(12) United States Patent
Cabrera Aquino et al.

(10) Patent No.: US 9,821,114 B2
(45) Date of Patent: Nov. 21, 2017

(54) COMPARTMENTALIZED METHOD OF NUCLEIC ACID DELIVERY AND COMPOSITIONS AND USES THEREOF

(71) Applicants: Jose Gustavo Cabrera Aquino, Mexico City (MX); Blanca Angelica Segura Pacheco, Mexico City (MX)

(72) Inventors: Jose Gustavo Cabrera Aquino, Mexico City (MX); Blanca Angelica Segura Pacheco, Mexico City (MX)

(73) Assignee: Global Bio Therapeutics, Inc., San Diego, CA (US)

( * ) Notice: Subject to any disclaimer, the term of this patent is extended or adjusted under 35 U.S.C. 154(b) by 0 days.

(21) Appl. No.: 13/815,206

(22) Filed: Feb. 7, 2013

(65) Prior Publication Data
US 2013/0211380 A1     Aug. 15, 2013

Related U.S. Application Data

(60) Provisional application No. 61/633,287, filed on Feb. 7, 2012.

(51) Int. Cl.
| | |
|---|---|
| A61K 31/70 | (2006.01) |
| A61M 5/00 | (2006.01) |
| A61M 31/00 | (2006.01) |
| A61B 19/00 | (2006.01) |
| A61M 5/178 | (2006.01) |
| A61K 35/76 | (2015.01) |
| A61K 48/00 | (2006.01) |
| A61M 39/00 | (2006.01) |
| A61M 5/30 | (2006.01) |

(52) U.S. Cl.
CPC .............. *A61M 5/178* (2013.01); *A61K 35/76* (2013.01); *A61K 48/0075* (2013.01); *A61K 48/005* (2013.01); *A61M 5/00* (2013.01); *A61M 5/30* (2013.01); *A61M 39/00* (2013.01); *A61M 2210/1071* (2013.01); *C12N 2799/022* (2013.01)

(58) Field of Classification Search
CPC ....... A61K 48/005; A61M 5/00; A61M 5/178; A61M 5/30; A61M 39/00; A61M 2210/1071
USPC ........ 514/44 R; 604/187, 246, 403, 508, 522
See application file for complete search history.

(56) References Cited

U.S. PATENT DOCUMENTS

| | | | |
|---|---|---|---|
| 3,667,471 A | 6/1972 | Doty et al. ................... 606/158 |
| 4,328,803 A | 5/1982 | Pape ............................. 604/28 |
| 4,342,832 A | 8/1982 | Goeddel et al. ........... 435/91.41 |
| 4,431,740 A | 2/1984 | Bell et al. ................. 435/252.33 |
| 4,517,295 A | 5/1985 | Bracke et al. ................ 435/101 |
| 4,522,811 A | 6/1985 | Eppstein et al. ............... 514/2.4 |
| 4,652,525 A | 3/1987 | Rutter et al. ............. 435/252.33 |
| 4,703,008 A | 10/1987 | Lin ................................ 435/360 |
| 4,738,927 A | 4/1988 | Taniguchi et al. ............. 435/243 |
| 4,965,195 A | 10/1990 | Namen et al. ............. 435/69.52 |
| 5,139,941 A | 8/1992 | Muzyczka et al. ........... 435/456 |
| 5,203,786 A | 4/1993 | Vernick ........................ 606/151 |
| 5,229,127 A | 7/1993 | McKinzie ..................... 424/427 |
| 5,273,056 A | 12/1993 | McLaughlin et al. ........ 128/898 |
| 5,282,851 A | 2/1994 | Jacob LaBarre ............ 623/6.56 |
| 5,292,362 A | 3/1994 | Bass et al. ............... 106/173.01 |
| 5,328,470 A | 7/1994 | Nabel et al. .................. 604/101 |
| 5,543,328 A | 8/1996 | McClelland et al. ...... 435/320.1 |
| 5,622,856 A | 4/1997 | Natsoulis ....................... 435/325 |
| 5,670,488 A | 9/1997 | Gregory et al. ............. 514/44 R |
| 5,704,908 A | 1/1998 | Hofmann et al. ............... 604/21 |
| 5,756,086 A | 5/1998 | McClelland et al. ........ 424/93.2 |
| 5,785,689 A | 7/1998 | de Toledo et al. ............ 604/158 |
| 5,792,453 A | 8/1998 | Hammond et al. ........ 424/93.21 |
| 5,801,029 A | 9/1998 | McCormick ................. 424/93.2 |
| 5,869,230 A | 2/1999 | Sukhatme ..................... 435/1.1 |
| 5,882,887 A | 3/1999 | Noeske et al. ............... 435/69.1 |
| 5,994,106 A | 11/1999 | Kovesdi et al. .............. 435/91.4 |
| 5,994,128 A | 11/1999 | Fallaux et al. ................ 435/325 |
| 5,998,205 A | 12/1999 | Hallenbeck et al. ......... 435/325 |
| 6,001,650 A | 12/1999 | Colosi .......................... 435/369 |
| 6,057,155 A | 5/2000 | Wickham et al. ............ 435/325 |
| 6,127,175 A | 10/2000 | Vigne et al. .................. 435/325 |
| 6,142,088 A | 11/2000 | Beyer ........................... 112/222 |
| 6,218,186 B1 | 4/2001 | Choi et al. ..................... 435/456 |
| 6,309,375 B1 | 10/2001 | Glines et al. ................. 604/187 |

(Continued)

FOREIGN PATENT DOCUMENTS

| | | |
|---|---|---|
| EP | 185 573 | 6/1986 |
| EP | 275 598 | 7/1988 |

(Continued)

OTHER PUBLICATIONS

Kay et al, Nature Genetics, 2000, 24:257-260.*
David, Best Practice and Research Clinical Obstetrics and Gynaecology, 2008, 22:203-218.*
Gagner et al, Surg Clin N Am, 2004, 84:451-462.*
Schiffelers et al, Nucleic Acids Research, 2004, 32:e149.*
Jiao et al, The American Journal of Surgery, 1999, 177:303-306.*
Papadakis et al, Current Gene Therapy, 2004, 4:89-113.*
Kota et al, Sci Transl Med, 2009, 6ra15.*
Kafri et al, Nature Genetics, 1997, 17:314-317.*
Berraondo et al, Human Gene Therapy, 2006, 17:601-610.*
Bruns et al, Tissue Engineering, 2005, 11:1718-1726.*

(Continued)

*Primary Examiner* — Shin Lin Chen
(74) *Attorney, Agent, or Firm* — Dentons US LLP; Stephanie Seidman

(57) ABSTRACT

Provided herein is a method of delivering nucleic acid molecules to a compartmentalized tissue or organ of a subject. Also provided herein are uses and processes for delivering a nucleic acid molecule to the parenchyma of a compartmentalized tissue or organ. The methods and uses can be used in the treatment of diseases and conditions and in industrial, agricultural and veterinary applications. Also provided herein are compositions containing an adenovirus or adeno-associated virus or other recombinant virus formulated for administration to the parenchyma of a tissue or organ.

75 Claims, 8 Drawing Sheets

(56) References Cited

U.S. PATENT DOCUMENTS

| | | |
|---|---|---|
| 6,322,536 B1 | 11/2001 | Rosengart et al. ...... 604/164.01 |
| 6,426,216 B1 | 7/2002 | Perricaudet et al. ...... 435/320.1 |
| 6,579,855 B1 | 6/2003 | Yla Herttuala et al. .... 514/44 R |
| 6,821,264 B1 | 11/2004 | Khurana et al. ............... 604/46 |
| 7,094,604 B2 | 8/2006 | Snyder et al. ............... 435/457 |
| 7,462,592 B2 | 12/2008 | Zuckermann et al. ........... 514/2 |
| 7,645,285 B2 | 1/2010 | Cosgrove et al. ............ 606/142 |
| 8,328,560 B2 | 12/2012 | Niblock et al. .............. 434/262 |
| 8,409,166 B2 | 4/2013 | Wiener et al. ............... 604/500 |
| 2002/0102729 A1 | 8/2002 | McLaughlin et al. ........ 435/455 |
| 2002/0168714 A1 | 11/2002 | Barbas et al. ............... 435/69.1 |
| 2003/0050271 A1 | 3/2003 | Sukhatme ...................... 514/44 |
| 2003/6104625 | 6/2003 | Cheng et al. ................ 435/456 |
| 2004/0053875 A1 | 3/2004 | Kreutzer ........................ 514/44 |
| 2005/0129660 A1 | 6/2005 | Hagstrom et al. .......... 424/93.2 |
| 2006/0188482 A1 | 8/2006 | Kay et al. .................... 424/93.2 |
| 2008/0009823 A1 | 1/2008 | McKay ......................... 604/500 |
| 2008/0025952 A1 | 1/2008 | Scheule et al. ............. 424/93.2 |
| 2008/0119880 A1 | 5/2008 | Chu ............................. 606/157 |
| 2008/0269718 A1 | 10/2008 | Weiner et al. ............... 604/506 |
| 2008/0281248 A1* | 11/2008 | Angheloiu et al. ......... 604/6.09 |
| 2010/0010068 A1 | 1/2010 | Ren et al. ................... 514/44 R |
| 2010/0234862 A1 | 9/2010 | Patel et al. .................. 606/151 |
| 2011/0119777 A1 | 5/2011 | Hermens et al. ............... 800/13 |
| 2011/0262399 A1 | 10/2011 | Fontanellas Romá et al. ............................ 424/93.2 |
| 2011/0305772 A1 | 12/2011 | Cameron ..................... 424/553 |
| 2012/0009268 A1 | 1/2012 | Asokan et al. .............. 424/499 |
| 2012/0308522 A1 | 12/2012 | Martin et al. ............... 424/93.2 |
| 2015/0045769 A1 | 2/2015 | Cabrera-Aquino et al. .. 604/506 |
| 2015/0066056 A1 | 3/2015 | Cabrera-Aquino et al. .. 606/140 |
| 2015/0352293 A9 | 12/2015 | Cabrera-Aquino et al. .. 606/140 |

FOREIGN PATENT DOCUMENTS

| | | |
|---|---|---|
| EP | 282 185 | 9/1988 |
| EP | 1 049 487 | 11/2000 |
| JP | H06-502078 | 3/1994 |
| JP | H08-511423 | 12/1996 |
| JP | 2004-537982 | 12/2004 |
| JP | 2006-501177 | 1/2006 |
| JP | 2007-530121 | 11/2007 |
| JP | 2008-521575 | 6/2008 |
| JP | 2008-526188 | 7/2008 |
| WO | WO 92/09616 | 6/1992 |
| WO | WO 93/14778 | 8/1993 |
| WO | WO 94/29471 | 12/1994 |
| WO | WO 95/26411 | 10/1995 |
| WO | WO 95/29993 | 11/1995 |
| WO | WO 95/34671 | 12/1995 |
| WO | WO 96/22378 | 7/1996 |
| WO | WO 96/40955 | 12/1996 |
| WO | WO 97/00326 | 1/1997 |
| WO | WO 97/25466 | 7/1997 |
| WO | WO 99/25860 | 5/1999 |
| WO | WO 2000/009675 | 2/2000 |
| WO | WO 00/26395 | 5/2000 |
| WO | WO 00/44895 | 8/2000 |
| WO | WO 01/00220 | 1/2001 |
| WO | WO 01/29058 | 4/2001 |
| WO | WO 01/30843 | 5/2001 |
| WO | WO 01/75164 | 10/2001 |
| WO | WO 01/92513 | 12/2001 |
| WO | WO 02/067861 | 9/2002 |
| WO | WO 02/085306 | 10/2002 |
| WO | WO 04/001049 | 12/2003 |
| WO | WO 2005/049094 | 6/2005 |
| WO | WO 2005/092425 | 10/2005 |
| WO | WO 2006/060641 | 6/2006 |
| WO | WO 2006/070023 | 7/2006 |
| WO | WO 2007/019646 | 2/2007 |
| WO | WO 2010/134806 | 11/2010 |
| WO | WO 2013/119880 | 8/2013 |

OTHER PUBLICATIONS

Kobayashi et al., 2007, World Journal of Gastroenterology, vol. 13, No. 25, p. 3487-3492.*

Letter/Written Disclosure of the Information Disclosure Statement for the above-referenced application, mailed on Jun. 19, 2013, 2 pages.

Abdalla et al., "Hepatic vascular occlusion: which technique?" Surg. Clin. N. Am., 84:563-585 (2004).

Adenovirus Wiki, "Human adenovirus genome sequences and annotations," Published on Dec. 1, 2010 [online][retrieved on Mar. 21, 2013] Retrieved from:<URL:binf.gmu.edu/wiki/index.php [2 pages].

Aihara, H. and Miyazaki, J., "Gene transfer into muscle by electroporation in vivo." Nat Biotechnol 16: 867-870 (1998).

Alexander et al. (2007) "Progress and prospects: gene therapy clinical trials (part 1)," Gene Ther. 14(20):1439-1447 (2007).

Assil et al., "Multivesicular liposomes. Sustained release of the antimetabolite cytarabine in the eye." Arch Ophthalmol. 105:400-403 (1987).

Barakat, M. and P. Kaiser, "VEGF inhibitors for the treatment of neovascular age-related macular degeneration." Expert Opin. Investig. Drugs 18(5):637-646 (2009).

Bass et al., "Recombinant adenovirus-mediated gene transfer to genitourinary epithelium in vitro and in vivo." Cancer Gene Ther., 2:97-104 (1995).

Baxley, S. and R. Serra, "Inhibiting breast cancer progression by exploiting TGFbeta signaling." Curr. Drug Targets 11(9):1089-1102 (2010).

Belghiti et al., "Continuous versus intermittent portal triad clamping for liver resection: a controlled study." Annals of Surgery, 229:369-375 (1999).

Bergelson et al., "Isolation of a common receptor for Coxsackie B viruses and adenoviruses 2 and 5," Science 275:1320-1323 (1997).

Berkner et al., "Abundant expression of polyomavirus middle T antigen and dihydrofolate reductase in an adenovirus recombinant," J. Virol. 61:1213-1220 (1987).

Berkner et al., "Expression of heterologous sequences in adenoviral vectors." Curr. Top. Micro. Immunol., 158:39-66 (1992).

Berkner et al., "Generation of adenovirus by transfection of plasmids," Nuc. Acids Res. 11:6003-6020 (1983).

Blaisdell et al., "The pathophysiology of skeletal muscle ischemia and the reperfusion syndrome: a review," Cardiovascular Surgery, 10:620-630 (2002).

Blomer et al., "Highly efficient and sustained gene transfer in adult neurons with a lentivirus vector," J. Virol., 71:6641-6449 (1997).

Blume et al., "Formulated collagen gel accelerates healing rate immediately after application in patients with diabetic neuropathic foot ulcers," Wound Repair Regen., 19:302-308 (2011).

Brekke, O. and I. Sandlie, "Therapeutic antibodies for human diseases at the dawn of the twenty-first century." Nat. Rev. Drug. Discov. 2(1):52-62 and Correction (2003).

Breyer et al., "Adenoviral vector-mediated gene transfer for human gene therapy," Current Gene Therapy, 1:149-162 (2001).

Brophy et al., Cloned transgenic cattle produce milk with higher levels of beta-casein and kappa-casein, Nature Biotechnology, 21:157-162 (2003).

Brunetti-Pierri et al., "Acute toxicity after high-dose systemic injection of helper-dependent adenoviral vectors into nonhuman primates," Hum Gene Ther.15(1):35-46 (2004).

Brunetti-Pierri et al., "Efficient, long-term hepatic gene transfer using clinically relevant HDAd doses by balloon occlusion catheter delivery in nonhuman primates," Molecular Therapy, 17:327-333 (2009).

Brunetti-Pierri et al., "Improved hepatic transduction, reduced systemic vector dissemination, and long-term transgene expression by delivering helper-dependent adenoviral vectors into the surgically isolated liver of nonhuman primates," Hum Gene Ther. 17:391-404 (2006).

Buchshacher, G. and F. Wong-Staal, "Development of lentiviral vectors for gene therapy for human diseases," Blood, 95:2499-2504 (2000).

(56) References Cited

OTHER PUBLICATIONS

Buell et al., "Is any method of vascular control superior in hepatic resection of metastatic cancers? Longmire clamping, pringle maneuver, and total vascular isolation," Arch. Surg., 136:569-575.
Burger et al., "Recombinant AAV viral vectors pseudotyped with viral capsids from serotypes 1, 2, and 5 display differential efficiency and cell tropism after delivery to different regions of the central nervous system," Mol. Ther., 10:302-317 (2004).
Campos et al., "Current advances and future challenges in Adenoviral vector biology and targeting." Curr. Gene Ther., 7:189-204 (2007).
Cantrell et al., "Cloning, sequence, and expression of a human granulocyte/macrophage colony-stimulating factor," Proc. Natl. Acad. Sci, 82:6250-6254 (1985).
Cassani et al., "Integration of retroviral vectors induces minor changes in the transcriptional activity of T cells from ADA-SCID patients treated with gene therapy," Blood, 114:3546-3556 (2009).
Cerullo et al., "Oncolytic adenovirus coding for granulocyte macrophage colony-stimulating factor induces antitumoral immunity in cancer patients," Cancer Res., 70:4297-4309 (2010).
Chaib et al., "The main indications and techniques for vascular exclusion of the liver," Arq Gastronenterol., 40:131-136 (2003).
Chan et al., "Surgical management of primary hepatocellular carcinoma," Hepatic Surgery, Hesham Abdeldayem (Ed.), p. 301-326 (2013).
Chia et al., "Adenoviral-mediated gene delivery to liver isografts: improved model of ex vivo gene transfer," Transplant Proc. 31:475-476 (1999).
Chillon et al. (1999) "Group D adenoviruses infect primary central nervous system cells more efficiently than those from group C," J. Virol., 73:2537-2540 (1999).
Chiorini et al., "Cloning and characterization of adeno-associated virus type 5," J. Virol., 73:1309-1319 (1999).
Chiorini et al., "Cloning of adeno-associated virus type 4 (AAV4) and generation of recombinant AAV4 particles," J. Virol., 71:6823-6833 (1997).
Cho et al., "Therapeutic nanoparticles for drug delivery in cancer," Clin. Cancer. Res., 14:1310-1316 (2008).
Choi et al., "Hybrid HIV/MSCV LTR enhances transgene expression of lentiviral vectors in human CD34(+) hematopoietic cells," Stem Cells, 19:236-246 (2001).
Chouillard et al., "Vascular clamping in liver surgery: physiology, indications and techniques," Annals of Surgical Innovation and Research, 4:2, 12 pages (2010).
Chowdhury et al., "Techniques for liver resection," BSMMU J., 3:112-119 (2010).
Chroboczek et al., "The sequence of the genome of adenovirus type 5 and its comparison with the genome of adenovirus type 2," Virology, 186:280-285 (1992).
Cline, M., "Perspectives for gene therapy: inserting new genetic information into mammalian cells by physical techniques and viral vectors," Pharmac. Ther. 29:69-92 (1985).
Clowes et al., "Long-term biological response of injured rat carotid artery seeded with smooth muscle cells expressing retrovirally introduced human genes," J. Clin. Invest. 93:644-651 (1994).
Corjon et al., "Cell entry and trafficking of human adenovirus bound to blood factor X is determined by the fiber serotype and not hexon:heparan sulfate interaction," PLoS One. 6:e18205, 19 pages.
Cotten et al., "Receptor-mediated transport of DNA into eukaryotic cells," Meth. Enzymol. 217:618-644 (1993).
Crettaz et al., "Intrahepatic injection of adenovirus reduces inflammation and increases gene transfer and therapeutic effect in mice," Hepatology, 44:623-632 (2006).
Curcio et al., "Oligonucleotides as modulators of cancer gene expression," Pharmacol Therapy, 74:317-332 (1997).
Curiel, D., "Strategies to adapt adenoviral vectors for targeted delivery," Ann NY Acad. Sci., 886:158-171 (1999).
Czubayko et al., "Adenovirus-mediated transduction of ribozymes abrogates HER-2/neu and pleiotrophin expression and inhibits tumor cell proliferation," Gene Therapy, 4:943-949 (1997).
Davidson et al., "Overproduction of polyomavirus middle T antigen in mammalian cells through the use of an adenovirus vector," J. Virol. 61:1226-1239 (1987).
Davison et al., "The DNA sequence of adenovirus type 40," J. Mol. Biol., 234:1308-1316 (1993).
Denardi et al., "Nephron-sparing surgery for renal tumours using selective renal parenchymal clamping," BJU Int. 2005 96:1036-1039 (2005).
Dixon et al., "Vascular occlusion to decrease blood loss during hepatic resection," Am J Surg. 190:75-86 (2005).
Dmitriev et al., "An adenovirus vector with genetically modified fibers demonstrates expanded tropism via utilization of a coxsackievirus and adenovirus receptor-independent cell entry mechanism," J. Virol., 72:9706-9712 (1998).
Duque et al., "Intravenous administration of self-complementary AAV9 enables transgene delivery to adult motor neurons," Mol. Ther., 17:1187-1196 (2009).
Eastman et al., "Development of catheter-based procedures for transducing the isolated rabbit liver plasmid DNA," Human Gene Therapy 13:2065-2077 (2002).
Echelard et al., "Production of recombinant therapeutic proteins in the milk of transgenic animals," Biopharm International, 19:36-45 (2006).
Eto et al., "Development of PEGylated adenovirus vector with targeting ligand," Int. J. Pharm., 354:3-8 (2008).
Fabre et al., "Hydrodynamic gene delivery to the pig liver via an isolated segment of the inferior vena cava," Gene Ther., 15:452-462 (2008).
Fallaux et al., "New helper cells and matched early region 1-deleted adenovirus vectors prevent generation of replication-competent adenoviruses," Hum. Gene Ther. 9:1909-1907 (1998).
Faraji, A. and P. Wipf, "Nanoparticles in cellular drug delivery," Bioorg. Med. Chem. 17(8):2950-2962 (2009).
Ferkol et al., "Transfer of the human Alpha1-antitrypsin gene into pulmonary macrophages in vivo," Am. J. Respir. Cell Mol. Biol., 18:591-601 (1998).
Ferry et al., "Retroviral-mediated gene transfer into hepatocytes in vivo," Proc. Natl. Acad. Sci. 88:8377-8381 (1991).
Finch, P. and J. Rubin, "Keratinocyte growth factor expression and activity in cancer: implications for use in patients with solid tumors," J. Natl. Cancer Inst. 98(12):812-824 (2006).
Fisher et al., "Recombinant adenovirus deleted of all viral genes for gene therapy of cystic fibrosis," J. Virol., 217:11-22 (1996).
Foust et al., "Intravascular AAV9 preferentially targets neonatal neurons and adult astrocytes," Nature Biotechnology, 27:59-65 (2009).
Franzen, S., "A comparison of peptide and folate receptor targeting of cancer cells: from single agent to nanoparticle," Expert Opin. Drug. Deliv. 8(3):281-298 (2011).
Fu et al., "Correction of neurological disease of mucopolysaccharidosis IIIB in adult mice by rAAV9 trans-blood-brain barrier gene delivery," Mol. Ther., 19:1025-1033 (2011).
Fujii et al., "Targeting of interstitial cells using a simple gene-transfer strategy," Nephrol Dial Transplant. 21:2745-2753 (2006).
Fujita et al., "Sendai virus-mediated gene delivery into hepatocytes via isolated hepatic perfusion," Biological & Pharmaceutical Bulletin, 29:1728-1734 (2006).
Fumoto et al., "Liver- and lobe-specific gene transfer following the continuous microinstillation of Plasmid DNA onto the liver surface in mice: effect of instillation speed," Biol. Pharm. Bull., 32:1298-1302 (2009).
Furlan et al., "Gene therapy-mediated modulation of immune processes in the central nervous system," Curr Pharm Des. 9:2002-2008 (2003).
Gao et al., "Clades of Adeno-associated viruses are widely disseminated in human tissues," J. Virol., 78:6381-6388 (2004).
Gao et al., "Novel adeno-associated viruses from rhesus monkeys as vectors for human gene therapy," Proc Natl. Acad. Sci., 99:11854-11859 (2002).
Genbank Accession No. AY530629.1, "Adeno-associated virus isolate hu.9 capsid protein VP1 (cap) gene, complete cds," Published on Jun. 24, 2004 [online][retrieved on Mar. 19, 2013] Retrieved from:<URL:ncbi.nlm.nih.gov/nuccore/AY530629.1[2 pages].

(56) References Cited

OTHER PUBLICATIONS

GENERX, "FGF-4 gene therapy GENERX—Collateral Therapeutics," BioDrugs 16:75-76 (2002).
George, D., "Receptor tyrosine kinases as rational targets for prostate cancer treatment: platelet-derived growth factor receptor and imatinib mesylate," Urology 60(3 Suppl. 1):115-121 (2002).
Ghosh-Choudhury et al., "Stable transfer of a mouse dihydrofolate reductase gene into a deficient cell line using human adenovirus vector," Biochem. Biophys. Res. Commun., 147:964-973 (1987).
Gilardi et al., "Expression of human alpha 1-antitrypsin using a recombinant adenovirus vector," FEBS Lett.267:60-62 (1990).
Golovan et al., "Pigs expressing salivary phytase produce low-phosphorus manure," Nature Biotechnology, 19:741-745 (2001).
Gondi, C. and J. Rao, "Concepts in in vivo siRNA delivery for cancer therapy," J. Cell Physiol. 220(2):285-291 (2009).
Gong et al., "Thirteen UDPglucuronosyltransferase genes are encoded at the human UGT1 gene complex locus," Pharmacogentics, 11:357-368 (2001).
Gorziglia et al., "Elimination of both E1 and E2 from adenovirus vectors further improves prospects for in vivo human gene therapy," J. Virology 70:4173-4178 (1996).
Goto et al., "Highly efficient electro-gene therapy of solid tumor by using an expression plasmid for the herpes simplex virus thymidine kinase gene," Proc Natl Acad Sci U S A 97:354-359 (2000).
Graham et al., "Characteristics of a Human Cell Line Transformed by DNA from Human Adenovirus Type 5," J. Gen. Virol. 36:59-71 (1977).
Graham, F., "Covalently closed circles of human adenovirus DNA are infectious," EMBO J. 3:2917-2922 (1984).
Grimm, D. and M. Kay, "From virus evolution to vector revolution: use of naturally occurring serotypes of adeno-associated virus (AAV) as novel vectors for human gene therapy," Current Gene Therapy, 3:281-304 (2003).
Groskreutz et al., "Genetically engineered proinsulin constitutively processed and secreted as mature, active insulin." J. Biol. Chem., 269:6241-6245 (1994).
Grossman et al., "A pilot study of ex vivo gene therapy for homozygous familial hypercholesterolaemia," Nat. Med., 1:1148-1154 (1995).
Grossman, M. and J. Wilson, "Retroviruses: delivery vehicle to the liver," Curr. Opin. in Genetics and Devel. 3:110-114 (1993).
Haj-Ahmad et al., "Development of a helper-independent human adenovirus vector and its use in the transfer of the herpes simplex virus thymidine kinase gene," J. Virol. 57:267-274 (1986).
Hampel, A., "The hairpin ribozyme: discovery, two-dimensional model, and development for gene therapy," Prog. Nucleic Acid Res. Mol. Biol., 58:1-39 (1998).
Harris et al., "Tissue-specific gene delivery via nanoparticle coating," Biomaterials, 31:998-1006 (2010).
Harvey et al., "Variability of human systemic humoral immune responses to adenovirus gene transfer vectors administered to different organs," J. Virol., 73:6729-6742 (1999).
Herbomel et al., "The rat albumin promoter is composed of six distinct positive elements within 130 nucleotides," Molecular and Cellular Biology, 9:4750-4758 (1989).
Hodges et al., "Local delivery of viral vector mitigates neutralization by antiviral antibodies and results in efficient transduction of rabbit liver," Mol. Ther. 12:1043-1051 (2005).
Hoffman et al., "Renal ischemic tolerance," AMA Arch. Surg., 109:550-551 (1974).
Hofherr et al., "Modification of adenoviral vectors with polyethylene glycol modulates in vivo tissue tropism and gene expression," Mol Ther. 16(7):1276-1282 (2008).
Holzer et al., "Assessment of renal oxygenation during partial nephrectomy using hyperspectral imaging," Journal of Urology, 186:400-404 (2011).
IUPAC-IUB Commission on Biochemical Nomenclature, "Symbols for amino-acid derivatives and peptides: recommendations (1971)," Biochem. 11(9):1726-1732 (1972).
James, H. and I. Gibson, "The therapeutic potential of ribozymes," Blood, 91:371-382 (1998).
Jimeno, A. and M. Hidalgo, "Pharmacogenomics of epidermal growth factor receptor (EGFR) tyrosine kinase inhibitors," Biochim. Biophys. Acta 1766(2):217-229 (2006).
Jin et al., "Nanoparticle-mediated drug delivery and gene therapy," Biotechnol. Prog., 23:32-41 (2007).
Johansson et al., "Adenoviral-mediated expression of porphobilinogen deaminase in liver restores the metabolic defect in a mouse model of acute intermittent porphyria," Mol. Ther. 10(2):337-343 (2004).
Jolly et al., "Viral vector systems for gene therapy." Cancer Gene Therapy, 1:51-64 (1994).
Joung et al., "Partial nephrectomy using parenchymal compression without renal pedicle clamping," Korean J. Urol., 28:265-269 (2007).
Kamimura, K. and D. Liu, "Physical approaches for nucleic acid delivery to liver," AAPS J.10:589-595 (2008).
Kanematsu et al., "A newly designed clamp facilitates hepatic resection," Jpn. J. Surg., 14:432-423 (1984).
Kiem et al., "Retrovirus-mediated gene transduction into canine peripheral blood repopulating cells," Blood 83:1467-1473 (1994).
Kieseier et al., "Interferon-beta and neuroprotection in multiple sclerosis—facts, hopes and phantasies," Exp. Neurol., 203:1-4 (2007).
Kim et al., "Preparation of multivesicular liposomes," Bioch. Bioph. Acta 728:339-348 (1983).
Kinoshita et al., "Targeted gene delivery to selected liver segments via isolated hepatic perfusion with clamping of the portal vein," Molecular Therapy 9: S119 (2004).
Kinoshita et al., "Targeted gene delivery to selected liver segments via isolated hepatic perfusion," J Surg. Res., 160:47-51 (2010).
Ko et al., "Efficacy of parenchymal compression in open partial nephrectomies: a comparison with conventional vascular clamping," Korean J. Urol., 51:8-14 (2010).
Kochanek et al., "A new adenoviral vector: Replacement of all viral coding sequences with 28 kb of DNA independently expressing both full-length dystrophin and beta-galactosidase," Proc. Natl. Acad. Sci., 93:5731-5736 (1996).
Kotin et al., "Site-specific integration by adeno-associated virus," Proc. Natl. Acad. Sci., 87:2211-2215 (1990).
Kotin, R., "Prospects for the use of adeno-associated virus as a vector for human gene therapy," Human Gene Therapy, 5:793-801 (1994).
Kozak et al., "Structural features in eukaryotic mRNAs that modulate the initiation of translation," J. Biol. Chem. 266: 19867-19870 (1991).3.
Krasnykh et al., "Genetic targeting of adenoviral vectors," Mol. Ther., 1:391-405 (2000).
Lai et al., "Generation of cloned transgenic pigs rich in omega-3 fatty acids," Nature Biotechnology, 24:435-436 (2006).
Lazaris et al., "Spider silk fibers spun from soluble recombinant silk produced in mammalian cells," Science, 295:472-476 (2002).
Lecollinet et al., "Improved gene delivery to intestinal mucosa by adenoviral vectors bearing subgroup B and d fibers," J Virol. 80(6):2747-2759 (2006).
Lee et al., "Temporal- and spatial-specific expression of bovine beta-casein/bovine growth hormone fusion gene in transgenic mice," Theriogenology, 47:225, 1 page (1997).
Lesurtel et al. (2009) "Clamping techniques and protecting strategies in liver surgery," HPB (Oxford). 11:290-295.
Levrero et al., Defective and nondefective adenovirus vectors for expressing foreign genes in vitro and in vivo, Gene 101:195-202 (1991).
Lewis, P. and F. Emerman, "Passage through mitosis is required for oncoretroviruses but not for the human immunodeficiency virus," J. Virol., 68:510-516 (1996).
Li, S. and L. Huang, "Gene therapy progress and prospects: non-viral gene therapy by systemic delivery," Gene Therapy, 13:1313-1319 (2006).
Lieber et al., "Recombinant adenoviruses with large deletions generated by Cre-mediated excision exhibit different biological

(56) References Cited

OTHER PUBLICATIONS properties compared with first-generation vectors in vitro and in vivo," J. Virol., 70:8944-8960 (1996).
Lillico et al., "Transgenic chickens as bioreactors for protein-based drugs," Drug Discovery Today, 10:191-196 (2005).
Liu et al., "Gene therapy of scarring: a lesson learned from fetal scarless wound healing," Yonsei Medical Journal, 42:634-645 (2001).
Lo et al., "EGFR signaling pathway in breast cancers: from traditional signal transduction to direct nuclear translocalization," Breast Canc. Res. Treat. 95(3):211-218 (2006).
Lo, H., "EGFR-targeted therapy in malignant glioma: novel aspects and mechanisms of drug resistance," Curr. Mol. Pharmacol. 3(1):37-52 (2010).
Loeffler, J. and J. Behr, "Gene transfer into primary and established mammalian cell lines with lipopolyamine-coated DNA," Meth. Enzymol. 217:599-618 (1993).
Maga et al., "Human lysozyme expressed in the mammary gland of transgenic dairy goats can inhibit the growth of bacteria that causes mastitis and the cold-spoilage of milk," Foodborne Pathog. Dis. 3:384-392 (2006).
Mandel et al., "Neutralization of animal viruses," Adv. Virus. Res., 23:205-268 (1978).
Manilla et al., "Regulatory considerations for novel gene therapy products: a review of the process leading to the first clinical lentiviral vector," Human Gene Therapy,16:17-25 and Corrections (2005).
Massie et al., "Construction of a helper-free recombinant adenovirus that expresses polyomavirus large T antigen," Mol. Cell. Biol. 6:2872-2883 (1986).
Mellstedt, H., "Monoclonal antibodies in human cancer," Drugs Today 39(Supl. C):1-16 (2003).
Meng et al., "Keratinocyte gene therapy for systemic diseases. Circulating interleukin 10 released from gene-transferred keratinocytes inhibits contact hypersensitivity at distant areas of the skin," J. Clin. Invest., 101(6):1462-1467 (1998).
Mercier, J., "Genetic engineering applied to milk producing animals: some expectations," Found in *Exploiting New Technologies in Animal Breeding*, Oxford University Press, New York, pp. 122-131 (1987).
Mingozzi et al., "Therapeutic in vivo gene transfer for genetic disease using AAV: progress and challenges," Nature Reviews Genetics, 12:341-355 and Corrigendum (2011).
Mir et al., "Long-term, high level in vivo gene expression after electric pulse-mediated gene transfer into skeletal muscle," C R Acad Sci III 321: 893-899 (1998).
Mittal et al., "Monitoring foreign gene expression by a human adenovirus-based vector using the firefly luciferase gene as a reporter," Virus Res. 28:67-90 (1993).
Mizuguchi et al., "Targeted adenovirus vectors," Hum. Gene Ther., 15:1034-1044 (2004).
Moreno et al., "Studies on the outflow tracts of the liver. I. On a method for the functional demonstration of the outflow tracts of the liver and its application to the study of hepatic hemodynamics in normal and cirrhotic rats," Ann Surg. 155:412-426 (1962).
Morral et al., "High doses of a helper-dependent adenoviral vector yield supraphysiological levels of alpha 1-antitrypsin with negligible toxicity," Hum. Gene Ther., 10:2709-2716 (1998).
Muramatsu et al., "Foreign gene expression in the mouse testis by localized in vivo gene transfer," Biochem Biophys Res Commun 233: 45-49 (1997).
Muramatsu et al., "Nucleotide sequencing and generation of an infectious clone of adeno-associated virus 3," Virol., 221:208-217 (1996).
Muzyczka, N., "Use of adeno-associated virus as a general transduction vector for mammalian cells," Curr. Top. Micro. Immunol., 1 58:97-129 (1992).
Nakai, H., "Hepatic Gene Therapy," pp. 343-370 in *Molecular Pathology of Liver Diseases* (S.P.S. Monga, ed.) Springer (2010).

Naldini et al., "In vivo gene delivery and stable transduction of nondividing cells by a lentiviral vector," Science, 272:263-267 (1996).
Nathwani et al., "Sustained high-level expression of human factor IX (hFIX) after liver-targeted delivery of recombinant adeno-associated virus encoding the hFIX gene in rhesus macaques," Blood, 100:1662-1669 (2002).
Nemerow, G., "Cell receptors involved in adenovirus entry," Virology 274:1-4 (2000).
Neumann et al., "Cytokine gene transfer in the therapy of autoimmune diseases," Gene Therapy and Molecular Biology, 9:61-76 (2005).
O'donnell et al., "Efficient, cardiac-specific adenoviral gene transfer in rat heart by isolated retrograde perfusion in vivo," Gene Therapy, 12:958-964 (2005).
Oh, Y. and T. Park, "siRNA delivery systems for cancer treatment," Adv. Drug. Deliv. Rev. 61(10):850-862 (2009).
Ohashi et al., "Modified infusion procedures affect recombinant adeno-associated virus vector type 2 transduction in the liver," Human Gene Therapy 16:299-306 (2005).
Palmiter et al., "Dramatic growth of mice that develop from eggs microinjected with metallothionein-growth hormone fusion genes," Nature, 300:611-615 (1982).
Parks et al., "A helper-dependent adenovirus vector system: removal of helper virus by Cre-mediated excision of the viral packaging signal," Proc. Natl. Acad. Sci., 93:13565-13570 (1996).
Pathak et al., "Nano-vectors for efficient liver specific gene transfer," Int. J. Nanomedicine, 3:31-49 (2008).
Prather et al., "Transgenic swine for biomedicine and agriculture," Theriogenology, 59:115-123 (2003).
Qi et al., "The clinical effect of recombinant human ad p53 agent-Gendicine in advanced cancer patients in 23 cases," Modern Oncology, 14:1259-1297 (2006). Article in Chinese and abstract in the English language.
Rasmussen et al., "TNFerade Biologic: preclinical toxicology of a novel adenovector with a radiation-inducible promoter, carrying the human tumor necrosis factor alpha gene," Cancer Gene Ther., 9:951-957 (2002).
Reid et al., "Hepatic arterial infusion of a replication-selective oncolytic adenovirus (dl1520): phase II viral, immunologic, and clinical endpoints," Cancer Res. 62:6070-6079 (2002).
Reid et al., "Intravascular adenoviral agents in cancer patients: lessons from clinical trials," Cancer Gene Ther. 9:979-986 (2002).
Rettinger et al., "In vivo hepatocyte transduction with retrovirus during in-flow occlusion," J Surg Res. 54:418-425 (1993).
Richt et al., "Production of cattle lacking prion protein." Nature Biotechnology, 25:132-138 (2007).
Rizzuto et al., "Efficient and regulated erythropoietin production by naked DNA injection and muscle electroporation," Proc Natl Acad Sci USA 96: 6417-6422 (1999).
Roberts et al., "DNA sequences from the adenovirus 2 genome," J. Biol. Chem., 259:13968-13975 (1984).
Roelvink et al., "The coxsackievirus-adenovirus receptor protein can function as a cellular attachment protein for adenovirus serotypes from subgroups A, C, D, E, and F," J. Virol. 72:7909-7915 (1998).
Rosewell et al., "Helper-dependent adenoviral vectors," J. Genet. Syndr. Gene Ther., S5:001, 16 pages (2011).
Rossi, J., "Therapeutic applications of catalytic antisense RNAs (ribozymes)," Ciba Found. Symp., 209:195-204 (1997).
Russell et al., "Oncolytic virotherapy," Nature Biotechnology, 30:658-670 (2012).
Russell, W., "Adenoviruses: update on structure and function," J Gen. Virol. 90:1-20 (2009).
Rutledge et al., "Infectious clones and vectors derived from adeno-associated virus (AAV) serotypes other than AAV type 2," J. Virol, 72:309-319 (1998).
Sachdeva et al., "Chimeric HIV-1 and HIV-2 lentiviral vectors with added safety insurance," Journal of Medical Virology, 79:118-126 (2007).
Saeki et al., "Functional expression of a Delta12 fatty acid desaturase gene from spinach in transgenic pigs," Proc. Natl. Acad. Sci., 101:6361-6366 (2004).

(56) References Cited

OTHER PUBLICATIONS

Sajja et al., "Development of multifunctional nanoparticles for targeted drug delivery and noninvasive imaging of therapeutic effect," Curr. Drug. Discov. Technol. 6(1):43-51(2009).
Salmons, B. and W. Gunzberg, "Targeting of retroviral vectors for gene therapy," Human Gene Therapy 4:129-141 (1993).
Sawyer et al., "Technical requirements for effective regional hydrodynamic gene delivery to the left lateral lobe of the rat liver," Gen Ther., 17:560-564 (2010).
Schilephake, H., "Bone growth factors in maxillofacial skeletal reconstruction," Int. J. Oral Maxillofac. Surg. 31(5):469-484 (2002).
Seglen, P., Chapter 4, "Preparation of Isolated Rat Liver Cells", *Methods in Cell Biology*, vol. XIII, Prescott, D., ed., Academic Press, pp. 29-83 (1976).
Segura-Pancheco et al., "HDAC inhibitor valproic acid upregulates CAR in vitro and in vivo," Genet. Vaccines Ther.5:10, 8 pages (2007).
Sferra et al., "Widespread correction of lysosomal storage following intrahepatic injection of a recombinant adeno-associated virus in the adult MPS VII mouse," Mol. Ther. 10:478-491 (2004).
Shayakhmetov et al., "Adenovirus Binding to Blood Factors Results in Liver Cell Infection and Hepatotoxicity," J. Virol. 79:7478-7491 (2005).
Shayakhmetov et al., "Analysis of adenovirus sequestration in the liver, transduction of hepatic cells, and innate toxicity after injection of fiber-modified vectors," J. Virol. 78:5368-5381 (2004).
Sheridan, C., "Gene therapy finds its niche," Nature Biotechnology, 29:121-128 and errata (2011).
Shichiri et al., "Intravenous gene therapy for familial hypercholesterolemia using ligand-facilitated transfer of a liposome:LDL receptor gene complex," Gene Ther., 10:827-831 (2003).
Shine, J. and L. Delgarno, "Determinant of cistron specificity in bacterial ribosomes," Nature 254(5495):34-38 (1975).
Shirakawa, T., "Clinical trial design for adenoviral gene therapy products," Drugs News Perspectives, 22(3):140-145 (2009).
Somers et al., "A comparison of the expression and metabolizing activities of phase I and II enzymes in freshly isolated human lung parenchymal cells and cryopreserved human hepatocytes," DMD, 35:1797-1805 (2007).
Somiari et al., "Theory and in vivo application of electroporative gene delivery," Mol Ther 2:178-187 (2000).
Song et al., "Effect of DNA-dependent protein kinase on the molecular fate of the rAAV2 genome in skeletal muscle," Proc. Natl. Acad. Sci., 98:4084-4088 (2001).
Song et al., "Ex vivo transduced liver progenitor cells as a platform for gene therapy in mice," Hepatology, 40:918-924 (2004).
Song et al., "Stable therapeutic serum levels of human alpha-1 antitrypsin (AAT) after portal vein injection of recombinant adeno-associated virus (rAAV) vectors," Gene Ther., 8:1299-1306 (2001).
Song et al., "Sustained secretion of human alpha-1-antitrypsin from murine muscle transduced with adeno-associated virus vectors," Proc. Natl. Acad. Sci., 95:14384-14388 (1998).
Sprengel et al., "Nucleotide sequence of human adenovirus type 12 DNA: comparative functional analysis," J. Virol., 68:379-389 (1994).
Sterman et al., "A phase I trial of repeated intrapleural adenoviral-mediated interferon-beta gene transfer for mesothelioma and metastatic pleural effusions," Mol. Ther., 18:852-860 (2010).
Sullenger (1995) "Revising messages traveling along the cellular information superhighway," Chem. Biol., 2:249-253.
Sullenger, B., "Ribozyme-mediated repair of RNAs encoding mutant tumor suppressors," Cytokines Mol. Ther., 2:201-205 (1996).
Suzuki et al., "Direct gene transfer into rat liver cells by in vivo electroporation," FEBS Lett 425: 436-440 (1998).
Thompson et al., "The impact of ischemia time during open nephron sparing surgery on solitary kidneys: a multi-institutional study," J. Urology, 177:471-476 (2006).
Titomirov et al., "In vivo electroporation and stable transformation of skin cells of newborn mice by plasmid DNA," Biochim Biophys Acta 1088: 131-134 (1991).
Toren et al., "Use of a novel parenchymal clamp for laparoscopic and open partial nephrectomy," Can. Urol. Assoc., 4:E133-E136 (2010).
Trojanowska, M and J. Varga, "Molecular pathways as novel therapeutic targets in systemic sclerosis," Curr. Opin. Rheumatol. 19(6):568-573 (2007).
Tronche et al., "The rat albumin promoter: cooperation with upstream elements is required when binding of APF/HNF1 to the proximal element is partially impaired by mutation or bacterial methylation," Molecular and Cellular Biology, 9:4759-4766 (1989).
Uniprot Accession No. P00451, "Coagulation factor VIII," Last Modified on Mar. 6, 2013 [online][retrieved on Mar. 19, 2013] Retrieved from:<URL:uniprot.org/uniprot/P00451 [22 pages].
Uniprot Accession No. P00750, "Tissue-type plasminogen activator," Last Modified on Mar. 6, 2013 [online][retrieved on Mar. 19, 2013] Retrieved from:<URL:uniprot.org/uniprot/P00750 [10 pages].
Uniprot Accession No. P01241, "Somatotropin," Last Modified on Mar. 6, 2013 [online][retrieved on Mar. 19, 2013] Retrieved from:<URL:uniprot.org/uniprot/P01241 [9 pages].
Uniprot Accession No. P01242, "Growth hormone variant," Last Modified on Mar. 6, 2013 [online][retrieved on Mar. 19, 2013] Retrieved from:<URL:uniprot.org/uniprot/P01242[6 pages].
Uniprot Accession No. P01308, "Insulin," Last Modified on Mar. 6, 2013 [online][retrieved on Mar. 19, 2013] Retrieved from:<URL:uniprot.org/uniprot/P01308 [11 pages].
Uniprot Accession No. P01583, "Interleukin-1 alpha," Last Modified on Mar. 6, 2013 [online][retrieved on Mar. 19, 2013] Retrieved from:<URL:uniprot.org/uniprot/P01583 [6 pages].
Uniprot Accession No. P01584, "Interleukin-1 beta," Last Modified on Mar. 6, 2013 [online][retrieved on Mar. 19, 2013] Retrieved from:<URL:uniprot.org/uniprot/P01584 [14 pages].
Uniprot Accession No. P01588, "Erythropoietin," Last Modified on Mar. 6, 2013 [online][retrieved on Mar. 19, 2013] Retrieved from:<URL:uniprot.org/uniprot/P01588 [6 pages].
Uniprot Accession No. P04141, "Granulocyte-macrophage colony-stimulating factor," Last Modified on Mar. 6, 2013 [online][retrieved on Mar. 19, 2013] Retrieved from:<URL:uniprot.org/uniprot/P04141 [5 pages].
Uniprot Accession No. P04275, "von Willebrand factor," Last Modified on Mar. 6, 2013 [online][retrieved on Mar. 19, 2013] Retrieved from:<URL:uniprot.org/uniprot/P04275 [12 pages].
Uniprot Accession No. P05112, "Interleukin-4," Last Modified on Mar. 6, 2013 [online][retrieved on Mar. 19, 2013] Retrieved from:<URL:uniprot.org/uniprot/P05112 [7 pages].
Uniprot Accession No. P08700, "Interleukin-3," Last Modified on Mar. 6, 2013 [online][retrieved on Mar. 19, 2013] Retrieved from:<URL:uniprot.org/uniprot/P08700 [5 pages].
Uniprot Accession No. P09919, "Granulocyte colony-stimulating factor," Last Modified on Mar. 6, 2013 [online][retrieved on Mar. 19, 2013] Retrieved from:<URL:uniprot.org/uniprot/P09919 [6 pages].
Uniprot Accession No. P13232, "Interleukin-7," Last Modified on Mar. 6, 2013 [online][retrieved on Mar. 19, 2013] Retrieved from:<URL:uniprot.org/uniprot/P13232 [5 pages].
Uniprot Accession No. P60568, "Interleukin-2," Last Modified on Mar. 6, 2013 [online][retrieved on Mar. 19, 2013] Retrieved from:<URL:uniprot.org/uniprot/P60568 [6 pages].
van Berkel et al., "Large scale production of recombinant human lactoferrin in the milk of transgenic cows," Nat. Biotech., 20:484-487 (2002).
van Gulik et al., "Vascular occlusion techniques during liver resection." Dig Surg. 24:274-281 (2007).
Vincent et al., "Rapid assessment of adenovirus serum neutralizing antibody titer based on quantitative, morphometric evaluation of capsid binding and intracellular trafficking: population analysis of adenovirus capsid association with cells is predictive of adenovirus infectivity," J. Virol., 75:1516-1521 (2001).

(56) References Cited

OTHER PUBLICATIONS

Von Seggern et al., "Complementation of a fibre mutant adenovirus by packaging cell lines stably expressing the adenovirus type 5 fibre protein," J. Gen. Virol. 79:1461-1468 (1998).
Vorburger, S. and K. Hunt, "Adenoviral gene therapy," The Oncologist, 7:46-59 (2002).
Wall et al., "Genetically enhanced cows resist intramammary *Staphylococcus aureus* infection," Nature Biotechnology, 23:445-451 (2005).
Wang et al., "Adenoviral vector systems for gene therapy," Gene Therapy and Mol. Biology, 9:291-300 (2005).
Whitehead et al., "Knocking down barriers: advances in siRNA delivery," Nat. Rev. Drug. Discov. 8(2):129-138 including corrigendum and errata (2009).
Wickham et al., "Increased in vitro and in vivo gene transfer by adenovirus vectors containing chimeric fiber proteins," J. Virol., 71:8221-8229 (1997).
Wickham, T., "Targeting adenovirus," Gene Ther., 7:110-114 (2000).
Willms-Kretschmer, K. and G. Majno, "Ischemia of the skin. Electron microscopic study of vascular injury." The American Journal of Pathology, 54:327-353 (1969).
Xiao et al., "Gene therapy vectors based on adeno-associated virus type 1," J. Virol., 73:3994-4003 (1999).
Yang et al., "An approach for treating the hepatobiliary disease of cystic fibrosis by somatic gene transfer," Proc. Natl. Acad. Sci. USA 90:4601-4605 (1993).
Yang et al., "MHC class I-restricted cytotoxic T lymphocytes to viral antigens destroy hepatocytes in mice infected with E1-deleted recombinant adenoviruses," Immunity, 1(5):433-442 (1994).
Yang et al., "Cellular and humoral immune responses to viral antigens create barriers to lung-directed gene therapy with recombinant adenoviruses." J. Virol., 69:2004-2015 (1995).
Yang et al., "Thrombospondin-1 mediates distal tubule hypertrophy induced by glycated albumin," Biochem. J., 379:89-97 (2004).
Ye et al., "Adenovirus-mediated gene transfer to renal glomeruli in rodents," Kidney International, 61:S16-S23 (2002).
Yla-Herttuala, S., "Endgame: glybera finally recommended for approval as the first gene therapy drug in the European union," Mol. Ther., 20:1831-1832 (2012).
Yoshino et al., "Naked plasmid DNA transfers to the porcine liver using rapid injection with large volume," Gene Ther.13:1969-1702 (2006).
Zhang et al., "Generation and identification of recombinant adenovirus by liposome-mediated transfection and PCR analysis," BioTechniques 15(5):868-872 (1993).
Zhang et al., "Alpha-1-antitrypsin expression in the lung is increased by airway delivery of gene-transfected macrophages," Gene Therapy, 10:2148-2152 (2003).
Zheng et al., "Antibody gene therapy: an attractive approach for the treatment of cancers and other chronic diseases," Cell Research, 17:303-306 (2007).
Zhu et al., "In vivo adenovirus-mediated gene transfer into normal and cystic rat kidneys," Gene Therapy, 3(4):298-304 (1996).
Letter/Written Disclosure of the Information Disclosure Statement for the above-referencd application, mailed on Oct. 21, 2013, 2 pages.
Best et al., "Assessment of renal oxygenation during partial nephrectomy using DLP hyperspectral imaging," Proc. SPIE, vol. 7932, Emerging Digital Micromirror Device Based Systems and Applications III, vol. 7932, 793202, published Feb. 11, 2011; doi:10.1117/12.873566, 8 pages.
Lee et al., "Laboratory evaluation of laparoscopic vascular clamps using a load-cell device—are all clamps the same?" J. Urol. 180:1267-1272 (2008).
Storm et al. "A simplified clamp for hepatic resection," Surg Gynecol Obstet.133(1):103-104 (1971).
Letter/Written Disclosure of the Information Disclosure Statement for the above-referenced application, mailed on Oct. 22, 2014, 3 pages.

Brooks et al., "Specific organ gene transfer in vivo by regional organ perfusion with herpes viral amplicon vectors: implications for local gene therapy." Surgery 129(3):324-334 (2001).
GenBank Accession No. AB685372.1, "Human adenovirus 5 gene hexon, partial cds, strain: 11_02402/Mongolia/hexon," Published on Oct. 8, 2013 [online][retrieved on Aug. 22, 2014] Retrieved from:<URL:http://www.ncbi.nlm.nih.gov/nuccore/AB685372.1 [2 pages].
Genbank accession No. AF517770.1, "Sus scrofa alpha-fetoprotein precursor, mRNA, complete cds," Published on Dec. 30, 2002 [online][retrieved on Aug. 22, 2014] Retrieved from:<URL:ncbi.nlm.nih.gov/nuccore/AF517770.1 [2 pages].
Genbank accession No. AY033476.1, "Sus scrofa serum albumin gene, promoter region," Published on May 5, 2002 [online][retrieved on Aug. 22, 2014] Retrieved from:<URL:ncbi/nlm/nih.gov/nuccore/AY033476.1 [1 page].
Invalidity Search Report prepared by a third-party, "Invalidity Search—Provisional Application—Gene Therapy Mechanism, Global Bio Therapeutics," redacted, dated May 21, 2014, 9 pages.
Miller, A., "Human gene therapy comes of age," Nature 357(6378):455-460 (1992).
Podevin et al., "Factors influencing immune response after in vivo retrovirus-mediated gene transfer to the liver," J Gene Med. 6(1):16-21 (2004).
Uniprot Accession No. P00740, "Coagulation factor IX," Last Modified on Jul. 9, 2014 [online][retrieved on Aug. 22, 2014] Retrieved from:<URL:uniprot.org/uniprot/P00740 [17 pages].
Uniprot Accession No. P00749, "Urokinase-type plasminogen activator," Last Modified on Jul. 9, 2014 [online][retrieved on Aug. 22, 2014] Retrieved from:<URL:uniprot.org/uniprot/P00749 [12 pages].
International Search Report and Written Opinion, dated May 23, 2013, in connection with corresponding International Patent Application No. PCT/US2013/025234, 24 pages.
Response to International Search Report and Written Opinion, dated Dec. 9, 2013, in connection with corresponding International Patent Application No. PCT/US2013/025234, 49 pages.
Written Opinion, dated Jan. 27, 2014, in connection with corresponding International Patent Application No. PCT/US2013/025234, 9 pages.
Response to Written Opinion, dated Mar. 27, 2014, in connection with corresponding International Patent Application No. PCT/US2013/025234, 45 pages.
International Preliminary Report on Patentability, dated May 6, 2014, in connection with corresponding International Patent Application No. PCT/US2013/025234, 10 pages.
U.S. Appl. No. 14/455,871, filed Aug. 8, 2014.
U.S. Appl. No. 14/455,865, filed Aug. 8, 2014.
Letter/Written Disclosure of the Information Disclosure Statement for the above-referenced application, mailed on Feb. 11, 2016, 3 pages.
Office Action, dated Dec. 17, 2015, in connection with Chinese Patent Application No. 201380028970.8, [Original document in Chinese with English translations] 14 pages.
Examination Report, issued Feb. 4, 2016, in connection with New Zealand Patent Application No. 715957, 2 pages.
Letter/Written Disclosure of the Information Disclosure Statement for the above-referenced application, mailed on Mar. 18, 2016, 2 pages.
Search Report and Written Opinion, dated Jan. 12, 2016, in connection with Singapore Patent Application No. 11201404741V, 21 pages.
Letter/Written Disclosure of the Supplemental Information Disclosure Statement for the above-referenced application, filed herewith on May 31, 2016, 2 pages.
Cabrera et al., "Adenoviral Mediated Compartmentalized Liver Transduction Improves Safety and Yields Longterm Transgene Expression in an Porcine Model," presented at the American Society for Gene and Cell Therapy Meeting, May 13, 2015. New Orleans, LA. Abstract 83, 1 page.

(56) References Cited

OTHER PUBLICATIONS

Cabrera et al., "Adenoviral Compartmentalized Liver Transduction Improves Safety and Yields Longterm Transgene Expression," presented at the American Society of Gene and Cell Therapy Meeting, May 14, 2015. New Orleans, LA. Abstract 323, 1 page.
Cabrera et al., "Correction of hyperglycemia through adenoviral-mediated compartmentalized liver transduction in a type 1 diabetes mellitus rodent model," presented at the European Society of Gene and Cell Therapy Meeting, Sep. 17-20, 2015. Helsinki, Finland. Abstract P130, 2 pages.
Cabrera et al., "Adenoviral mediated compartmentalized liver transduction resolves viremia, biodistribution, toxicity and yields long terms transgene expression in a porcine model," presented at the European Society of Gene and Cell Therapy Meeting, Sep. 17-20, 2015. Helsinki, Finland. Abstract P232, 1 page.
News Article, "Spotlight: Global BioTherapeutics—Cultivating Entrepreneurship in Gene Therapy," Published Sep. 30, 2015 [online][Retrieved May 25, 2016][Retrieved from:<URL:http://mexicosalud.com/spotlight-global-biotherapeutics-cultivating-entrepreneurship-in-gene-therapy/, 6 pages.
Response, filed May 20, 2015, to Rules 161(1) and 162 Communication, dated May 20, 2015, in connection with European Patent Application No. 13 706 130.5, 30 pages.
Response, filed Jan. 13, 2016, to Examination Report, dated May 6, 2015, in connection with New Zealand Patent Application No. 627992, 39 pages.
Examination Report, dated Feb. 4, 2016, in connection with New Zealand Patent Application No. 627992, 2 pages.
Response, filed Feb. 9, 2016, to Examination Report, dated Feb. 4, 2016, in connection with New Zealand Patent Application No. 627992, 1 page.
Examination Report, dated Feb. 29, 2016, in connection with New Zealand Patent Application No. 627992, 2 pages.
Response, filed Nov. 17, 2015, to Search Report and Written Opinion, dated Jun. 5, 2015, in connection with Singapore Patent Application No. 11201404741V, 20 pages.
Letter/Written Disclosure of the Supplemental Information Disclosure Statement for the above-referenced application, filed herewith on Jul. 26, 2016, 3 pages.
Examination Report, dated Jun. 29, 2016, in connection with European Patent Application No. 13 706 130.5, 6 pages.
Letter/Written Disclosure of the Supplemental Information Disclosure Statement for the above-referenced application, filed herewith on Sep. 22, 2016, 3 pages.
Examination Report, dated Aug. 24, 2016, in connection with Australian Patent Application No. 2013216920, 4 pages.
Notice of Acceptance, dated Sep. 7, 2016, in connection with Australian Patent Application No. 2013216920, 2 pages.
Letter/Written Disclosure of the Supplemental Information Disclosure Statement for the above-referenced application, filed herewith on Oct. 25, 2016, 3 pages.
Office Action, dated Sep. 6, 2016, in connection with Chinese Patent Application No. 201380018970.8 [Original document in Chinese with English translation], 13 pages.
Examination Report, dated Sep. 8, 2016, in connection with Singapore Patent Application No. 11201404741V, 19 pages.
Letter/Written Disclosure of the Information Disclosure Statement for the above-referenced application, mailed on Jul. 27, 2015, 2 pages.
Search Report and Written Opinion, dated Jun. 5, 2015, in connection with Singapore Patent Application No. 11201404741V, 16 pages.
Letter/Written Disclosure of the Information Disclosure Statement for the above-referenced application, mailed on Jun. 4, 2015, 2 pages.
Examination Report, dated May 6, 2015, in connection with New Zealand Patent Application No. 627992, 3 pages.
Letter/Written Disclosure of the Supplemental Information Disclosure Statement for the above-referenced application, filed herewith on Jun. 8, 2017, 2 pages.

Adams et al., "Metabolic hormones and tissue concentrations of mRNA for IGF-I in lines of sheep that differ in their protein synthesis response to feed intake," J. Endocrinol. 167(2):315-320 (2000).
Hirano et al., "Persistent gene expression in rat liver in vivo by repetitive transfections using HVJ-liposome," Gene Therapy 5(4):459-464 (1998).
Sugiyama et al., "Defective adenoassociated viral-mediated transfection of insulin gene by direct injection into liver parenchyma decreases blood glucose of diabetic mice," Horm. Metab. Res. 29(12): 599-603 (1997).
Examiner's Report, dated Dec. 21, 2016, in connection with Canadian Patent Application No. 2,863,964, 5 pages.
Response, filed Jul. 1, 2016, to Office Action, dated Dec. 17, 2015, in connection with Chinese Patent Application No. 201380018970.8 [English instructions and document as filed in Chinese], 47 pages.
Supplementary Response, filed Aug. 8, 2016, to Office Action, dated Dec. 17, 2015, in connection with Chinese Patent Application No. 201380018970.8 [English letter and document as filed in Chinese], 4 pages.
Response, filed Jan. 23, 2017, to Office Action, dated Sep. 6, 2016, in connection with Chinese Patent Application No. 201380018970.8 [English instructions with document as filed in Chinese], 33 pages.
Response, filed Mar. 8, 2017, to Examination Report, dated Jun. 29, 2016, in connection with European Patent Application No. 13706130.5, 24 pages.
Office Action, dated Mar. 18, 2017, in connection with Eurasian Patent Application No. 201400871 [English summary and original document in Russian], 3 pages.
Office Action, dated Dec. 6, 2016, in connection with Japanese Patent Application No. 2014-556699 [Original document in Japanese and English translation], 12 pages.
Response, filed Nov. 5, 2016, to Examination Report, dated Feb. 29, 2016, in connection with New Zealand Patent Application No. 627992, 28 pages.
Notice of Acceptance, dated Feb. 9, 2017, in connection with New Zealand Patent Application No. 627992, 1 page.
Response, filed Jun. 13, 2016, to Search Report and Written Opinion, dated Jan. 12, 2016, in connection with Singapore Patent Application No. 11201404741V, 25 pages.
Response, dated May 31, 2017, to Office Action, dated Dec. 6, 2016, in connection with Japanese Patent Application No. 2014-556699 [English instructions and original document in Japanese], 50 pages.
Letter/Written Disclosure of the Supplemental Information Disclosure Statement for the above-referenced application, filed herewith on Aug. 3, 2017, 2 pages.
Decision to Grant, issued Jul. 4, 2017, in connection with Japanese Patent Application No. 2014-556699 [English reporting letter and original document in Japanese], 5 pages.
Letter/Written Disclosure of the Supplemental Information Disclosure Statement for the above-referenced application, filed herewith on Aug. 30, 2017, 3 pages.
Miyanohara et al., "Direct gene transfer to the liver with herpes simplex virus type 1 vectors: transient production of physiologically relevant levels of circulating factor IX," The New Biologist 4(3):238-246 (1992).
Sobrevals et al., "AAV vectors transduce hepatocytes in vivoas efficiently in cirrhotic as in healthy rat livers," Gene Therapy 19:411-417 (2012).
Examination Report, issued Aug. 1, 2017, in connection with corresponding European Patent Application No. 13 706 130.5, 7 pages.
Notice of Acceptance, issued Aug. 24, 2017, in connection with corresponding New Zealand Patent Application No. 715957, 1 page.
Office Action, issued Jul. 21, 2017, in connection with corresponding Chinese Patent Application No. 201380018970.8 [English translation and original document in Chinese], 12 pages.
Letter/Written Disclosure of the Supplemental Information Disclosure Statement for the above-referenced application, filed herewith on Oct. 5, 2017, 3 pages.
Vetrini, F. and P. Ng, "Liver-directed gene therapy with helper-dependent adenoviral vectors: current state of the art and future challenges," Curr. Pharm. Des. 17(24):2488-2499 (2011).

(56) References Cited

OTHER PUBLICATIONS

Search Report and Written Opinion, issued Sep. 25, 2017, in connection with corresponding Singapore Patent Application No. 10201604810U, 10 pages.

* cited by examiner

PANEL A

PANEL B

PANEL A

PANEL B

PANEL A

PANEL B

I.V.

COMPARTMENTALIZED

COMPARTMENTALIZED METHOD OF NUCLEIC ACID DELIVERY AND COMPOSITIONS AND USES THEREOF

RELATED APPLICATIONS

Benefit of priority is claimed to U.S. Provisional Application No. 61/633,287, filed Feb. 7, 2012, entitled "Compartmentalized Method of Nucleic Acid Delivery and Compositions and Uses Thereof."

This application is related to International PCT Application Serial No. PCT/US2013/025234, filed the same day herewith, entitled "Compartmentalized Method of Nucleic Acid Delivery and Compositions and Uses Thereof," which claims priority to U.S. Provisional Application No. 61/633,287.

The subject matter of each of the above-noted related applications is incorporated by reference in its entirety.

FIELD OF THE INVENTION

Provided herein is a method of delivering nucleic acid molecules to a compartmentalized tissue or organ of a subject. Also provided herein are uses and processes for delivering a nucleic acid molecule to the parenchyma of a compartmentalized tissue or organ. The methods and uses can be used in the treatment of diseases and conditions and in industrial, agricultural and veterinary applications. Also provided herein are compositions containing a adenovirus or adeno-associated virus or other recombinant virus formulated for administration to the parenchyma of a tissue or organ.

BACKGROUND

Gene therapy is a therapeutic method by which nucleic acid molecules are administered to a subject to supplement or alter genes within the individual. In particular, gene therapy is used for the purpose of the treatment of diseases. Gene therapy is regarded as fundamental to treating genetic diseases, which develop due to mutation or deletion of a gene. Various procedures of introducing a gene encoding a protein into a subject necessary for therapy have been tried, but there are few examples in which satisfactory therapeutic effect is obtained. Thus, there is a need for alternative methods of delivering nucleic acid molecules to subjects for gene therapy applications.

SUMMARY

Provided herein is a method of delivering a nucleic acid molecule to a subject. The method can be used in gene therapy applications, including in applications to treat diseases and conditions as well as in industrial, agricultural and veterinary applications. As provided herein, the method includes a) compartmentalizing a tissue or organ or portion of the tissue or organ from systemic circulation of the host; and b) administering a delivered agent directly to the parenchyma of the tissue or organ or portion of the tissue or organ, wherein the delivered agent contains the nucleic acid molecule, whereby the delivered agent enters parenchymal cells of the compartmentalized tissue or organ or portion of the tissue or organ. Compartmentalizing the tissue or organ or portion of the tissue or organ can be effected prior to, simultaneous or subsequent to administering the delivered agent. Generally, compartmentalization of the tissue or organ or portion of the tissue or organ is initiated prior to administering the delivered agent, and typically no more than 5 minutes, 4 minutes, 3 minutes, 2 minutes, 1 minute or 30 seconds before delivery of the delivered agent containing a nucleic acid molecule.

The method provided can further include a step of restoring communication between the tissue, organ or portion of the tissue or organ with the systemic circulation. The step of restoring communication is generally a predetermined time after administering the delivered agent. The predetermined time is a time period that is sufficient for the administered delivered agent to enter parenchymal cells (e.g. by transduction), whereby upon restoration of communication no more than 20% of the delivered agent has not entered a parenchymal cell. For example, no more than 15%, 14%, 13%, 12%, 11%, 10%, 9%, 8%, 7%, 6%, or 5% of the delivered agent has not entered a parenchymal cell. In some examples, the predetermined times is a time period sufficient for the administered delivered agent to enter parenchymal cells, whereby upon restoration of communication no more than 20% of the delivered agent is exposed to the systemic circulation. For example, no more than 15%, 14%, 13%, 12%, 11%, 10%, 9%, 8%, 7%, 6%, or 5% of the delivered agent is exposed to the systemic circulation. Typically in the methods herein, the predetermined time is at least or at least about 1, 2, 4, 5, 10, 15, 20, 25, 30, 35, 40, 45, 50, 55, 60, 65, 70, 75, 80, 85, 90, 95, 100, 105, 110, 115, or 120 minutes. In particular examples, the predetermined time is at least or at least about or is or is about 30 minutes, and generally not greater than 30 minutes to 60 minutes.

In the methods herein, the tissue or organ or portion of the tissue or organ that is compartmentalized is the liver, brain spinal cord, pancreas, heart, skin, kidney, lung, blood vessel, bone, muscle, uterus, cervix, prostate, urethra, or intestine. In particular examples, the tissue or organ or portion of the tissue or organ is the liver. For example, in examples of the method herein, the tissue or organ or portion of the tissue or organ is the liver; and the predetermined time is at least or at least about or is or is about 30 minutes, and generally not greater than 30 minutes to 60 minutes. In such examples, the predetermined time is a time period sufficient for virtually all of the delivered agent, and generally at least 80% of the delivered agent, to enters the hepatocytes of the liver parenchyma. In examples of the method herein, a portion of the tissue or organ is compartmentalized. For example, a portion of the liver is compartmentalized and the portion is a lobe, segment or a portion of a lobe or segment of the liver. The lobe or portion of a lobe can be the right lobe, the left lobe, the quadrate lobe and the caudate lobe or portion thereof.

In any of the methods described herein, compartmentalizing a tissue or organ or portion of a tissue or organ is achieved by blocking any one or more arteries, veins, ducts and/or vessels in the tissue or organ or portion of the tissue or organ, whereby blood supply and flow to the tissue or organ or portion thereof is reduced or eliminated. Generally, compartmentalization is effected when all arteries, veins, ducts and/or vessels servicing or traversing the tissue or organ or portion of the tissue or organ that is to be compartmentalized are blocked. The blocking of an artery, vein, duct and/or vessel can be effected with a device or technique such a manual compression, a parenchymal clamp, an arterial or venous clamp, an occlusion catheter, a stapling device, a band, a tourniquet or a cable. Generally, in the methods herein, a tissue or organ or portion of a tissue or organ is compartmentalized by clamping with a parenchymal clamp. The clamp can be a laparoscopic clamp. In any of the methods herein, compartmentalization of a tissue or organ from the systemic circulation also can include applying suction to reduce or eliminate blood in the tissue or organ or portion thereof.

In any of the methods provided herein, the delivered agent can be a non-viral vector, a virus, a virus-like particle, a minicircle, a nanoparticle and a whole cell that contain the nucleic acid molecule. In one example, the delivered agent is a non-viral vector and the non-viral vector is an expression vector. In another example, the delivered agent is a nanoparticle and the nanoparticle is targeted or radiolabeled. In a further example, the delivered agent is a virus. In examples herein where the delivered agent is a virus, the virus can be an adenovirus, an adeno-associated virus (AAV), a retrovirus, vaccinia virus or herpes simplex virus. For example, the virus can be a retrovirus that is a lentivirus. The virus is generally a recombinant virus that contains a nucleic acid molecule that is heterologous to its genome. The virus can be a replication-defective virus. The virus can be a virus that replicates in the nucleus of a cell in the subject. The virus also includes those that infect non-dividing cells, such as liver hepatocytes. In some examples, the virus infects dividing cells. In such examples, the method can include a step to stimulate division of cells. In particular examples herein, such as when the liver is the target organ for practice of the method, the virus is one that exhibits tropism for the liver and can enter hepatocytes.

For example, in examples of the method provided herein, a virus is an adenovirus containing a heterologous nucleic acid in its genome that is administered to a compartmentalized tissue or organ or portion of a tissue or organ. The adenovirus can be any serotype, such as a serotype 1 to a serotype 51 (e.g. 1, 2, 4, 5 . . . 51). For example, the adenovirus is an adenovirus type 2 or adenovirus type 5. Any of the adenoviruses used in the methods herein include those with a deletion in any one or more of the E1, E2a, E2b, E3, or E4 coding regions. For example, the adenovirus contains a deletion in the E1 coding region. As the delivered agent in the methods herein, the virus contains the nucleic acid molecule.

In any of the methods herein, the delivered agent contains the nucleic acid molecule that is delivered to the subject for gene therapy. In some examples, the nucleic acid molecule encodes a polypeptide. The encoded polypeptide can be a therapeutic polypeptide. For example, the encoded polypeptide can be an enzyme, a hormone, coagulation or clotting factor, a growth factor, an antibody or portions of antibodies, an angiogenesis modulator, an immunomodulator, a pain modulator, a receptor, a transport protein, a regulatory protein, an antigen or an allergen. In particular, the encoded polypeptide can be an interleukin, interferon, growth factor or portions thereof, and growth factor receptor or portions thereof. Exemplary of nucleic acid molecules include, but are not limited to, those that encode adenosine deaminase, cystic fibrosis transmembrane conductance regulator (CTFR), galsulfase, laronidase, N-acetylgalactosamine 6-sulfatase, phenylalanine ammonia lyase, acid alpha glucosidase, imiglucerase, alglucosidase alpha, thyrotropin, growth hormone, insulin, thyroid hormone, erythropoietin (EPO), interleukin-1 (IL-1), IL-2, IL-3, IL-4, IL-5, IL-7, an interferon-α (IFN-α), IFN-β, IFN-γ, tumor necrosis factor (TNF), IL-12, IL-18, fms-related tyrosine kinase 3 (flt3), neuropilin-2 (NP2), a bone morphogenic protein (BMP), epidermal growth factor (EGF), erythropoietin (EPO), fibroblast growth factor (FGF), granulocyte colony stimulating factor (G-CSF), granulocyte macrophage colony stimulating factor (GM-CSF), hepatocyte growth factor (HGF), insulin-like growth factor (IGF), platelet derived growth factor (PDGF), transforming growth factor α or β, vascular endothelial growth factor (VEGF), epidermal growth factor receptor (EGFR), fibroblast growth factor receptor (FGFR), FGFR antagonist (sFGFR), transforming growth factor receptor (TGFR), vascular endothelial growth factor receptor (VEGFR), plasminogen activator, urokinase, Factor VIII, Factor IX, von Willebrand factor, growth hormone, metalloproteinase thrombospondin motifs 1 (METH-1), METH-2, tryptophanyl-tRNA synthetase (TrpRS) fragments, proliferin-related protein, prolactin fragment, pigment epithelium-derived factor (PEDF), vasostatin, angiostatin, endostatin, kininostatin, fibrinogen-E fragment, thrombospondin, tumstatin, canstatin, restin, soluble fms-like tyrosine kinase-1 (sFlt-1), soluble vascular endothelial growth factor receptors (sFlk), soluble Neuropilin 1 (sNRP1), Interferon gamma-induced protein 10 (IP-10), Platelet factor 4 (PF-4), Gro-beta, soluble Ephrin type-B receptor 4 (sEphB4), sephrinB2, IGF-1, herpes simplex virus thymidine kinase (HSV-TK), carboxypeptidase G2 (CPG2), carboxylesterase (CA), cytosine deaminase (CD), cytochrome P450 (cyt-450), deoxycytidine kinase (dCK), nitroreductase (NR), purine nucleoside phosphorylase (PNP), thymidine phosphorylase (TP), varicella zoster virus thymidine kinase (VZV-TK), xanthine-guanine phosphoribosyl transferase (XGPRT), Aspartylglucosaminidase, α-Galactosidase A, Palmitoyl Protein Thioesterase, Tripeptidyl Peptidase, Lysosomal transmembrane protein, cysteine transporter, Acid ceramidase, acid α-L-fucosidase, protective protein/cathepsin A, acid β-glucosidase or glucocerebrosidase, acid β-galactosidase, iduronate-2-sulfatase, α-L-Iduronidase, galactocerebrosidase, acid α-mannosidase, acid β-mannosidase, arylsulfatase B, arylsulfatase A, N-Acetylgalactosamine-6-sulfate sulfatase, N-Acetlylglucosamine-1-phosphotransferase, Acid sphingomyelinase, Niemann-Pick disease, type C1 (NPC-1), β-Hexosaminidase B, Heparan N-sulfatase, α-N-Acetylglucosaminidase (NaGlu), Acetyl-CoA:αglucosamininde N-acetyltransferase, N-Acetylglucosamine-6-sulfate sulfatase, β-Glucuronidase, acid lipase, neprilysin, insulin-degrading enzyme insulysin, thimet oligopeptidase, calbindin D28, parvalbumin, hypoxia induced factor 1-alpha (HIF1-alpha), sirtuin-2 (SIRT-2), survival motor neuron protein-1 (SMN-1), SMN-2, glial cell-derived neurotrophic factor (GDNF), ciliary neurotrophic factor (CNF), low density lipoprotein receptor (LDLR), lipoprotein lipase (LPL), Alpha-1-Antitrypsin (AAT), UDP-glucuronyl-transferase (UGT), UGT1A1, glucose-6 phosphatase, phosphoenolpyruvate-carboxykinase, galactose-1 phosphate uridyl transferase, phenylalanine hydroxylase, branched chain alpha-ketoacid dehydrogenase, fumarylacetoacetate hydrolase, methylmalonyl-CoA mutase, ornithine transcarbamylase, argininosuccinic acid synthetase, adenosine deaminase, hypoxanthine guanine phosphoribosyl transferase, biotinidase, beta-glucocerebrosidase, beta-gluronidase, porphobilinogen deaminase (PBDG) or p53.

In other examples, the encoded polypeptide can be one that is involved in industrial, veterinary or agricultural applications. For example, the nucleic acid molecule can encode a polypeptide that increases muscle production in an animal, increases hair or wool production in an animal, growth of an animal, or is involved in nutrient synthesis or utilization. In such examples, the encoded polypeptide can be a myostatin inhibitor, growth hormone, IGF-1, growth hormone releasing factor, chicken Ski, serine transacetylase or o-acetylserine sulphydrylase. The myostatin inhibitor can be a follistatin.

In examples of the method provided herein, the nucleic acid molecule can be a DNA molecule, a RNA molecule, and an aptamer. For example, the nucleic acid molecule can be a microRNA, a small interfering RNA, a ribozyme and an antisense nucleic acid. Such nucleic acid molecules also can effect a therapeutic effect in a subject and hence are therapeutic nucleic acid molecules.

In any of the methods provided herein, the method also can optionally include a step of imaging the tissue or organ to identify the parenchymal tissue prior to administration of the delivered agent. Such methods can be used to minimize administration of the delivered agent, and nucleic acid molecule, to the lumen of a duct, artery or vessel. For example, magnetic resonance imaging (MRI), sonography (ultrasound), or computed tomography (CT) can be performed. In particular examples, Doppler sonography can be used in practice of the methods herein.

In addition, in practice of any of the methods herein, the techniques, methods and reagents can be used to facilitate or increase the efficiency of delivery of the delivered agent to cells of the parenchyma of a tissue or organ. For example, the delivered agent can be formulated with lipids, polymer reagents or other agents to facilitate entry into the parenchymal cells. In addition or alternatively, the delivered agent can be delivered in the presence of a physical method to facilitate entry into parenchymal cells, such as electroporation, sonoporation, pressure, ultrasound or "gene gun."

In further examples of any of the methods herein, an agent that promotes cellular uptake of the delivered agent can be administered to the subject. The agent can be administered prior to, simultaneously or subsequent to administration of the delivered agent. In some examples, the agent is a transcriptional enhancer of a virus-specific cell surface receptor. For example, the agent is a histone deacetylase (HDAC) inhibitor. Exemplary HDAC inhibitor, include but are not limited to, trischostatin A, vorinostat (SAHA), belionostat (PXD101), LAQ824, panobinostat (LBH589), entinostat (MS-275), C199, mocetinostat (MGCD0103), romidepsin (lstodax), valproic acid, PCI-24781, SB939, resminostat, givinostat, CUDC-101, AR-42, CHR-2845, CHR-3996, 4SC-202, CG200745, Kevetrin, and trichostatin A (TSA).

In practice of the methods herein, delivery of the delivered agent to a compartmentalized tissue means that lower dosages of agent can be administered, which can be further controlled because the kinetics of agent administered and protein expressed is linear. This is in contrast to existing gene therapy methods where agents are predominantly delivered intravenously. For example, the amount of agent that is administered by the methods herein is greater than 100-fold less than the amount of the same delivered agent administered intravenously. For example, the amount of delivered agent is up to 200-fold, 500-fold, 1000-fold, 5000-fold, 10000-fold or less than the amount of the same delivered agent administered intravenously.

In particular examples, where the delivered agent is an adenovirus or adeno-associated virus (AAV) containing a heterologous nucleic acid in its genome, the amount of delivered agent administered is or is about between 10 to $1\times10^{12}$ particles, 10 to $1\times10^{6}$ particles, $1\times10^{3}$ to $1\times10^{12}$ particles, $1\times10^{6}$ to $1\times10^{10}$ particles, or $1\times10^{7}$ to $1\times10^{9}$ particles; or is or is about between 10 to $1\times10^{12}$ pfu, 10 to $1\times10^{6}$ pfu, $1\times10^{3}$ to $1\times10^{12}$ pfu, $1\times10^{6}$ to $1\times10^{10}$ pfu, or $1\times10^{7}$ to $1\times10^{9}$ pfu. For example, the amount of delivered agent administered is less than $1\times10^{12}$ particles, $1\times10^{11}$ particles, $1\times10^{10}$ particles, $1\times10^{9}$ particles, $1\times10^{8}$ particles, $1\times10^{7}$ particles, $1\times10^{6}$ particles, $1\times10^{5}$ particles, $1\times10^{4}$ particles, $1\times10^{3}$ particles or less; or is less than $1\times10^{12}$ pfu, $1\times10^{11}$ pfu, $1\times10^{10}$ pfu, $1\times10^{9}$ pfu, $1\times10^{8}$ pfu, $1\times10^{7}$ pfu, $1\times10^{6}$ pfu, $1\times10^{5}$ pfu, $1\times10^{4}$ pfu, $1\times10^{3}$ pfu or less.

In examples of any of the methods provided herein, the delivered agent can be administered to more than one locus in the compartmentalized tissue, organ or portion of the tissue or organ. The methods also can include a step of removing from the parenchyma of the tissue or organ or portion of the tissue or organ any extracellular delivered agent. Such a step can further reduce or minimize exposure of the delivered agent to the systemic circulation, which otherwise could occur upon removal of the compartmentalization if delivered agent has not entered cells. Typically, the removal step is performed prior to restoring communication of the tissue, organ or portion of the tissue or organ with the systemic vasculature. Compartmentalization is terminated by restoring communication with the systemic circulation after the predetermined time. The step of restoring communication with the systemic circulation can include removing the device or technique used to block an artery, vein, duct and/or vessel. In any of the methods herein, any of the steps provided herein can be repeated a plurality of times. In some examples, in a subsequent iteration of the method, the delivered agent is administered to the same compartmentalized locus or a different compartmentalized locus.

The methods provided herein of delivering a delivered agent containing a nucleic acid molecule can result in the functional action or expression of the nucleic acid molecule in the cells in which it is delivered. In some cases, the nucleic acid molecule can encode a protein that is secreted from the cells into the tissue, and which in some instances can reach or access the systemic circulation. Thus, the methods provided herein can be used in diverse applications and in particular in applications where local or systemic expression of a polypeptide is desired. For example, in the methods herein, delivery of the nucleic acid molecule effects production of a polypeptide, whereby the delivered agent contains a nucleic acid molecule that encodes the polypeptide. In practice of the methods herein, expression of the polypeptide is sustained for at least 3 months, 4 months, 5 months, 6 months, 7 months, 8 months, 9 months, 10 months, 11 months, 12 months, 18 months, 24 months, 36 months, 48 months, 60 months, 72 months, 84 months, 96 months, 10 years, 15 years or more after restoring communication with the systemic circulation.

Hence, in examples of the method provided herein, delivery of the nucleic acid molecule effects treatment of a disease or condition. The disease or condition can be a genetic deficiency or other disease or condition that is caused by aberrant cellular or protein activity. The disease or condition can be an inherited enzyme deficiency, inherited immune deficiency, cancer, a retrovirus infection, hemophilia, diabetes, a muscular dystrophy, a cardiovascular disorder, cystic fibrosis, a neurodegenerative disorder, trauma, pain, sickle cell anemia, autoimmune disease, inflammatory disease, or hypertension. Exemplary of such diseases or conditions include, but are not limited to, hemophilia A and B, type I diabetes mellitus, alpha-1-antitrypsin (AAT) deficiency, hemochromatosis, Wilson's disease, Crigler-Najjar syndrome type I, ornithine transcarbamylase deficiency, type II, familial hypercholesterolemia, afibrinogenemia, glycogen storage disease (GSD) type Ia, GSD type Ib, GSD type II (Pompe), mucopolysaccharidosis (MPS1), MPS IIIA, MPS IIIB, MPS VII, Fabry disease, Gaucher's disease, Niemann-Pick syndrome, ornithine transcarbamylase deficiency (OTC) deficiency, phenylketonuria, liver fibrosis, liver ischemia reperfusion injury, Alzheimer's disease, Amyotrophic Lateral Sclerosis (ALS), galactosemia, phenylketonuria, maple syrup urine disease, tyrosinemia type 1, methylmalonic acidemia, citrullinemia, Gout and Lesch Nyan syndrome, Sly syndrome, Zellweger syndrome, Human immunodeficiency virus (HIV) infection, combined immunodeficiency disease (SCID), cystic fibrosis, acute intermittent porphyria, multiple sclerosis, lipoprotein lipase deficiency (LPLD) or Parkinson's Disease. In particular examples of the method herein, the subject is a human child under the age of 18. In some examples, the subject is a fetus. For example, the subject can be one that has been diagnosed with a genetic deficiency.

In any of the methods provided herein, the method can be performed via laparoscopy.

Provided herein are uses and compositions containing a delivered agent containing a nucleic acid molecule for use in direct parenchymal administration of the nucleic acid molecule to a compartmentalized tissue, organ or portion of a tissue or organ. The uses and compositions for use in direct parenchymal administration of a nucleic acid molecule to a compartmentalized tissue, organ or portion of a tissue or organ can effect treatment of a disease or condition, overproduce a heterologous polypeptide in a subject, increase muscle production in an animal, increase hair growth in an animal, increase wool production in an animal, increase growth of an animal, or effect nutrient synthesis or utilization in an animal.

In the uses and compositions provided herein for use in delivering a nucleic acid to the parenchyma of a compartmentalized tissue or organ, the compartmentalized tissue or organ or portion of the tissue or organ can be the liver, brain spinal cord, pancreas, heart, skin, kidney, lung, blood vessel, bone, muscle, uterus, cervix, prostate, urethra, and intestine or portion thereof. In particular, the tissue or organ or portion of the tissue or organ is the liver. For examples, the uses and compositions for use provided herein can be used for direct parenchymal delivery of a nucleic acid to a portion of liver that is compartmentalized, such as a lobe, segment or a portion of a lobe or segment of the liver. The lobe or portion of a lobe can be the right lobe, the left lobe, the quadrate lobe and the caudate lobe or portion thereof. The compartmentalized tissue or organ is one in which the tissue or organ or a portion of the tissue or organ is isolated from the systemic circulation, whereby the arteries, veins, ducts and/or vessels servicing or traversing the tissue or organ or portion of the tissue or organ are blocked. For example, the tissue or organ or portion of the tissue or organ is one that is compartmentalized by isolation from the systemic circulation by a clamp of the parenchyma.

In examples of uses and compositions provided herein for use in delivering a nucleic acid to the parenchyma of a compartmentalized tissue or organ or portion of the tissue or organ, the delivered agent that contains the nucleic acid molecule can be a non-viral vector, a virus, a virus-like particle, a minicircle, a nanoparticle and a whole cell that contain the nucleic acid molecule. In one example, the delivered agent is a non-viral vector and the non-viral vector is an expression vector. In another example, the delivered agent is a nanoparticle and the nanoparticle is targeted or radiolabeled. In a further example, the delivered agent is a virus. For example, the virus is an adenovirus, an adeno-associated virus (AAV), a retrovirus, vaccinia virus and herpes simplex virus. The retrovirus can be a lentivirus. The delivered agent is generally a recombinant virus in which the nucleic acid molecule is heterologous to its genome. In some examples, the virus is one that is replication-defective. In other examples, the virus is one that can replicate in the nucleus of the cell. In examples herein, the virus is one that can infect non-dividing cells, for example, the virus is one that exhibits tropism for the liver and can enter hepatocytes.

In examples of the uses and compositions for use provided herein, the composition contains a delivered agent that is an adenovirus containing a heterologous nucleic acid molecule in its genome for use in delivery to a compartmentalized tissue or organ or portion of a tissue or organ. The adenovirus can be any serotype, such as a serotype 1 to a serotype 51 (e.g. 1, 2, 3, 4, 5, . . . 51). For example, that adenovirus is an adenovirus type 2 or adenovirus type 5. Any of the adenoviruses for use in the compositions or uses herein include those with a deletion in any one or more of the E1, E2a, E2b, E3, or E4 coding regions. For example, the adenovirus contains a deletion in the E1 coding region. As the delivered agent in the compositions and uses herein, the virus contains the nucleic acid molecule and the nucleic acid molecule is heterologous to the virus genome.

In any of the uses or compositions provided herein, the composition contains a delivered agent that contains a nucleic acid molecule that encodes a polypeptide. The encoded polypeptide can be an enzyme, a hormone, a coagulation or clotting factor, a growth factor, an antibody or portion thereof, an angiogenesis modulator, an immunomodulator, a pain modulator, a receptor, a transport protein, a regulatory protein, an antigen or an allergen. For example, the encoded polypeptide can be an interleukin, interferon, growth factor or portion thereof or growth factor receptor or portion thereof. Exemplary of nucleic acid molecules in the uses and compositions herein, include but are not limited to, any that encode adenosine deaminase, cystic fibrosis transmembrane conductance regulator (CTFR), galsulfase, laronidase, N-acetylgalactosamine 6-sulfatase, phenylalanine ammonia lyase, acid alpha glucosidase, imiglucerase, alglucosidase alpha, thyrotropin, growth hormone, insulin, thyroid hormone, erythropoietin (EPO), interleukin-1 (IL-1), IL-2, IL-3, IL-4, IL-5, IL-7, interferon-α (IFN-α), IFN-β, IFN-γ, tumor necrosis factor (TNF), IL-12, IL-18, fms-related tyrosine kinase 3 (flt3), neuropilin-2 (NP2), bone morphogenic proteins (BMPs), epidermal growth factor (EGF), erythropoietin (EPO), fibroblast growth factor (FGF), granulocyte colony stimulating factor (G-CSF), granulocyte macrophage colony stimulating factor (GM-CSF), hepatocyte growth factor (HGF), insulin-like growth factor (IGF), platelet derived growth factor (PDGF), transforming growth factor α or β, vascular endothelial growth factor (VEGF), epidermal growth factor receptor (EGFR), fibroblast growth factor receptor (FGFR), FGFR antagonist (sFGFR), transforming growth factor receptor (TGFR), vascular endothelial growth factor receptor (VEGFR), plasminogen activator, urokinase, Factor VIII, Factor IX, von Willebrand factor, growth hormone, metalloproteinase thrombospondin motifs 1 (METH-1), METH-2, tryptophanyl-tRNA synthetase (TrpRS) fragments, proliferin-related protein, prolactin fragment, pigment epithelium-derived factor (PEDF), vasostatin, angiostatin, endostatin, kininostatin, fibrinogen-E fragment, thrombospondin, tumstatin, canstatin, restin, soluble fms-like tyrosine kinase-1 (sFlt-1), soluble vascular endothelial growth factor receptors (sFlk), soluble Neuropilin 1 (sNRP1), Interferon gamma-induced protein 10 (IP-10), Platelet factor 4 (PF-4), Gro-beta, soluble Ephrin type-B receptor 4 (sEphB4), and sephrinB2, IGF-1, herpes simplex virus thymidine kinase (HSV-TK), carboxypeptidase G2 (CPG2), carboxylesterase (CA), cytosine deaminase (CD), cytochrome P450 (cyt-450), deoxycytidine kinase (dCK), nitroreductase (NR), purine nucleoside phosphorylase (PNP), thymidine phosphorylase (TP), varicella zoster virus thymidine kinase (VZV-TK), xanthine-guanine phosphoribosyl transferase (XGPRT), Aspartylglucosaminidase, α-Galactosidase A, Palmitoyl Protein Thioesterase, Tripeptidyl Peptidase, Lysosomal transmembrane protein, cysteine transporter, Acid ceramidase, acid α-L-fucosidase, protective protein/cathepsin A, acid β-glucosidase or glucocerebrosidase, acid β-galactosidase, iduronate-2-sulfatase, α-L-Iduronidase, galactocerebrosidase, acid α-mannosidase, acid β-mannosidase, arylsulfatase B, arylsulfatase A, N-Acetylgalactosamine-6-sulfate sulfatase, N-Acetylglucosamine-1-phosphotransferase, Acid sphingomyelinase, Niemann-Pick disease, type C1 (NPC-1), β-Hexosaminidase B, Heparan N-sulfatase,α-N-Acetylglucosaminidase (Na-Glu), Acetyl-CoA:αglucosamininde N-acetyltransferase, N-Acetylglucosamine-6-sulfate sulfatase, β-Glucuronidase, acid lipase, neprilysin, the insulin-degrading enzyme insulysin, thimet oligopeptidase, calbindin D28, parvalbumin, hypoxia induced factor 1-alpha (HIF1-alpha), sirtuin-2 (SIRT-2), survival motor neuron protein-1 (SMN-1), SMN-2, glial cell-derived neurotrophic factor (GDNF), ciliary neurotrophic factor (CNF), low density lipoprotein receptor (LDLR), lipoprotein lipase (LPL), Alpha-1-Antitrypsin (AAT), UDP-glucuronyl-transferases (UGT), UGT1A1, glucose-6 phosphatase, phosphoenolpyruvate-carboxykinase, galactose-1 phosphate uridyl transferase, phenylalanine hydroxylase, branched chain alpha-ketoacid dehydrogenase, fumarylacetoacetate hydrolase, methylmalonyl-CoA mutase, ornithine transcarbamylase, argininosuccinic acid synthetase, adenosine deaminase, hyposanthine guanine phosphoribosyl transferase, biotinidase, beta-glucocerebrosidase, beta-gluronidase, porphobilinogen deaminase (PBDG) or p53.

In examples of the uses or compositions provided herein, the composition contains a delivered agent that contains a nucleic acid molecule that encodes a polypeptide that increases muscle production in an animal, increases hair production in an animal, increases wool production in an animal, increases growth of an animal, or is involved in nutrient synthesis or utilization. For example, the encoded polypeptide can be a myostatin inhibitor, growth hormone, IGF-1, growth hormone releasing factor, chicken Ski, serine transacetylase and o-acetylserine sulphydrylase. In specific examples, the myostatin inhibitor is follistatin.

In examples of the uses or compositions provided herein, the composition contains a delivered agent that contains a nucleic acid molecule that is a DNA molecule, a RNA molecule, or an aptamer. The nucleic acid molecule can be a microRNA, a small interfering RNA, a ribozyme or an antisense nucleic acid.

In addition, the compositions provided herein for uses and compositions for use can include an agent or reagent that facilitates or increases the efficiency of delivery of the delivered agent to cells of the parenchyma of a tissue or organ. For example, the delivered agent can be formulated with lipids, polymer reagents or other agents to facilitate entry into the parenchymal cells. In examples where the use or compositions are for delivery to the liver, the parenchymal cells can be hepatocytes. In other examples, the delivered agent can be formulated with an agent that promotes cellular uptake of the delivered agent. For example, the delivered agent can be formulated with an agent that is a transcriptional enhancer of a virus-specific cell surface receptor. Exemplary of such an agent is a histone deacetylase (HDAC) inhibitor. The HDAC inhibitor can be trischostatin A, vorinostat (SAHA), belionostat (PXD101), LAQ824, panobinostat (LBH589), entinostat (MS-275), C199, mocetinostat (MGCD0103), romidepsin (lstodax), valproic acid, PCI-24781, SB939, resminostat, givinostat, CUDC-101, AR-42, CHR-2845, CHR-3996, 4SC-202, CG200745, Kevetrin, or trichostatin A (TSA).

In any of the examples of the uses or compositions provided herein, the delivered agent in the composition is generally in an amount that is greater than 100-fold less than the amount of the same delivered agent in a composition formulated for intravenous administration. For example, the amount of delivered agent in the composition is up to 200-fold, 500-fold, 1000-fold, 5000-fold, 10000-fold or less than the amount of the same delivered agent in a composition formulated for intravenous administration. In particular examples, the uses or compositions include a delivered agent that is an adenovirus or an adeno-associated virus that contains a heterologous nucleic acid molecule in its genome, where the amount of virus in the composition is or is about $2\times10^3$ pfu/mL to $1\times10^{14}$ pfu/mL, $2\times10^3$ pfu/mL to $1\times10^{12}$ pfu/mL, $2\times10^3$ pfu/mL to $2\times10^{11}$ pfu/mL, $1\times10^4$ pfu/mL to $5\times10^{11}$ pfu/mL, $1\times10^5$ pfu/mL to $1\times10^{11}$ pfu/mL, $2\times10^6$ pfu/mL to $2\times10^{10}$ pfu/mL, or $1\times10^8$ to $1\times10^{10}$ pfu/mL; or is or is about between $2\times10^3$ particles/mL to $1\times10^{14}$ particles/mL, $2\times10^3$ particles/mL to $1\times10^{12}$ particles/mL, $2\times10^3$ particles/mL to $2\times10^{11}$ particles/mL, $1\times10^4$ particles/mL to $5\times10^{11}$ particles/mL, $1\times10^5$ particles/mL to $1\times10^{11}$ particles/mL, $2\times10^6$ particles/mL to $2\times10^{10}$ particles/mL, or $1\times10^8$ to $1\times10^{10}$ particles/mL. The composition can be a liquid composition provided in a volume that is or is about between 0.02 mL to 100 mL, 0.05 mL to 50 mL, 1 mL to 10 mL, 0.05 mL to 5 mL or 0.02 mL to 1 mL. The composition for use provided herein can be formulated for single dosage administration or for multiple dosage administration. For example, the composition can contain an amount of adenovirus or adeno-associated virus for single dosage administration where the amount of adenovirus in the composition is or is about 10 to $1\times10^{12}$ particles, 10 to $1\times10^6$ particles, $1\times10^3$ to $1\times10^{12}$ particles, $1\times10^6$ to $1\times10^{10}$ particles, or $1\times10^7$ to $1\times10^9$ particles; or is or is about 10 to $1\times10^{12}$ pfu, 10 to $1\times10^6$ pfu, $1\times10^3$ to $1\times10^{12}$ pfu, $1\times10^6$ to $1\times10^{10}$ pfu, or $1\times10^7$ to $1\times10^9$ pfu. For example, the amount of adenovirus or adeno-associated virus in the composition is less than $1\times10^{12}$ particles, $1\times10^{11}$ particles, $1\times10^{10}$ particles, $1\times10^9$ particles, $1\times10^8$ particles, $1\times10^7$ particles, $1\times10^6$ particles, $1\times10^5$ particles, $1\times10^4$ particles, $1\times10^3$ particles or less; or is less than $1\times10^{12}$ pfu, $1\times10^{11}$ pfu, $1\times10^{10}$ pfu, $1\times10^9$ pfu, $1\times10$ pfu, $1\times10^7$ pfu, $1\times10^6$ pfu, $1\times10^5$ pfu, $1\times10^4$ pfu, $1\times10^3$ pfu or less.

In examples of the uses or compositions for use herein, the composition is formulated for administration to a human patient. The composition can be formulated for administration to children under 18 years of age. The compositions can be formulated for administration to a fetus.

In examples of the uses or compositions for use herein, the use of a delivered agent containing a nucleic acid molecule for use in direct parenchymal administration to a compartmentalized tissue can be used to express a polypeptide in a subject. The nucleic acid molecule can be a therapeutic nucleic acid molecule. The nucleic acid molecule can encode a therapeutic polypeptide. Hence, the uses or compositions for use herein for direct delivery to the parenchyma of a compartmentalized tissue or organ or portion thereof can effect treatment of a disease or condition. Exemplary of such diseases and conditions include, but are not limited to an inherited enzyme deficiency, inherited immune deficiency, a virus infection, cancer, hemophilia, diabetes, a muscular dystrophy, a cardiovascular disorder, cystic fibrosis, a neurodegenerative disorder, trauma, pain, sickle cell anemia, autoimmune disease, inflammatory disease, or hypertension. For example, the disease or condition can be hemophilia A and B, type I diabetes mellitus, alpha-1-antitrypsin (AAT) deficiency, hemochromatosis, Wilson's disease, Crigler-Najjar syndrome type I, ornithine transcarbamylase deficiency, type II, familial hypercholesterolemia, afibrinogenemia, glycogen storage disease (GSD) type Ia, GSD type Ib, GSD type II (Pompe), mucopolysaccharidosis (MPS1), MPS IIIA, MPS IIIB, MPS VII, Fabry disease, Gaucher's disease, Niemann-Pick syndrome, ornithine transcarbamylase deficiency (OTC) deficiency, phenylketonuria, liver fibrosis, liver ischemia reperfusion injury, Alzheimer's disease, Amyotrophic Lateral Sclerosis (ALS), galactosemia, phenylketonuria, maple syrup urine disease, tyrosinemia type 1, methylmalonic acidemia, citrullinemia, Gout and Lesch Nyan syndrome, Sly syndrome, Zellweger syndrome, human immunodeficiency virus (HIV) infection, severe combined immunodeficiency disease (SCID), cystic fibrosis, acute intermittent *porphyria*, multiple sclerosis, lipoprotein lipase deficiency (LPLD) or Parkinson's Disease.

Provided herein is a container containing an adenovirus or adeno-associated virus composition formulated for direct parenchymal administration in an amount between or about between 10 to $1\times10^{12}$ pfu, $1\times10^3$ pfu to $1\times10^{12}$ pfu, $1\times10^2$ pfu to $1\times10^{10}$ pfu, $1\times10^3$ pfu to $1\times10^{10}$ pfu, $1\times10^3$ pfu to $1\times10^9$ pfu, $1\times10^3$ pfu to $1\times10^8$ pfu, or $1\times10^6$ pfu to $1\times10^9$ pfu; or is between or about between 10 to $1\times10^{12}$ particles, $1\times10^3$ particles to $1\times10^{12}$ particles, $1\times10^2$ particles to $1\times10^{10}$ particles, $1\times10^3$ particles to $1\times10^{10}$ particles, $1\times10^3$ particles to $1\times10^9$ particles, $1\times10^3$ particles to $1\times10^8$ particles, or $1\times10^6$ particles to $1\times10^9$ particles. The adenovirus or adeno-associated virus generally contains a heterologous nucleic acid molecule in its genome. The container is one that is sterile and sealed. The container can be a syringe or vial. The container also can contain a needle for injection of the composition. The container can contain a capillary device. For example, the container can include a capillary device to penetrate the Glisson's capsule of the liver, for example, to intraparenchymally deliver the delivered agent.

In particular examples of containers provided herein, the composition contains an amount of adenovirus or adeno-associated virus that is less than $1\times10^{12}$ pfu, and is at least or about at least $1\times10^3$ pfu, $1\times10^4$ pfu, $1\times10^5$ pfu, $1\times10^6$ pfu, $1\times10^7$ pfu, $1\times10^8$ pfu, $1\times10^9$ pfu, $1\times10^{10}$ pfu, $1\times10^{11}$ pfu or more; or that is less than $1\times10^{12}$ particles, and is at least or about at least $1\times10^3$ particles, $1\times10^4$ particles, $1\times10^5$ particles, $1\times10^6$ particles, $1\times10^7$ particles, $1\times10^8$ particles, $1\times10^9$ particles, $1\times10^{10}$ particles, $1\times10^{11}$ particles or more.

In examples provided herein where the composition in the container contains an adenovirus, the adenovirus can be any available or known serotype. For example, the adenovirus is a serotype that is a serotype 1 to a serotype 51 (e.g. 1, 2, 3, 4, 5 . . . 51). The adenovirus can be adenovirus type 2 or adenovirus type 5. Generally, the adenovirus in the compositions provided in the containers herein contains a deletion in any one or more of the E1, E2a, E2b, E3, or E4 coding regions. For example, the adenovirus contains a deletion in the E1 coding region. The heterologous nucleic acid molecule can be inserted or contained in any one or more of the deleted regions.

In examples of the containers provided herein, the compositions contain a delivered agent that contains a nucleic acid molecule. For example, for viruses, the nucleic acid molecule is one that is heterologous to its genome. In some examples, the nucleic acid molecule can be any nucleic acid molecule that encodes a polypeptide. The encoded polypeptide can be an enzyme, a hormone, a coagulation or clotting factor, a growth factor, an antibody or portion thereof, an angiogenesis modulator, an immunomodulator, a pain modulator, a receptor, a transport protein, a regulatory protein, an antigen and an allergen. For example, the encoded polypeptide is an interleukin, interferon, growth factor or portion thereof and growth factor receptor or portion thereof. Exemplary nucleic acid molecules in the compositions provided in the containers herein include, but are not limited to, any that encode adenosine deaminase, cystic fibrosis transmembrane conductance regulator (CTFR), galsulfase, laronidase, N-acetylgalactosamine 6-sulfatase, phenylalanine ammonia lyase, acid alpha glucosidase, imiglucerase, alglucosidase alpha, thyrotropin, growth hormone, insulin, thyroid hormone, erythropoietin (EPO), interleukin-1 (IL-1), IL-2, IL-3, IL-4, IL-5, IL-7, interferon-α (IFN-α), IFN-β, IFN-γ, tumor necrosis factor (TNF), IL-12, IL-18, fms-related tyrosine kinase 3 (flt3), neuropilin-2 (NP2), bone morphogenic proteins (BMPs), epidermal growth factor (EGF), erythropoietin (EPO), fibroblast growth factor (FGF), granulocyte colony stimulating factor (G-CSF), granulocyte macrophage colony stimulating factor (GM-CSF), hepatocyte growth factor (HGF), insulin-like growth factor (IGF), platelet derived growth factor (PDGF), transforming growth factor α or β, vascular endothelial growth factor (VEGF), epidermal growth factor receptor (EGFR), fibroblast growth factor receptor (FGFR), FGFR antagonist (sFGFR), transforming growth factor receptor (TGFR), vascular endothelial growth factor receptor (VEGFR), plasminogen activator, urokinase, Factor VIII, Factor IX, von Willebrand factor, growth hormone, metalloproteinase thrombospondin motifs 1 (METH-1), METH-2, tryptophanyl-tRNA synthetase (TrpRS) fragments, proliferin-related protein, prolactin fragment, pigment epithelium-derived factor (PEDF), vasostatin, angiostatin, endostatin, kininostatin, fibrinogen-E fragment, thrombospondin, tumstatin, canstatin, restin, soluble fms-like tyrosine kinase-1 (sFlt-1), soluble vascular endothelial growth factor receptors (sFlk), soluble Neuropilin 1 (sNRP1), Interferon gamma-induced protein 10 (IP-10), Platelet factor 4 (PF-4), Gro-beta, soluble Ephrin type-B receptor 4 (sEphB4), sephrinB2, IGF-1, herpes simplex virus thymidine kinase (HSV-TK), carboxypeptidase G2 (CPG2), carboxylesterase (CA), cytosine deaminase (CD), cytochrome P450 (cyt-450), deoxycytidine kinase (dCK), nitroreductase (NR), purine nucleoside phosphorylase (PNP), thymidine phosphorylase (TP), varicella zoster virus thymidine kinase (VZV-TK), xanthine-guanine phosphoribosyl transferase (XGPRT), Aspartylglucosaminidase, α-Galactosidase A, Palmitoyl Protein Thioesterase, Tripeptidyl Peptidase, Lysosomal transmembrane protein, cysteine transporter, Acid ceramidase, acid α-L-fucosidase, protective protein/cathepsin A, acid β-glucosidase or glucocerebrosidase, acid β-galactosidase, iduronate-2-sulfatase, α-L-Iduronidase, galactocerebrosidase, acid α-mannosidase, acid β-mannosidase, arylsulfatase B, arylsulfatase A, N-Acetylgalactosamine-6-sulfate sulfatase, N-Acetylglucosamine-1-phosphotransferase, Acid sphingomyelinase, Niemann-Pick disease, type C1 (NPC-1), β-Hexosaminidase B, Heparan N-sulfatase,α-N-Acetylglucosaminidase (NaGlu), Acetyl-CoA:αglucosamininde N-acetyltransferase, N-Acetylglucosamine-6-sulfate sulfatase, β-Glucuronidase, acid lipase, neprilysin, the insulin-degrading enzyme insulysin, thimet oligopeptidase, calbindin D28, parvalbumin, hypoxia induced factor 1-alpha (HIF1-alpha), sirtuin-2 (SIRT-2), survival motor neuron protein-1 (SMN-1), SMN-2, glial cell-derived neurotrophic factor (GDNF), ciliary neurotrophic factor (CNF), low density lipoprotein receptor (LDLR), lipoprotein lipase (LPL), Alpha-1-Antitrypsin (AAT), UDP-glucuronyl-transferases (UGT), UGT1A1, glucose-6 phosphatase, phosphoenolpyruvate-carboxykinase, galactose-1 phosphate uridyl transferase, phenylalanine hydroxylase, branched chain alpha-ketoacid dehydrogenase, fumarylacetoacetate hydrolase, methylmalonyl-CoA mutase, ornithine transcarbamylase, argininosuccinic acid synthetase, adenosine deaminase, hyposanthine guanine phosphoribosyl transferase, biotinidase, beta-glucocerebrosidase, beta-gluronidase, porphobilinogen deaminase (PBDG) or p53.

In some cases, the compositions in the containers provided herein encode a polypeptide that increases muscle production in an animal, increases hair production in an animal, increases wool production in an animal, increases growth of an animal, or is involved in nutrient synthesis or utilization. the encoded polypeptide can be a myostatin inhibitor, growth hormone, IGF-1, growth hormone releasing factor, chicken Ski, serine transacetylase or o-acetylserine sulphydrylase. In specific examples, the myostatin inhibitor is follistatin.

Figure 1:
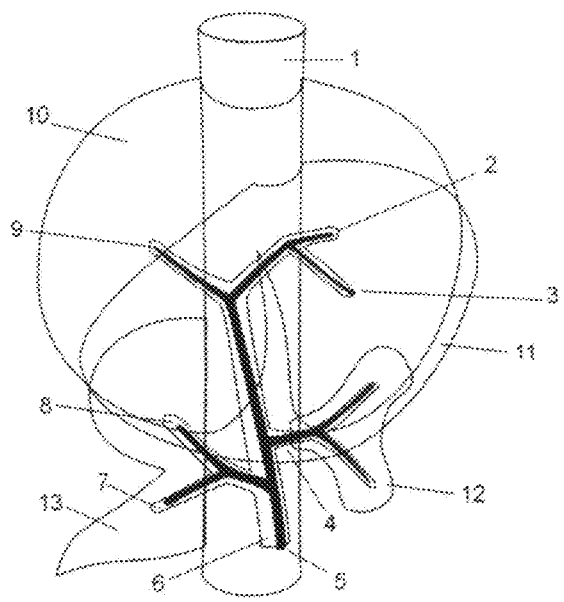
FIG. 1A is a diagram of the anatomy of a liver depicting the separate lobes and the blood supply to each lobe. The liver is traditionally divided into four lobes: a left anatomical lobe, a right anatomical lobe, the caudate lobe and the quadrate lobe. In the rat liver, these anatomically separate lobes are: the median lobe (10), the left lateral lobe (11), the right lobe (13), and the caudate lobe (12). The median lobe is situated directly under the diaphragm. It is fixed to the diaphragm via the faciform ligament, which forms the interlobular fissure and separates the lobe into a left and right portion. The median lobe represents nearly 40% of the total liver mass. The left lateral lobe is positioned below to the median lobe and above the caudate lobe. Interlobular ligaments fix the left lateral lobe with the superior portion of the caudate lobe. The left lateral lobe represents roughly 30% of the total liver mass. The right lobe is located to the right of the vena cava (1) and contains two well defined portions, the right superior lobe and the right inferior lobe. The right superior lobe is spherically shaped. Its fixation element is the hepato-diaphragmal ligament. The right inferior lobe has a triangular shape with the tip pointing to the vena cava. The right lobe represents 20% of the total liver mass. The caudate lobe is located to the left of the vena cava directly below the left lateral lobe. The lobe is divided into two portions: an upper caudate portion and a lower caudate portion. The upper caudate lobe is fixed to the left lateral lobe via an interlobular ligament and to the stomach via a hepato-gastric ligament. The lower portion of the caudate lobe is located behind the stomach. The caudate lobe represents 7% of the total mass of the liver.
Figure 1:
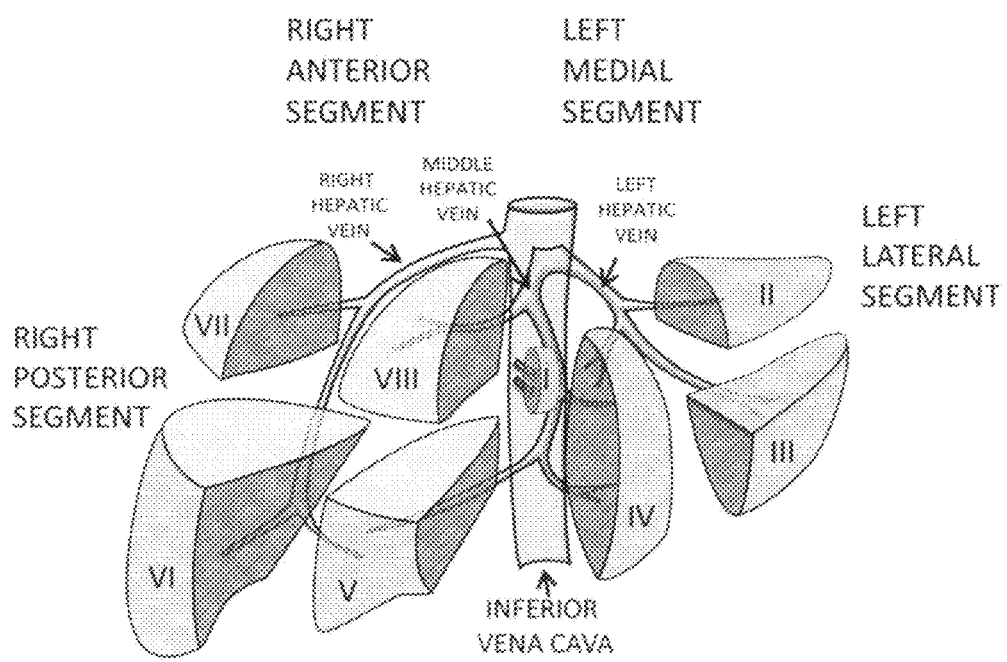

In-flow of blood to the liver is via the portal vein (6) and the hepatic artery (5), which, upon entry into the liver, branch off to the right and to the left to supply the various lobes. The first branch stems to the right as the right inferior portal vein (7) and right superior portal vein (8) to supply the right lobe. The second branch stems to the left as the caudate portal vein (4), which splits into two veins: an upper caudate branch and a lower caudate branch. The portal vein continues onto its main bifurcation giving the right median portal vein (9) that supplies the right portion of the median lobe and the left portal vein that releases the left median portal vein (2) and the left lateral portal vein (3) supplying the corresponding lobes. The arterial irrigation of the liver is provided by the hepatic artery, which once it enters the livers, branches to the right and left to supply the lobes and follows the same distribution as the portal veins.

FIG. 1B depicts further divisions of the liver based on the functional/vascular features of the liver. The three main hepatic veins (right hepatic vein, middle hepatic vein and left hepatic vein) divide the human liver into four sections or segments (the right posterior segment, the right anterior segment, the left medial segment and the left lateral segment) each of which is supplied by a corresponding branch of the portal system. Further branching of the portal veins subdivide the human liver into eight anatomically independent subsegments each with its own efferent hepatic venous system, afferent portal venous systems, afferent arterial system and a biliary duct system. Subsegments I and IV correspond to the left medial segment, subsegments II and III correspond to the left lateral segment, subsegments V and VIII which correspond to the right anterior segment and subsegments VI and VII which correspond to the right posterior segment.

Figure 2:
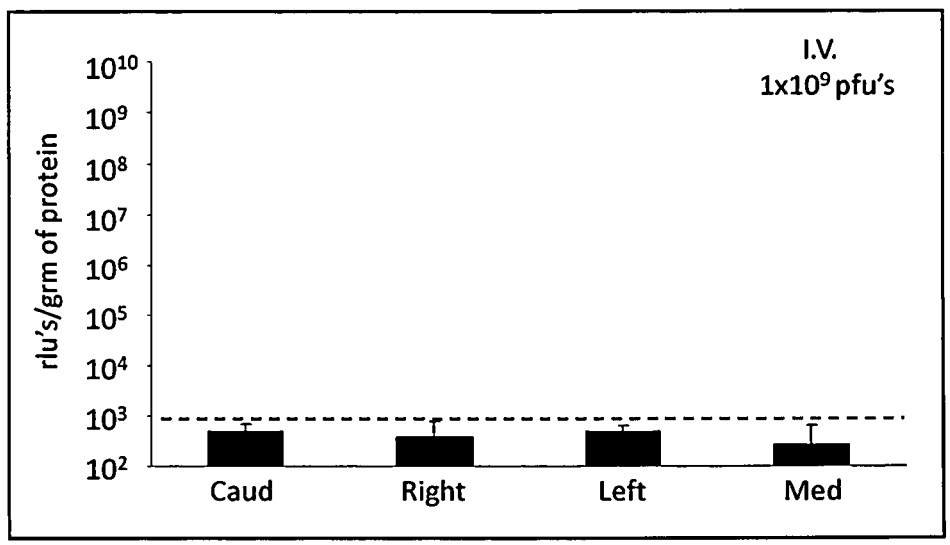
Figure 2:
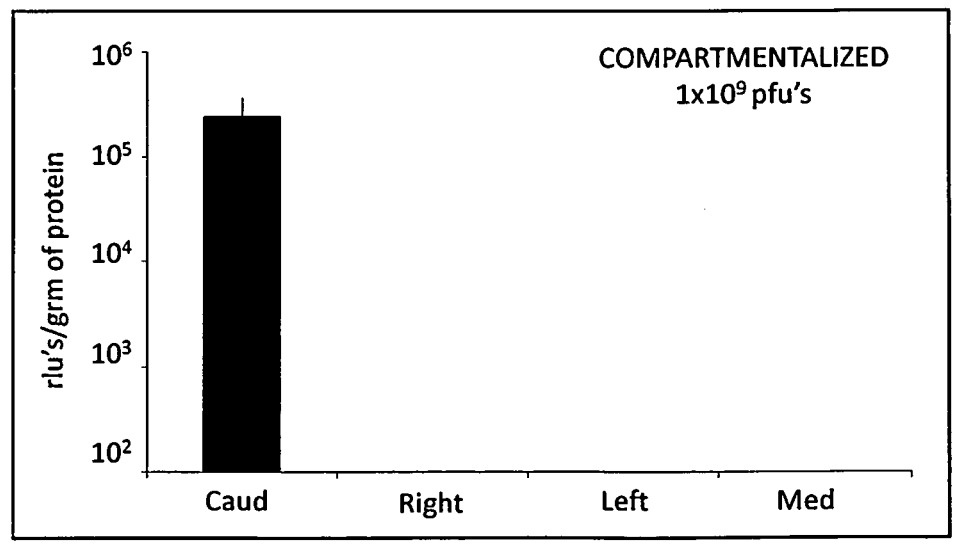

FIG. 2 depicts a comparison of luciferase activity upon delivery of a recombinant adenovirus by intravenous administration into the vena cava (FIG. 2A) or by interstitial administration into the parenchyma of the caudate lobe while blocking blood flow through the caudate lobe with a pedicle clamp (FIG. 2B). The results show expression of luciferase only in the caudate lobe following temporal compartmentalization.

Figure 3:
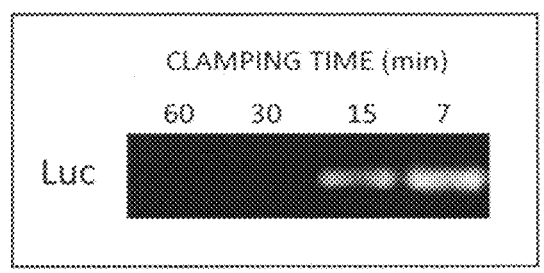
Figure 3:
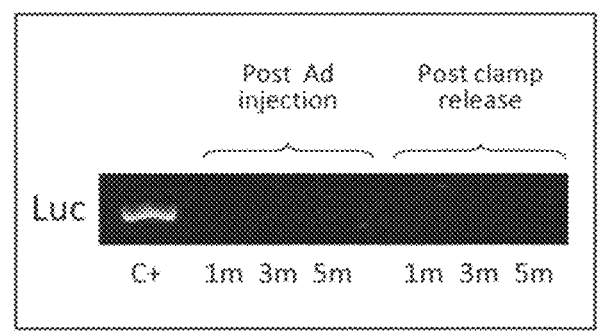

FIG. 3 depicts the presence of adenoviral DNA in systemic circulation when delivered by the compartmentalized method. Specifically, FIG. 3A shows no presence of adenoviral DNA upon termination of vascular isolation of the caudate lobe after 30 minutes or 60 minutes, but that adenovirus DNA was detected systemically upon termination of vascular isolation of the caudate lobe after 7 minutes or 15 minutes. FIG. 3B shows the kinetics of adenovirus DNA presence following initiation and termination of a 30 minute vascular isolation (via pedicle clamp). The results show no presence of adenovirus DNA in the peripheral blood 1, 3 and 5 minutes post adenoviral injection (during clamping) and at 1, 3 and 5 minutes after release of the clamp (post clamp release).

Figure 4:
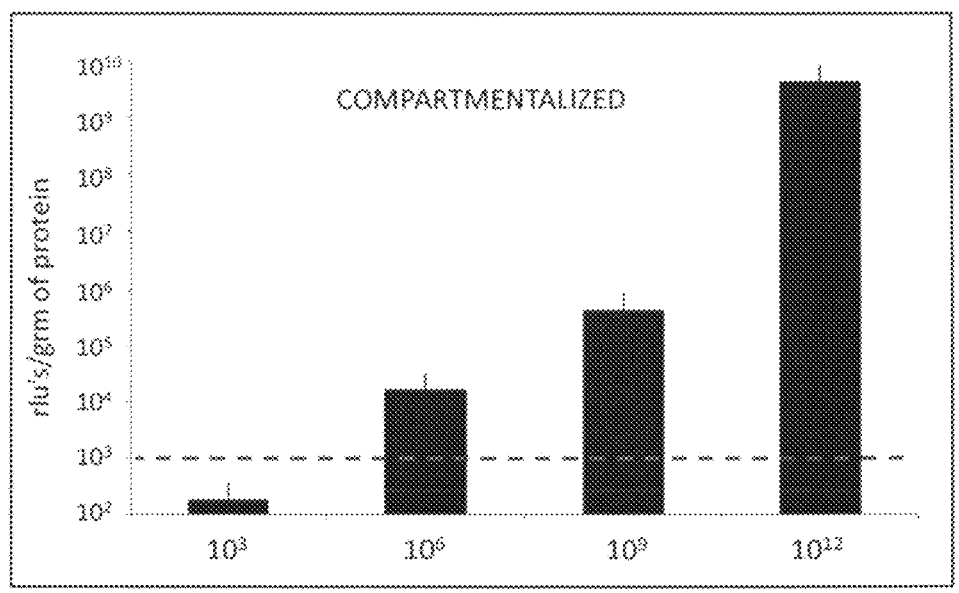

FIG. 4 shows luciferase activity levels in the caudate lobe upon parenchymal administration of various doses of recombinant adenovirus to the caudate lobe of rats during vascular isolation. The dashed line shows the maximum amount of expression achieved using intravenous infusion of the same vector at any dose. The results show that vascular isolation markedly increases the expression of the nucleic acid and provides controlled level of protein expression in a dose-dependent manner based on the amount of viral vector provided.

Figure 5:
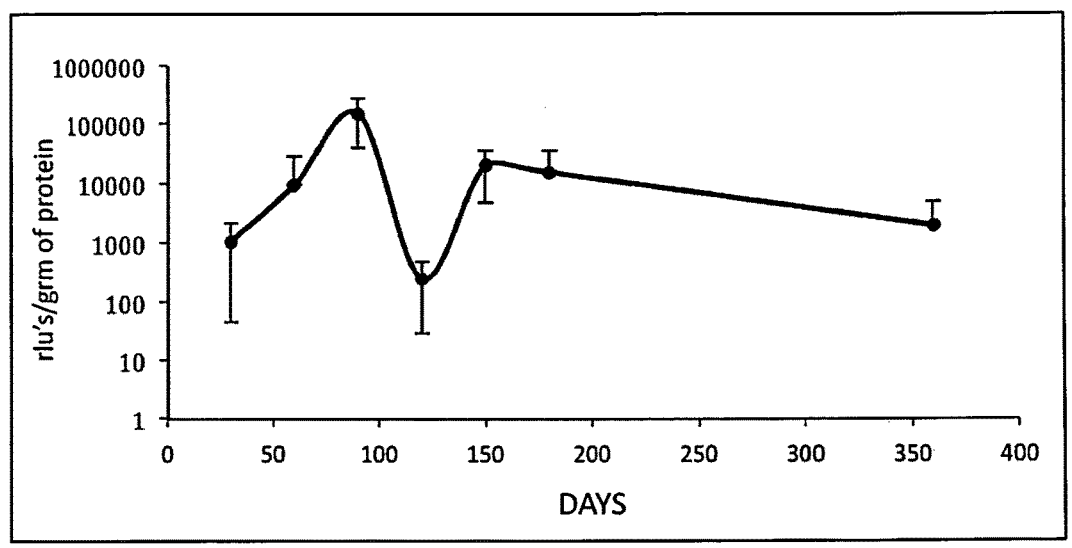

FIG. 5 shows the sustained luciferase expression in the caudate lobe up to 1 year in the compartmentalized model of hepatic gene therapy following parenchymal administration of recombinant adenovirus to the caudate lobe of rats during vascular isolation.

Figure 6:
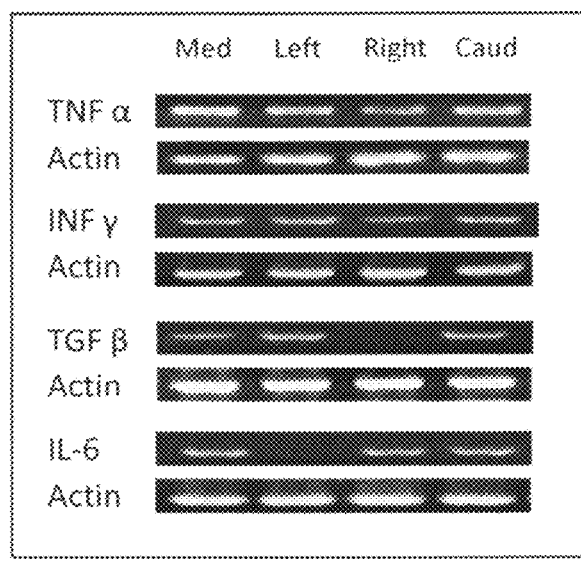
Figure 6:
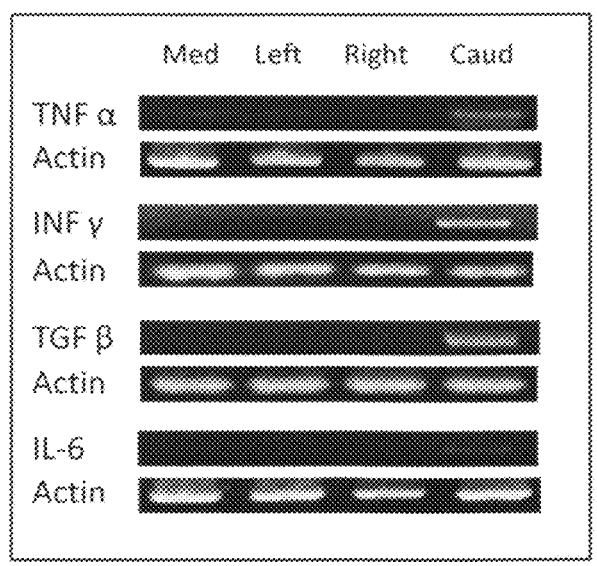

FIG. 6 depicts the cytokine expression levels (TNFα, IFNγ, TGFβ and IL-6) induced in the lobes of the liver upon delivery of recombinant adenovirus to the compartmentalized caudate lobe or upon delivery of recombinant adenovirus intravenously (IV). Expression of β-actin was used as a positive control. The results show robust cytokine expression in all lobes of the groups administered adenovirus intravenously. In the groups where adenovirus was administered to the compartmentalized lobe, reduced cytokine expression was observed, which was present only in the caudate lobe.

Figure 7:
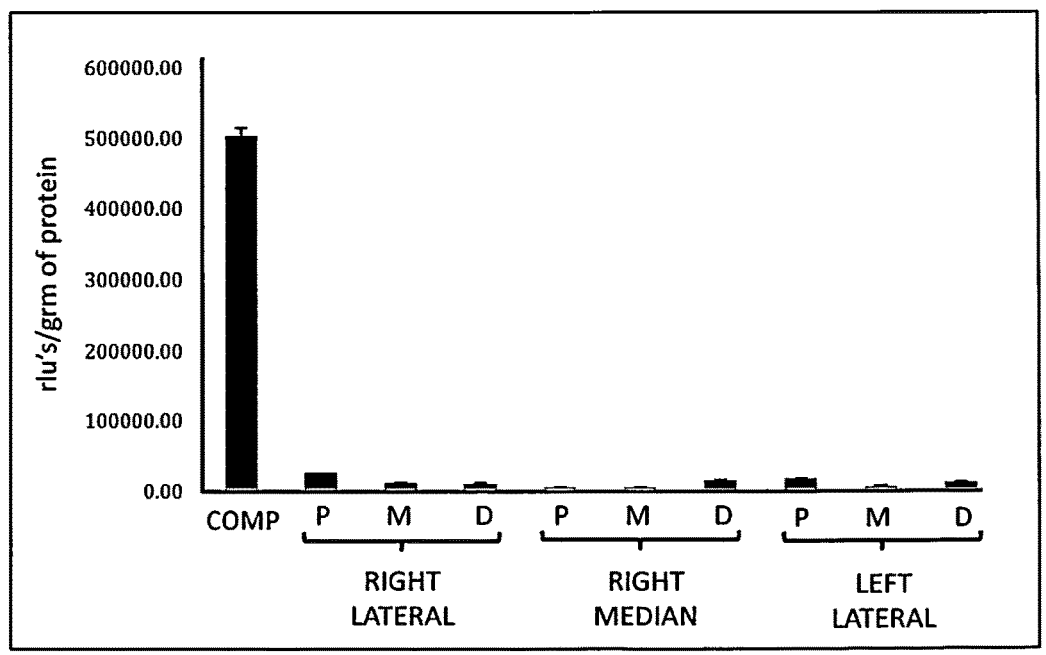

FIG. 7 depicts a comparison of luciferase gene expression in tissue samples from the left median lobe (comp; site of injection), the left lateral lobe, right lateral lobe, and right median lobe at sites proximal, medial, and distal to the site of injection upon delivery of a recombinant adenovirus into the parenchyma of the left median lobe of pigs while blocking blood flow with a parenchymal clamp. The results show expression of luciferase only at the site of injection.

Figure 8:
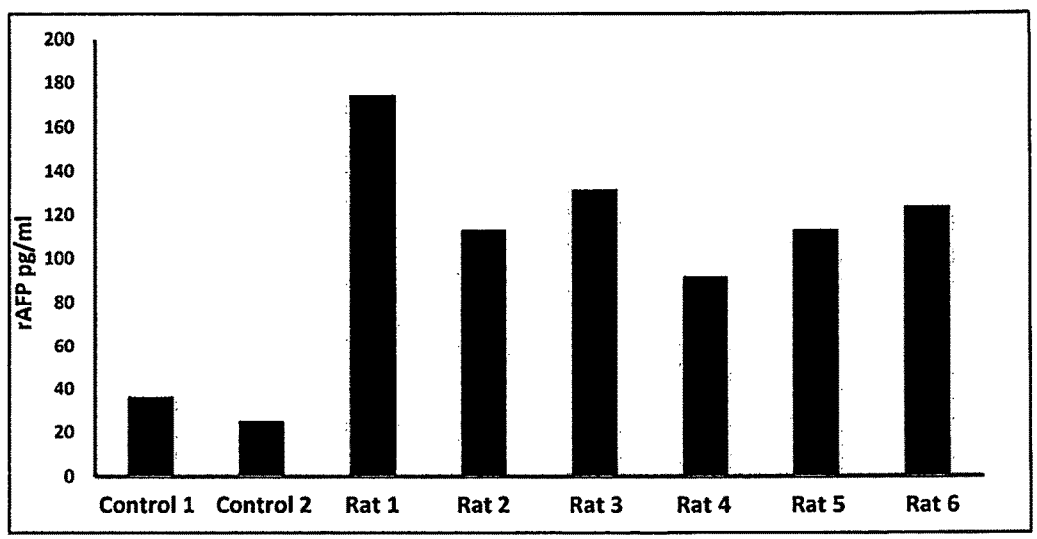

FIG. 8 depicts the alpha fetoprotein (AFP) protein levels in the serum of rats seven (7) days after delivery of a recombinant adenovirus encoding AFP to the compartmentalized caudate lobe of the liver of rats.

DETAILED DESCRIPTION

Outline
A. Definitions
B. Delivery of Nucleic Acid and Gene Therapy
1. Existing Gene Therapy Methods
2. Delivery Directly to a Compartmentalized Tissue or Organ
C. Compartmentalized Method of Nucleic Acid Delivery
1. Compartmentalization of a Tissue or Organ
   a. Liver
   b. Other Organs
2. Delivery of Nucleic Acid by Administering a Delivered Agent
   a. Delivery Methods and Routes of Administration
   b. Methods to Facilitate Delivery
   c. Dosages and Regimens for Delivery
3. Termination/Release of Compartmentalization
D. Delivered Agents
1. Nucleic Acid Molecule
2. Vehicles and Constructs Containing the Nucleic Acid Molecule
   a. Virus and Viral Vector
      i. Adenovirus
      ii. Adeno-associated virus (AAV)
      iii. Retrovirus
      iv. Lentivirus
   b. Non-Viral Vectors
      Nanoparticle
   c. Whole Cell
3. Exemplary Gene Therapy Agents
E. Compositions, Systems and Kits
1. Dosage Formulations
2. Combinations
3. Articles of Manufacture and Kits
F. Assessing Delivery, Expression or Efficacy
1. Monitoring of Delivered Agent
2. Host Toxicity and Immune Activation
G. Applications and Methods of Use
1. Treating Diseases and Disorders
   a. Hemophilia A and B
   b. Familial Hypercholeroloemia
   c. Type I Diabetes Mellitus
   d. Alpha-1-Antitrypsin (AAT) Deficiency
   e. Angiogenesis and Cancer
   f. Autoimmune and Inflammatory Disorders (e.g. Multiple Sclerosis)
   g. Acute Intermittent Porphyria (AIP)
   h. Sanfilippo Syndrome (Mucopolysaccharidosis type III; MPSIII)
   i. Lipoprotein Lipase Deficiency (LPLD)
2. Protein Expression and Production
3. Veterinary and Agricultural Applications
H. Examples

A. Definitions

Unless defined otherwise, all technical and scientific terms used herein have the same meaning as is commonly understood by one of skill in the art to which the invention(s) belong. All patents, patent applications, published applications and publications, Genbank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

As used herein, "compartmentalization" or "compartmentalized", or grammatical variations thereof, (also referred to herein as circulatory isolation or vasculature isolation) with reference to a tissue or organ or portion thereof refers to isolation of a tissue or organ or portion thereof from the systemic circulation. The isolation can be achieved by blocking or occluding one or more, and generally all, arteries, veins, ducts or vessels that traverse a tissue or organ or portion thereof, and that empty into, access or otherwise communicate with the systemic circulation. Compartmentalization of a tissue or organ is characterized by a stop or arrest of blood flow to the tissue or organ, or a portion or region of the tissue or organ. The compartmentalization disrupts communication or access between and among the tissue and organ, or a portion or region of the tissue or organ, and the rest of the body through the systemic circulation. Compartmentalization can be achieved by any method that blocks or occludes one or more arteries, veins, ducts or vessels, such as by using occlusion catheters, bands, tourniquets or clamps.

As used herein, recitation that "blood flow to a tissue or organ or portion thereof is reduced or eliminated," or similar such language, means that there is an interference or block in blood supply or flow from the arteries, veins, ducts and/or vessels servicing or traversing the tissue or organ or portion thereof, thereby depriving the tissue or a portion of the tissue access to substances carried in the blood. Such block can result in anoxia or ischemia to the tissue or organ or portion of the tissue or organ. It is within the level of a skilled artisan to monitor the reduction or elimination of blood flow to a tissue or organ. For example, reduction or elimination of blood flow can be monitored based on the color of tissue; electron paramagnetic resonance (EPR) oximetry using India ink or other reportable dye; using a Tissue Spectroscope (TiSpec); perfusion magnetic resonance imaging, positron emission tomography, near-infrared (NIR) spectroscopy, optical Doppler tomography, ultrasound and other methods known to a skilled artisan. For purposes of the methods herein, blood flow to a tissue or organ or a portion of a tissue or organ should be decreased more than 75%, 80%, 85%, 90%, 95% and up to about or 100% during compartmentalization of the tissue or organ or portion thereof.

As used herein, "systemic circulation" or "general circulation" refers to the general circulation that carries oxygenated blood from the left ventricle to the body tissues, and returning venous blood to the right atrium.

As used herein, an organ or tissue refers to differentiated parts of the body of a subject that performs a specific function. Tissues generally are a group of specialized cells that group together to form a specialized function. For example, muscle tissue is a specialized tissue that can contract. Organs are made up of tissues that perform a function. Examples of organs, include but are not limited to, the eyes, ears, lungs, liver, kidney, heart, or skin.

As used herein, reference to a "portion of a tissue or organ" refers to part of a tissue or organ of the body of a subject. The part can be a region, segment, lobe, section or other part of a tissue or organ. The portion is generally one that can be mobilized or isolated separate from the rest of the tissue or organ in order to permit compartmentalization of the portion from the rest of the tissue or organ. It also is a portion that is sufficient to effect delivery of the agent. It is within the skill of one in the art to determine the appropriate size of a portion of a tissue or organ sufficient to compartmentalize and/or to effect delivery of the agent, and it depends upon the particular organ, the instrument used for compartmentalization, the indication treated, the dosage, the size of the subject and other parameters. Typically, a portion of a tissue or organ has a volume of at least about 5 mm$^3$, 10 mm$^3$ or more. For example, the portion can be any area of a tissue or organ that has a length ranging from 0.5 cm to 25 cm, a height (or thickness) of 0.5 cm to 20 cm and/or a depth from 0.5 cm to 15 cm. As an example, a portion of a liver lobe or segment is one that has a length of 5 cm to 10 cm, a height of 1 cm to 3 cm and a depth (from the tip) of 1.5 cm to 3 cm. Smaller regions or portions are also contemplated so long as the portion is able to be compartmentalized.

As used herein, restoring communication with reference to compartmentalization refers to the process by which compartmentalization of a tissue or organ or portion of a tissue or organ is terminated so as to restore or resume access of the systemic circulation with the tissue or organ. This can be achieved by removal of the device, apparatus or process used to block or occlude one or more, and generally all, arteries, veins, ducts or vessels that traverse a tissue or organ or portion thereof.

As used herein, predetermined time with reference to termination of compartmentalization before restoration of communication with the systemic circulation means a limited time that is known before and can be controlled. Typically, the predetermined time is a time subsequent to administration or delivery of a delivered agent in which at least or about at least 80%, 85%, 90%, 95% or more of the delivered agent is intracellular in cells of the parenchyma of a tissue or organ (e.g. hepatocytes of the liver). Generally, such time is a time in which less than 10%, 5% or less of the delivered agent is present in the systemic circulation upon restoration of communication by termination of the compartmentalization. Such time can be empirically determined by one of skill in the art, and is a function, for example, of the particular target organ and delivered agent. In particular examples, the predetermined time is at least about or 15 minutes, 20 minutes, 25 minutes, 30 minutes, 35 minutes, 40 minutes, 45 minutes, 50 minutes or 60 minutes subsequent to initiation of compartmentalization and/or administration of the delivered agent. The predetermined time can be controlled by methods, mechanism or techniques that increase uptake of a delivered agent by cells. Such methods are known to one of skill in the art and are described herein. Thus, in some examples, the predetermined time can be less than 15 minutes, such as 5 minutes to 15 minutes.

As used herein, parenchyma refers to the portions of the tissue and associated cells of an organ that conducts the specific function of the organ and that makes up the bulk of the organ. Hence, the parenchyma is the main underlying functional tissue of an organ. These can include the epithelial tissue, muscle tissue, nervous tissue and associated cells thereof. Parenchyma is distinct from the stroma, which is the connective tissue, blood vessels, nerves and ducts. Hence, parenchyma does not include connective tissue, blood vessels, nerves and ducts. For example, the parenchyma of the liver includes hepatocytes, the parenchyma of the heart includes cardiac muscle cells such as myocytes, the parenchyma of the kidney includes nephrons. The parenchyma of the skin is the epidermis.

As used herein, "parenchymal cell" refer to the cells that are contained in or that make up the parenchyma of a tissue or organ. For example, hepatocytes are cells of the main tissue of the liver, which make up 70-80% of the livers mass. In the lung, 75% of all lung cells are contained in the parenchyma. These include, for example, fibroblasts of the interstitium and epithelial cells that line that alveoli, such as type 1 and type 2 cells (pneumocytes) and brush cells. In the skin, cells found in the parenchyma include epidermal cells such as keratinocytes. One of skill in the art is familiar with the parenchyma of various tissue and organs and cells therein.

As used herein, parenchymal administration refers to administration to the parenchyma of a tissue or organ. Administration to the parenchyma is typically by injection or capillary diffusion.

As used herein, a clamp refers to a device, such as a surgical device, used to compress a structure, such as an organ, vessel or tissue. A clamp generally has opposing sides or parts that can be mobilized or adjusted to effect pressure or force on opposite sides of a structure in order to compress the structure. A clamp can have serrated jaws, locking handles and/or inflatable balloons. Generally, the clamping force or pressure can be adjusted.

As used herein, "parenchymal clamp" refers to a clamp that can compress the parenchyma of a tissue or organ. Parenchymal clamps include pedicle clamps.

As used herein, laparoscopic surgery refers to surgery performed through small incisions (e.g. between 0.5 to 1.5 cm) and that use a laparoscope.

As used herein, "delivered agent" refers to the agent or conduit, such as vehicle, vector, or construct, that contains a nucleic acid molecule for gene therapy in and that facilitates entry of the nucleic acid molecule into cells and/or expression thereof. Hence, the delivered agent is the entity that is administered to a subject and that contains the nucleic acid molecule packaged therein or associated therewith. Examples of delivered agents include, but are not limited to, a virus, virus-like particles, mini-circles, a plasmid or vector, a liposome and/or nanoparticle. For example, a delivered agent can include a lipid-based or other polymer-based composition, such as liposome, micelle or reverse micelle, that is associated with a nucleic acid molecule or other agent, such as a non-viral vector or virus provided herein, for delivery into a host subject. In some examples, a naked DNA can be a delivered agent. The uptake of delivered agents can be further increased or facilitated using various mechanical techniques such as electroporation, sonoporation or "gene gun."

As used herein, "genetic therapy" or "gene therapy" involves the transfer of a nucleic acid molecule, such as heterologous DNA to certain cells, target cells, of a mammal, particularly a human, with a disorder or condition for which such therapy is sought. The DNA is introduced into the selected target cells in a manner such that the heterologous DNA is expressed and a therapeutic product encoded thereby is produced. Alternatively, the heterologous DNA can in some manner mediate expression of DNA that encodes the therapeutic product, it can encode a product, such as a peptide or RNA that in some manner mediates, directly or indirectly, expression of a therapeutic product. Genetic therapy also can be used to deliver nucleic acid encoding a gene product to replace a defective gene or supplement a gene product produced by the mammal or the cell in which it is introduced. The introduced nucleic acid can encode a therapeutic compound (e.g. a growth factor inhibitor thereof, or a tumor necrosis factor or inhibitor thereof, such as a receptor therefor), that is not normally produced in the mammalian host or that is not produced in therapeutically effective amounts or at a therapeutically useful time. The heterologous DNA encoding the therapeutic product can be modified prior to introduction into the cells of the afflicted host in order to enhance or otherwise alter the product or expression thereof.

As used herein, nucleic acid molecule refers to single-stranded and/or double-stranded polynucleotides, such as deoxyribonucleic acid (DNA) and ribonucleic acid (RNA), as well as analogs or derivatives of either RNA or DNA. Also included in the term "nucleic acid" are analogs of nucleic acids such as peptide nucleic acid (PNA), phosphorothioate DNA, and other such analogs and derivatives. Nucleic acids can encode gene products, such as, for example, polypeptides, regulatory RNAs, microRNAs, small inhibitory RNAs (siRNAs) and functional RNAs. Hence, nucleic acid molecule is meant to include all types and sizes of DNA molecules including siRNA, aptamers, ribozymes, complementary DNA (cDNA), plasmids and DNA including modified nucleotides and nucleotide analogs.

As used herein, a therapeutic nucleic acid is a nucleic acid molecule that encodes a therapeutic product or is capable of producing a therapeutic effect. The product can be nucleic acid, such as a regulatory sequence or gene, or can encode a protein that has a therapeutic activity or effect. For example, therapeutic nucleic acid can be a ribozyme, antisense, double-stranded RNA, a nucleic acid encoding a protein and others.

As used herein, a therapeutic product is a compound that is capable of producing a therapeutic effect. The compound can be a polypeptide, peptide, DNA or RNA.

As used herein, a heterologous nucleic acid with reference to nucleic acid contained in the genome of a virus (also referred to as exogenous nucleic acid or foreign nucleic acid) refers to a nucleic acid that is not normally produced in vivo by an organism or virus from which it is expressed or that is produced by an organism or a virus but is at a different locus, or that mediates or encodes mediators that alter expression of endogenous nucleic acid, such as DNA, by affecting transcription, translation, or other regulatable biochemical processes. Hence, heterologous nucleic acid is often not normally endogenous to an organism or a virus into which it is introduced. Heterologous nucleic acid can refer to a nucleic acid molecule from another virus in the same organism or another organism, including the same species or another species. Heterologous nucleic acid, however, can be endogenous, but is nucleic acid that is expressed from a different locus or altered in its expression or sequence (e.g., a plasmid). Thus, heterologous nucleic acid includes a nucleic acid molecule not present in the exact orientation or position as the counterpart nucleic acid molecule, such as DNA, is found in a genome. Generally, although not necessarily, such nucleic acid encodes RNA and proteins that are not normally produced by the organism or virus or in the same way in the virus in which it is expressed. Any nucleic acid, such as DNA, that one of skill in the art recognizes or considers as heterologous, exogenous or foreign to the virus in which the nucleic acid is expressed is herein encompassed by heterologous nucleic acid. Examples of heterologous nucleic acid include, but are not limited to, nucleic acid that encodes exogenous peptides/proteins, including diagnostic and/or therapeutic agents. Proteins that are encoded by heterologous nucleic acid can be expressed within the virus, secreted, or expressed on the surface of the virus in which the heterologous nucleic acid has been introduced.

As used herein, a detectable label or detectable moiety refers to an atom, molecule or composition, wherein the presence of the atom, molecule or composition can be directly or indirectly measured. Detectable labels can be used included in any of the delivered agents herein. Detectable labels include, for example, chemiluminescent moieties, bioluminescent moieties, fluorescent moieties, radionuclides, and metals. For example, detectable moieties include, for example, luciferase, green fluorescent protein, red fluorescent protein, colloidal gold, iron, gadolinium, and gallium-67. Methods for detecting labels are well known in the art. Such a label can be detected, for example, by visual inspection, by fluorescence spectroscopy, by reflectance measurement, by flow cytometry, by X-rays, by a variety of magnetic resonance methods such as magnetic resonance imaging (MRI) and magnetic resonance spectroscopy (MRS). Methods of detection also include any of a variety of tomographic methods including computed tomography (CT), computed axial tomography (CAT), electron beam computed tomography (EBCT), high resolution computed tomography (HRCT), hypocycloidal tomography, positron emission tomography (PET), single-photon emission computed tomography (SPECT), spiral computed tomography, and ultrasonic tomography. Direct detection of a detectable label refers to, for example, measurement of a physical phenomenon of the detectable label itself, such as energy or particle emission or absorption of the label itself, such as by X-ray or MRI. Indirect detection refers to measurement of a physical phenomenon of an atom, molecule or composition that binds directly or indirectly to the detectable label, such as energy or particle emission or absorption, of an atom, molecule or composition that binds directly or indirectly to the detectable label. In a non-limiting example of indirect detection, a detectable label can be biotin, which can be detected by binding to avidin. Non-labeled avidin can be administered systemically to block non-specific binding, followed by systemic administration of labeled avidin. Thus, included within the scope of a detectable label or detectable moiety is a bindable label or bindable moiety, which refers to an atom, molecule or composition, wherein the presence of the atom, molecule or composition can be detected as a result of the label or moiety binding to another atom, molecule or composition.

As used herein, a DNA construct is a single or double stranded, linear or circular DNA molecule that contains segments of DNA combined and juxtaposed in a manner not found in nature. DNA constructs exist as a result of human manipulation, and include clones and other copies of manipulated molecules.

As used herein, vector (or plasmid) refers to discrete elements that are used to introduce a heterologous nucleic acid into cells for either expression or replication thereof. The vectors typically remain episomal, but can be designed to effect integration of a gene or portion thereof into a chromosome of the genome. Vectors include non-viral vectors, such as non-viral expression vectors. Also contemplated are vectors that are artificial chromosomes, such as yeast artificial chromosomes and mammalian artificial chromosomes. Vector also includes "virus vectors" or "viral vectors." Selection and use of such vehicles are well known to those of skill in the art.

As used herein, an expression vector includes vectors capable of expressing DNA that is operatively linked with regulatory sequences, such as promoter regions, that are capable of effecting expression of such DNA fragments. Such additional segments can include promoter and terminator sequences, and optionally can include one or more origins of replication, one or more selectable markers, an enhancer, a polyadenylation signal, and the like. Expression vectors are generally derived from plasmid or viral DNA, or can contain elements of both. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, "virus," refers to any of a large group of infectious entities that cannot grow or replicate without a host cell. Viruses typically contain a protein coat surrounding an RNA or DNA core of genetic material, but no semipermeable membrane, and are capable of growth and multiplication only in living cells. Viruses include those that are formed when, such as when a vector containing all or a part of a viral genome, is transduced into an appropriate cell or cell line for the generation of such particles. The resulting viral particles have a variety of uses, including, but not limited to, transferring nucleic acids into cells either in vitro or in vivo. Thus, a virus is a packaged viral genome. A virus can refer to a single particle, a stock of particles or a viral genome.

As used herein, viral vector refers to a nucleic acid vector construct that includes at least one element of viral origin and can be packaged into a viral vector particle or virus. Reference to viral vector herein is used interchangeably with virus when it is packaged inside a protein coat. The viral vector particles or virus can be used for the purpose of transferring DNA, RNA or other nucleic acids into cells either in vitro or in vivo. Viral vectors include, but are not limited to, retroviral vectors, vaccinia vectors, lentiviral vectors, herpes virus vectors (e.g., HSV), baculoviral vectors, cytomegalovirus (CMV) vectors, papillomavirus vectors, simian virus (SV40) vectors, Sindbis vectors, Semliki Forest virus vectors, phage vectors, adenoviral vectors, and adeno-associated viral (AAV) vectors. Suitable viral vectors are described, for example, in U.S. Pat. Nos. 6,057,155, 5,543,328 and 5,756,086. Viral vectors typically include engineered viruses that are operatively linked to exogenous genes to transfer (as vehicles or shuttles) the exogenous genes into cells.

As used herein, operably or operatively linked when referring to nucleic acid arranged with regulatory and effector sequences of nucleotides, such as promoters, enhancers, transcriptional and translational stop sites, and other signal sequences refers to the relationship between such nucleic acid, such as DNA, and such sequences of nucleotides so that they function in concert for their intended purposes, e.g., transcription initiates in the promoter and proceeds through the coding segment to the terminator. For example, operative linkage of nucleic acid to a promoter refers to the physical relationship between the DNA and the promoter such that the transcription of such DNA is initiated from the promoter by an RNA polymerase that specifically recognizes, binds to and transcribes the DNA. Thus, operatively linked or operationally associated refers to the functional relationship of a nucleic acid, such as DNA, with regulatory and effector sequences of nucleotides, such as promoters, enhancers, transcriptional and translational stop sites, and other signal sequences. In order to optimize expression and/or transcription, it can be necessary to remove, add or alter 5' untranslated portions of the clones to eliminate extra, potentially inappropriate, alternative translation initiation (i.e., start) codons or other sequences that can interfere with or reduce expression, either at the level of transcription or translation. In addition, consensus ribosome binding sites can be inserted immediately 5' of the start codon and can enhance expression (see e.g., Kozak *J. Biol. Chem.* 266: 19867-19870 (1991) and Shine and Delgarno, *Nature* 254 (5495):34-38 (1975)). The desirability of (or need for) such modification can be empirically determined.

As used herein, antisense refers to nucleic acid (DNA, RNA or chemical analog) that is complementary to the messenger RNA (mRNA) of a gene of interest and can bind and inactivate it.

As used herein, small interfering RNA (siRNA) refers to a class of 20-25 nucleotide-long double stranded RNA molecules that can interfere with the expression of a gene.

As used herein, aptamer refers to oligonucleotides (DNA or RNA) that bind to a target such as a small molecule, protein, nucleic acid, cell or tissue. Aptamers can be engineered and selected against a target molecule by in vitro selection methods, such as by using systematic evolution of ligands by exponential enrichment (SELEX). Aptamers against various targets are known to one of skill in the art.

As used herein, ribozyme refers to an RNA molecule that has a unique hairpin or hammerhead shaped active center and a unique secondary structure that allows them to cleave other RNA molecules at specific sequences. Ribozymes include natural ribozymes as well as ribozymes that are engineered or designed to cleave any RNA molecule.

As used herein, virus-like particle (VLPs) refers to a non-infectious agent that resembles a virus but does not contain any viral genetic material. For example, VLPs can be assembled from expression of viral structural proteins (e.g. envelope or capsid). VLPs include those produced from Parvoviridae (e.g. adeno-associated virus), Retroviridae (e.g. HIV) and Flaviviridae (e.g. Hepatitis C virus).

As used herein, minicircle refers to small circular plasmids or DNA vectors that are episomal and are produced as a circular expression cassette devoid of any bacterial plasmid backbone. They can be generated from a parental bacterial plasmid that contains a heterologous nucleic acid and two recombinase target sites by intramolecular (cis-) recombination using a site-specific recombinase, such as PhiC31 integrase. Recombination between the two sites generates a minicircle and a leftover miniplasmid. The minicircle can be recovered separate from the miniplasmid. One of skill in the art is familiar with minicircles and methods of making them.

The term "naked" polynucleotide, DNA or RNA, refers to sequences that are free from any delivery vehicles, complexes or agents that acts to assist, promote, or facilitate entry into the cell, including viral sequences, viral particles, liposome formulations, lipofectin or precipitating agents.

As used herein, viral particles (VP) refers to the total number of viral particles, including live and dead combined. The number of viral particles can be determined using an OD260 assay from a purified virus stock.

As used herein, plaque forming unit (pfu) or infectious unit (IU) refers to the number of infectious or live viruses. It thus reflects the amount of active virus in the preparation. The pfu can be determined using a plaque formation assay or an end-point dilution assay, which are standard assays known to one of skill in the art.

As used herein, "adenovirus vector" and "adenoviral vector" are used interchangeably and are well understood in the art to mean a polynucleotide containing all or a portion of an adenovirus genome. An adenoviral vector, refers to nucleic acid encoding a complete genome or a modified genome or one that can be used to introduce heterologous nucleic acid when transferred into a cell, particularly when packaged as a particle. An adenoviral vector can be in any of several forms, including, but not limited to, naked DNA, DNA encapsulated in an adenovirus capsid, DNA packaged in another viral or viral-like form (such as herpes simplex, and AAV), DNA encapsulated in liposomes, DNA complexed with polylysine, complexed with synthetic polycationic molecules, conjugated with transferrin, complexed with compounds such as PEG to immunologically "mask" the molecule and/or increase half-life, or conjugated to a non-viral protein.

As used herein, the term "adenovirus" or "adenoviral particle" is used to include any and all viruses that can be categorized as an adenovirus, including any adenovirus that infects a human or an animal, including all groups, subgroups, and serotypes. Depending upon the context reference to "adenovirus" can include adenoviral vectors. There are at least 51 serotypes of adenovirus that are classified into several subgroups. For example, subgroup A includes adenovirus serotypes 12, 18, and 31. Subgroup B includes adenovirus serotypes 3, 7, 11a, 11p, 14, 16, 21, 34, 35 and 50. Subgroup C includes adenovirus serotypes 1, 2, 5, and 6. Subgroup D includes adenovirus serotypes 8, 9, 10, 13, 15, 17, 19, 19p, 20, 22-30, 32, 33, 36-39, 42-49 and 51. Subgroup E includes adenovirus serotype 4. Subgroup F includes adenovirus serotypes 40 and 41. Thus, as used herein an adenovirus or adenovirus particle is a packaged vector or genome. For purposes herein, the viruses typically are recombinant adenoviruses containing a heterologous nucleic acid molecule in its genome and formed when an adenovirus vector is encapsulated in an adenovirus capsid.

Included among adenoviruses are any and all viruses that can be categorized as an adenovirus, including any adenovirus that infects a human or an animal, including all groups, subgroups, and serotypes. Thus, as used herein, "adenovirus" and "adenovirus particle" refer to the virus itself and derivatives thereof and cover all serotypes and subgroups and naturally occurring and recombinant forms, except where indicated otherwise. Included are adenoviruses that infect human cells. Adenoviruses can be wildtype or can be modified in various ways known in the art or as disclosed herein. Such modifications include, but are not limited to, modifications to the adenovirus genome that is packaged in the particle in order to make an infectious virus. Exemplary modifications include deletions known in the art, such as deletions in one or more of the E1a, E1b, E2a, E2b, E3, or E4 coding regions. Other exemplary modifications include deletions of all of the coding regions of the adenoviral genome. Such adenoviruses are known as "gutless" adenoviruses. The terms also include replication conditional adenoviruses, which are viruses that preferentially replicate in certain types of cells or tissues but to a lesser degree or not at all in other types.

As used herein, a "targeting molecule" or "targeting ligand" refers to any protein, polypeptide, or portion thereof that binds to a cell surface molecule, including, but not limited to, proteins, carbohydrates, lipids or other such moiety. Targeting ligands include, but are not limited to growth factors, cytokines, adhesion molecules, neuropeptides, protein hormones and single-chain antibodies (scFv).

As used herein, a nanoparticle refers to a colloidal particle for delivery of a molecule that is microscopic in size of between or about between 1 and 1000 nanometers (nm), such as 1 and 100 nm, and that behave as a whole unit in terms of transport and properties. Nanoparticles include monolithic nanoparticles (nannospheres) in which the molecule is absorbed, dissolved or dispersed throughout the matrix and nanocapsules in which the molecule is confined to an aqueous or oily core surrounded by a shell-like wall. Alternatively, the molecule can be covalently attached to the surface or into the matrix. Nanoparticles include, for example, liposomes, dendrimers, polymeric micelles, nanocapsules, nanospheres and solid lipid nanoparticles. Generally, nanoparticles are made from biocompatible and biodegradable materials such as natural or synthetic polymers (e.g. gelatin, albumin, polylactides, polyalkylcyanoacrylates) or solid lipids. Nanoparticles include those that contain a targeting molecule attached to the outside.

As used herein, a compound conjugated to a moiety refers to a complex that includes a compound bound to a moiety, where the binding between the compound and the moiety can arise from one or more covalent bonds or non-covalent interactions such as hydrogen bonds, or electrostatic interactions. A conjugate also can include a linker that connects the compound to the moiety. Exemplary compounds include, but are not limited to, nanoparticles and siderophores. Exemplary moieties, include, but are not limited to, detectable moieties and therapeutic agents.

As used herein, tropism with reference to a delivered agent, such as a virus, refers to the selective infectivity or binding that is conferred on the particle by a capsid protein, such as the fiber protein and/or penton.

As used herein, "entry," "uptake" or "enters" with respect to a cell refers to the process whereby the delivered agent is introduced into a cell. Hence, such terms mean that the delivered agent is intracellularly located.

As used herein, transduction refers to the transfer of genetic material into cells by a virus.

As used herein, "sustained' expression with reference to a delivered nucleic acid molecule refers to the period of time after introduction of the nucleic acid into the organ during which at least 70%, 80%, 85%, 90%, 91%, 92%, 93%, 94%, 95%, 96%, 97%, 98%, 99% or more of the peak expression is observed. Typically, expression is sustained if the encoded protein is expressed over a length of time of greater than 6 months, 7 months, 8 months, 9 months, 10 months, 11 months, 12 months, 16 months, 24 months or more.

As used herein, the term promoter means a portion of a gene containing DNA sequences that provide for the binding of RNA polymerase and initiation of transcription. Promoter sequences are commonly, but not always, found in the 5' non-coding region of genes.

As used herein, production by recombinant means by using recombinant DNA methods means the use of the well known methods of molecular biology for expressing proteins encoded by cloned DNA.

As used throughout, subject can be a vertebrate, more specifically a mammal (e.g., a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject in need of a therapeutic agent. The term patient or subject includes human and veterinary subjects. Both therapeutic, industrial, veterinary and agricultural (e.g., meat production) uses are disclosed herein.

As used herein, a patient refers to a human subject.

As used herein, a composition refers to any mixture. It can be a solution, suspension, liquid, powder, paste, aqueous, non-aqueous or any combination thereof.

As used herein, a combination refers to any association between or among two or more items. The combination can be two or more separate items, such as two compositions or two collections, can be a mixture thereof, such as a single mixture of the two or more items, or any variation thereof. The elements of a combination are generally functionally associated or related.

As used herein, a kit is a packaged combination that optionally includes other elements, such as additional reagents and instructions for use of the combination or elements thereof. Kits optionally include instructions for use.

As used herein, "disease or disorder" refers to a pathological condition in an organism resulting from cause or condition including, but not limited to, infections, acquired conditions, genetic conditions, and characterized by identifiable symptoms.

As used herein, a "disease or disorder treatable by a nucleic acid" refers to any disease or disorder that is amenable to treatment by an exogenously delivered nucleic acid by altering (increasing or decreasing) expression of a gene associated or involved in the etiology or a disease or condition, expressing a gene product for ameliorating a disease or condition, or replacing a gene product that is defective or missing in a disease or condition. Hence, a disease or disorder treatable by a nucleic acid is intended to encompass known gene therapy methods and applications including, for example, treating genetic deficiencies by replacing a defective or missing gene product or exogenously administering a therapeutic agent or product. A skilled artisan is familiar with such diseases and disorders. Exemplary diseases and disorders treatable by a nucleic acid are described herein.

As used herein, "treating" a subject with a disease or condition means that the subject's symptoms are partially or totally alleviated, or remain static following treatment. Hence treatment encompasses prophylaxis, therapy and/or cure. Prophylaxis refers to prevention of a potential disease and/or a prevention of worsening of symptoms or progression of a disease.

As used herein, treatment means any manner in which the symptoms of a condition, disorder or disease or other indication, are ameliorated or otherwise beneficially altered.

As used herein therapeutic effect means an effect resulting from treatment of a subject that alters, typically improves or ameliorates the symptoms of a disease or condition or that cures a disease or condition. A therapeutically effective amount refers to the amount of a composition, molecule or compound which results in a therapeutic effect following administration to a subject.

As used herein, amelioration of the symptoms of a particular disease or disorder by a treatment, such as by administration of a pharmaceutical composition or other therapeutic, refers to any lessening, whether permanent or temporary, lasting or transient, of the symptoms that can be attributed to or associated with administration of the composition or therapeutic.

As used herein, prevention or prophylaxis refers to methods in which the risk of developing disease or condition is reduced.

As used herein, an effective amount is the quantity of a therapeutic agent necessary for preventing, curing, ameliorating, arresting or partially arresting a symptom of a disease or disorder.

As used herein, unit dose form refers to physically discrete units suitable for human and animal subjects and packaged individually as is known in the art.

As used herein, direct administration means administration without further dilution.

As used herein, a single dosage formulation refers to a formulation for direct administration.

As used herein, a multiple dosage formulation refers to a formulation for use in repeat administrations.

As used herein, an "article of manufacture" is a product that is made and sold. As used throughout this application, the term is intended to encompass delivered agents, such as adenovirus particles, contained in articles of packaging.

As used herein, the singular forms "a," "an" and "the" include plural referents unless the context clearly dictates otherwise. Thus, for example, reference to a compound, comprising "an extracellular domain" includes compounds with one or a plurality of extracellular domains.

As used herein, the term "or" is used to mean "and/or" unless explicitly indicated to refer to alternatives only or the alternatives are mutually exclusive.

As used herein, ranges and amounts can be expressed as "about" a particular value or range. About also includes the exact amount. Hence "about 5 bases" means "about 5 bases" and also "5 bases."

As used herein, "optional" or "optionally" means that the subsequently described event or circumstance does or does not occur, and that the description includes instances where said event or circumstance occurs and instances where it does not. For example, an optionally substituted group means that the group is unsubstituted or is substituted.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:1726).

For clarity of disclosure, and not by way of limitation, the detailed description is divided into the subsections that follow.

B. Delivery of Nucleic Acid and Gene Therapy

Provided herein is a method of delivering to a subject a delivered agent (that is or includes a nucleic acid molecule) to an organ or a portion of an organ that is compartmentalized from the general vasculature by vascular isolation of the organ from the general circulation. Specifically, provided herein are methods based on the finding that expression of an exogenous delivered nucleic acid molecule can be sustained and stable, upon administration of a delivered agent (that is or includes the nucleic acid molecule) to an organ or portion thereof when the organ or portion thereof is temporarily compartmentalized (i.e., vascularly deprived or isolated). Further, practice of the compartmentalized method of nucleic acid delivery achieves a linear kinetic dose-response that has not been previously achieved. The nucleic acid molecule that is delivered can be a therapeutic nucleic acid, including a nucleic acid that encodes a therapeutic polypeptide to a subject. Thus, the methods can be used for cellular expression in vivo of a selected polypeptide. In some examples, the polypeptide agent can be useful in therapeutic settings where the polypeptide treats or ameliorates a disorder or condition in a subject or otherwise improves the quality of life in a subject. In other examples, the polypeptide agent can be useful in agriculture setting, for example, applications that improve the quality or quantity of meat production.

The method described herein offers several advantages over traditional gene therapy methods by eliminating the need to infuse a viral vector systemically (thereby reducing viremia and immunologic responses), allowing a markedly reduced quantity of viral vector (thereby reducing necrosis at the site of administration), allowing control over the amount of agent delivered, providing for quantitative control of gene expression, and providing sustained expression of the selected agent.

1. Existing Gene Therapy Methods

A basic challenge for biotechnology is to develop approaches for delivering genetic information to cells in vivo. The purposeful delivery of genetic material to somatic cells for the purpose of treating disease or for biomedical investigation has been termed gene therapy. Gene therapy promises to be a significant advance in the treatment of disease, including somatic and hereditary genetic diseases. To be successful, the nucleic acid molecule must be delivered to a therapeutically significant percentage of the affected cells in a manner that is both efficient and safe. The delivered nucleic acid molecule can then compensate for a missing or partially or non-functional endogenous gene, provide a beneficial function or block activity of a dominant negative endogenous gene or gene of an infectious organism.

Existing gene therapy methods deliver a nucleic acid molecule to a tissue or organ intravenously. Intravenous delivery of nucleic acids, using non-viral or viral vectors, is complicated by several problems that have hindered its widespread application. For example, systemic delivery of nucleic acid vectors can result in the initiation of immune responses that result in severe toxic side effects, neutralization of transgene products (e.g. due to generation of antibodies against expressed proteins), reduced cellular uptake of the nucleic acid or vector, loss of gene expression and/or transient expression requiring repeat infusion, the need for large doses of nucleic acid to be injected into the subject's circulation, tissue damage, elevated pressures within the target organ during therapy, viremia, and/or difficulty targeting specific cell types within the body. These problems can be more severe when the nucleic acid is delivered in a viral vector, such as an adenoviral vector. In addition, in existing gene therapy methods there is a lack of correlation between vector dose and protein output.

For example, systemic administration of a delivered agent containing a nucleic acid molecule, such as a virus, can result in transduction of immune cells and activation of an unwanted immune response. Innate immune cells involved in the first line of defense to foreign infection, including phagocytic cells (e.g. macrophages, neutrophils) and natural killer (NK) cells, become activated by exposure to foreign material (e.g. viral-based vectors). Activation of the innate immune response acts to limit the infection by killing infected cells and by secreting pro-inflammatory cytokines and chemokines (e.g. interferons, IL-1, IL-6, TNF-α, MIP-2, MIP-1α). The cytokine and cellular response results in tissue damage, apoptosis of infected cells, recruitment of other effector cells such as dendritic cells and the initiation of the adaptive immune response. Antigen-presenting cells (APCs), such as immature dendritic cells present in the blood and tissues, recognize and uptake foreign antigen material, thereby stimulating signal transduction pathways activating NF-κB, secretion of inflammatory cytokines and chemokines, and upregulation of T-cell activating molecules such as MHC molecules and costimulatory molecules.

The result is activation of the cellular and humoral immune responses. Humoral immunity can result in the generation of antibodies that can bind to and inactivate antigen directly (neutralizing antibodies) or activate other cells of the immune system to destroy the antigen. Cellular immunity is mediated by cytotoxic T cells that recognize foreign peptides on the surface of infected cells and once recognized eliminate any cells producing foreign antigen. Thus, the result of immune activation is the activation of effector cells such as cytotoxic T cells that eliminate transduced cells, as well as the generation of antibody secreting plasma cells that produce neutralizing antibodies preventing readministration of the nucleic acid (e.g. viral vector). The culmination of the immune responses, and extent of such responses, can cause systemic and local toxicity.

This toxicity also can be exacerbated when the delivery is widespread, whereby several tissues or organs become transduced with the nucleic acid. While such tissues or organs can be excised to limit localized toxicity, in cases where several organs are involved having multiple sites of transduction, it can be impossible to treat any toxic effects by removal of transduced tissue. Even where delivery of a nucleic acid is targeted to the vasculature of a target organ, unwanted immune responses and toxicity can occur. Also, the entire organ can be subjected to toxic effects.

Systemic administration requires higher doses in order to achieve sufficient transduction efficiency of cells and confer efficient gene transfer. For example, for viral delivery, such as administration of adenoviral vectors, $10^{10}$-$10^{13}$ viral particles (vp) per kg (vp/kg) are administered, and generally $10^{12}$ to $10^{13}$ vp/kg in order to achieve measurable and reproducible cellular transduction and expression at the tissue site, such as hepatocyte transduction and expression in the liver. The requirement for higher doses is because the vector is removed from the blood by the immune responses prior to reaching tissue cells, such as liver hepatocytes. At higher doses, the phagocytic cells of the blood and tissue (e.g. Kupffer cells) become saturated and permit high level hepatocyte transduction. Also, systemic delivery of nucleic acid can result in delivery and distribution throughout the body, which is not ideal if the resulting therapeutic is only required at a target locus. In such cases, it is often necessary to increase dosage in order to achieve therapeutic efficacy. Increasing dosage, however, increases the likelihood of eliciting unwanted toxicity or other side effects.

While others have attempted efforts to localize delivery to an organ or portion thereof in order to avoid some of these problems, none have been successful in addressing all of these complications. For example, methods of targeting delivery of viral vectors (e.g. lentivirus or adenovirus) to the liver by isolated intravenous or hepatic artery perfusion following occlusion of a hepatic vein or artery resulted in elevation of liver enzymes, cytokines, some lymphocyte infiltrates and/or contamination of non-targeted organs or portions of organs (see e.g. U.S. Patent Application No. US2008/0025952, US2010/0010068 and US2006/0188482; Kinoshita et al. (2010) *J Surg. Res.*, 160:47-51). Methods of hydrodynamic gene delivery to the liver by intravenous delivery of a nucleic acid, which generates "pores" in the plasma membrane of the surrounding parenchyma cells to achieve delivery to parenchymal cells, also can lead to contamination of other organs. Such methods are not effective in all species and have yet to be shown to be applicable to viral vectors (Fabre et al. (2008) *Gene Ther.*, 15:452-62). Further, hydrodynamic gene delivery methods have been shown to require outflow obstruction to be effective, such that the invasive technique is not feasible in the clinic (Sawyer et al. (2010) *Gen Ther.*, 17:560-4). Other methods that rely principally on direct parenchymal administration and intrahepatic injection of nucleic acid also can result in elevated liver enzymes, elevated cytokines, and/or contamination of other organs or portions thereof (see e.g. Crettaz et al. (2006) *Hepatology*, 44:623-32; Fumoto et al. (2009) *Biol. Pharm. Bull.*, 32:1298-302).

2. Delivery Directly to a Compartmentalized Tissue or Organ

Provided herein are methods of compartmentalized delivery of a nucleic acid molecule by administering a delivered agent directly to cells in an organ or portion thereof that is compartmentalized by isolation from the vasculature, lymph and/or ducts. In the methods herein, the method is characterized by 1) blocking blood flow to and from an organ or portion thereof to prevent or substantially prevent communication with the systemic circulation; 2) directly administrating the delivered agent to tissue parenchymal cells of the tissue or portion thereof; and 3) maintaining vascular isolation for a time period sufficient to permit cellular uptake of the selected agent. The effect of these aspects means that the delivered agent, such as viral vector, is not exposed to the general circulation, such that systemic immune responses are not initiated, systemic toxicity is avoided and there is no contamination of other non-targeted organs or tissues. Further, by directly administering the delivered agent to parenchymal cells of the compartmentalized tissue or organ, cellular uptake is maximized. Maximizing cellular uptake of the agent means that, upon release of the tissue or organ compartmentalization, virtually all of the delivered nucleic acid molecule is available for transgene expression in the cell, and the amount of delivered agent that could escape into the systemic circulation is reduced or eliminated. Thus, the methods provided herein permit targeting of only the desired cells within the target organ and expression of a transgene produce for a sustained length of time.

The method is based on the finding herein that delivery of nucleic acid to a tissue or organ compartmentalized for a time selected as appropriate for a target organ of interest, provides sustained expression of the nucleic acid molecule that is delivered, which is far longer than expression using methods available in the prior art; reduces the amount of delivered agent that must be administered to cause appreciable uptake and expression of the nucleic acid molecule; avoids side effects related to systemic administration of a delivered agent, such as a viral vector, or a genetically modified cell; and for the first time provides an opportunity to adjust the amount of polypeptide expression by adjusting the amount of delivered agent administered to the subject. These are significant improvements that provide new opportunities in the field of gene therapy.

The present methods of delivering a nucleic acid molecule that encodes a polypeptide provides an advantage over methods of directly administering a polypeptide. For example, because expression of the resulting encoded polypeptide is sustained, the delivery of the nucleic acid molecule to the subject does not necessarily require repeated infusions or injections over the course of a treatment. Additionally, because the polypeptide is expressed in the methods herein by the subject's own transduced cells (e.g., hepatocytes), the encoded polypeptides are properly post-translationally modified.

In addition, gene delivery to individual lobes or segments of an organ, such as a liver, has advantages. For example, regional delivery means that any unexpected harmful effects of gene delivery will either be of no consequence or can be readily treated by removal of the targeted lobe. In the method, compartmentalized delivery permits non-targeted parts of the tissue or organ to serve as an internal control. It also permits removal of the targeted lobe, thereby providing formal proof that gene delivery to the targeted lobe was responsible for the effect.

These features of the method are exemplified herein with direct hepatic administration of an adenovirus delivery agent containing a heterologous nucleic acid molecule. The results herein show that direct administration of an adenovirus to interstitial parenchymal cells of a liver lobe under vascular isolation or compartmentalization by parenchymal clamping, for a time sufficient to permit cellular uptake of virtually all of the administered adenovirus, exhibits numerous advantages over existing methods. In particular, higher efficiency hepatic transduction was observed as compared to systemic injections. Using this approach sustained and robust gene expression was achieved without immune-suppression, high levels of protein synthesis were observed, and low doses of administered virus of less than 1011 particles, such as less than $10^{10}$ particles, $10^9$ particles $10^8$ particles, $10^7$ particles, $10^6$ particles, $10^5$ particles, $10^4$ particles, $10^3$ particles, or less was sufficient and effective to confer high-level transgene expression in the targeted lobe or region. In particular, the results herein show that less virus is required without compromising protein output. The results also show that there is a correlation between the vector dose and the protein output. For example, using the present method of administration with compartmentalization, lower amounts of viral vector (e.g., less than $10^{10}$ particles and as low as $10^3$ particles, $10^2$ particles or less) resulted in polypeptide expression, with a positive correlation between the amount of viral vector administered and the amount of expression. Also, by practice of the method side effects such as viremia, inflammatory hepatic response, hepatic cytokine expression, general liver damage and necrosis at the site of administration and systemic toxicity were not observed. Given the non-toxicity and long-term transgene expression, this approach can be used for gene therapy applications by targeting expression of a transgene in the liver for treating liver diseases or other diseases in mammalian subjects, including humans.

The following sections describe in further detail the steps of the compartmentalized method of nucleic acid delivery as provided herein, and exemplary delivery agents and compositions for use in performing the method. It is understood that the description of additional steps or alternative steps that can be performed in the method are contemplated as being performed with any specific method steps or combination of method steps of the disclosed methods, and that such combination or subset of combinations is specifically contemplated. Also described below are methods and applications of the compartmentalized delivery method for use in expressing nucleic acid molecules encoding polypeptides for therapeutic or industrial, veterinary or agricultural applications. The various steps and reagents used in the method, including the targeted organ and delivered agent, can be adapted by one of skill in the art based on the description herein for use in any amenable organ or portion thereof depending on the delivered agent, the particular application or therapeutic indication and the particular subject and other similar considerations.

C. Compartmentalized Method of Nucleic Acid Delivery

Provided herein is a method of delivering a nucleic acid molecule by administering a selected delivered agent to a subject including the steps of (1) compartmentalizing a tissue, organ or portion thereof by isolation or near complete isolation from the vasculature, lymph and/or ductal systems; (2) administering the selected delivered agent directly to the compartmentalized organ or portion thereof; (3) maintaining the compartmentalization for a time period subsequent to the administration of the delivered agent before removing the isolation, e.g. restoring vascular circulation to the organ or portion thereof. In the method, compartmentalization of the tissue or organ or portion thereof is maintained for a time period subsequent to the administration of the nucleic agent sufficient so that less than 10% of the delivered agent is exposed to the systemic circulation and/or to allow cellular uptake of greater than 80% of the selected delivered agent by cells of the organ or portion thereof. The method provided herein permits sustained expression of a transgene product in the tissue or organ or portion thereof for more than 60 days, more than 90 days, more than 6 months, more than 9 months, or more than one year.

In practice of the method herein, optionally, immunosuppressive agents can be administered to subjects prior to and following dosing with a delivered agent, such as a viral vector, in order to minimize or reduce the possibility of immune responses. For example, agents can be administered that suppress cytotoxic lymphocytes. Exemplary immunosuppressive agents include, but are not limited to, cyclosporine (Neoral®, Sandimmune®), prednisone (Novo Prednisone®, Apo Prednisone®), azathioprine (Imuran®), tacrolimus or FK506 (Prograf®), mycophenolate mofetil (CellCept®), sirolimus (Rapamune®), OKT3 (Muromorab CO3®, Orthoclone®), ATGAM or Thymoglobulin. It is within the level of skill of the treating physician to determine if an immunosuppressive agent is required. Effective immunosuppressive regimes are routinely practiced in the art, and the particular regime will depend on factors that include, for example, the particular target organ, the particular delivered agent, the particular genetic therapy, and the subject being treated.

The method of delivering a nucleic acid provided herein can be performed on any mammalian subject. Exemplary of such subjects include, but are not limited to, mice, rats, cows, pigs, sheep, goats, horses and humans. In particular, the methods provided herein are performed in human subjects. In particular, the methods can be performed on human subjects that are children under the age of 18, such as infants, toddlers and younger children. In some examples, the method can be performed in utero on a fetus. Since the method provided herein permits sustained and long-term high level expression of a transgene product, the method can be used in diverse applications, including, but not limited to, medical applications, including applications to replace a defective gene product or in applications to exogenously administer a therapeutic agent; production of organs for transplant; production of therapeutic proteins in transgenic animals (e.g. bioreactors); and in agricultural or veterinary applications as well as industrial applications.

The compartmentalized methods of nucleic acid delivery to a subject provided herein can be performed once, or can be performed a plurality times. For example, the method provided herein can be effected multiple times over the course of a protein production protocol or over the course of a treatment regime. In some examples, as described elsewhere herein, the method is repeated to effect delivery at multiple target loci, particularly where high levels of transduction or expression is sought throughout the tissue or organ. In such examples, the method is generally repeated within minutes, hours or days of the first application of the method. In other examples, the method can be repeated weeks, months or years after the first application. Escalation schemes can be added if the pathology requires. In examples where the method is repeated to the same target locus, a sufficient period of time is provided in order for the tissue or organ to recover from the previous vascular isolation. In other examples, when repeated, the method is applied to a target tissue or organ or region that has not previously been subjected to vascular isolation.

Description of steps of the method, and various exemplary non-limiting embodiments thereof, is provided in the following subsections.

1. Compartmentalization of a Tissue or Organ

As a first step in the method provided herein, a tissue, organ or portion thereof is compartmentalized by isolating it from the vasculature system. In some examples, compartmentalization is also additionally achieved by isolation from the ductal system and/or lymph system. Initiation of the compartmentalization precedes administration of the selected agent and is not released or ended to restore vascular circulation to the organ or portion thereof until after a period of time sufficient to allow cellular uptake of the selected agent.

Any tissue or organ or portion thereof can be used in the compartmentalized methods herein for delivery of nucleic acids. Such tissues or organs include, but are not limited to, liver, lung, CNS (brain or spinal cord), peripheral nervous system (e.g., nerve), pancreas, gall bladder, endocrine glads (pituitary, adrenal, thyroid, etc.), cardiovascular organs (e.g., heart and blood vessels), skin, urogential organs (kidney, uterus, cervix, prostate, urethra), organs of the respiratory system (e.g., lung or airways), bone, muscle, and intestine. This list is not intended to be exhaustive, as one of skill in the art will recognize additional target organs and lobes thereof. In particular examples, the tissue or organ or portion thereof for use in the compartmentalized method herein is the liver or a portion thereof.

Generally, the tissue or organ or portion thereof that is compartmentalized is one that is amenable to vascular isolation for a time period sufficient so that less than 10%, and generally less than 5%, 4%, 3%, 2%, 1% or less of the delivered agent is exposed to the systemic circulation. Generally, this predetermined time period is such that virtually all of the delivered agent is taken up by the tissue cells, for example, at least 80%, 85%, 90%, 91%, 92%, 93%, 94%, 95%, 96%, 97%, 98%, 99% or more of the delivered agent is taken up by the tissue cells. The predetermined time period to permit tissue cellular uptake and prevent release or exposure of the agent to the systemic circulation is a function of the particular organ or portion thereof, the particular delivered agent and the particulars of the direct delivery to tissue cells (e.g use of electroporation). It is within the level of one of skill in the art to empirically determine the time period required such that less than 10% of the delivered agent is exposed to the systemic circulation. For example Section F provided herein describes exemplary assays and methods for assessing delivery of the delivered agent. In particular examples herein, compartmentalization of an organ or portion thereof is maintained for at least 10 minutes, 15 minutes, 20 minutes, 25 minutes, 30 minutes, minutes, 40 minutes, 45 minutes, 50 minutes, 55 minutes or 60 minutes, or more. Generally, compartmentalization is for at least 20 minutes but not longer than 60 minutes. For example, compartmentalization of an organ or portion thereof, such as the liver or portion thereof, is for at least 30 minutes and generally for not longer than 60 minutes. Thus, depending on the particular delivered agent, the compartmentalization is maintained under conditions that can result in ischemia to the organ tissue or portion thereof for a brief time period. Hence, the organ or portion thereof used in the methods herein is one that is amenable to periods of brief ischemia.

Initiation of the compartmentalization precedes administration of the selected agent. In the methods herein, compartmentalization is initiated immediately prior to delivery of the delivered agent to the tissue. For example, compartmentalization is initiated no more than 5 minutes prior to delivery of the delivered agent, and typically no more than 4 minutes, 3 minutes, 2 minutes, 1 minute or 30 seconds prior to delivery of the delivered agent. In particular examples, the device used to effect vascular isolation can be adapted or modified or made to be compatible with a delivery device in order to permit faster or more efficient delivery of the delivered agent following vascular isolation.

In the methods provided herein of administering a selected delivered agent to an organ or portion thereof of a subject, the methods include the steps of reducing, blocking, or isolating blood flow through the organ or portion thereof or otherwise disturbing access or communication of the tissue or organ or portion thereof with the circulation. This can be achieved by isolation of the tissue or organ or portion thereof from the vasculature system, ductal system and/or lymph system. The isolation can be for a predetermined time. Typically, compartmentalization is effected by methods that achieve total vascular exclusion for a predetermined time. The tissue or organ or portion thereof can be compartmentalized by any number of methods. In one example, isolation can be achieved using one or more arterial or venous clamps, occlusion catheters, or by vascular stapling devices to seal individual veins or arteries. Typically, to block blood flow, the arteries and veins or ducts servicing the organ or portion thereof are clamped. In other examples, vascular isolation can be effected using one or more parenchymal or pedicle clamps to cut off the blood supply and flow through the tissue. For a reasonably isolated organ or portion thereof having a single blood supply (e.g., the arteries and vessels supplying the organ or portion thereof are within a pedicle that can be clamped) a single clamp or occlusion catheter is sufficient. In other organs or portions thereof with complex vasculature or with collateral circulation, multiple clamps or occlusion catheters can be needed. Methods of isolating a tissue or portion thereof from the vasculature are well-known in the art, and are used in various medical procedures such as tissue resection and transection procedures.

The methods to achieve compartmentalization of a tissue or organ can include selective or non-selective methods to block the blood flow through the organ or portion thereof. For example, selective clamping of a lobe, section or segment of an organ, such as the liver, can be performed. The benefit of selective clamping is that ischemic injury, if any, can be limited to the selected area that is compartmentalized (Chouillard et al. (2010) *Annals of Surgical Innovation and Research,* 4:2).

In particular examples, compartmentalization is achieved by parenchymal compression. For example, manual compression can be performed, such as by using finger fracture techniques. In additional examples, a tourniquet, cable or banding device can be applied to a region or portion of an organ. In other examples, a parenchymal clamp can be used to compress blood vessels, arteries, ducts or lymph vessels and block blood flow to a region, lobe, section or segment of a tissue or organ. Such clamps include pedicle clamps and other clamps that can selectively clamp a region or segment of an organ. Clamps for use in vascular isolation and exclusion methods are well known and available to one of skill in the art. These include commercially available clamps from manufacturers such as Aesculap (Center Valley, Pa.), Klein Surgical Systems (San Antonio, Tex.) or Karl Storz (Germany). Exemplary clamps include, but are not limited to, a Kelly clamp, micro-serrefine clamp, Bulldog clamps, a Debakey-Satinsky clamp, Longmire clamp, Lin or Chu liver clamp, or the Inokuchi liver clamp. Inflatable balloon clamps also can be employed. The choice and size of clamp is dependent on the particular subject, the size of the subject, the surgical method used, and the particular organ or portion thereof to be compartmentalized by the method herein. It is within the level of one of skill in the art to empirically identify and choose a clamp that is compatible with the particular application.

In the examples herein of parenchymal compression, the pressure that is applied to the parenchymal tissue is enough to stop blood flood, but is not so much as to cause serious damage to the surrounding tissue. It is within the level of one of skill in the art, such as a skilled surgeon, to determine the ideal pressure to achieve optimal compartmentalization of an organ or portion thereof while minimizing tissue damage or trauma. Generally, the clamp is one that can achieve even pressure across the distal, middle and proximal jaw positions of the clamp. The clamp, and pressure applied, also should be capable of compartmentalizing a region or segment of a tissue or organ from adjacent tissue areas and from the surrounding vasculature. This compartmentalization should be maintained throughout the duration of its application, and generally at least up to 30 minutes to 60 minutes. If desired, the force of a clamp can be determined using procedures known in the art, such as by using a compression load cell transducer, for example a 2.2. button style compression load transducer (Interface Advanced Force Measurement; Scottsdale, Az). Also, the pressure in mm Hg required to achieve compartmentalization (leak pressure) can be determined ex vivo or in vivo using a pressure gauge, such as a Cole Parmer digital pressure measuring device (e.g. Cole-Parmer®; Vernon Hills, Ill.).

Compartmentalization can be assessed by injecting a dye, such as methylene blue or bromophenol blue or other similar dye, into the target region or segment that is compartmentalized and assessing its localization to that region. For example, after removal of the clamp, the tissue on both sides where the clamp had been placed can be dissected and analyzed for the presence of the dye. Compartmentalization is achieved when the dye does not penetrate a portion or region of the isolated tissue. It is understood that some leakage of the dye (indicative of blood flow) can occur at the peripheral regions around the boundary of the clamp, so long as there is a region or portion of the tissue that is isolated from the vasculature for the entire period of parenchymal compression. Ideally, compartmentalization is achieved so that the dye does not penetrate the adjacent tissue beyond the boundary of the clamp. This is exemplified in Example 6.

In addition to clamps and occlusion catheters, suction can be used to reduce or eliminate blood flow to the organ of portion thereof. In further examples, flushing can be used to perfuse or partially perfuse the isolated organ or tissue to dilute the blood and to further minimize exposure of the delivered agent to the circulation. Flushing can be achieved using any physiologically appropriate solution, such as saline. The suction or flushing can be performed prior to administration or delivery of the delivered agent. In addition, in examples of the methods herein, the step of compartmentalizing an organ or portion thereof from the general circulation can be aided by imaging devices, such as ultrasonography, computed tomography or magnetic resonance imaging. In one example, an intra-operative ultrasound can be used to locate vascular patterns and other anatomical features of the tissue or organ in order to aid in blocking blood flow.

In some examples, ischaemic preconditioning (IP) can be performed prior to total vascular isolation for a predetermined time that is likely to result in a prolonged ischaemic event. The preconditioning results in increased tolerance of the organ or portion thereof to longer periods of ischaemia that can occur in practice of the method herein to ensure the delivered agent is taken up by tissue cells. In such methods, blood flow to the tissue or portion thereof is blocked for a length of time less than the predetermined time for vascular isolation in the method herein, but for a time that results in a low level, mild or moderate ischaemia. For example, the tissue or organ is preconditioned by blocking blood flow for at least or up to 2 minutes, 3 minutes, 5 minutes, 10 minutes, 15 minutes, 20 minutes, 25 minutes, 30 minutes or more. Then, the tissue or organ is immediately reperfused within 10 minutes of the ischaemia to produce a state of sustained ischaemia-reperfusion injury. The reperfusion is for at least or up to 2 minutes, 3 minutes, 4 minutes, 5 minutes, 6 minutes, 7 minutes, 8 minutes, 9 minutes, 10 minutes, 12 minutes, 15 minutes, 20 minutes or more. Immediately after the preconditioning characterized by a period of mild to moderate ischaemia followed by reperfusion, the organ or portion thereof is subjected to compartmentalization using any of the methods herein for a predetermined time sufficient to ensure the delivered agent is taken up by tissue cells as described herein.

In other examples of the method herein, where the organ or portion thereof is particularly sensitize to hypoxia or anoxia, the organ or portion thereof is compartmentalized by providing extracorporeal perfusion of the organ or portion thereof. This method is utilized, for example, in cardiac by-pass surgery where systemic circulation is maintained. In the methods herein, the extracorporeal perfusion can act to maintain blood flow in a closed loop to the target organ or portion thereof. Also, the extracorporeal perfusion can include oxygenating the blood.

The methods of blocking blood flow to effect compartmentalization of an organ or portion thereof can be performed by general surgical procedures known in the art, including open surgical procedures or laparoscopic techniques.

The above-described methods of organ compartmentalization, for example by vascular isolation from the general circulation, can be performed on any organ or portion thereof. Exemplary of such organs include, but are not limited to, the liver, kidney, pancreas, lung or spleen or a portion thereof. The following subsections exemplify practice of vascular isolation of exemplary organs.

a. Liver

In humans and other animals, the liver is a reddish brown lobulated organ. The liver has a wide range of functions, including detoxification, protein synthesis and production of biochemicals necessary for digestion. Using the methods herein, the liver is a particularly good organ to target for delivery of the delivered agent for several reasons. It is the largest organ in the body (2% to 3% of overall body weight), has at least one lobe that is readily accessible and compartmentalizable, has fairly slow cellular turnover, is proficient at secreting proteins, and tolerates anoxia and hypoxia for long periods of time. In addition, the liver is an important target organ for delivery of nucleic acid molecules because of its central role in metabolism and production of serum proteins. There are a large number of known diseases, some of which are caused by defects in liver-specific gene products, that could benefit from liver production of a secreted or intracellular protein. These include, for example, familial hypercholesterolemia, hemophilia, Gaucher's and Fabry's diseases and urea cycle disorders and glycogen storage diseases. Nevertheless, despite these benefits, targeted delivery of nucleic acid to the liver is hampered by the inability to achieve long term gene expression of the delivered nucleic acid.

The liver is located in the upper right quadrant of the abdominal cavity just below the diaphragm. It is a well vascularized structure. It is characterized by a dual afferent blood inflow through the portal vein and the hepatic artery and a single efferent blood outflow through the hepatic veins that coalesce into the hepatic veins which drain into the superior vena cava. The result of the dual vascular inflow results in a blood flow of 1500 mL/minute with 75% provided by the portal vein and 25% by the hepatic artery (Abdalla et al. (2004) *Surg. Clin. N. Am.*, 84:563-585). FIG. 1, panel A depicts the anatomical and vascular organization of the rat liver. Once the portal vein enters the liver, it divides into branches to the right and to the left to supply the various lobes. The first branch stems to the right as the right inferior portal vein and right superior portal vein to supply the right lobe. The second branch stems to the left as the caudate portal vein, which splits into two veins: an upper caudate branch and a lower caudate branch. The portal vein continues onto its main bifurcation giving the right median portal vein that supplies the right portion of the median lobe and the left portal vein that releases the left median portal vein and the left lateral portal vein supplying the corresponding lobes. The arterial irrigation of the liver is provided by the hepatic artery, which once it enters the livers, branches to the right and left to supply the lobes and follows the same distribution as the portal veins.

Traditional human gross anatomy divides the liver into four lobes based on surface features. On its anterior side, the falciform ligament divides the liver into a left anatomical lobe, and a right anatomical lobe. If the liver is flipped over to the visceral surface there are two additional lobes between the right lobe and left lobe, these are the caudate lobe and the quadrate lobe.

Further divisions are possible based on the functional/vascular features of the liver (FIG. 1, panel B). The three main hepatic veins (right hepatic vein, middle hepatic vein and left hepatic vein) divide the human liver into four sections or segments (the right posterior segment, the right anterior segment, the left medial segment and the left lateral segment) each of which is supplied by a corresponding branch of the portal system. Further branching of the portal veins subdivide the human liver into eight anatomically independent subsegments each with its own efferent hepatic venous system, afferent portal venous systems, afferent arterial system and a biliary duct system. Subsegments I and IV correspond to the left medial segment, subsegments II and III correspond to the left lateral segment, subsegments V and VIII which correspond to the right anterior segment and subsegments VI and VII which correspond to the right posterior segment.

The parenchyma of the liver is made up of a connective tissue capsule (called the Glisson's capsule) that form septae through the liver that is divided into small units called lobules. This parenchyma also is traversed by blood vessels, lymphatic vessels and bile ducts. Each lobule contains a hexagonal arrangement of hepatocytes that form stacks or plates one or two cells thick radiating outward from the central vein. The plates of cells are separated by a system of sinusoids. Hepatocytes have an average life span of about five months. These cells are also capable of robust regeneration when the liver substance is lost. Present at each lobule vertex is the portal triad, which contains a bile duct and a terminal branch of the hepatic artery and portal vein (interlobular vessels). Vessels originating from the interlobular vessels are distributed around the periphery of the lobule, which provide blood flow to inlet vessels into the sinusoids and toward the central vein.

In the methods provided herein, compartmentalization of the liver, or a lobe, region or segment thereof, can be achieved by isolation of the liver or lobe or segment thereof from communication with the general circulation, such as by isolation from the vasculature, ductal or lymph system. Methods to achieve compartmentalization include vascular and/or parenchymal clamping procedures. Methods to effect liver vascular isolation and occlusion are well known in the art (see e.g. Buell et al. (2001) *Arch. Surg.*, 136:569-575; Belghiti et al. (1999) *Annals of Surgery*, 229:369-375; Chowdhury (2010) *BSMMU J.*, 3:112-119; Chouillard et al. (2010) *Annals of Surgical Innovation and Research*, 4:2-12; Chaib et al. (2003) *Arq Gastronenterol.*, 40:131; Abdalla et al. (2004) *Surg Clin. N. Am*, 84:563-585). Such methods include, but are not limited to hepatic vascular exclusion, hemihepatic vascular occlusion, pedicle clamping, segmental vascular occlusion, total vascular exclusion and hepatic vascular exclusion with caval flow preservation.

In examples of the method herein, compartmentalization of a segment or portion of the liver can be achieved by methods that result in compression of the parenchyma. For example, manual compression can be performed, such as finger-fracture where the liver parenchyma is crushed between the thumb and one finger. In another example, pedicle clamping is used, either by compression of the pedicle between the fingers or by the use of a clamp or other similar device capable of delivering pressure to the pedicle. In a further example, compartmentalization can be performed by placement of a parenchymal compression clamp or occlusion clamp across the lobe. Exemplary clamps that can be used for parenchymal compression of a liver lobe include, but are not limited to a Longmire-Storm clamp (V. Mueller, Stainliss, Germany, catalog #SU-9080), the Lin or Chu liver clamp (Pilling no. 604113-61995), a Inokuchi liver clamp (Kanematsu et al. (1984) *Jpn. J. Surg.*, 14:432-3), the Doty clamp (U.S. Pat. No. 3,667,471) and Vernick clamp (U.S. Pat. No. 5,203,786). In some examples, further segmental vascular isolation can be achieved by placing a smaller volume of parenchyma within the clamp.

Typically, in practice of the method herein, a lobe can be mobilized from the other lobes in order to selectively compartmentalize a region or portion of the liver. Mobilization allows access to the lobe or region in order to permit parenchymal compression or clamping. The ability to mobilize only a portion or region of the liver also means that methods to achieve selective delivery of a delivered agent is possible. Due to the segmented anatomy of the liver into self-contained units, compartmentalization of a specific lobe, segment or portion thereof can be achieved, while maintaining blood flow to the other segments. For example, selective clamping or occlusion of a pedicle, each segmented pedicle, or a parenchymal region can be performed to achieve compartmentalization of a region or segment. Mobilization can require dividing the associated ligaments and/or other associated glands. Procedures and techniques for mobilizing or isolating the various lobes or segments of the liver are well known to one of skill in the art. For example, the caudate lobe, the left lobe, or the left median lobe, are all reasonably vascularly isolated and accessible. Differences in liver anatomy between mammalian species can render a particular region or lobe more amenable to isolation in one species than another. One of skill in the art would recognize comparable lobes in other animals, and could identify a lobe or segment suitable for mobilizing or isolating for compartmentalization using the methods herein.

In particular examples herein, the caudate lobe, left lobe or left median lobe, or portion thereof, is compartmentalized. If necessary, retraction and dissection of the liver lobe or segment from its surrounding attachments can be performed to permit access to a region that can be properly compartmentalized from the vasculature without damaging or affecting other regions of the tissue or organ or surrounding structures. For example, the caudate lobe lies posterior to segment IV and is closely associated to the inferior vena cava and portal veins. Mobilization of the caudate lobe can be achieved by division of the gastrohepatic omentum and dorsal caudate-caval ligament. The left lobe of the liver can be mobilized by dividing the left triangular ligament. Similar procedures can be used to mobilize the comparable lobe in the human or other subject.

Once the liver, region, lobe or segment thereof is compartmentalized, the delivered agent can be delivered to the compartmentalized lobe, region or segment as described further below.

b. Other Organs

The methods provided herein can be used in a wide variety of organs depending upon a variety of factors, including the target of the nucleic acid or the encoded polypeptide, the accessibility of the organ and its vasculature, the disorder or disease to the treated, the nature of the encoded polypeptide and other factors. In addition to the liver, the targeted organ or portion thereof to effect vascular isolation and compartmentalization can be the CNS (brain or spinal cord), peripheral nervous system (e.g., nerve), pancreas, gall bladder, endocrine glands (pituitary, adrenal, thyroid, etc.), cardiovascular organs (e.g., heart and blood vessels), skin, urogenital organs (kidney, uterus, cervix, prostate, and urethra), organs of the respiratory system (e.g., lung or airways); bone, muscle, and intestine. This list is not intended to be exhaustive, as one of skill in the art will recognize additional target organs and lobes thereof.

The skin is a target organ for practice of the compartmentalized method herein. For example, keratinocytes of the skin are suitable target cells for gene therapy, and treatment thereof can be appropriate for diseases or conditions caused by genetic defects, systemic diseases by production of proteins that can be released into the circulation, and wounds or scars (e.g. Meng et al. (1998) *J. Clin. Invest.*, 101:1462;

Liu et al. (2001) *Yonsei Medical Journal*, 42:634-645). The skin also has been shown to be amenable to periods of brief ischemia that can result from the compartmentalization methods herein (see e.g. Willms-Kretschmer and Majno (1969) *The American Journal of Pathology*, 54:327). For example, in the methods herein, the compartmentalization is maintained for a time period sufficient for transduction of cells or entry of the delivered agent into or by cells (e.g. keratinocytes). For example, the time period of compartmentalization can be less than 2 hours, and generally at least 10 minutes, 15 minutes, 20 minutes, 30 minutes or 60 minutes.

Compartmentalization of the skin can be effected by any of the techniques described herein that are capable of cutting of the skin from the peripheral circulation. In particular examples, clamps can be used. In such examples, folds of the skin can be isolated or mobilized and fit between the clamp. The pressure of the clamp can be adjusted as described herein such that isolation from the systemic circulation is achieved (see e.g. Willms-Kretschmer and Majno (1969) *The American Journal of Pathology*, 54:327).

The lung is a target organ for practice of the compartmentalized method herein. Gene therapy of the lung can be targeted for therapy of acute and chronic diseases, including cancer, asthma, cystic fibrosis, alpha-1-antitrypsin deficiency and respiratory distress syndrome, among others. In the methods herein, the compartmentalization is typically performed on a segment or region of the lung, while maintaining ventilation through the lung. For example, a bronchial segment of the lung can be compartmentalized. Compartmentalization can be effected by occlusion of the bronchial arteries, use of vascular clamps, and/or by direct parenchymal clamping of the bronchus.

Gene therapy of the kidney can be used to treat renal diseases, including hereditary renal diseases (e.g. Alport syndrome). Compartmentalization of the kidney can be achieved, for example, by renal pedicle occlusion, for example by clamping the renal pedicle; regional parenchymal compression by clamping renal parenchyma using a vascular clamp, such as a long curved vascular clamp; or a renal cable tie, tourniquet or banding device. For parenchymal clamping, laparoscopic parenchymal clamps can be used, including, but not limited to, the Satinsky- or Debakey-style clamp (see e.g. Toren et al. (2010) *Can. Urol. Assoc.*, 4:E133-E136; Ko et al. (2010) *Korean J. Urol.*, 51:8-14 and Joung et al. (2007) *Korean J. Urol.*, 28:265-269).

2. Delivery of a Nucleic Acid Molecule by Administering a Delivered Agent

In the methods herein, the nucleic acid is delivered to cells in the organ or tissue or portion thereof by administering a delivered agent directly to tissue cells. The delivered agent can be administered prior to, simultaneously, intermittently or subsequently to initiating compartmentalization of an organ or portion thereof. Typically, in the methods herein, the delivered agent is administered immediately after initiating compartmentalization of an organ or portion thereof, such as within or no more than 10 minutes and generally no more than 5 minutes after initiating compartmentalization of an organ or portion thereof. For example, the delivered agent is delivered to a subject no more than 30 seconds, 1 minute, 2 minutes, 3 minutes, 4 minutes or 5 minutes, 6 minutes, 7 minutes, 8 minutes, 9 minutes or 10 minutes after initiating compartmentalization.

a. Delivery Methods and Routes of Administration

Delivery of the nucleic acid molecule by administering a delivered agent is by any method or administration route that is capable of delivering the delivered agent to the cells of the compartmentalized organ or portion thereof of a subject, and in particular, to the relevant target tissue cells for gene expression therefrom. For example, delivery is directly to the parenchymal cells. In the case of the liver, target parenchymal cells are hepatocytes, while non-parenchymal cells include vascular endothelial cells, Kupffer cells and supporting stromal cells.

In some examples, delivery of the delivered agent into a patient can be direct, in which case the subject is directly exposed to the delivered agent (e.g. in vivo delivery). For example, the delivered agent can be delivered by direct injection into the parenchyma or interstitial space of tissues. In other examples, delivery of the delivered agent can be indirect, in which case cells are first transformed with the delivered agent in vitro, then transplanted into the patient (e.g. ex vivo delivery). For example, for ex vivo gene therapy methods, parenchymal cells can be removed from the body and exposed to the delivered agent ex vivo, followed by reimplantation of the cells to the compartmentalized tissue or organ or portion thereof.

In particular examples, the delivered agent is delivered by direct tissue or organ injection. For example, the delivered agent is delivered by direct injection into the tissue or organ parenchyma, such as by intraparenchymal administration into compartmentalized tissues or organs, or portions thereof, such as muscle (intramuscular), liver, brain, kidney and others as described herein or known in the art. Interstitial delivery into the parenchyma has advantages over systemic delivery methods. Systemic delivery of nucleic acid, such as by intravenous, intraportal and intra-arterial administration of delivered agents, increases exposure of the delivered agent to the general circulation. This can result in non-selective tissue targeting, decreased or lower efficiency of cellular uptake leading to decreased gene expression, the need for high amounts or dosages of delivered agent to ensure uptake by tissue cells, exposure to immune cells and activation of an unwanted immune response, and other problems associated with systemic delivery methods. It is found herein that direct injection into the interstitial space, coupled with the compartmentalization of the tissue cells (e.g. by vascular exclusion and isolation), increases the frequency and efficiency of uptake of the delivered agent by the tissue cells while minimizing exposure to the general circulation.

For example, in addition to increasing the frequency and efficiency of uptake of the delivered agent by tissue cells, parenchymal delivery also can avoid exposure of the delivered agent to immune cells. For example, for delivery of the nucleic acid molecule to the liver or a portion thereof, interstitial delivery by direct parenchymal injection of a delivered agent, such as by intrahepatic injection, can avoid Kupfer cell engulfment (see e.g. Crettaz et al. (2006) *Hepatology*, 44:623-632). Kupfer cells, which are phagocytic macrophages of the liver, are present in the liver sinusoids and thus are exposed to delivered agent that is administered intravenously. In contrast, the hepatocyte tissue cells of the liver are separated from the sinusoids by the space of Disse. Therefore, direct targeting of the delivered agent to the hepatocytes that reside in the interstitial space avoids the unwanted proinflammatory response that can be initiated by Kupfer cell activation, and increases the uptake by the resident tissue cells. Similarly, direct delivery of the delivered agent to interstitial cells of other organs, is also contemplated. Hence, in the methods herein, delivered agent or compositions thereof are delivered directly to the tissue parenchyma.

Typically, the delivered agent that is delivered is provided as a composition. Exemplary of such delivered agents and compositions are those described in Sections D and E, respectively. The delivered agent can be delivered in a pharmaceutically acceptable liquid or aqueous carrier. The delivered agent can be introduced directly into a tissue or organ or portion thereof, by injection using a needle or other similar device. The volume of the delivered agent in the carrier to be delivered is or is about 0.5 mL to 100 mL, such as 0.5 mL to 50 mL, 1 mL to 20 mL, 5 mL to 50 mL, or 5 mL to 20 mL.

b. Methods to Facilitate Delivery

Generally the methods herein utilize injection methods that avoid injection into arteries, veins and other associated vasculature, and also into vessels of the duct and lymphatic system. The delivery of delivered agents by parenchymal injection can be aided by the use of imaging techniques that differentiate the parenchymal tissue and cells from the surrounding vasculature and associated architecture. The imaging can be performed immediately prior to injection, coincident with injection and/or subsequent to injection. Such imaging techniques include, but are not limited to, magnetic resonance imaging (MRI), ultrasound and sonography techniques, including Doppler sonography. For example, B-glow, 3-D imaging or color Doppler can be used. If necessary, contrast agents can be injected to facilitate imaging. For example, such methods also can be used to minimize the possibility of introduction of the agent into the lumen of the vascular or ductal systems.

In the methods provided herein, if necessary, the efficacy of delivery agent uptake by tissue cells can be increased using various techniques known to one of skill in the art. It is understood that procedures that enhance delivery agent uptake can reduce the compartmentalization time (discussed above) because less time will be required to ensure sufficient delivered agent is taken up by the cells. The choice of particular procedure can be empirically determined by one of skill in the art and depends on the particular delivered agent that is delivered, the route of administration (e.g. particular tissue or organ) and the dosage or amount of agent administered. In one example, the delivered agent can be formulated with lipids, polymer transfection reagents, or other agents. In other examples, physical methods can be used to enhance delivery. Exemplary physical methods to enhance delivery of a delivered agent include, but are not limited to, "gene gun" method, electroporation, sonoporation, pressure or ultrasound. Alternatively to enhance in vivo gene delivery with minimal tissue damage the pharmaceutical composition can be administered using a femtosecond infrared laser (LBGT technology).

In one example, the uptake of delivered agents, and in particular delivered agents that are viruses or virus-like particles, such as adenovirus, can be enhanced by the presence of various agents. For example, the delivered agent can be administered with an agent or compound that is a transcriptional enhancer of the virus-specific cell surface receptor. Such agents or compounds include, for example, a histone deacetylase (HDAC) inhibitors. HDAC inhibitors include those of the class of hydroxamic acids, cyclic tetrapeptides, benzamides, electrophilic ketones or aliphatic acid compounds. For example, HDAC inhibitors include, but are not limited to, trischostatin A, vorinostat (SAHA), belionostat (PXD101), LAQ824, panobinostat (LBH589), entinostat (MS-275), C199, mocetinostat (MGCD0103), romidepsin (lstodax), valproic acid, PCI-24781, SB939, resminostat, givinostat, CUDC-101, AR-42, CHR-2845, CHR-3996, 4SC-202, CG200745, Kevetrin, or trichostatin A (TSA). Exemplary of an HDAC inhibitor is valproic acid, which is a transcriptional enhancer of the adenovirus receptor CAR and the therapeutic transgene. Studies have shown that adenoviral uptake is increased in the presence of valproic acid (Segura-Pancheco et al. (2007) *Genet. Vaccines Ther.*, 5:10). In such examples, the viral vector is formulated together or separately with the agent. In examples where the viral vector is formulated separately, the transcriptional enhancer agent or compound is delivered prior to delivery of the delivered agent. The transcriptional enhancer agent can be administered at or between about 1 mg/kg to 100 mg/kg, for example, at or about 20 mg/kg to 60 mg/kg, such as 40 mg/kg. The dosage can be divided and administered separately to achieve the total dose. For example, the cycle of administration can be 1 time a day, 2 times, 3 times, 4 times, or 5 times a day. The frequency of administration can be daily for at least 3 days, 4 days, 5 days, 6 days, 7 days, or 2 weeks. The agent can be administered by any route of administration, such as, subcutaneously, intravenously, orally or topically. In particular examples, the agent is administered by direct parenchymal administration.

In some examples, the delivered agent is formulated with an agent or delivery vehicle that binds to or complexes with the delivered agent and mediates its entry into cells. Exemplary agents include, but are not limited to, cationic liposomes and lipids, lipoproteins, synthetic polymers or polypeptides, mineral compounds or vitamins. Exemplary of polymers include polycations or polyanions. For example, a delivered agent can be formulated with polyamine, calcium phosphate precipitate, histone protein, protamine, polyethylenemine, polylysisne, polyarginine, polyornithine, DEAE dextrane, polybrene, polyampholyte complex, spermine, spermidine, purtrescine, human serum albumin, DNA binding proteins, non-histone chromosomal proteins, coat proteins from DNA viruses and polymers of N-substituted glycines.

For example, the delivered agent can be encapsulated in lipids or packaged in liposomes prior to delivery to the subject or to cells derived therefrom. Lipid encapsulation is generally accomplished using liposomes that are able to stably bind or entrap and retain nucleic acid. The ratio of condensed nucleic acid delivered agent to lipid preparation can vary but will generally be around 1:1 (mg DNA: micromoles lipid) or more of lipid. Liposomal preparations include cationic (positively charged), anionic (negatively charged) and neutral preparations. Such preparations are well known to one of skill in the art and readily available. For example, exemplary cationic lipids include, but are not limited to, N[1-2,3-dioleyloxy)propyl]-N,N,N-triethyammonium (DOTMA; available under the product line Lipofectin®); DDAB/DOPE and DOTAP/DOPE. Anionic and neutral liposomes also are readily available and can be prepared from phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), such as the commercially available preparation Avanti Polar Lipids. The liposomes include multilamellar vesicles (MLVs), small unilamellar vesicles (SUVs), or large unilainellar vesicles (LUCs).

In some examples, the delivered agent can be a nanoparticle that contains a functional group or targeting agent to further assist and increase cellular delivery of the agent, for example, a targeting molecule that binds to receptors expressed in the cells to be targeted. Functional groups or targeting agents include, for example, a cell targeting moiety that enhances the association of the agent or complex with a cell. The cell targeting moiety can be, but is not limited to, a protein, peptide, lipid, steroid, sugar, carbohydrate, (non-expressing) polynucleic acid or synthetic compound. For example, cell targeting signals can include ligands that enhance cellular binding to receptors. Such ligands include, but are not limited to, insulin, growth factor (e.g. EGF or FGF), transferrin, peptides that include the RGD sequence. Other targeting moieties include, but are not limited to, chemical groups that react with thiol, sulfhydryl or disulfide groups on cells, folate and other vitamins.

In examples herein, injection can be facilitated by electroporation. Electroporation is a technique that involves the application of a pulsed electric field to create transient pores in the cellular membrane without causing permanent damage to the cell and thereby allows for the introduction of exogenous molecules. By adjusting the electrical pulse generated by an electrophoretic system, delivered agents can find their way through passageways or pores in the cell that are created during the procedure. Methods using electroporation for in vivo delivery of delivered agents, including to muscle, liver, skin and other tissues or organs, are known in the art (see e.g., U.S. Pat. No. 5,704,908; published U.S. application No. US2002/0102729; Titomirov, A. V., et al. (1991) *Biochim Biophys Acta* 1088: 131-134; Muramatsu, T., et al. (1997) *Biochem Biophys Res Commun* 233: 45-49; Suzuki, T., et al. (1998) *FEBS Lett* 425: 436-440; Aihara, H. and Miyazaki, J. (1998) *Nat Biotechnol* 16: 867-870; Mir, L. M., et al. (1998) *C R Acad Sci* 111321: 893-899; Rizzuto, G., et al. (1999) *Proc Natl Acad Sci USA* 96: 6417-6422; Goto, T., et al (2000) *Proc Natl Acad Sci USA* 97:354-359; Somiari, S., et al. (2000) *Mol Ther* 2:178-187).

In examples where delivery is to cells ex vivo, generally cells isolated from the subject, any method of delivery of a nucleic acid to cells known to one of skill in the art can be used, including any of the described methods applicable to in vivo delivery. For example, delivery of nucleic acid can be achieved using dextran-mediated transfection, calcium phosphate precipitation, polybrene mediated transfection, protoplast fusion, electroporation, encapsulation into liposomes or direct microinjection of DNA. Also, for viral DNA delivery, cells can be transduced with viral particle. The transformed cell is then the delivered agent for use in the methods herein. Methods for the ex vivo delivery and reimplantation of delivered agent transformed cells into a subject are known in the art and described (see e.g. International Publication No. WO93/14778).

c. Dosages and Regimens for Delivery

The amount or dosage of delivered agent that is administered can be empirically determined based on the particular application. By virtue of the method herein, the dose-response kinetics are linear such that there is a direct correlation between the amount of delivered agent, for example virus, such as adenovirus or adeno-associated virus or other virus, that is administered and the transgene product that is produced. For example, it is found that 40 genomes of transduced virus is sufficient to produce a therapeutic amount of protein (see e.g. Nathwani et al. (2002) *Blood*, 100:1662). Hence, in the methods herein, the method permits administration of lower amounts of virus to achieve a sufficient genome copy number by viral transduction of cells, for example liver hepatocytes, to produce a therapeutically amount of encoded protein. For example, the amount is sufficient to transduce cells with 40 genomes per cell or higher of virus. The methods herein can further increase the genome copy per cell, and thereby further increase sustained expression of product with a lower dosage than existing methods. Thus, using the instant methods, it is possible to precisely correlate the amount of particle injected, the intracellular genomes and the amount of protein expressed.

This is advantageous compared to existing gene therapy methods in the art. For example, in existing methods, for delivery of adenovirus, such for delivery to the liver, there is a nonlinear dose response to hepatic transduction whereby low doses result in undetectable protein expressions whereas high doses achieve transgene expression (Rosewell et al. (2011) *J. Genet. Syndr. Gene Ther.*, S5:1-16). The high doses, however, also initiate immune activation and toxicity. Thus, using existing methods of adenoviral gene delivery dosages levels must balance the level required to achieve sufficient transgene expression, while achieving a level that does not result in toxic lethality. Generally, in existing methods these amount of adenovirus administered to achieve sufficient protein production are relatively high, and are about or about between greater than $1.5 \times 10^{12}$ virus particles per kilogram (vp/kg), and generally at least $1 \times 10^{11}$ virus particles (vp) per kilogram (kg) (vp/kg), such as at least $5 \times 10^{11}$ vp/kg or greater. For example, administration of AAV encoding Factor IX in macaques at a dose of $4 \times 10^{12}$ vp/kg intravenously was necessary to achieve sustained expression to restore 8% of Factor IX activity (Nathwani et al. (2002) *Blood,* 100:1662). Human clinical trials have shown that dosages of $4 \times 10^{11}$ vp/kg are required to correct 10% of Factor IX activity for only a few days and expression last for only 2 to 6 weeks (Mingozzi et al. (2011) *Nature Reviews Genetics,* 12:341). Also, these amounts, which are typically given by intravenous delivery methods, still suffer from some mild toxicity, immune activation, and/or tissue damage.

In particular, in the compartmentalized methods herein, the dose or amount of delivered agent that is administered is such that a level of protein product is produced that is capable of delivering a therapeutic or prophylactic effect. Typically, in the methods herein the level is sustained for at least 6 months, 7 months, 8 months, 9 months, 10 month, 11 months, 12 months, 14 months, 16 months, 18 months, 20 months, 24 months, 36 months, 48 months, 60 months, 72 months, 84 months, 96 months, 10 years, 15 years or more. Since there is a linear relationship in administered delivered agent and the amount of product produced, such dosages can be determined by one of skill in the art. Considerations in determining the dosage can include the particular genetic therapy and the therapeutic product, half-life of the protein product, the promoter used to express the transgene product, the particular 1.0 delivered agent and other similar factors.

Where the delivered agent is non-viral nucleic acid, an effective dosage amount of DNA or RNA is in the range of from about or from 0.005 mg/kg body weight to about or 50 mg/kg body weight. Generally, the dosage is from about or from 0.005 mg/kg to about or 20 mg/kg and more generally from about or from 0.05 mg/kg to about or 5 mg/kg. For example, for non-viral nucleic acid (e.g. plasmid, naked DNA, siRNA, shRNA or antisense nucleic acid), 0.01 mg to 2000 mg is delivered, such as 0.05 mg to 1500 mg, 1 mg to 1000 mg, 10 mg to 1500 mg, or 100 mg to 1000 mg.

Where the delivered agent is a virus, such as an adenovirus or an adeno-associated virus or other virus, dosages are typically provided by number of virus particles (vp) or plaque forming units (pfu) and dosages generally are less than $1 \times 10^{12}$ total particles or $1 \times 10^{12}$ pfu, and are generally in the range from about or from to $1 \times 10^{12}$ particles, 10 to $1 \times 10^6$ particles, $1 \times 10^3$ to $1 \times 10^{12}$ particles, such as $1 \times 10^6$ to $1 \times 10^{10}$ particles, or $1 \times 10^7$ to $1 \times 10^9$ particles or in the range from about or from 10 to $1 \times 10^{12}$ pfu, 10 to $1 \times 10^6$ pfu, $1 \times 10^3$ to $1 \times 10^{12}$ pfu, such as $1 \times 10^6$ to $1 \times 10^{10}$ pfu, or $1 \times 10^7$ to 1×10$^9$ pfu. Lower or higher doses than those recited can be required. Specific dosage and treatment regimens for any particular subject or patient can depend upon a variety of factors, including the specific genetic therapy and its therapeutic product, the activity of the specific compound or agent, the age, body weight, general health status, sex, diet, time of administration, rate of excretion, drug combination, the severity and course of the disease, condition or symptoms, the subject or patient's disposition to the disease, conditions or symptoms, method of administration and the judgment of the treating physician. It is within the level of the treating physician skilled in the art to determine the exact dosage.

Generally, using the compartmentalized methods herein, a markedly reduced quantity of delivered agent can be administered compared to existing methods to achieve optimal delivery of a nucleic acid molecule, such as a therapeutic nucleic acid molecule. In addition, the amount of delivered agent that is administered can be controlled due to the linear relationship between the dose of delivered agent and the amount of therapeutic product that is produced. The result is that up to 100-fold or less of delivered agent can be administered using the methods herein than is achieved by administration of the same delivered agent intravenously. For example, the amount of delivered agent that is administered in the methods herein can be up to 10-fold, 100-fold, 200-fold, 300-fold, 400-fold, 500-fold, 600-fold, 700-fold, 800-fold, 900-fold, 1000-fold, 5000-fold, 10000-fold or less than the amount of the same delivered agent that is administered intravenously to the target organ or tissue. It is within the level of one of skill in the art to determine the particular amount of delivered agent that is administered in the methods herein, based on the particular delivered agent, the nucleic acid molecule, and the disease or condition that is treated.

One of skill in the art is familiar with applications of various gene therapy vectors and agents for use in treating various diseases or disorders. Based on the dosages and amounts of agents that are administered in existing protocols in the art by intravenous delivery (or other administration methods), one of skill in the art can alter by reducing the dosage of the same vector or agent for use in parenchymal administration to a compartmentalized tissue or organ or portion thereof using the methods herein. For example, for liver-targeted gene therapy with adenovirus, such as a recombinant adenovirus containing a heterologous nucleic acid molecule in its genome, dosages of adenovirus from or from about 2×10$^9$ to 6×10$^{11}$ vp/kg, corresponding to about 1.5×10$^{11}$ vp to 4.5×10$^{13}$ vp for an average human subject of 75 kg, have been administered to humans, and generally with little success due to toxicity and/or lethality or due to inefficient hepatocyte transduction (Brunetti-Pierri et al. (2009) *Molecular Therapy*, 17:327-333). In the methods herein, for example, adenovirus, such as a recombinant adenovirus containing a heterologous nucleic acid molecule in its genome, is administered to the liver or other tissue or organ or portion thereof at less than 1×10$^{12}$ vp or less than 1×10$^{12}$ pfu, and typically less than 1×10$^{10}$ vp or less than 1×10$^{10}$ pfu. For example, using the compartmentalized methods herein, less than 1×10$^{12}$ vp, 1×10$^{11}$ vp, 1×10$^{10}$ vp, 1×10$^9$ vp, 1×10$^8$ vp, 1×10$^7$ vp, 1×10$^6$ vp, 1×10$^5$ vp, 1×10$^4$ vp, 1×10$^3$ vp or less adenovirus can be administered in liver-targeted gene therapy methods. In another example, using the compartmentalized methods herein, less than 1×10$^{12}$ pfu, 1×10$^{11}$ pfu, 1×10$^{10}$ pfu, 1×10$^9$ pfu, 1×10$^8$ pfu, 1×10$^7$ pfu, 1×10$^6$ pfu, 1×10$^5$ pfu, 1×10$^4$ pfu, 1×10$^3$ pfu or less adenovirus can be administered in liver-targeted gene therapy methods. In such examples, the amount can be for administration to a human subject.

Methods of titering viruses for the purposes of preparing compositions thereof and/or determining dosage amounts are well known to one of skill in the art. For example, titers can be determined by an OD$_{260}$ assay, which measures the concentration of viral DNA and protein. To perform such an assay, stocks of purified virus are required, since serum and other factors in growth media can interfere with the absorbance reading. For example, virus can be purified by banding using a CsCl density-gradient or other methods known to one of skill in the art. Typically, dilutions of virus are made. The optical particle units (opu) or viral particle (vp) per mL can be determined from the absorbance. For example, for adenovirus, the vp/mL is determined by multiplying 1.1×10$^{12}$ with the OD$_{260}$ absorbance and viral dilution factor. OD$_{260}$ assay does not distinguish between live and dead virus. In another example, titer can be determined by performing a plaque assay using standard procedures known in the art. Typically, cells that can be grown in a monolayer, for example 293 cells, are plated at a moderately high density (e.g. at or about or above 70%) followed by infection with a viral stock at various dilutions. After sufficient time to allow infection and transduction of cells, an agarose solution is added to the cells. Plaques, which are formed by lysis of the cells, are visible in several days and up to 10 days can be counted (typically by using a dye that can differentiate the plaque areas). Titer is calculated as plaque forming units (pfu) per mL by dividing the number of plaques by the dilution factor. In an addition example, an end-point dilution assay can be used. This assay is similar to a plaque assay, except greater numbers of dilutions are made (generally from 10$^{-3}$ to 10$^{-10}$). Also, instead of an agarose overlay to identify plaques, the infected plate of cells is manually visualized under a microscope to identify wells for cytopathic effect (CPE). The wells of the plate can be scored to determine the end-point dilution based on the Spearman-Karber method.

Dosage treatment can be a single dose schedule or multiple dose schedule. Frequency of dosing can depend on the agent being administered, the progression of the disease or conditions in the subject, and other considerations known to those of skill in the art. For example, delivered agents or compositions can be delivered 1 time, or can be delivered in multiple administrations, such as at least or about or 2, 3, 4, 5, 6, 7 or 8 administrations. Treatment can also be at a single target locus, or at multiple target locus. For example, delivery of a delivered agent can be single injection per target site, or can be repeated injection of the target site. By way of example, in the treatment of a lung disease like cystic fibrosis, it can be necessary to target at least 25, 50, 75, 80, 85, 90, or 95% of the lung with multiple injections to achieve enough transgene product and/or functional improvement in the subject. Thus, multiple injection sites can be used. The repeat injections can be effected in succession, such as immediately following a prior injection, or can be delayed over the course of minutes, hours, days or years. In some examples, the delivered agent is administered to more than one locus in the organ or portion thereof, particularly where high levels of transduction or expression is sought. For example, in some embodiments, in addition to the first administration site, a composition containing a delivered agent is administered to another site or locus. The other site or locus can be at a site that is adjacent to or near the first site in the same region or portion of a target tissue, or can be at a site removed from the first locus while still in the same target organ (e.g. a different lobe or region of the liver or lung).

3. Termination/Release of Compartmentalization

After delivery of the delivered agent, the compartmentalization of the tissue or organ or portion thereof is maintained for a time period sufficient to allow sufficient uptake of the delivered agent and/or minimize exposure of the delivered agent to the systemic circulation. For example, compartmentalization is for a sufficient time to allow entrance of the delivered agent to the cell while avoiding systemic circulation. The effect of this compartmentalization means that toxicity and immune activation is minimized. Generally, the compartmentalization of the tissue or organ or portion thereof is maintained to limit, minimize or avoid toxicity and immune activation (e.g. as assessed by local or systemic cytokine expression, inflammatory infiltrates such as neutrophil and lymphocyte infiltrates, and/or tissue enzymes). It is within the level of one of skill in the art to empirically determine the precise time period to maintain the compartmentalization based on factors that include the particular delivered agent that is administered, the target tissue or organ or portion thereof, the subject being treated or the particular application. Methods and techniques to assess gene expression and parameters associated with immune activation and toxicity are known to one of skill in the art, and exemplary of such are described in Section F.

In examples herein, the duration of compartmentalization of the tissue or organ or portion thereof is maintained for a time period sufficient so that less than 10%, and generally less than 5%, 4%, 3%, 2%, 1% or less of the delivered agent is exposed to the systemic circulation. Methods of assessing systemic levels of, delivered agent or transgene products are provided in Section F. Further, Example 2 exemplifies assays to detect delivered agent in the systemic circulation, such as in the peripheral blood.

In examples herein, the duration of compartmentalization of the tissue or organ or portion thereof is maintained to allow cellular uptake of greater than or about greater than or 80, 85, 90, or 95% of the selected delivered agent by cells of the tissue organ or portion thereof. For example, the duration of compartmentalization of the tissue or organ or portion thereof is maintained such that at least 80%, 81%, 82%, 83%, 84%, 85%, 86%, 87%, 88%, 89%, 90%, 91%, 92%, 93%, 94%, 95%, 96%, 97%, 98%, 99% or more of the delivered agent is present intracellularly by resident cells of the tissue or organ. For example, for delivery to the liver, the duration of compartmentalization of the liver or portion thereof is maintained such that at least 80%, 81%, 82%, 83%, 84%, 85%, 86%, 87%, 88%, 89%, 90%, 91%, 92%, 93%, 94%, 95%, 96%, 97%, 98%, 99% or more of the delivered agent is taken up intracellularly by hepatocytes. Methods of assessing the intracellular presence and localization of delivered agents are described in Section F.

The method provided herein can achieve long term gene expression in the tissue or organ or portion thereof for more than 60 days, more than 90 days, more than 6 months, more than 7 months, more than 8 months, more than 9 months, more than months, more than 11 months, more than 12 months, more than 18 months, or more than 24 months. Typically, the compartmentalization of a tissue or organ or portion thereof is maintained for a time period sufficient so as to achieve expression of a gene products for at least a year.

The optimal duration of compartmentalization can vary depending on a variety of factors that include the particular target organ or tissue or portion thereof, the delivered agent, and the particular method used for delivery. For example, different tissue or organ resident cells exhibit different endocytic abilities and kinetics for intracellular uptake of a delivered agent. This endocytic function can be influenced or differ depending on the particular delivered agent. For example, for a delivered agent that is a viral vector such as adenovirus, the kinetics of adenovirus infection is initiated upon binding and interaction with its receptors, which for adenovirus subgroups A, C-F, is the Coxsackie virus B Ad receptor (CAR). Binding to the primary receptor mediates endocytosis of the associated virus. Within 1 minute post-transduction, generally about 2% of the virus is intracellular. Disassembled adenovirus escapes to the cytosol by release of the endosomal contents into the cytoplasm. Within or before 30 minutes post-transduction, about 80% of the virus is intracellular. Upon further disassembly, the capsid is transported through the cytoplasm where it finally delivers the viral DNA into the cellular nucleus. Within or before 60 minutes post-transduction, all of the transgene is delivered into the nucleus.

It is understood herein that the delivered agent that is delivered to a tissue or cell is one that is capable of uptake by resident cells. If necessary, the delivered agent can be modified to increase or mediate entry by a particular cell. For example, fiber capsomer modifications of adenovirus are known in the art to permit attachment of the viral vector to cell targets for efficient virus entry (see e.g. Campos et al. (2007) *Curr Gene Ther.*, 7:189-204; Russell W C, (2009) *J. Gen. Virol.*, 90:1-20). Further, it is understood that the time period of intracellular uptake can be reduced with the use of agents that promote uptake. Such agents include electroporation, gene gun, sonoporation, lipoplexes, polyplexes, detergents, or formulation with agents or compounds that increase transcription of an uptake receptor and other methods known to those of skill in the art such as described above. The kinetics of delivered agent entry into a cell, such as into a tissue or organ resident cell in vivo, can be determined by methods known in the art (see e.g. Section F).

In addition, the optimal duration of vascular compartmentalization can depend on the tolerance of the organ or tissue or portion thereof, and resident cells therein, to ischemic conditions and is a consideration in the methods herein. Some organs or tissues exhibit less tolerance to ischemic conditions than others. For example, hepatocytes generally are viable longer than neurons or cardiomyocytes subject to vascular isolation. The liver generally tolerates interruption of blood flow for up or more than 60 minutes (Abdalla et al. (2004) *Surg. Clin. N. Am,* 84:563-585). For the kidney, vascular isolation can be performed for a predetermined time to permit virtually all of the nucleic acid to be taken up by tissue cells. The kidney typically tolerates periods of ischemia of up to 2 hours, but generally no more than 1 hour or no more than 30 minutes (Hoffman et al. (1974) *AMA Arch. Surg.,* 109:550-551; Thompson et al. (2006) *J. Urology,* 177:471-476). Muscle is tolerant to ischemia for up to 4 hours (Blaisdell F. W. (2002) *Cardiovascular Surgery,* 10:620-630). One of skill in the art can monitor and assess the tissue or organ to determine a time period that achieves sufficient cellular uptake, minimizes systemic exposure and results in no ischemia or acceptable ischemia to the organ or portion thereof that is reversible or recoverable. For example, digital light processing (DLP®) hyperspectral imaging (HSI) can be used to construct a "real time" tissue oxygenation map of the tissue or organ or portion thereof (Best et al. (2011) *Proc. SPIE,* 7932, 793202).

In particular examples, in the methods herein compartmentalization of a tissue or organ or portion thereof is for greater than 15 minutes. For example, the time period to maintain compartmentalization of a tissue or organ or portion thereof as described herein above is for at least or at least about or up to 15, 20, 25, 30, 35, 40, 45, 50, 55, 60, 65, 70, 75, 80, 85, 90, 95, 100, 105, 110, 115, or 120 minutes subsequent to initiation of compartmentalization and/or the administration of the delivered agent. It is understood that the time period to maintain compartmentalization can be shorter than 15 minutes in the presence of agents that can facilitate uptake or entry. Thus, in examples herein, the time period to maintain compartmentalization of a tissue or organ or portion thereof is for at least or at least about or up to 5, 6, 7, 8, 9, 10, 11, 12, 13, 14, 15 minutes or more. In certain embodiments the compartmentalization is maintained for at least about or up to 30 minutes. Generally, in any of the methods herein, compartmentalization of a tissue or organ or portion thereof is for no longer than 60 minutes, such as greater than 15 minutes but less than 60 minutes.

For example, in examples herein where the liver or portion thereof is compartmentalized by the methods herein, the time period to maintain compartmentalization of the liver is at least or at least about or up to 15 minutes, 20 minutes, 25 minutes, 30 minutes, 35 minutes, 40 minutes, 45 minutes, 50 minutes or 60 minutes subsequent to initiation of compartmentalization and/or administration of the delivered agent. Generally, in any of the methods herein, compartmentalization of the liver or a portion thereof is for no longer than 60 minutes, such as at least or at least about 15 minutes, 20 minutes, 25 minutes, 30 minutes, 35 minutes, 40 minutes, 45 minutes, 50 minutes, but less than 60 minutes. For example, compartmentalization can be from or from about 15 minutes to 60 minutes, 15 minutes to 50 minutes, 15 minutes to 40 minutes, 15 minutes to 30 minutes, 20 minutes to 60 minutes, 20 minutes to 40 minutes, and generally is for about or approximately 30 minutes.

In some examples herein, the method provided herein can further include removing from the organ or portion thereof, or from the surgical field, extracellular delivered agent (i.e., that portion of the delivered agent administered but that was not taken up by the cells of the compartmentalized organ or portion thereof). The removal step can include absorbing, suctioning, or flushing so that, once the vascular circulation to the organ or portion thereof is restored, little to no delivered agent will reach the general circulation. Thus, the removal step is performed prior to restoring vascular circulation to the organ or portion thereof.

After the period of compartmentalization, compartmentalization to the organ or portion thereof is terminated. This is effected by restoring communication of the tissue or organ or portion thereof with the systemic circulation. For example, compartmentalization is terminated by restoring vascular circulation to the organ or portion thereof. Restoration of vascular isolation can be achieved by removal of the device, apparatus or process used to block blood flow to the tissue or portion thereof. For example, the parenchymal clamp can be released from the tissue. In other examples, compression of the region or portion of the tissue can be released. It is within the level of a skilled physician to carefully remove the device, apparatus or process used to block blood flow to the tissue or organ or portion thereof so that damage to the underlying tissue, vessels, veins or arteries, or ducts does not occur. For example, the pressure of a parenchymal clamp can be carefully released to control restoration of blood flow to the tissue, organ or portion thereof.

D. Delivered Agents

The delivered agent for use in the methods, uses or compositions herein can be any desired nucleic acid molecule, or a vehicle, construct or complex containing any nucleic acid molecule. In particular, the delivered agent is a nucleic acid molecule or includes a nucleic acid molecule that has a desired function or that encodes a selected polypeptide with a desired function. The delivered agent can be a DNA (e.g., double stranded circular or linear), RNA, a ribozyme, or an aptamer. Further the delivered agent can be in any forms including, but not limited to, naked DNA, a microRNA, a small interfering RNA, or an antisense nucleic acid. The delivered agent can be provided as a construct containing a heterologous nucleic acid molecule. There are a number of constructs that are known to one of skill in the art for delivery of nucleic acid to cells, either in vitro or in vivo. Such constructs include viral based delivery systems and non-viral based deliver systems. For example, the delivered agent can be a construct containing a nucleic acid molecule that is delivered in a nanoparticle (e.g., a targeted or radiolabeled nanoparticle), a plasmid or a vector (e.g., a viral vector or an expression vector). Such constructs are well known in the art and readily adaptable for use with the compositions and methods described herein.

It is understood that the choice of delivered agent that is used is dependent on the target tissue or organ locus. It is within the level of one of skill in the art to empirically determine and identify a delivered agent and/or delivery method that is compatible with cell uptake by the target tissue or organ cells. For example, it is known to one of skill in the art that retrovirus-based vectors generally only transduce actively dividing cells. Liver cells are generally quiescent, and thus delivery of a retrovirus-based vector to liver cells requires procedures whereby the method includes steps of stimulating cell division (e.g. partial hepatectomy). In contrast, adenoviral-based vectors are capable of being delivered to non-dividing cells.

In particular examples, the delivered agent used in the method herein is typically one that will not integrate into the host genome nor contain sequences that allow for replication. It is found herein that even in the absence of integration into the genome, the compartmentalized delivery method provided herein achieves sustained gene expression of the introduced nucleic acid molecule for greater than 6 months, and generally for up to 1 year or greater than 1 year. If desired, however, nucleic acid that integrates into the genome can be used in the methods herein.

1. Nucleic Acid Molecule

The particular delivered agent that is used in the methods, uses or compositions herein is or includes a nucleic acid molecule whereby delivery and/or expression thereof effects an activity or property that is useful when present in the target organ or when secreted into the bloodstream. For example, delivery and/or expression of a nucleic acid molecule effects replacement of a missing or defective (e.g. partially or non-functional) gene product, achieves overproduction of a gene product, acts as a DNA vaccine, encodes a polypeptide that has a desired effect or therapeutic activity, or inhibits gene expression. For example, the nucleic acid molecule can be one that is selected for that encodes a polypeptide for a desired effect or therapeutic outcome. In another example, the nucleic acid molecule is a nucleic acid-based inhibitor of a gene or of a gene product, such as an inhibitor of transcription or translation of a gene. For example, the delivered agent can be a short-interfering RNA (siRNA) sequence, antisense sequence or a micro-RNA (miRNA) sequence. In additional examples, the delivered agent can be used prophylactically to deliver prophylaxic proteins. In a further example, delivery and/or expression of the nucleic acid molecule can encode proteins for use in agriculture application, for example, to improve meat production (e.g., by blocking production of myostatin). It is within the level of one of skill in the art to select a nucleic acid molecule depending on the particular application or the particular disease or disorder that is being treated, such as any described in Section G.

The nucleic acid molecule can be delivered as a naked DNA, or can be delivered in a vehicle or as a complex or construct. Hence, it is understood that the delivered agent is or includes the nucleic acid molecule. For example, the nucleic acid molecule can include a vector or plasmid containing the nucleic acid molecule, such as a viral vector or non-viral vector. The nucleic acid molecule can be encapsulated in liposomes. The nucleic acid molecule can be complexed to other agents, such as target ligands or other moieties and delivered as a nanoparticle.

The nucleic acid molecule can be driven by a promoter to enhancer to control or regulate expression. The promoter is operably linked to the coding region. Any strong promoter known to those skilled in the art can be used for driving the expression of DNA. The promoter can be a constitutive promoter, such as a CMV promoter, a tissue-specific promoter, an inducible or regulatable promoter. In a specific embodiment, the nucleic acid molecule is to be introduced for purposes of gene therapy contains an inducible promoter operably linked to the coding region, such that expression of the nucleic acid is controllable by controlling the presence or absence of the appropriate inducer of transcription. Generally the promoter is a regulated promoter and transcription factor expression system, such as the published tetracycline-regulated systems or other regulatable systems (see e.g. published International PCT Appl. No. WO 01/30843), to allow regulated expression of the encoded polypeptide. Exemplary of other promoters, are tissue-selective promoters, such as those described in U.S. Pat. No. 5,998,205, including, for example, a fetoprotein, DF3, tyrosinase, CEA, surfactant protein and ErbB2 promoters. An exemplary regulatable promoter system is the Tet-On (and Tet-Off) system available, for example, from Clontech (Palo Alto, Calif.). This promoter system allows the regulated expression of the transgene controlled by tetracycline or tetracycline derivatives, such as doxycycline. Other regulatable promoter systems are known (see e.g., published U.S. Application No. 2002-0168714, entitled "Regulation of Gene Expression Using Single-Chain, Monomeric, Ligand Dependent Polypeptide Switches," which describes gene switches that contain ligand binding domains and transcriptional regulating domains, such as those from hormone receptors). Other suitable promoters that can be employed include, but are not limited to, adenoviral promoters, such as the adenoviral major late promoter and/or the E3 promoter; or heterologous promoters, such as the cytomegalovirus (CMV) promoter; the Rous Sarcoma Virus (RSV) promoter; inducible promoters, such as the MMT promoter, the metallothionein promoter; heat shock promoters; the albumin promoter; and the ApoAI promoter.

In some examples, the delivered agent in the methods, uses or compositions herein is or includes a nucleic acid molecule that encodes a desired polypeptide. Upon delivery of the delivered agent in the methods herein, the encoded polypeptide can be one that can be used as a biologic therapy or drug. The nucleic acid molecule can encode any desired gene product, such as a cytokine, clotting factor or coagulation factor, hormone, growth factor, enzyme, transport protein, regulatory protein, receptor, or antigen. The nucleic acid molecule can encode hormonal proteins to regulate cell growth, cell differentiation or metabolism. The choice of particular nucleic acid molecule encoding a desired therapeutic polypeptide depends on the particular disease or condition that is treated, and is within the level of one of skill in the art. For example, the nucleic acid molecule encodes insulin if the subject to be treated has Type I diabetes, a specific blood clotting factor if the subject has hemophilia, dopamine if the subject has Parkinson's Disease, or LDL receptor if the subject being treated has familial hypercholesterolemia. One of skill in the art would know how to select the needed polypeptide and the nucleic acid that encodes it based on the particular needs of the subject to be treated. Exemplary nucleic acid molecules encode immunomodulatory proteins, enzymes, hormones, cytokines, receptor, an antibody or an anti-angiogenic agent. The nucleic acid molecule can encode a protein that is a fusion protein.

The selected nucleic acid molecule can encode a polypeptide that is an immunostimulating protein or that exhibits immunomodulatory properties. Such nucleic acid molecules include, but are not limited to, genes that encode cytokines, for example, an interleukin, interferon, granulocyte colony stimulating factor or thereof, such as interleukin (IL)-1, IL-2, IL-4, IL-5, IFN-β, IFN-γ, IFN-α, TNF, IL-12, IL-18, and flt3; proteins that stimulate interactions with immune cells (B7, cluster of differentiation 28 (CD28), major histocompatibility complex class I (MHC class I), MHC class II, Transporter associated with antigen processing (TAPs)); tumor-associated antigens (immunogenic polypeptides from melanoma antigen recognized by T-cells 1 (MART-1), gp100 (Melanocyte protein pmel-17); tyrosinase, tyrosinase-related protein 1, tyrosinase-related protein 2, melanocyte-stimulating hormone receptor, melanoma-associated antigen 1 (MAGE1), MAGE2, MAGE3, MAGE12, B melanoma antigen (BAGE), cancer-germline antigens (GAGE), cancer-testis antigen NY-ESO-1, β-catenin, Mutated melanoma-associated antigen 1 (MUM-1), cyclin-dependent kinase 4 (CDK-4), caspase 8, antigen identified by monoclonal antibody Ki-67 (KIA) 0205, human leukocyte antigen (HLA)-A2R1701, α-fetoprotein, telomerase catalytic protein, G-250, mucin 1 (MUC-1), carcinoembryonic protein, p53, Her2/neu, triosephosphate isomerase, cell division control protein 27 (CDC-27), low density lipid receptor-GDP-1-fucose:β-d-galactoside 2-α-1-fucosyltransferase fusion protein (LDLR-FUT), telomerase reverse transcriptase, and prostate-specific membrane antigen (PSMA)), cDNA encoding antibodies that block inhibitory signals (Cytotoxic T-Lymphocyte Antigen 4 (CTLA4) blockade), chemokines (Macrophage inflammatory protein (MIP1), MIP3, CCR7 ligand, and calreticulin), and other proteins.

The nucleic acid molecule can encode a polypeptide that is a growth factor or portions thereof that bind to the receptor or a growth factor receptor or portions thereof that bind to ligand. Growth factors and growth factor receptors are known in the art. See e.g., Baxley and Serra, *Curr. Drug Targets* 11(9):1089-102 (2010); Lo, *Curr. Mol. Pharmacol.* 3(1):37-52 (2010); Barakat and Kaiser, *Expert Opin. Investig. Drugs* 18(5):637-46 (2009); Trojanowska and Varga, *Curr. Opin. Rheumatol.* 19(6):568-73 (2007); Jimeno and Hidalgo, *Biochim. Biophys. Acta* 1766(2):217-29 (2006); Finch and Rubin, *J. Natl. Cancer Inst.* 98(12):812-24 (2006); Lo et al., *Breast Canc. Res. Treat.* 95(3):211-8 (2006); Schilephake, *Int. J. Oral Maxillofac. Surg.* 31(5): 469-84 (2002); George, *Urology* 60(3 Suppl. 1):115-21 (2002). Growth factors include, for example, bone morphogenic protein (BMPs), epidermal growth factor (EGF), erythropoietin (EPO), fibroblast growth factor (FGF), granulocyte colony stimulating factor (G-CSF), granulocyte macrophage colony stimulating factor (GM-CSF), hepatocyte growth factor (HGF), insulin-like growth factor (IGF), platelet derived growth factor (PDGF), transforming growth factor α and β, and vascular endothelial growth factor (VEGF). Growth factor receptors include, for example, epidermal growth factor receptor (EGFR), fibroblast growth factor receptor (FGFR), or transforming growth factor receptor (TGFR).

The nucleic acid molecule can encode a polypeptide that is an antibody or antibody fragment, including a single chain antibody or an anti-idiopathic antibody. Antibodies are known in the art. See e.g., Brekke and Sandlie, *Nat. Rev. Drug. Discov.* 2(1):52-62 (2003); Mellstedt, *Drugs Today* 39(Supl. C):1-16 (2003); Therapeutic Antibodies: Methods and Protocols; Ed. Dimitrov, A. S., Humana Press, Springer, New York, N.Y. (2009); Zheng et al. (2007) *Cell Research,* 17:303-306. Non-limiting examples of encoded antibodies or fragments thereof include, for example, anti-thymocyte globulin, muromonab, Abciximab, Adalimumab, Alemtuzumab, Basiliximab, Bevacizumab, Cetuximab, Certolizumab, Dacliziuma, Eculizumab, Efalizumab, Gemtuzumab, Ibritumomab tiuxetan, Infliximab, Muromonab-CD3, Natalizumab, Omalizumab, Palivizumab, Panitumumab, Ranibizumab, Rituximab, Tositumomab or Trastuzumab.

The nucleic acid molecule can encode a polypeptide that is, but is not limited to, an enzyme (e.g., galsulfase, laronidase, N-acetylgalactosamine 6-sulfatase, phenylalanine ammonia lyase, acid alpha glucosidase, imiglucerase, alglucosidase alpha), a hormone (e.g., thyrotropin, growth hormone, insulin, thyroid hormone, erythropoietin), an angiogenesis modulator, an immunomodulator (denileukin diftitox; interleukin-2), a pain modulator (e.g., NP2), a fusion protein (e.g., insulin-like growth factor 2 and acid alpha glucosidase (IGF2-GAA); abatacept; alefacept; etanercept), a poly (ADP-ribose) polymerase (PARP) inhibitor, a hylan or other derivative of hyaluronan, or an allergen (e.g., a peanut or other food allergen).

For example, the nucleic acid molecule can encode human erythropoietin or a variants thereof (see e.g. U.S. Pat. No. 4,703,008, Accession No. P01588), human G-CSF or variants thereof (see e.g., Accession No. P09919); human GM-CSF or variants thereof (see e.g. Cantrell et al. (1985) Proc. Natl. Acad. Sci, 82:6250-4; Accession No. P04141); plasminogen activator or variants thereof (see e.g., Accession No. P00750); urokinase or variants thereof (see e.g. Accession No. P00749); insulin or variants thereof (see e.g., U.S. Pat. No. 4,652,525, U.S. Pat. No. 4,431,740, Groskreutz et al. (1994) *J. Biol. Chem.,* 269:6241-5, Accession No. P01308); interleukins such as interleukin-1 or variants thereof (see e.g. Accession Nos. P01583, P01584), interleukin-2 or variants thereof (see e.g. Accession No. P60568, U.S. Pat. No. 4,738,927), interleukin-3 or variants thereof (see e.g. Accession No. P08700, EP Publ. EP275,598 or 282,185), interleukin-4 or variants thereof (see e.g., Accession No. P05112), interleukin 7 or variants thereof (see e.g. Accession No. P13232, U.S. Pat. No. 4,965,195), an interferon or variants thereof, a Factor VIII or variants thereof (see e.g. Accession No. P00451), Factor IX or variants thereof (see e.g. P00740), von Willebrand factor or variants thereof (see e.g. Accession No. P04275), or human growth hormone or variants thereof (see e.g. Accession No. P01241, P01242, U.S. Pat. No. 4,342,832).

Other nucleic acid molecules of interest, include those that encode anti-angiogenic or suicide proteins. Anti-angiogenic proteins include, for example, METH-1, METH-2, TrpRS fragments, proliferin-related protein, prolactin fragment, PEDF, vasostatin, various fragments of extracellular matrix proteins and growth factor/cytokine inhibitors. Various fragments of extracellular matrix proteins include, but are not limited to, angiostatin, endostatin, kininostatin, fibrinogen-E fragment, thrombospondin, tumstatin, canstatin, and restin. Growth factor/cytokine inhibitors include, but are not limited to, VEGF/VEGFR antagonist, sFlt-1, sFlk, sNRP1, angiopoietin/tie antagonist, sTie-2, chemokines (IP-10, PF-4, Gro-beta, IFN-gamma (Mig), IFN, FGF/FGFR antagonist (sFGFR), Ephrin/Eph antagonist (sEphB4 and sephrinB2), PDGF, TGF and IGF-1. A suicide protein is a protein that can lead to cell death, as with expression of diphtheria toxin A, or the expression of the protein can render cells selectively sensitive to certain drugs, e.g., expression of the herpes simplex thymidine kinase gene (HSV-TK) renders cells sensitive to antiviral compounds, such as acyclovir, ganciclovir and FIAU (1-(2-deoxy-2-fluoro-f-D-arabinofuranosil)-5-iodouracil). Other suicide proteins include carboxypeptidase G2 (CPG2), carboxylesterase (CA), cytosine deaminase (CD), cytochrome P450 (cyt-450), deoxycytidine kinase (dCK), nitroreductase (NR), purine nucleoside phosphorylase (PNP), thymidine phosphorylase (TP), varicella zoster virus thymidine kinase (VZV-TK), and xanthine-guanine phosphoribosyl transferase (XGPRT). Other encoded proteins, include, but are not limited to, herpes simplex virus thymidine kinase (HSV-TK), which is useful as a safety switch (see, U.S. patent application Ser. No. 08/974,391, filed Nov. 19, 1997, which published as PCT Publication No. WO 99/25860), Nos, FasL, and sFasR (soluble Fas receptor).

In other examples herein, the nucleic acid molecule is one that encodes a protein that is involved in a lysosomal storage disorder, and in particular an enzyme that is defective therein, including, but not limited to, Aspartylglucosaminidase, α-Galactosidase A, Palmitoyl Protein Thioesterase, Tripeptidyl Peptidase, Lysosomal transmembrane protein, cysteine transporter, Acid ceramidase, acid α-L-fucosidase, protective protein/cathepsin A, acid β-glucosidase or glucocerebrosidase, acid β-galactosidase, iduronate-2-sulfatase, α-L-Iduronidase, galactocerebrosidase, acid α-mannosidase, acid β-mannosidase, arylsulfatase B, arylsulfatase A, N-Acetylgalactosamine-6-sulfate sulfatase, N-Acetylglucosamine-1-phosphotransferase, Acid sphingomyelinase, Niemann-Pick disease, type C1 (NPC-1), β-Hexosaminidase B, Heparan N-sulfatase, α-N-Acetylglucosaminidase (Na-Glu), Acetyl-CoA:αglucosaminide N-acetyltransferase, N-Acetylglucosamine-6-sulfate sulfatase, β-Glucuronidase, and acid lipase. The role of such enzymes in various lysosomal storage diseases are known to one of skill in the art (see e.g. published U.S. Patent Appl. No. US2008/0025952; US20120009268). The choice of enzyme depends on the particular lysosomal disorder. Non-limiting examples of nucleic acid molecules of interest include any that encode: a β-glucuronidase for treatment of mucopolysaccharidosis disorder (e.g., Sly syndrome); α-L-iduronidase for treatment of Hurler Syndrome; α-L-iduronidase for treatment of Scheie Syndrome or Hurler-Scheie Syndrome; iduronate sulfatase for treatment of Hunter's Syndrome; heparin sulfamidase for treatment of Sanfilippo Syndrome A (MPSIIIA); N-acetylglucosaminidase for treatment of Sanfilippo Syndrome B (MPSIIIB); acetyl-CoA:α-glucosaminide acetyltransferase for treatment of Sanfilippo Syndrome C (MPSIIIC); N-acetylglucosamine-6-sulfatase for treatment of Sanfilippo Syndrome D (MPSIIID); galactose-6-sulfate sulfatase for treatment of Morquio Syndrome A; β-galactosidase for treatment of Morquio Syndrome B; N-acetylgalactosamine-4-sulfatase for treatment of Maroteaux-Lamy Syndrome; α-galactosidase for treatment of Fabry disease; glucocerebrosidase for treatment of Gaucher's disease, or lysosomal acid α-glucosidase for treatment of a glycogen storage disorder (e.g., Pompe disease).

Other exemplary nucleic acids molecules of interest include, but are not limited to, any that encode: a protein for treatment of Alzheimer's disease such as a metalloendopeptidase, for example, amyloid-beta degrading enzyme neprilysin, the insulin-degrading enzyme insulysin, or thimet oligopeptidase; a protein or peptide that can act as a anti-retroviral agent to treat virus infection such as infection by human immunodeficiency virus (HIV), for example, enfuvirtide (Fuzeon®); a protein for treatment of Amyotrophic Lateral Sclerosis (ALS) such as, but not limited to, insulin growth factor-1 (IGF-1), calbindin D28, parvalbumin, HIF1-alpha, SIRT-2, VEGF, SMN-1, SMN-2, GDNF or ciliary neurotrophic factor (CNF); a protein that is deficient in subjects having hemophilia, such as, but not limited to, Factor VIII or Factor IX; a protein for treatment of type I diabetes, such as the furin-cleavable insulin gene; a protein for treatment of familial hypercholesterolemia, such as low density lipoprotein receptor (LDLR); a protein for treatment of lipoprotein lipase deficiency (LPLD), such as lipoprotein lipase (LPL); a protein for treatment of Alpha-1-Antitrypsin (AAT) deficiency, such as AAT; a protein for the treatment of Crigler Najar Syndrome Type I or Type II, such as hepatic bilirubin UDP-glucuronyl-transferase or a functional variant thereof, for example, UGT1A1 (Gong et al. (2001) Pharmacogentics, 11:357-68); a protein for treatment of glycogen storage deficiency type 1A such as glucose-6 phosphatase; a protein for treatment of Pepck deficiency such as phosphoenolpyruvate-carboxykinase; protein associated with galactosemia such as galactose-1 phosphate uridyl transferase; protein associated with phenylketonuria such as phenylalanine hydroxylase, protein associated with maple syrup urine disease such as branched chain alpha-ketoacid dehydrogenase; protein associated with tyrosinemia type 1 such as fumarylacetoacetate hydrolase; protein associated with methylmalonic acidemia such as methylmalonyl-CoA mutase; protein associated with ornithine transcarbamylase deficiency such as ornithine transcarbamylase; protein associated with citrullinemia such as argininosuccinic acid synthetase; protein associated with severe combined immunodeficiency disease such as adenosine deaminase; protein associated with Gout and Lesch Nyan syndrome such as hyposanthine guanine phosphoribosyl transferase; protein associated with biotinidase deficiency such as biotinidase; protein associated with Gaucher disease such as beta-glucocerebrosidase; protein associated with Sly syndrome such as beta-gluronidase; protein associated with Zellweger syndrome such as peroxisome membrane protein 70 kDa; protein associated with acute intermittent *porphyria* such as porphobilinogen deaminase (PBDG); protein associated with alpha-1 antitrypsin deficiency (emphysema) such as alpha 1 antitrypsin, protein associated with cancer such as a tumor suppressor gene such as p53; protein encoding glutamic acid decarboxylase (GAD) for the treatment of Parkinson's disease; or a protein that is deficient in a lysosomal storage disease, and in particular Sanfilippo Syndrome (also called Mucopolysaccharidosis type III, MPSIII), such as lysosomal sulfamidase, and α-N-acetylglucosaminidase (NaGlu).

Alternatively, a therapeutic nucleic acid can exert its effect at the level of RNA, for instance, by encoding an antisense message or ribozyme, a protein that affects splicing or 3' processing (e.g., polyadenylation), or a protein that affects the level of expression of another gene within the cell, e.g. by mediating an altered rate of mRNA accumulation, an alteration of mRNA transport, and/or a change in post-transcriptional regulation. These include RNA, such as RNAi and other double-stranded RNA, antisense and ribozymes, which among other capabilities can be directed to mRNAs encoding proteins essential for proliferation, such as structural proteins, transcription factors, polymerases, genes encoding cytotoxic proteins, genes that encode an engineered cytoplasmic variant of a nuclease (e.g. RNase A) or protease (e.g. trypsin, papain, proteinase K and carboxypeptidase).

For example, the nucleic acid molecule can be a nucleic acid-based inhibitor of a gene or of a gene product, such as an inhibitor of transcription or translation of a gene. The delivered agent can be a short-interfering RNA (siRNA) sequence, antisense sequence or a micro-RNA (miRNA) sequence. The RNA can be 10 to 30 nucleotides long, such as 19-25 or 21-25 nucleotides in length. siRNA-mediated gene silencing methods, where expression products of a gene are targeted by specific double stranded derived siRNA nucleotide sequences that are complementary a nucleotide segment of the target gene transcript (e.g. to at least a 19-25 nucleotide long segment), including the 5' untranslated (UT) region, the ORF, or the 3' UT region, are known in the art (see e.g. PCT International Patent Publication Nos. WO00/44895, WO01/75164, WO01/92513, or WOO 1/29058. A siRNA sequence typically binds a unique sequence within a target mRNA with exact complementarity and results in the degradation of the target mRNA molecule. A siRNA sequence can bind anywhere within the mRNA molecule. Sequences targeted by the siRNA include genes expressing a polypeptide of interest, or an upstream or downstream modulator of such a gene. Examples of upstream or downstream modulators of a gene include a transcription factor that binds a gene promoter, a kinase or phosphatase that interacts with a polypeptide of interest, and polypeptides involved in regulatory pathways capable of influencing the polypeptide of interest. A miRNA sequence typically binds a unique sequence within a target mRNA with exact or less than exact complementarity and results in the translational repression of the target mRNA molecule. A miRNA sequence can bind anywhere within mRNA sequence, but generally binds within the 3' untranslated region of the mRNA molecule.

A nucleotide siRNA or miRNA sequence (e.g. 21-25 nucleotides in length) can, for example, be produced from an expression vector by transcription of a short-hairpin RNA (shRNA) sequence, a longer (e.g. 60-80 nucleotide) precursor sequence, which is subsequently processed by the cellular RNAi machinery to produce either a siRNA or miRNA sequence. Alternatively, a nucleotide siRNA or miRNA sequence (e.g. 21-25 nucleotides in length) can, for example, be synthesized chemically. Chemical synthesis of siRNA or miRNA sequences is commercially available from such corporations as Dharmacon, Inc. (Lafayette, Colo.), Qiagen (Valencia, Calif.), and Ambion (Austin, Tex.). Methods of delivering siRNA or miRNA molecules are known in the art. See e.g., Oh and Park, *Adv. Drug. Deliv. Rev.* 61(10):850-62 (2009); Gondi and Rao, *J. Cell Physiol.* 220(2):285-91 (2009); and Whitehead et al., *Nat. Rev. Drug. Discov.* 8(2): 129-38 (2009).

For example, the nucleic acid molecule can be an antisense nucleic acid sequence. By hybridization interactions, antisense nucleic acid block expression of a cellular or pathogen mRNA. Antisense nucleic acid molecules can, for example, be transcribed from an expression vector to produce an RNA which is complementary to at least a unique portion of the target mRNA and/or the endogenous gene which encodes the target. Hybridization of an antisense nucleic acid under specific cellular conditions results in inhibition of target protein expression by inhibiting transcription and/or translation. Examples of antisense nucleic acids include, but are not limited to, the following Isis Pharmaceuticals, Inc. products: Mipomersen for high cholesterol; ISIS-CRP$_{Rx}$ for coronary artery disease, inflammation, and renal disease; ISIS-APOCIII$_{Rx}$ for high triglycerides; ISIS-FXI$_{Rx}$ for clotting disorders; BMS-PCSK9$_{Rx}$ for coronary artery disease; ISIS-SGLT2$_{Rx}$, ISIS-PTP1B$_{Rx}$, ISIS-GCGR$_{Rx}$, and ISIS-GCCR$_{Rx}$ for Type 2 diabetes; ISIS-FGFR4$_{Rx}$ for obesity; OGX-011 f, LY2181308, ISIS-EIF4E$_{Rx}$, OGX-427, ISIS-STAT3$_{Rx}$ for cancer; ISIS-SOD1$_{Rx}$ for ALS; ISIS-TTR$_{Rx}$ for TTR amyloidosis; ISIS-SMN$_{Rx}$ for spinal muscular atrophy; Vitravene for CMV retinitis; Alicaforsen for ulcerative colitis; ACHN-490 for severe bacterial infection; ATL1102 for multiple sclerosis; EXC 001 for local fibrosis; iCo-007 for ocular disease; and ATL1103 for acromegaly. Examples of microRNAs that can be administered using the methods taught herein include, but are not limited to, the following Santaris Pharma products: Miravirsen for Hepatitis C; EZN-2968 for solid tumors; EZN-3042 for cancer; EZN-4176 for androgen receptor; SPC 4955 and SPC 5001 for high cholesterol. Additional therapeutic microRNAs include the following Mirna Therapeutics, Inc. products for the treatment of cancer: let-7, miR-34, miR-Rx02, miR-16, miR-Rx-01, miR-Rx-03, miR-Rx-06, and miR-Rx-07.

In other examples, the nucleic acid molecule can be a ribozyme (e.g. a hammerhead or a hairpin-based ribozyme) designed either to repair a defective cellular RNA or to destroy an undesired cellular or pathogen-encoded RNA (see e.g. Sullenger (1995) *Chem. Biol.*, 2:249-253; Czubayko et al. (1997) *Gene Therapy*, 4:943-9; Rossi (1997) *Ciba Found. Symp.*, 209:195-204; James and Gibson (1998) *Blood*, 91:371-82; Sullenger (1996) *Cytokines Mol. Ther.*, 2:201-5; Hampel (1998) *Prog. Nucleic Acid Res. Mol. Biol.*, 58:1-39; or Curcio et al. (1997) *Pharmacol Therapy*, 74:317-32).

In some examples, the nucleic acid molecule encodes a polypeptide that is detectable. Exemplary of such polypeptides include, but are not limited to, luciferase or a fluorescent protein, such as a green fluorescent protein (GFP). In particular examples, the delivered agent is a viral vector, such as an adenoviral vector, that contains a nucleic acid molecule. Exemplary of such a delivered agent is Ad-CMV-Luc (see e.g. Example 1). Such an adenovirus can be further modified to contain a further or different nucleic acid molecule, such as any known in the art or described herein above. For example, the luciferase transgene expressed therein can be replaced or swapped to contain a nucleic acid molecule encoding a nucleic acid molecule.

2. Vehicles and Constructs Containing the Nucleic Acid Molecule

The nucleic acid molecule can be provided in a vector, construct or other vehicle of delivery. Exemplary of such are viral vectors, non-viral vectors, nanoparticles or whole cells. Methods of generating such constructs or vehicles for delivery are well-known to a skilled artisan. For example, nucleic acid molecules can be inserted into non-viral or viral vectors using standard methods well-known to one of skill in the art. In some instances, routine molecular biology and recombinant DNA techniques can be used (see e.g. Ausubel et al., Current Protocols in Molecular Biology, John Wiley & Sons, New York, N.Y., 1998, Sambrook et al., Molecular Cloning: A Laboratory Manual, Cold Spring Harbor, N.Y. (1989). In other instances, the nucleic acid molecule can be inserted so it is under the control of any appropriate regulatory sequence or sequences. In other examples, the nucleic acid molecules are inserted as part of an expression cassette that includes regulatory elements, such as promoters or enhancers. Appropriate regulatory elements can be selected by one of ordinary skill in the art based on, for example, the desired level of expression. In particular examples, the regulatory elements can be selected to include tissue-specific promoters, such as liver-specific promoters, to limit gene expression to tissue-specific cells.

a. Virus and Viral Vectors

A virus can be used as a delivered agent in the methods, uses and compositions herein as the delivered agent, whereby an exogenous nucleic acid sequence is inserted into a viral vector. Viruses are useful in delivering nucleic acid molecules in vivo because they are efficient at transferring viral DNA into host cells, they can infect and be taken up by specific target cells depending on the viral attachment proteins (e.g. capsid or glycoproteins), and they can be manipulated to remove non-essential genes and add heterologus nucleic acid molecules. Many viral vectors are known to those skilled in the art. Examples of viruses that can be used in the methods herein include, but are not limited to, adenoviruses, adeno-associated viruses, alphaviruses, baculoviruses, hepadenaviruses, baculoviruses, poxviruses, herpesviruses, retroviruses, lentiviruses, orthomyxoviruses, papovaviruses, paramyxoviruses, and paroviruses. In particular examples, the virus is an adenovirus. The choice of virus is within the level of one of skill in the art and is dependent on a number of factors, such as the desire for replication or integration of viral DNA, the tropism of the virus, and/or the immunogenicity of the virus. Such viruses and derivatives thereof, are well-known and available to one of skill in the art. For example, many are available from the American Type Culture Collection (ATCC, Rockville, Md.) or from commercial vendors (e.g. Vector Biolabs, Philadelphia, Pa.; Applied Biological Materials, Inc., Richmond, British Columbia, Canada).

Viral vectors for use in generating recombinant viruses include replication-competent viruses and replication-defective viruses. In replication-defective viruses, the virus typically lacks one or more genes associated with viral replication and cannot replicate beyond the first cycle of infection. In some cases, in order to produce replication-defective viruses, transfer vectors, packaging vectors or helper virus are required. For example, a packaging vector can be provided as a cosmid or in a cell line that provides the viral structural proteins for packaging of the defective vector.

The viral vectors used in the method herein also can contain expression cassettes that include regulatory elements, such as promoters and enhancers, operably linked to a transgene of choice. As discussed above, any suitable promoter can be used. Suitable promoters and enhancers are widely available in the art for use in the viral vector of choice. Typically the promoter is constitutive promoter. Exemplary promoters include, but are not limited to, a CMV promoter, a truncated CMV promoter, a human serum albumin promoter or an α-1-antitrypsin promoter. For example, the promoter is a truncated CMV promoter in which binding sites for known transcriptional repressors have been deleted. In other examples, the promoter is an inducible promoter. For example, the promoter is the inducible ecdysone promoter. Other examples of promoters include steroid promoters, such as estrogen and androgen promoters, and metallothionein promoters. The enhancer can be a tissue specific- or non-specific enhancer. For example, the enhancer is a liver-specific enhancer element. Exemplary enhancer elements include, but are not limited to, human serum albumin (HAS) enhancers, human prothrombin (HPrT) enhancers, α-1-microglobulin enhancers, intronic aldolase enhancers and apolipoprotein E hepatic control region.

i. Adenovirus

Adenoviruses are viral vectors that can be used as delivered agents containing a nucleic acid molecule of interest in the methods, uses and compositions herein. Adenovirus is a nuclear DNA virus with a genome of about 36 kb, which has been well-characterized through studies in classical genetics and molecular biology (Horwitz, M. S., "Adenoviridae and Their Replication," in Virology, 2nd edition, Fields, B. N., et al., eds., Raven Press, New York, 1990). The genome is classified into early (known as E1-E4) and late (known as L1-L5) transcriptional units, referring to the generation of two temporal classes of viral proteins. The demarcation between these events is viral DNA replication.

Adenoviruses exhibit a natural tropism for epithelial cells of the respiratory and gastrointestinal tract. Adenovirus also can infect liver cells, such as hepatocytes and endothelial cells, which can occur upon clearance of the virus into the liver after systemic administration. In particular, in the methods herein, direct injection into the parenchyma facilitates selective liver cell uptake by hepatocytes. Penton base and fiber proteins on the surface of the virus are responsible for the virus tropism. Multiple interactions between adenoviral particles and the host cell are required to promote efficient cell entry (Nemerow (2000) *Virology* 274:1-4). For subgroup C adenoviruses, such as adenovirus 2 and 5 (Ad2 or Ad5), the viral entry pathway has been well characterized and is believed to involve two separate cell surface events. First, a high affinity interaction between the adenoviral fiber knob and coxsackie-adenovirus receptor (CAR) mediates the attachment of the adenovirus particle to the cell surface. A subsequent association of penton with the cell surface integrins $\alpha_v\beta_3$ and $\alpha_v\beta_5$, which act as co-receptors, potentiates virus internalization. CAR, which is expressed in many human tissues including lung epithelial cells (Bergelson et al., (1997) *Science* 275: 1320-1323), appears to function as a cellular receptor for most adenoviral subgroups, except subgroup B (Bergelson et al., (1997) *Science* 275: 1320-1323; Roelvink et al, (1998) *J. Virol.* 72:7909-7915).

Adenovirus includes over 50 serotypes that are grouped into six distinct subgroups, A to F. Any of these adenovirus serotypes, which are available from the American Type Culture Collection (ATCC, Rockville, Md.) and other commercial and non-commercial providers can be used in the methods herein or used as a source for further modification as is known in the art. Also, any other serotype of adenovirus available from any other source can be used or further modified. For instance, an adenovirus can be of subgroup A (e.g., serotypes 12, 18, 31), subgroup B (e.g., serotypes 3, 7, 11a, 11p, 14, 16, 21, 34, 35, 50), subgroup C (e.g., serotypes 1, 2, 5, 6), subgroup D (e.g., serotypes 8, 9, 10, 13, 15, 17, 19, 19p, 20, 22-30, 32, 33, 36-39, 42-49, 51), subgroup E (e.g., serotype 4), subgroup F (e.g., serotypes 40, 41), or any other adenoviral serotype. In certain embodiments, the adenovirus is a subgroup C adenovirus or derived from a subgroup C adenovirus. Subgroup C adenoviruses, include, but are not limited to, Ad2 and Ad5.

Adenoviral vectors are available in the art (e.g. available from the American Type Culture Collection (ATCC, Rockville, Md.), and the sequences of the wild-type adenovirus Proteins from many different adenovirus serotypes are well known in the art (see e.g. Roberts et al. (1984) J. Biol. Chem., 259:13968-13975; Chroboczek et al. (1992) Virology, 186:28-285; Sprengel et al. (1994) J. Virol., 68:379-389; Chillon et al. (1999) J. Virol., 73:2537-2540; Davison et al. (1993) J. Mol. Biol., 234:1308-1316; binf.gmu.edu/wiki/index.php/Human_Adenovirus_Genome_Sequences_and_Annotations). The adenoviral vectors are widely available to the skilled artisan, for example from the American Type Culture Collection (ATCC) or other commercial or non-commercial provider. From the ATCC, adenoviruses are available as ATCC numbers VR-1 to VR-1616. For example, wild type adenovirus type 2 is available from the ATCC as VR-846 and type 5 is available as VR-5 and VR-1082. Any of a number of recombinant or modified adenoviruses can be generated that are derived from any of the above serotypes, as described in the art and herein or by any suitable method known to one of skill in the art.

Adenoviral vectors have several advantages for use as gene delivery vehicles, including tropism for both dividing and non-dividing cells, minimal pathogenic potential, ability to replicate to high titer for preparation of vector stocks, and the potential to carry large inserts (see e.g. Berkner (1992) *Curr. Top. Micro. Immunol.,* 158:39-66; Jolly et al. (1994) *Cancer Gene Therapy,* 1:51-64).

For example, adenovirus vectors include defective adenovirus vector containing at least one deletion in the first early gene region (E1-E4). Modifications to adenoviral vectors include deletions known in the art, such as deletions in one or more of the E1, E2a, E2b, E3, or E4 coding regions. For example, adenovirus vectors for gene therapy can be prepared by substitution of a heterologous nucleic acid molecule in place of the E1, E2a, E2b, E3 and/or E4 genes. Deletion can be effected using restriction endonucleases. For example, the E1a region can be deleted using convenient restriction endonuclease sites within the E1a region. Often, a portion of E3 is also deleted by restriction endonuclease addition so as to permit the insertion of a larger piece of foreign DNA while still satisfying the size constraints required for packaging into new viral particles. Due to deletion of these regions, the cloning capacity of an adenovirus vector can be about 8 kb. Such adenoviral vectors are typically referred to as replication defective adenovirus due to the at least one deletion in the first viral early gene region, such as E1, which includes the E1a and E1b regions.

Deletion of the early genes, such as viral E1 region, renders the recombinant adenovirus defective for replication and incapable of producing infectious viral particles in subsequently infected target cells. Thus, to permit early gene-deleted adenovirus genome replication, such as E1-deleted adenovirus genome replication, and to produce virus particles requires a system of complementation which provides the missing gene product. For example, E1 complementation is typically provided by a cell line expressing E1, such as the human embryonic kidney packaging cell line, i.e. an epithelial cell line, called 293 (deposited with the ATCC under Accession No. CRL-1573). Cell line 293 contains the E1 region of adenovirus, which provides E1 gene region products to "support" the growth of E1-deleted virus in the cell line (see e.g., Graham et al., *J. Gen. Virol.* 36: 59-71, 1977). Additionally, cell lines that are usable for production of defective adenovirus having a portion of the adenovirus E4 region have been reported (see e.g. International published Appl. No. WO 96/22378). E3 also can be deleted from the vector, but since it is not required for vector production, it can be omitted from the complementing producer cell.

The benefit of the use of replication deficient viruses as vectors is that they are limited in the extent to which they can spread to other cell types, since they can replicate within an initial infected cell, but are unable to form new infectious viral particles. Multiple deficient adenoviral vectors and complementing cell lines have also been described (see e.g.

published Appl. Nos. WO 95/34671, U.S. Pat. No. 5,994, 106). The construction of replication-defective adenoviruses has been described (Berkner et al., *J. Virol.* 61:1213-20 (1987); Massie et al., *Mol. Cell. Biol.* 6:2872-83 (1986); Haj-Ahmad et al., *J. Virol.* 57:267-74 (1986); Davidson et al., *J. Virol.* 61:1226-39 (1987); Zhang et al., *BioTechniques* 15:868-72 (1993); Berkner (1983) (1984) *Nuc. Acids Res.* 11:6003; Ghosh-Choudhury (1987) *Biochem. Biophys. Res. Commun.*, 147:964; Gilardi et al. (1990) *FEBS Lett.* 267:60; Mittal (1993) *Virus Res.* 28:67; Yang (1993) *Proc. Natl. Acad. Sci. USA* 90:4601; and International published PCT WO1995/026411).

Adenovirus vectors also include "gutless" or "gutted" vectors in which all viral genes are removed leaving only the ITRs necessary for vector propagation and the Ψ. Such adenoviral vectors are designated pseudoadenoviral vectors (PAVs) because they are derived from the genome of an adenovirus that contain minimal cis-acting nucleotide sequences required for the replication and packaging of the vector genome. PAVs vectors contain the 5' inverted terminal repeat (ITR) and the 3' ITR nucleotide sequences that contain the origin of replication, and the cis-acting nucleotide sequences required for packaging of the PAV genome. They can be modified to contain one more transgenes with appropriate regulatory elements (e.g. promoter or enhancers). PAVs have a carrying capacity of far more than 8 kb in size and up to 36 kb in size, since they contain deletions of most viral coding sequences. (see e.g. U.S. Pat. No. 5,882, 887 or 5,670,488; PCT Publication No. WO96/40955, WO97/25466, WO95/29993, WO97/00326; Morral et al. (1998) *Hum. Gene Ther.*, 10:2709-2716, Kochanek et al. (1996) *Proc. Natl. Acad. Sci.*, 93:5731-5736; Parks et al. (1996) *Proc. Natl. Acad. Sci.*, 93:13565-13570; Lieber et al. (1996) *J. Virol.*, 70:8944-8960 or Fisher et al. (1996) *J. Virol.*, 217:11-22).

Adenovirus vectors also include "gutless" or "gutted" vectors in which all viral genes are removed leaving only the ITRs necessary for vector propagation and the Ψ. Such adenoviral vectors are designated pseudoadenoviral vectors (PAVs) because they are derived from the genome of an adenovirus that contain minimal cis-acting nucleotide sequences required for the replication and packaging of the vector genome. PAVs vectors contain the 5' inverted terminal repeat (ITR) and the 3' ITR nucleotide sequences that contain the origin of replication, and the cis-acting nucleotide sequences required for packaging of the PAV genome. They can be modified to contain one more transgenes with appropriate regulatory elements (e.g. promoter or enhancers). PAVs have a carrying capacity of far more than 8 kb in size and up to 36 kb in size, since they contain deletions of most viral coding sequences. (see e.g. U.S. Pat. No. 5,882, 887 or 5,670,48; PCT Publication No. WO96/40955, WO97/25466, WO95/29993, WO97/00326; Morral et al. (1998) *Hum. Gene Ther.*, 10:2709-2716, Kochanek et al. (1996) *Proc. Natl. Acad. Sci.*, 93:5731-5736; Parks et al. (1996) *Proc. Natl. Acad. Sci.*, 93:13565-13570; Lieber et al. (1996) *J. Virol.*, 70:8944-8960 or Fisher et al. (1996) *J. Virol.*, 217:11-22).

PAVs are grown by co-infection of the producing cells with a "helper" virus (such as using an E1-deleted adenovirus vector), where the packaging cells express the E1 gene products. The helper virus trans-complements the missing adenovirus functions, including production of the viral structural proteins needed for particle assembly. For example, a helper adenovirus vector genome and a gutless adenoviral vector genome are delivered to packaging cells. The cells are maintained under standard cell maintenance or growth conditions, whereby the helper vector genome and the packaging cell together provide the complementing proteins for the packaging of the adenoviral vector particle. Such gutless adenoviral vector particles are recovered by standard techniques. The helper vector genome can be delivered in the form of a plasmid or similar construct by standard transfection techniques, or it can be delivered through infection by a viral particle containing the genome. Such viral particle is commonly called a helper virus. Similarly, the gutless adenoviral vector genome can be delivered to the cell by transfection or viral infection.

Adenoviruses also include replication-conditional adenoviruses, which are viruses that replicate in certain types of cells or tissues but not in other types as a result of placing adenoviral genes essential for replication under control of a heterologous promoter (discussed above; see, also U.S. Pat. No. 5,998,205, U.S. Pat. No. 5,801,029 and U.S. application Ser. No. 10/081,969, published as US 2003-0104625 and corresponding published International PCT application No. WO 2002/067861).

Adenoviruses also include those that have been modified to contain a targeting ligand to increase infection of specific target cells that express receptors (proteins, lipids, carbohydrates, or portions thereof) for the targeting ligand, for example, to alter the tropism of the virus. While adenoviral vectors and others, hold much promise for therapeutic applications, their usefulness is limited by the widespread tissue distribution of CAR, which restricts delivery of adenoviral vectors to specific cell types. Furthermore, the absence of CAR and/or a, integrin receptors on certain cells in vivo restricts the cell or tissue types that can be targeted by adenoviral vectors. Thus, adenovirus also include those that have been modified by reducing or ablating binding to native receptors and/or engineering capsid proteins, such as the HI loop, C terminus of fiber, the L1 loop of hexon or the RGD loop of penton base, or the capsid protein IX, to incorporate target ligands for a desired cell receptor or tissue-specific receptor (see e.g. Krasnykh et al. (2000) *Mol. Ther.*, 1:391-405; Wickham et al. (2000) *Gene Ther.*, 7:110-4; Dmitriev et al. (1998) *J. Virol.*, 72:9706-12; Mizuguchi et al. (2004) *Hum. Gene Ther.*, 15:1034-44; Wickham et al. (1997) *J. Virol.*, 71:8221-9; Curiel (1999) *Ann NY Acad Sci.*, 886:158-71). A capsid protein can be modified, for example, by addition of a target ligand or substitution of the fiber with other types of adenovirus fiber. The target ligand can be any protein, or portion thereof, that binds to a moiety in or on a cell, such as a cell surface protein, lipid, carbohydrate or other moiety. For example, the target ligand includes, but is not limited to, growth factors, adhesion molecules, cytokines, protein hormones, neuropeptides (neurotransmitters) and single-chain antibodies, or a suitable portion thereof. In other examples, adenovirus vectors can be conjugated with adaptor molecules, such as antibody and fusion protein containing an anti-Ad single-chain antibody (scFv) or the extracellular domain of CAR with the targeting ligand, or chemically modified with polymers, e.g. polyethylene glycol (PEG) moieties, that contain the targeting ligands (see e.g. Mizuguchi et al. (2004) *Hum. Gene Ther.*, 15:1034-44; Eto et al. (2008) *Int. J. Pharm.*, 354:3-8).

Any of the above adenoviruses, or any known in the art, can be modified to contain a desired heterologous nucleic acid molecule for use as a delivered agent herein. The adenovirus containing the desired heterologous nucleic acid sequence can be prepared by any technique known to persons skilled in the art (Levrero et al., *Gene* 101 (1991) 195, EP 185 573; Graham, *EMBO J.* 3 (1984) 2917; International Published PCT Application No. WO95/26411). In particular, such viruses can be prepared by homologous recombination between an adenovirus vector and a plasmid carrying the heterologous DNA sequence. The homologous recombination can occur after cotransfection of the adenovirus vector and plasmid into an appropriate cell line. The cell line used is generally one that is transformable. The transfection can be performed in the presence of a reagent that directs adenoviral particle entry into producer cells. Such reagents include, but are not limited to, polycations and bifunctional reagent. In some examples, if the adenovirus is a defective adenovirus (due to deletion of an early gene or fiber protein), the cell line also contains the sequences capable of complementing the defective adenovirus genome part, such as in integrated form in order to avoid risks of recombination. Examples of complementing cell lines include, but are not limited to, the human embryonic kidney line 293 (Graham et al., *J. Gen. Virol.* 36 (1977) 59) which contains the left-hand part of the genome of an Ad5 adenovirus. A complementing cell also includes, for example, a cell of the PER.C6 cell line, which contains the adenoviral E1 gene (PER.C6 is available, for example, from Crucell, The Netherlands; deposited under ECACC accession no. 96022940; see, also Fallaux et al. (1998) *Hum. Gene Ther.* 9:1909-1907; see, also, U.S. Pat. No. 5,994,128) or an AE1-2a cell (see, Gorziglia et al. (1996) *J. Virology* 70:4173-4178; and Von Seggern et al. (1998) *J. Gen. Virol.* 79:1461-1468)). Then, the adenoviruses which have multiplied are recovered and purified according to conventional molecular biology techniques.

References illustrating the use of adenoviruses in gene therapy include, but are not limited to, Vorburger and Hunt (2002) *The Oncologist*, 7:46-59; Breyer et al. (2001) *Current Gene Therapy*, 1:149-162; Shirakawa (2009) *Drugs News Perspectives*, 22:140-5; Wang et al. (2005) *Gene Therapy and Mol. Biology*, 9:291-300; and Sheridan (2011) *Nature Biotechnology*, 29:121).

ii. Adeno-Associated Virus (AAV)

Viral vectors for use as a delivered agent in the methods, compositions and uses herein include adeno-associated virus (AAV). AAV is a single-stranded human DNA parvovirus whose genome has a size of 4.6 kb. The AAV genome contains two major genes: the rep gene and the cap gene. The rep gene codes for the rep proteins (Rep 76, Rep 68, Rep 52 and Rep 40). The cap gene codes for AAV replication, rescue, transcription and integration, while the cap proteins form the AAV viral particle. AAV derives its name from its dependence on an adenovirus or other helper viruses (e.g. herpesviruses) to supply essential gene products that permit AAV to undergo a productive infection (i.e. reproduce itself in the host cell). In the absence of helper virus, AAV integrates as a provirus into the host cell's chromosome until it is rescued by superinfection of the host cell with a helper virus, usually adenovirus (Muzyczka (1992) *Curr. Top. Micro. Immunol.*, 158:97-129).

AAV viruses can be integrated into the cellular genome. The mechanism of integration is mediated by the presence of inverted terminal repeat (ITRs) at both ends of the AAV genome, which contain cis-acting nucleotide sequences required for virus replication, rescue, packaging and integration. The integration function of the ITR mediated by the rep protein in trans permits the AAV genome to integrate into a cellular chromosome after infection in the absence of helper virus. The site of integration for AAV is well-established and has been localized to chromosome 19 of humans (Kotin et al. (1990) *Proc. Natl. Acad. Sci.*, 87:2211-2215). Knowledge of the integration site reduces the danger of random insertional events into the cellular genome that can activate or inactivate host genes or interrupt coding sequences. AAV also is useful for gene therapy applications because its host range is broad, exhibiting tropism for many cell types. AAV also can infect both non-dividing and dividing cells.

AAV vectors can be derived from any naturally occurring AAV serotype, including AAV-1, AAV-2, AAV-3, AAV-4, AAV-5, AAV-6, AAV-7, AAV-8 or AAV-9. Such viruses are well known and available to one of skill in the art (see e.g. Grimm et al. (2003) *Current Gene Therapy*, 3:281-304; Muramatsu et al. (1996) *Virol.*, 221:208-217; Chiorini et al. (1997) *J. Virol.*, 71:6823-6833; Chiorini (1999) *J. Virol.*, 73:1309-1319; Rutledge et al. (1998) *J. Virol*, 72:309-319; Xiao et al. (1999) *J. Virol.*, 73:3994-4003; Gao et al. (2002) *Proc Natl. Acad. Sci.*, 99:11854-11859; Kotin (1994) *Human Gene Therapy*, 5:793-801). Other serotypes also are known and available and include AAV-8 to AAV-12. For example, many AAV vectors are available from American Type Culture Collection (ATCC, Rockville, Md.; see e.g. VR-197, VR-645, VR-646, VR-680, VR-681, VR-1449, VR-1523, VR-1616). Also available are compatible host cells and helper virus. AAV vectors also include "pseudotyped" AAV vectors, in which the AAV-2 vector genome is cross-packaged into the capsids of the other AAV serotypes (Burger et al. (2004) Mol. Ther., 10:302-17; U.S. Pat. No. 7,094,604). Such pseudotyped AAV vectors overcome limitations of AAV-2-derived serotypes, such as their inefficiency at transducing some cells, such as liver or muscle cells.

Many AAV vectors exhibit widespread transduction throughout multiple tissues, such as skeletal and cardiac muscles, following delivery methods that achieve systemic expression. These include, for example, AAV serotypes-6, -8 and -9. In particular, AAV vectors include an adenovirus-associated serotype 9 (AAV-9; GenBank Accession No. AY530629.1; Gao et al. (2004) J. Virol., 78:6381-6388). AAV-9 is a vector that can bypass the blood brain barrier to target the central nervous system (CNS) (see e.g. Foust et al., (2009) *Nature Biotechnology*, 27:59-65; Duque et al. (2009) *Mol. Ther.*, 17:1187-1196). Hence, in examples of neurodegenerative diseases or other diseases herein that affect or are associated with the brain or CNS, AAV-9 can be used as the delivered agent to encode a protein of interest for delivery systemically (e.g. delivery to the liver or portion thereof for expression in the blood).

AAV vectors include recombinant AAV vectors that contain a heterologous nucleic acid of interest. Procedures for generating such vectors are known to one of skill in the art. For example, standard approaches to the generation of AAV vectors requires transfection of a host cell with an AAV vector genome containing a nucleic acid molecule of interest flanked by the AAV ITR sequences, transfection of the host cell by a plasmid encoding the genes for the AAV rep and cap proteins that are required in trans, and infection of the transfected cell with a helper virus to supply the non-AAV helper functions required in trans (Muzyczka (1992) *Curr. Top. Micro. Immunol.*, 158:97-129; U.S. Pat. No. 5,139, 941). The helper virus can be an adenovirus or other helper virus. The helper virus proteins activate transcription of the AAV rep gene, and the rep proteins then activate transcription of the AAV cap genes. The cap proteins then utilize the ITR sequences to package the AAV genome into a viral particle.

Alternatively, recombination of AAV virions can be helped using a plasmid containing helper function genes, in combination with infection by one of the well-known helper viruses that can be used as the source of replicative functions (see e.g. U.S. Pat. Nos. 5,622,856 and 5,139,941). Similarly, the skilled artisan can make use of a plasmid containing accessory function genes, in combination with infection by wt AAV, to provide the necessary replicative functions. A triple transfection method also can be used to produce rAAV virions, which is a method that does not require helper virus (see e.g., U.S. Pat. No. 6,001,650). This is accomplished by use of three vectors for rAAV virion production: an AAV helper function vector, an accessory function vector, and a rAAV vector.

References illustrating the use of AAV viruses in gene therapy include, but are not limited to, Sheridan (2011) *Nature Biotechnology,* 29:121 iii. Retrovirus

Viral vectors for use as a delivered agent in the methods, compositions and uses herein include a retroviral vector (see e.g., Miller (1992) *Nature,* 357:455-460). Retroviral vectors are well suited for delivering nucleic acid into cells because of their ability to deliver an unrearranged, single copy gene into a broad range or rodent, primate and human somatic cells. Retroviral vectors integrate into the genome of host cells. Unlike other viral vectors, they only infect dividing cells.

Retroviruses are RNA viruses such that the viral genome is RNA. When a host cell is infected with a retrovirus, the genomic RNA is reverse transcribed into a DNA intermediate, which is integrated very efficiently into the chromosomal DNA of infected cells. This integrated DNA intermediate is referred to as a provirus. Transcription of the provirus and assembly into infectious virus occurs in the presence of an appropriate helper virus or in a cell line containing appropriate sequences permitting encapsulation without coincident production of a contaminating helper virus. A helper virus is not required for the production of the recombinant retrovirus if the sequences for encapsulation are provided by co-transfection with appropriate vectors.

The retroviral genome and the proviral DNA have three genes: the gag, the pol and the env, which are flanked by two long terminal repeat (LTR) sequences. The gag gene encodes the internal structural (matrix, capsid, and nucleocapsid) proteins and the env gene encodes viral envelope glycoproteins. The pol gene encodes products that include the RNA-directed DNA polymerase reverse transcriptase that transcribes the viral RNA into double-stranded DNA, integrase that integrate the DNA produced by reverse transcriptase into host chromosomal DNA, and protease that acts to process the encoded gag and pol genes. The 5' and 3' LTRs serve to promote transcription and polyadenylation of the virion RNAs. The LTR contains all other cis-acting sequences necessary for viral replication.

Retroviral vectors are described by Coffin et al., *Retroviruses,* Cold Spring Harbor Laboratory Press (1997). Exemplary of a retrovirus is Moloney murine leukemia virus (MMLV) or the murine stem cell virus (MSCV). Retroviral vectors can be replication-competent or replication-defective. Typically, a retroviral vector is replication-defective in which the coding regions for genes necessary for additional rounds of virion replication and packaging are deleted or replaced with other genes. Consequently, the viruses are not able to continue their typical lytic pathway once an initial target cell is infected. Such retroviral vectors, and the necessary agents to produce such viruses (e.g. packaging cell line) are commercially available (see e.g. retroviral vectors and systems available from Clontech, such as Catalog number 634401, 631503, 631501, and others, Clontech, Mountain View, Calif.).

Such retroviral vectors can be produced as delivered agents by replacing the viral genes required for replication with the nucleic acid molecule to be delivered. The resulting genome contains an LTR at each end with the desired gene or genes in between. Methods of producing retrovirus are known to one of skill in the art (see e.g. International published PCT Application No. WO1995/026411). The retroviral vector can be produced in a packaging cell line containing a helper plasmid or plasmids. The packaging cell lines provides the viral proteins required for capsid production and the virion maturation of the vector (e.g. gag, pol and env genes). Typically, at least two separate helper plasmids (separately containing the gag and pol genes; and the env gene) are used so that recombination between the vector plasmid cannot occur. For example, the retroviral vector can be transferred into a packaging cell line using standard methods of transfection, such as calcium phosphate mediated transfection. Packaging cell lines are well known to one of skill in the art, and are commercially available. An exemplary packaging cell line is GP2-293 packaging cell line (Catalog Numbers 631505, 631507, 631512, Clontech). After sufficient time for virion product, the virus is harvested. If desired, the harvested virus can be used to infect a second packaging cell line, for example, to produce a virus with varied host tropism. The end result is a replicative incompetent recombinant retrovirus that includes the nucleic acid of interest but lacks the other structural genes such that a new virus cannot be formed in the host cell.

References illustrating the use of retroviral vectors in gene therapy include: Clowes et al., (1994) *J. Clin. Invest.* 93:644-651; Kiem et al., (1994) *Blood* 83:1467-1473; Salmons and Gunzberg (1993) *Human Gene Therapy* 4:129-141; Grossman and Wilson (1993) *Curr. Opin. in Genetics and Devel.* 3:110-114; Sheridan (2011) *Nature Biotechnology,* 29:121; Cassani et al. (2009) *Blood,* 114:3546-3556.

iv. Lentivirus

Lentiviruses are a subclass of retroviruses. Exemplary of lentiviruses are HIV, SIV and FIV. Unlike other retroviruses, lentiviruses are able to integrate into the genome of non-dividing cells. Thus, for example, lentiviral vectors have been reported to deliver genes to primary livers cells efficiently and permanently, integrating into the genome of non-dividing primary liver cells (Lewis and Emerman (1994) *J. Virol.,* 68:510-6). Lentiviral vectors also do not suffer from the same transcription silencing mechanism as MMLV retroviral vectors. Lentiviruses differ from other retroviruses in that they have karyophilic determinants contained in several virion proteins, such as matrix or VPR, which interact with the nuclear import machinery and mediate active transportation of the viral pre-integration complex through the nucleopore. Therefore, lentiviral integration into the genome of the host cells is not dependent on cell division.

Similar to other retroviruses, lentiviruses contain gag, pol and env genes that are the main genes coding for viral proteins. In addition, there also are other accessory genes that are involved in regulation of synthesis, processing of viral RNA and other replicative functions (e.g. Tat and Rev in HIV). These are flanked by two long terminal repeat (LTR) sequences. The replication cycle is initiated by binding of a viral glycoprotein to a host cell receptor, fusion of the membranes, and entry of the virus into the cell. Upon entry the virus is uncoated and reverse transcription takes place leading to the formation of a pre-integration complex (PIC). It is the other accessory genes that play a role in the formation of a PIC and the ability of lentiviruses to infect non-dividing cells by actively entering the nucleus of a cell through the nuclear envelope via the PIC. Once the provirus enters the nuclear envelope, it integrates itself into the host genome.

Exemplary lentivirus vectors are based on HIV-1, HIV-2, SIV or FIV. In order to generate safe lentiviral vectors, packaging cell lines are created that contain several plasmid vectors, for example a four plasmid vector system. For example, a first plasmid contains accessory proteins (e.g. tat, brf, vpr and nef) deleted such that it contains only the promoter, gag and pol and the Psi packaging sequence that allows the transcribed viral RNA to be incorporated into the assembly of new virus, a second plasmid contains the reverse transcriptase, a third plasmid contains the env gene replaced with the Vesicular Stomatitis Virus Envelope Protein (VSV-G), and a fourth plasmid is the vector of interest by replacing the viral genes required for replication with the nucleic acid molecule to be delivered.

Such lentiviral vectors, and systems and methods of producing lentivirus, are known in the art (see e.g. Buchshacher and Wong-Staal (2000) *Blood*, 95:2499-2504; Blomer et al. (1997) *J. Virol.*, 71:6641-9; Choi et al. (2001) *Stem Cells*, 19:236-46; U.S. Pat. No. 6,218,186). The lentiviral vectors are replication defective and do not contain the genes required for replication. To produce a lentivirus, several packaging plasmids are transfected into a packaging cell line, generally derivatives of HEK 293 or other similar cell line (e.g. 293FT cells, Catalog number R700-07, Invitrogen, Life Technologies, Carlsbad, Calif.); 293LTV cell line, catalog number LTV-100, Cell Biolabs, Inc., San Diego, Calif.; Lenti-Pac 293Ta Cell Line, Catalog Number CLv-PK-01, GeneCopoeia, Rockville, Md.). The packaging plasmids separately encode virion proteins (e.g. capsid and reverse transcriptase) and the nucleic acid molecule to be delivered by the vector (which can be transfected into the packaging cell lines). A single-stranded RNA viral genome is transcribed, which is packaged into the virion. Methods of generating lentiviral vectors are well known to one of skill in the art (see e.g. Naldine et al. (1996) *Science*, 272:263-267). Lentiviral vectors and systems for producing virus are commercially available (see e.g., Lentivrial expression vectors such as pSMPUW Lentiviral vector and derivatives thereof and Lentiviral Expression and Packaging Systems available from Cell Biolabs, Inc.).

Lentiviral vectors have been used in gene therapy applications (see e.g. Manilla et al. (2005) *Human Gene Therapy*, 16:17-25; Sheridan (2011) *Nature Biotechnology*, 29:121). In particular, lentiviral vectors have been used for the delivery of short-interfering RNA (siRNA) (Sachdeva et al. (2007) *Journal of Medical Virology*, 79:118-26).

b. Non-Viral Vectors

Non-viral based agents can be used as delivered agents in the methods, uses and compositions herein. These include non-viral expression vectors. Non-viral expression vectors contain a nucleic acid of interest, e.g. a nucleic acid encoding a polypeptide, an antisense DNA or an siRNA, wherein the nucleic acids are operably linked to an expression control sequence (e.g. promoter). Suitable vector backbones include, for example, those routinely used in the art such as plasmids, minicircles, and artificial chromosomes (e.g. mammalian artificial chromosomes (MACs), bacterial artificial chromosomes (BACs), yeast artificial chromosomes (YACs), or plant artificial chromosomes (PACs). Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

Vectors typically contain one or more regulatory regions, which are functionally inked to the encoding region. Regulatory regions include, without limitation, promoter sequences, enhancer sequences, SMARS (scaffold matrix attachment regions), insulators, response elements, protein recognition sites, inducible elements, protein binding sequences, 5' and 3' untranslated regions (UTRs), transcriptional start sites, termination sequences, polyadenylation sequences, and introns.

Promoters controlling transcription from vectors in mammalian host cells may be obtained from various sources, for example, the genomes of viruses such as polyoma, Simian Virus 40 (SV40), adenovirus, retroviruses, hepatitis B virus, and most preferably cytomegalovirus (CMV), or from heterologous mammalian promoters, e.g. 3-actin promoter or EF1α promoter, or from hybrid or chimeric promoters (e.g., CMV promoter fused to the β-actin promoter). Promoters from the host cell or related species are also useful herein.

Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 base pairs (bp) in length, and they function in cis. Enhancers usually function to increase transcription from nearby promoters. Enhancers can also contain response elements that mediate the regulation of transcription. While many enhancer sequences are known from mammalian genes (globin, elastase, albumin, fetoprotein, and insulin), typically, one will use an enhancer from a eukaryotic cell virus for general expression. Examples are the SV40 enhancer on the late side of the replication origin, the cytomegalovirus early promoter enhancer, the polyoma enhancer on the late side of the replication origin, and adenovirus enhancers.

The promoter and/or the enhancer can be inducible (e.g. chemically or physically regulated). A chemically regulated promoter and/or enhancer can, for example, be regulated by the presence of alcohol, tetracycline, a steroid, or a metal. A physically regulated promoter and/or enhancer can, for example, be regulated by environmental factors, such as temperature and light. Optionally, the promoter and/or enhancer region can act as a constitutive promoter and/or enhancer to maximize the expression of the region of the transcription unit to be transcribed. In certain vectors, the promoter and/or enhancer region can be active in a cell type specific manner. Optionally, in certain vectors, the promoter and/or enhancer region can be active in all eukaryotic cells, independent of cell type. Examples of promoters of this type are the CMV promoter, the SV40 promoter, the β-actin promoter, the EF1α promoter, and the retroviral long terminal repeat (LTR).

The vectors also can include, for example, origins of replication and/or markers. A marker gene can confer a selectable phenotype on a cell (e.g., antibiotic resistance) or be otherwise detectable. Examples of detectable markers include the *E. coli* lacZ gene, green fluorescent protein (GFP), and luciferase. In addition, an expression vector can include a tag sequence designed to facilitate manipulation or detection (e.g., localization) of the expressed polypeptide. Tag sequences, such as GFP, glutathione S-transferase (GST), polyhistidine, c-myc, hemagglutinin, or FLAG™ tag (Kodak; New Haven, Conn.) sequences typically are expressed as a fusion polypeptide, including the encoded polypeptide and the marker. Such tags can be inserted anywhere within the encoded polypeptide including at either the carboxyl or amino terminus.

In particular, a desired nucleic acid molecule expression vector containing a desired nucleic acid molecule of interest, for example, encoding a gene of interest, antisense DNA or siRNA or other nucleic acid molecule, can be delivered as naked DNA can be used as a delivered agent. The efficiency of delivery of the naked DNA in the methods herein can be increased by using various methods well-known to one of skill in the art (see e.g. Li and Huang (2006) *Gene Therapy*, 13:1313-1319). Such methods include, for example, such as electroporation, sonoporation or "gene gun" approaches as described elsewhere herein and known to one of skill in the art. Also, the efficiency of delivery can be increased by encapsulation in liposomes or complexing with polymers as described herein. In a particular example, the nucleic acid can be delivered as a nanoparticle.

References illustrating the use of non-vectors in gene therapy include: Sheridan (2011) *Nature Biotechnology*, 29:121.

Nanoparticle

Non-viral-based delivered agents include nanoparticles (generally of 3-200 nm) where the nucleic acid molecule is encapsulated or conjugated to a particular carrier that contain a targeting molecule for specific targeting to cells of interest. The generation of nanoparticles for gene therapy is well known in the art (see e.g. Cho et al. (2008) *Clin. Cancer. Res.*, 14:1310; Jin et al. (2007) *Biotechnol. Prog.*, 23:32-41). The nanoparticle can be made as a polymer, such as by using polymer carriers (e.g. polylactic acid, polysaccharides, poly(cyanoactylates, poly(lactide-co-glycolide)) or branched polymers to generate dendrimers, such as by growth polymerization steps from poly(L-glutamic acid (PGA), polyamidoamine (PAMAM), poly(ethylene glycol) (PEG) and polyethylenimine (PEI). Biodegradable polymers can be used which include, for example, polylactic acid, polyglycolic acid, polylactic-glycolic acid (PLGA) or poly(methyl methacrylate) (PMMA). Other types of nanoparticles can be generated as a liposome using various lipid mixtures; as a magnetic nanoparticle using iron oxide, as a silica nanoparticle using $SiO_2$ or as a gold nanoparticle using chlorauric acid or sodium citrate. Nanoparticle systems are well known to one of skill in the art.

The nanoparticles can be functionalized by conjugating or coating a targeting molecule onto the surface, for example, a targeting molecule that is a ligand for or otherwise binds to receptors expressed in the cells to be targeted. Such targeting molecules include, but are not limited to, ligands, antibodies, or peptides. In particular examples, a dual-ligand approach can be used to increase the selectivity for a cell. An example of a targeting molecule could be a growth factor, e.g., a fibroblast growth factor, that targets a fibroblast growth factor receptor. The choice of targeting molecule depends on the particular application, including the tissue or organ to be targeted, and can be empirically determined by one of skill in the art. Targeted nanoparticles are known in the art (see e.g., Franzen (2011) *Expert Opin. Drug. Deliv.* 8(3):281-98; Faraji and Wipf (2009) *Bioorg. Med. Chem.* 17(8):2950-62; Saija et al., (2009) *Curr. Drug. Discov. Technol.* 6(1):43-51). In particular, methods for tissue-specific gene delivery of nanoparticles are known in the art (see e.g. Harris et al. (2010) *Biomaterials*, 31:998-1006. For example, parenchymal hepatocytes express asialoglycoprotein receptor (ASGP-R) and hepatic lectins. Thus, liver-specific nanoparticles are known in the art and can include functionalization with agents that recognize the asialoglycoprotein receptor (ASGP-R) and other receptors including, for example, asialo-feutin, asialo-transferrin, asialo-ceruloplasmin, asialo-lactoferrin, asialo-orosomucoid, lac-BSA, hepatoglobulin, antibodies and galactose (see e.g. Pathak et al. (2008) *Int. J. Nanomedicine*, 3:31-49).

c. Whole Cell

The methods herein can be used to deliver cells containing ex vivo delivered nucleic acid as the delivered agent. For example, cells isolated from a patient or a donor introduced with an exogenous heterologous nucleic acid can be delivered directly to a patient by the methods herein. The advantage of the present method is that the immune response to the cells is reduced by the vascular compartmentalization. Thus, provided herein is a method of administering a genetically modified cell or cells to a compartmentalized organ or portion thereof in the subject. The method includes compartmentalizing an organ or portion thereof, administering a genetically modified cell or cells to the compartmentalized organ or portion thereof, maintaining the compartmentalization for a time period subsequent to the administration of the genetically modified cell or cells as described herein; and restoring vascular circulation to the organ or portion thereof. The amount of cells that are delivered depends on the desired effect, the particular nucleic acid, the subject being treated and other similar factors, and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, or fetal liver. For example, the genetically modified cells can be pluripotent or totipotent stem cells (including induced pluripotent stem cells) or can be embryonic, fetal, or fully differentiated cells. The genetically modified cells can be cells from the same subject or can be cells from the same or different species as the recipient subject. In a preferred example, the cell used for gene therapy is autologous to the patient. Methods of genetically modifying cells and transplanting cells are known in the art.

Typically, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, *Meth. Enzymol.* (1993) 217:599-618; Cotten et al., *Meth. Enzymol.* (1993) 217:618-644; Cline, *Pharmac. Ther.* (1985) 29:69-92) and can be used provided that the necessary developmental and physiological functions of the recipient cells are not disrupted. In particular examples, the method is one that permits stable transfer of the nucleic acid to the cell, so that the nucleic acid is expressible by the cell and heritable and expressible by its cell progeny.

3. Exemplary Gene Therapy Agents

The delivered agent containing a nucleic acid molecule for use in the methods, uses or compositions herein can be any viral or non-viral vector encoding a nucleic acid of interest, such as any gene therapy agent that is known to the skilled artisan. It is within the level of a skilled artisan to choose an appropriate gene therapy agent depending on the particular disease or condition that is being treating. Hundreds of gene therapy agents are in clinical trials, and several have received market approval in Europe (e.g. Glybera®, AdLPL) and China (e.g. rAd53, Gendicine®) (see e.g. Sheridan (2011) Nature Biotechnology, 29:121).

For example, exemplary gene therapy vectors include adenovirus- or AAV-based therapeutics. Non-limiting examples of adenovirus-based or AAV-based therapeutics for use in the methods, uses or compositions herein include, but are not limited to: rAd-p53, which is a recombinant adenoviral vector encoding the wild-type human tumor suppressor protein p53, for example, for the use in treating a cancer (also known as Gendicine®, Genkaxin®, Qi et al. (2006) *Modern Oncology*, 14:1295-1297); Ad5_d11520, which is an adenovirus lacking the E1B gene for inactivating host p53 (also called H101 or ONYX-015; see e.g. Russell et al. (2012) *Nature Biotechnology*, 30:658-670); AD5-D24-GM-CSF, an adenovirus containing the cytokine GM-CSF, for example, for the use in treating a cancer (Cerullo et al. (2010) *Cancer Res.*, 70:4297); rAd-HSVtk, a replication deficient adenovirus with HSV thymidine kinase gene, for example, for the treatment of cancer (developed as Cerepro®, Ark Therapeutics, see e.g. U.S. Pat. No. 6,579,855; developed as ProstAtak™ by Advantagene; International PCT Appl. No. WO2005/049094); rAd-TNFα, a replication-deficient adenoviral vector expressing human tumor necrosis factor alpha (TNF-α) under the control of the chemoradiation-inducible EGR-1 promoter, for example, for the treatment of cancer (TNFerade™, GenVec; Rasmussen et al. (2002) *Cancer Gene Ther.*, 9:951-7; rAd-FGF4, an adenoviral vector serotype 5 encoding FGF-4, for example, for the treatment of angiogenesis and coronary artery disease (GENERX, *BioDrugs*, 2002, 16:75-6; U.S. Pat. No. 5,792,453); rAd-VEGF-D, an adenoviral vector 5 containing a gene encoding vascular endothelial growth factor (VEGF-D), for example, for use in treating angiogenesis-related diseases and conditions (Trinam®, Ark Therapeutics; U.S. Patent Publication No. US20120308522); rAd-PDGF, an adenoviral vector 5 containing a gene encoding PDGF-B, for example, for the treatment of wounds (Excellarate, GAM501 Tissue Repair Co.; Blume et al. (2011) *Wound Repair Regen.*, 19:302-308); Ad-IFNβ, an adenovirus serotype 5 vector from which the E1 and E3 genes have been deleted expressing the human interferon-beta gene under the direction of the cytomegalovirus (CMV) immediate-early promoter, for example for treating cancers (BG00001 and H5.110CMVhIFN-beta, Biogen; Sterman et al. (2010) *Mol. Ther.*, 18:852-860); an AAV containing a gene encoding the lipoprotein lipase deficiency (LPLD) gene, for example, for treatment of subjects with LPLD or familial hyperchylomicronemia (alipogene tiparvovec, Glybera®, Amsterdam Molecular Therapeutics; see e.g. International Published Appl. No. WO2010/134806; WO2001000220, Yla-Herttuala (2012) *Mol. Ther.*, 20:1831-2); AMT-021, an AAV containing a gene encoding the enzyme porphobilinogen deaminase (PBGD), for example, for treatment of subjects with Acute Intermittent *Porphyria* (AIP) (see e.g. U.S. Patent Publication No. US2011/0262399; European Patent No. EP1049487); rAAV9-CMV-hNaGlu, an AAV-9 containing a gene encoding NaGlu under the control of the CMV promoter (see e.g. Fu et al. (2011) *Mol. Ther.*, 19:1025-33).

Other exemplary gene therapy agents for use in the methods, uses and compositions herein include, but are not limited to, rAd-H1F1α (Genzyme/Sunway), V930/V932 (Merck), NLX-P101 (Neurologix), Toca-511 (Tocagen, San Dieog), LentiGlobin (Bluebird Bio), ProSavin (Oxford Bio-Medica), rAAV-1-CB-hAAT (Applied Genetic Technologies), rAAV2-CB-human retinal pigment epithelium specific 65 dalton protein (RPE65) (Applied Genetic Technologies), AMT-101 (Amsterdam Molecular), Ad5CMV-p53 (Aventis), CERE-120 (Ceregene, San Diego), CERE-110 (Ceregene, San Diego), SERCA-2a (Celladon, La Jolla), AAV2-sFLT01 (Genzyme), tgAAG76 (Targeted Genetics, Seattle), tgAAC94 (Targeted Genetics, Seattle), GX-12 (Genexine, Seoul, Korea), SC 1B1 (ScanCell, Nottingham, UK), Allovectin-7 (Vical, San Diego), VM202 (ViroMed, Minnetonka, Minn.) or Rexin-G nanoparticle (Epeius Biotechnologies, San Marino, Calif.).

E. Compositions, Systems and Kits

Compositions containing the delivered agents for use in delivery to a tissue or organ or portion thereof by the compartmentalized method herein are provided. The compositions provided herein are suitable for administration in vivo. The compositions are formulated for parenchymal administration. Typically, the compositions herein are provided as injectables. Injectables can be prepared in conventional forms, either as liquid solutions or suspensions, solid forms suitable for solution or suspension in liquid prior to injection, or as emulsions. Generally, the delivered agent compositions provided herein are in liquid form.

The compositions can contain a pharmaceutically acceptable carrier. For injection, the carrier will typically be a liquid. In particular, the pharmaceutical carrier is any carrier that is not biologically or otherwise undesirable, i.e. the composition is administered to a subject without causing undesirable side effects or interacting in a deleterious manner with the other components of the pharmaceutical composition in which it is contained. The carrier is selected to minimize degradation of the active ingredient and to minimize adverse side effects to the subject. For example, pharmaceutically acceptable carriers for administration to cells typically is a carrier acceptable for delivery by injection, and do not include agents such as detergents or other compounds that could damage cells.

Suitable carriers and their formulations are described in *Remington: The Science and Practice of Pharmacy*, 21$^{st}$ Edition, David B. Troy, ed., Lippicott Williams & Wilkins (2005). Compositions for administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. As an injection medium, it is general carriers include water that contains additives usual for injection solutions, such as stabilizing agents, salts or saline, and/or buffers. Exemplary physiologically acceptable carriers include sterile water, saline, buffered solutions or dextrose solution. For example, exemplary physiological carriers include physiological saline, phosphate buffered saline, balanced salt solution (BSS), or Ringer's solution and solutions containing thickening and solubilizing agents, such as glucose, polyethylene glycol, and polypropylene glycol and mixtures thereof. The pH of the solution is generally about 5 to about 8 or from about 7 to 7.5. If necessary, the pH of the formulation can be adjusted with pharmaceutically acceptable acids, bases or buffers to enhance the stability of the formulated compound of its delivery form.

The delivered agent (that is the nucleic acid molecule or contains the nucleic acid molecule) can be formulated as the sole pharmaceutically active ingredient in the composition or can be combined with other active agents for the particular disorder treated. Optionally, other medicinal agents, pharmaceutical agents, carriers, adjuvants, diluents can be included in the compositions provided herein. For example, any one or more of a wetting agents, emulsifiers and lubricants, such as sodium lauryl sulfate and magnesium sterate, as well as coloring agents, release agents, coating agents, sweetening, flavoring and perfuming agents, preservatives, antioxidants, chelating agents and inert gases also can be present in the compositions. Exemplary other agents and excipients that can be included in the compositions include, for example, water soluble antioxidants, such as ascorbic acid, cysteine hydrochloride, sodium bisulfate, sodium metabisulfite, sodium sulfite; oil-soluble antioxidants, such as ascorbyl palmitate, butylated hydroxyanisole (BHA), butylated hydroxytoluene (BHT), lecithin, propyl gallate, α-tocopherol; and metal chelating agents, such as citric acid, ethylenediamine tetraacetic acid (EDTA), sorbitol, tartaric acid and phosphoric acid.

The compositions also can be formulated for sustained release formulations, such as adsorbed to biodegradable supports, including collagen sponges, or in liposomes. Sustained release formulations can be formulated for multiple dosage administration, so that during a selected period of time, such as a month or up to about a year, several dosages are administered. Thus, for example, liposomes can be prepared such that a total of about two to up to about five or more times the single dosage is administered in one injection.

The compositions can be prepared with carriers that protect them against rapid elimination from the body, such as time release formulations or coatings. Such carriers include controlled release formulations, such as, but not limited to, microencapsulated delivery systems, and biodegradable, biocompatible polymers, such as ethylene vinyl acetate, polyanhydrides, polyglycolic acid, polyorthoesters, polylactic acid and other types of implants that can be placed directly into the body. The compositions also can be administered in pellets, such as ELVAX pellets (ethylene-vinyl acetate copolymer resin).

Liposomal suspensions, including tissue-targeted liposomes, also can be suitable as pharmaceutically acceptable carriers. For example, liposome formulations can be prepared by methods known to those of skill in the art (see e.g., Kim et al. (1983) Bioch. Bioph. Acta 728:339-348; Assil et al. (1987) Arch Ophthalmol. 105:400; and U.S. Pat. No. 4,522,811). The delivered agent can be encapsulated into the aqueous phase of liposome systems.

The active materials also can be mixed with other active materials, that do not impair the desired action, or with materials that supplement the desired action or have other actions, including viscoelastic materials, such as hyaluronic acid, which is sold under the trademark HEALON, which is a solution of a high molecular weight (MW) of about 3 millions fraction of sodium hyaluronate (manufactured by Pharmacia, Inc; see e.g., U.S. Pat. Nos. 5,292,362, 5,282,851, 5,273,056, 5,229,127, 4,517,295 and 4,328,803). Additional active agents can be included.

1. Dosage Formulations

Provided herein are compositions containing a delivered agent formulated for parenchymal administration to a tissue or organ in an amount that is less than 100-fold or less than the amount of the same delivered agent that is administered intravenously. For example, compositions are provided containing a delivered agent formulated for parenchymal administration to a tissue or organ in an amount that is less than 100-fold, 200-fold, 300-fold, 400-fold, 500-fold, 600-fold, 700-fold, 800-fold, 900-fold, 1000-fold, 5000-fold, 10000-fold or less than the amount of the same delivered agent that is administered intravenously to the target organ or tissue. The compositions can be provided as single dosage formulations or multiple dosage formulations.

For example, compositions are provided containing an amount of a delivered agent that is an adenovirus or adeno-associated virus. In particular, the adenovirus or adeno-associated virus is one that contains at least one heterologous nucleic acid molecule in its genome, such as a therapeutic nucleic acid molecule. The amount of adenovirus in the composition for single dosage administration is 10 pfu to $1\times10^{12}$ pfu, $1\times10^{2}$ pfu to $1\times10^{10}$, $1\times10^{3}$ pfu to $1\times10^{10}$ pfu, $1\times10^{3}$ pfu to $1\times10^{9}$ pfu, $1\times10^{3}$ pfu to $1\times10^{8}$ pfu, or $1\times10^{6}$ pfu to $1\times10^{9}$ pfu, or is 10 particles to $1\times10^{12}$ particles, $1\times10^{2}$ particles to $1\times10^{10}$ particles, $1\times10^{3}$ particles to $1\times10^{10}$ particles, $1\times10^{3}$ particles to $1\times10^{9}$ particles, $1\times10^{3}$ particles to $1\times10^{8}$ particles, or $1\times10^{6}$ particles to $1\times10^{9}$ particles. Generally, the amount of adenovirus in the composition for single dosage administration is 10 vp to $1\times10^{12}$ vp, $1\times10^{2}$ vp to $1\times10^{10}$ vp, $1\times10^{3}$ vp to $1\times10^{12}$ vp, $1\times10^{3}$ vp to $1\times10^{1}$ vp, $1\times10^{3}$ vp to $1\times10^{9}$ vp, $1\times10^{3}$ vp to $1\times10^{8}$ vp, $1\times10^{3}$ vp to $1\times10^{6}$ vp, $1\times10^{6}$ vp to $1\times10^{12}$ vp, $1\times10^{6}$ vp to $1\times10^{10}$ vp, or is less than or about less than $1\times10^{12}$ vp, $1\times10^{11}$ vp, $1\times10^{10}$ vp, $1\times10^{9}$ vp, $1\times10^{8}$ vp, $1\times10^{7}$ vp, $1\times10^{6}$ vp, $1\times10^{5}$ vp, $1\times10^{4}$ vp, $1\times10^{3}$ vp, $1\times10^{2}$ vp, 10 vp or less. In other examples, the amount of adenovirus in the composition for single dosage administration is 10 pfu to $1\times10^{12}$ pfu, $1\times10^{2}$ pfu to $1\times10^{10}$ pfu, $1\times10^{3}$ pfu to $1\times10^{12}$ pfu, $1\times10^{3}$ pfu to $1\times10^{10}$ pfu, $1\times10^{3}$ pfu to $1\times10^{9}$ pfu, $1\times10^{3}$ pfu to $1\times10^{8}$ pfu, $1\times10^{3}$ pfu to $1\times10^{6}$ pfu, $1\times10^{6}$ pfu to $1\times10^{12}$ pfu, $1\times10^{6}$ pfu to $1\times10^{10}$ pfu, or is less than or about less than $1\times10^{12}$ pfu, $1\times10^{11}$ pfu, $1\times10^{10}$ pfu, $1\times10^{9}$ pfu, $1\times10^{8}$ pfu, $1\times10^{7}$ pfu, $1\times10^{6}$ pfu, $1\times10^{5}$ pfu, $1\times10^{4}$ pfu, $1\times10^{3}$ pfu, $1\times10^{2}$ pfu, 10 pfu or less. The composition can be formulated in 10 μL to 5 mL, such as 20 μL to 1 mL or 50 μL to 500 μL. In such compositions, the adenovirus is formulated for parenchymal administration. In particular examples, the adenovirus is formulated for parenchymal administration to the liver.

2. Combinations

The compositions containing a delivered agent formulated for parenchymal administration can be provided in combination with other agents. The other agents can be agents that increase the efficiency or facilitate entry of the delivered agent by parenchymal cells, or regulate or modulate the immune response to the delivered agent.

For example, combinations are provided herein containing a composition containing a delivered agent formulated for parenchymal administration and an agent or delivery vehicle that binds to or complexes with the delivered agent and mediates its entry into cells. Exemplary agents include, but are not limited to, cationic liposomes and lipids, lipoproteins, synthetic polymers or polypeptides, mineral compounds or vitamins. Exemplary of polymers include polycations or polyanions. For example, a delivered agent can be provided as a combination with polyamine, calcium phosphate precipitate, histone protein, protamine, polyethylenemine, polylysisne, polyarginine, polyornithine, DEAE dextrane, polybrene, polyampholyte complex, spermine, spermidine, purtrescine, human serum albumin, DNA binding proteins, non-histone chromosomal proteins, coat proteins from DNA viruses and polymers of N-substituted glycines. The agents can be formulated separately or together.

In a further example, expression of the therapeutic transgene can be enhanced with transcriptional enhancers, such as histone deacetylase (HDAC) inhibitors, for example, hydroxamic acid, cyclic tetrapeptide, valproic acid and others. Thus, the delivered agent can be provided in combination with an agent or compound that is a transcriptional enhancer of the virus-specific cell surface receptor. Such agents or compounds include, for example, a histone deacetylase (HDAC) inhibitors. HDAC inhibitors include those of the class of hydroxamic acids, cyclic tetrapeptides, benzamides, electrophilic ketones or aliphatic acid compounds. For example, HDAC inhibitors include, but are not limited to, trischostatin A, vorinostat (SAHA), belionostat (PXD101), LAQ824, panobinostat (LBH589), entinostat (MS-275), C199, mocetinostat (MGCD0103), romidepsin (lstodax), valproic acid, PCI-24781, SB939, resminostat, givinostat, CUDC-101, AR-42, CHR-2845, CHR-3996, 4SC-202, CG200745, Kevetrin, or trichostatin A (TSA). Exemplary of an HDAC inhibitor is valproic acid, which is a transcriptional enhancer of the adenovirus receptor CAR. Studies have shown that adenoviral uptake is increased in the presence of valproic acid (Segura-Pancheco et al. (2007) *Genet. Vaccines Ther.,* 5:10). In such examples, the composition containing the delivered agent is formulated together or separately with the additional agent or compound (e.g. transcriptional enhancer agent). The transcriptional enhancer agent can be provided in an amount between or about between 50 mg to 8000 mg, such as or about between 100 mg to 5000 mg, 1000 mg to 4000 mg. The agent or compound composition in the combination can be formulated for single or multiple dosage administration. The additional agent or compound composition can be formulated for any route of administration that is acceptable and known to one of skill in the art. For example, the transcriptional enhancer can be formulated for oral administration, intravenous administration, subcutaneous administration or parenchymal administration.

In a further example, combinations are provided herein containing a composition containing a delivered agent formulated for parenchymal administration and a composition containing an immunosuppressive agent. Exemplary immunosuppressive agents include, but are not limited to, cyclosporine (Neoral®, Sandimmune®), prednisone (Novo Prednisone®, Apo Prednisone®), azathioprine (Imuran®), tacrolimus or FK506 (Prograf®), mycophenolate mofetil (CellCept®), sirolimus (Rapamune®), OKT3 (Muromorab CO3®, Orthoclone®), ATGAM & Thymoglobulin. In such examples, the composition containing the delivered agent is formulated together or separately with the immunosuppressive agent. The additional composition containing an immunosuppressive agent can be formulated for any route of administration that is acceptable and known to one of skill in the art. For example, the immunosuppressive agent can be formulated for oral administration, intravenous administration, subcutaneous administration or parenchymal administration.

3. Articles of Manufacture and Kits

The compositions or combinations can be packaged for storage and/or use. The packaging material for use in packaging the agents are well known to those of skill in the art. Examples of packaging materials include ampoules, bottles, tubes, vials, containers, syringes, and any packaging material suitable for a selected formulation and parenchymal administration. For example, the compositions or combinations can be enclosed in ampoules, disposable syringes or multiple or single dose vials made of glass, plastic or other suitable material. The packaging material can include a needle or other injection device so as to facilitate administration for parenchymal administration purposes. The choice of package depends on the particular delivered agent. In general, the packaging is non-reactive with the compositions contained therein. Also, the composition and packaging material is sterile.

For example, the composition containing a delivered agent can be provided in a container, such as a sealed sterile vial or syringe containing an amount such that upon administration a sufficient amount of delivered agent (e.g. viral particles) is delivered. The amount of delivered agent, such as an adenovirus or adeno-associated virus, in the composition is between or about between 10 pfu to $1 \times 10^{12}$ pfu, $1 \times 10^2$ pfu to $1 \times 10^{10}$, $1 \times 10^3$ pfu to $1 \times 10^{10}$ pfu, $1 \times 10^3$ pfu to $1 \times 10^9$ pfu, $1 \times 10^3$ pfu to $1 \times 10^8$ pfu, or $1 \times 10^6$ pfu to $1 \times 10^9$ pfu; or is between or about between 10 particles to $1 \times 10^{12}$ particles, $1 \times 10^2$ particles to $1 \times 10^{10}$ particles, $1 \times 10^3$ particles to $1 \times 10^{10}$ particles, $1 \times 10^3$ particles to $1 \times 10^9$ particles, $1 \times 10^3$ particles to $1 \times 10^8$ particles, or $1 \times 10^6$ particles to $1 \times 10^9$ particles. The volume of the composition in the container can be 50 µL to 50 mL, 50 µL to 5 mL, 50 µL to 500 µL, 100 µL to 10 mL, 100 µL to 5 mL, 100 µL to 2 mL, 100 µL to 1 mL, 200 µL to 4 mL, 200 µL to 2 mL, 1 mL to mL or 1 mL to 2 mL. For example, the container can be provided for single use or for multiple use administration. The volume of agent in the container can be 100 µL to 10 mL, where about 20 to 5 mL, such as 20 to 500 µl, 50 to 150 µl, 100 µL to 10 mL or 200 µl to 2 mL, containing at least about 10 to $10^{10}$ plaque forming units (pfu) or particles, such as $10^2$ to $10^6$ plaque forming units (pfu) or particles in such volume are delivered.

Compositions or combinations containing a delivered agent can be packaged as articles of manufacture containing packaging material, an amount of agent formulated for parenchymal administration for single or multiple dosage administration, and a label that indicates the delivered agent is for use in delivering a particular nucleic acid molecule and/or for use in a particular application.

Such enclosed compositions, combinations and articles of manufacture can be provided in kits. In particular, kits containing ampoules, bottles, tubes, vials, containers, syringes with a delivered agent composition enclosed therein are provided. The kits can optionally be supplied with a device that permits administration of the delivered agent such as a syringe, needle, or other injection device. The compositions can be contained in the item for administration or can be provided separately to be added later. The kit can, optionally, include instructions for application including dosages, dosing regimens and instructions for administration. Other reagents also can be provided. For example, the kits can optionally include a device that effects compartmentalization of a tissue or organ or portion thereof, implements for effecting mobilization of a tissue or organ, a timer in order to monitor compartmentalization and other reagents for use in practice of the method. For example, the kit can include a parenchymal clamp.

F. Assessing Delivery, Expression or Efficacy

In performing the compartmentalized method herein, any number of parameters can be monitored or assessed to confirm delivery of the delivered agent, expression of the nucleic acid molecule and/or to otherwise validate practice of the method. For example, entry of the delivered agent into cells can be monitored, the presence of the delivered agent in the parenchyma or in the systemic circulation can be assessed, expression of an encoded polypeptide can be assessed, toxicity of the tissue can be monitored or assessed and/or activation of the immune system can be determined.

One of skill in the art is familiar with such methods and techniques. Such methods and techniques can be optionally performed.

1. Monitoring of Delivered Agent

For example, upon delivery or administration of a delivered agent using the compartmentalized method herein, the presence of the delivered agent in the subject can be assessed or detected. For example, assays as exemplified herein to measure systemic release of the delivered agent or expressed transgene product in the peripheral blood prior to, during and after release of vascular isolation can be performed. Typically, in the methods herein, less than 10%, and generally less than 5%, 4%, 3%, 2% or 1% of the transgene product is detected in the systemic circulation following direct administration of the delivered agent to a tissue or portion herein using the methods herein.

Detection of the delivered agent can be facilitated by conjugation or operable linkage of the delivered agent or nucleic acid molecule to a detectable moiety. Detectable moieties are well-known to one of skill in the art, and include but are not limited to, chemiluminescent moieties, bioluminescent moieties, fluorescent moieties, radionuclides, and metals. For example, detectable moieties include, for example, luciferase, green fluorescent protein, red fluorescent protein, colloidal gold, iron, gadolinium, and gallium-67 and other moieties well-known to a skilled artisan.

The delivered agent can be monitored from a tissue or bodily fluid sample. For example, parenchymal tissue, and in particular a compartmentalized region, can be harvested and processed (e.g. by homogenization) and RNA or DNA isolated or purified therefrom. Bodily fluids that can be assayed include, for example, peripheral blood. Methods of extracting RNA and DNA from tissue or bodily fluids are well known to one of skill in the art. For example, TRIzol®-based methods are typically used for extract RNA from biological material (e.g. TRIzol® reagent, Life Technologies, Carlsbad, Calif.). For example, gene-specific primers or probes can be designed and the delivered agent or nucleic acid molecule can be detected using PCR and other standard methods known to one of skill in the art. This is exemplified herein in the Examples where PCR was performed using primers against luciferase.

Detection thereof in a tissue (e.g. homogenized sample) or biological fluid sample can also be effected using a fluorometer, luminometer, colorimetric plate reader, Geiger counter, liquid scintillation counter. The choice of method depends on the particular detectable moiety and is within the level of skill of one in the art. For example, luciferase activity can be assessed using a luminometer as exemplified herein in the Examples. Furthermore, detection is optionally performed by detecting expression of polypeptide encoded by the delivered agent in a biological sample from the subject. The polypeptide can be detected using procedures known to one of skill in the art, including, but not limited to, western blot, immunohistochemistry, immunofluorescence or ELISA.

In particular examples, parenchymal cells from tissues or organs also can be isolated and assessed for intracellular presence of the delivered agent. In particular, isolation of parenchymal cells typically is by enzyme digestion of tissues using trypsin, collagenases and/or other protease. Such procedures are well known to one of skill in the art (see e.g. Somers et al. (2007) DMD, 35:1797-1805; Methods in Cell Biology, vol XIII, David M. Prescott ed., Academic Press, 1976; Chapter 4, "Preparation of Isolated Rat Liver Cells", pp 29-83). For example, the tissue can be perfused, such as with phosphate-buffered saline, to remove any blood. The tissue can be minced with scissor and digested in a digestion medium containing a protease. This typically results in a cell suspension that can be filtered to collect the cells. Any residual protease can be inactivated, such as by collection of cells in fetal bovine serum. The cells can then be washed and cultured in a cell culture medium of choice that is known to be compatible with the particular cell. Cell viability can be assessed, and the freshly isolated cells can be assayed for the intracellular presence of delivered agents. The presence of intracellular agents can be assessed by fixation and permeabilization of the cell membranes (e.g. using commercially available reagents such as ORTHOPermeaFix™ (OPF) or the FIX&PERM Cell Permeabilization Kit®; An Der Grub Bio Research GmbH, Imtec). The cells can be assessed by flow cytometry, by using a plate reader device (e.g. fluorometer, luminometer or colorimetric plate reader), or by assessing radioactivity. In addition, if desired, microscopy methods can be used. In addition, cell homogenates can be prepared and used for Western Blot analysis.

2. Host Toxicity and Immune Activation

Tissue toxicity and immune responses initiated upon administration of the delivered agent also can be assessed. For example, toxicity can be assessed by histopathology of the underlying tissue or organ or portion thereof. Tissue samples can be obtained by biopsy and stained for histological analysis, typically using hematoxylin and eosin. Cellular abnormalities can be assessed. For example, histopathological analysis can identify inflammatory cell infiltrates, such as lymphocytic or neutrophil infiltrates, associated with immune activation. Comparisons can be made to a region of the same tissue or organ of the same subject that was not compartmentalized. In other examples, tissues from control subjects that were not treated by the method herein can be used.

Toxicity also can be monitored by assessing the expression of factors or markers that are upregulated, present or associated with injury of the tissue or organ. For example, biochemical markers of tissue injury can be assessed. Such markers are known to one of skill in the art and will vary depending on the particular tissue or organ. For example, with respect to the liver, known biomarkers associated with liver injury or damage include, for example, alanine transferase (ALT), aminotransferase (AST), alkaline phosphatase or bilirubin. Baseline levels of such markers can be determined in the subject prior to initiation of the procedures herein. Normal control subjects also can be used as a measure of normal levels of such enzymes. Further, the level of markers can be compared between areas of the tissue or organ that have been compartmentalized versus areas that have not been compartmentalized. Typically, levels of an marker, such as ALT, that is at least twice that of control is indicative of tissue damage such as liver damage.

In a further example, other markers of immune activation can be assessed. The markers of immune activation can be assessed in the local tissue. In other examples, markers of immune activation can be assessed in the systemic circulation. In the methods herein, following administration of the delivered agent, markers of immune activation, such as cytokine expression, are not significantly elevated or not elevated in the systemic circulation of the subject. In addition, while some increase in the organ or portion thereof to which the delivered agent is administered, the local immune activation that is observed is less than is observed in existing gene therapy methods. A baseline value for such markers can be determined from normal subjects or from the treated subject prior to administration of the delivered agent in the method herein. Further, effects of the compartmentalization can be determined by comparing immune markers in portions of the tissue or organ that have been compartmentalized versus portions of the tissue or organ that have not been compartmentalized.

For example, the presence of neutralizing antibodies to the delivered agent can be assessed or determined. In particular examples, virus-specific neutralizing antibodies can be detected. Typically, serum is collected from a subject that has been administered virus, such as the method herein. Various assays are known to one of skill in the art to assess the presence and amount of neutralizing antibody in the serum. For example, neutralizing antibodies can be detected based on sera inhibition of viral function (Mandel et al. (1978) Adv. Virus. Res., 23:205-68), using a plaque assay (Harvey et al. (1999) J. Virol., 73:6729-6742), Western Blot of adenoviral capsid proteins by human sera (Vincent et al. (2001) J. Virol., 75:1516-1521) and based on quantitative morphological criteria (Vincent et al. (2001). Serum levels of neutralizing antibodies also can be assessed using anti-virus-specific antibodies. For example, an anti-Ad5 antibody can be used (e.g. 65H6, Thermo Scientific, Rockford, Ill.).

In other examples, the expression of cytokines, and particularly proinflammatory cytokines, can be assessed. Tissue or bodily fluid (e.g. peripheral blood) can be processed for DNA or RNA. PCR, such as RT-PCR, can be performed. Various arrays are commercially available containing reagents for RT-PCR of cytokines (see e.g. TaqMan® arrays from Life Technologies, Carlsbad, Calif.). Also, primers can be designed against any cytokine of interest. In another example, enzyme-linked immunosorbent assays (ELISA), enzyme immunoassay (EIA) or Western Blot assays can be used to assess cytokine expression. Reagents for assessing cytokines and other immune proteins are well known and commercially available. For example, EIA and ELISA kits are commercially available for numerous cytokines that include, but are not limited to, IL-6, IL-1α, IL-1β, IL-2, TNF-α and others. For tissue preparation for use in such assays, tissue homogenization procedures can be used, which are known to one of skill in the art. Tissue can be homogenized in a homogenization buffer, centrifuged to remove debris and insoluble material and total protein concentration can be determined (e.g. using a Coomassie Protein staining assays, BCA method, or other method known to one of skill in the art). The aliquots of the centrifuged supernatant can be processed for Western Blot, or can be diluted and used directly for an ELISA-based assay.

G. Applications and Methods of Use

The compartmentalized method provided herein permits sustained and long-term high level expression of a transgene product. Accordingly, the method can be used in diverse applications, including, but not limited to, medical applications, including applications to replace a defective gene product or in applications to exogenously administer a therapeutic agent; production of organs for transplant; production of therapeutic proteins in transgenic animals (e.g. bioreactors); and in agricultural, veterinary and industrial applications. For example, the methods can be used for cellular expression in vivo of a selected polypeptide. In some examples, the polypeptide agent can be useful in therapeutic settings where the polypeptide treats or ameliorates a disorder or condition in a subject or otherwise improves the quality of life in a subject. In other examples, the polypeptide agent can be useful in agriculture setting, for example, applications that improve the quality or quantity of meat production.

The method can be performed on any subject or patient that is in need of gene therapy treatment and is amenable to treatment by the method herein. Exemplary of such subjects include, but are not limited to, mice, rats, cows, pigs, sheep, goats, horses and humans. In particular examples, children under age 18, including infants, toddlers or young children, are contemplated herein for the treatment of diseases or conditions associated with genetic deficiencies.

Exemplary applications of the method herein are provided below. It is understood that other applications exist depending on the particular nucleic acid molecule that is being administered. It is within the level of skill in the art to choose a nucleic acid molecule of interest based on any desired application. The description herein below is for exemplification only.

1. Treating Diseases and Disorders

Provided herein are methods of treating a disease, disorder or condition by delivering a nucleic acid molecule to a subject using the compartmentalized methods provided herein. The disease, disorder or condition that is treated is any that is amenable to treatment by an exogenously delivered nucleic acid molecule. For example, such diseases or conditions include any in which treatment is effected by decreasing or increasing expression of a gene associated with the condition, decreasing or increasing the activity of a gene product associated with the condition or otherwise countering the alteration associated with the condition (e.g. signs, symptoms or effects associated with the disease or condition). For example, gene therapy can be used to treat diseases or conditions associated with genetic deficiencies, including monogenic diseases, (e.g. hemophilia A and B, type I diabetes mellitus, alpha-1-antitrypsin (AAT), cystic fibrosis, muscular dystrophy and numerous others) or can be used to treat diseases or conditions by encoding a therapeutic protein associated with ameliorating the disease or condition (e.g. cancers).

In any of such examples herein, the delivered agent is a nucleic acid molecule or contains a nucleic acid molecule that is a therapeutic nucleic acid or that encodes a therapeutic polypeptide. Thus, provided herein is a method of treating a subject with a disease or disorder by compartmentalizing an organ or portion thereof of a subject; administering a selected delivered agent that is or that contains a nucleic acid molecule of interest directly to the compartmentalized organ or portion thereof for a predetermined time period subsequent to the administration of the nucleic agent as described herein; and restoring vascular circulation to the organ or portion thereof.

The methods provided herein can be used to treat a wide variety of diseases and disorders. The delivered agent, and nucleic acid molecule therein, is selected based on the disorder or disease to be addressed, and the particular organ affected. As described elsewhere herein, one of skill in the art can determine the type of nucleic acid molecule depending on the particular disease or disorder that is being treated. As further exemplification, for example, the compartmentalized method is used to deliver a nucleic acid encoding CFTR for treating cystic fibrosis, a nucleic acid encoding NP2 for treatment of pain, a nucleic acid encoding an angiogenesis inhibitor or tumor suppressor for the treatment of cancer, a nucleic acid encoding an insulin or exendin-4 for treatment of diabetes.

Further, it is known to one of skill in the art the particular tissue or organ to compartmentalize based on the disease or disorder to be treated, and the particular delivered agent that is administered. In some cases, a delivered agent does not exhibit tissue or organ transduction, and thus is delivered directly to the affected tissue or organ. In other instances, a particular delivered agent is chosen that exhibits tissue tropism or transduction following systemic expression. For example, AAV-4, AAV-6, AAV-8 and AAV-9 exhibit widespread transduction to multiple tissues, including lung, heart, liver, kidney, skeletal and cardiac, and thus can be a delivered agent for systemic expression to achieve treatment of skeletal or cardiac diseases and disorders. In another example, AAV-9 is capable of bypassing the blood brain barrier to transduce the central nervous system (CNS), and thus is a delivered agent for systemic expression to achieve treatment of neurodegenerative disorders or other CNS diseases and disorders.

In particular, the lung is an important target organ for gene therapy of many acute and chronic diseases, including cancer, asthma, cystic fibrosis, alpha-1-antitrypsin deficiency and respiratory distress syndrome, among others. The muscle is a target organ for gene therapy for treatment of muscular or motor disorders like muscular dystrophy or charcot-Marie-Tooth (CMT) disease. The brain is an important target organ for gene therapy of motor neuron diseases (e.g. spinal muscular atrophy (AMA), amyotrophic lateral sclerosis (ALS), X-linked adrenoleukodystrophy (ALD)), Parkinson's Disease, or diseases and conditions associated with a missing or defective gene, including metabolic or lysosomal disorders such as Sanfilippo (mucopolysaccharaidosis type III; MSPIII) or Canavan disease. The skin is a target organ for gene therapy for chronic wounds, hypertrophic scars, keloids, cancer, genetic diseases and systemic diseases. For example, growth factors (e.g. PDGF-B, FGF2, VEGF) can be targeted to the skin for wound repair (Liu et al. (2001) *Yonsei Medican Journal*, 42:634-645). The liver is a target organ for gene therapy of numerous inherited, genetic and metabolic liver diseases and disorders including, but not limited to, hemochromatosis, hemophilia A and B, alpha 1 antitrypsin deficiency, Wilson's disease, Crigler-Najjar syndrome type I, ornithine transcarbamylase deficiency, type IIa familial hypercholesterolemia, afibrinogenemia, lysosomal storage diseases, glycogen storage diseases, phenylketonuria, Tay-Sachs disease, induced hepatitis.

Gene therapy of a delivered agent containing a nucleic acid of interest to a particular tissue or organ can effected for systemic expression. For example, gene therapy delivery to the liver can be used to treat non-liver associated systemic diseases or conditions, since the cellular machinery of the liver can produce and secrete a large quantity of proteins into the blood. Thus, targeting the liver can be used to produce therapeutic proteins into the blood circulation for treatments of various diseases and conditions, including but not limited to, blood coagulation factors, hormones, growth factors, cytokines, metabolic enzymes and anti-proteases. The liver also can be used to differentiate hepatocytes into insulin-secreting β cells in the liver. Gene therapy has been used to treat a number of disease and conditions by targeting the liver (Nakai H., "*Hepatic Gene Therapy,*" pp. 343-370 in Molecular Pathology of Liver Diseases (S. P. S. Monga, ed.). In another example, systemic diseases can be treated by targeting skin because keratinocytes can produce large amounts of protein that can be released into the circulation. Thus, gene therapy of the skin can be used to delivery nucleic acid encoding cytokines (e.g. interferon or interleukins or other cytokines), hormones (e.g. insulin, growth hormone and other hormones), coagulation factors and other proteins to treat neoplastic, viral, inflammatory and genetic diseases. For example, genetic defects such as hemophilia B can be treated by delivery of Factor IX into keratinocytes.

Furthermore, the amount of delivered agent administered is adjusted based on the desired therapeutic dosage of the therapeutic nucleic acid or therapeutic polypeptide encoded by the nucleic acid molecule. As described herein, by using the compartmentalized method provided herein, the dose of delivered agent and the protein output is linear. Hence, the particular dosage of delivered agent can be empirically determined based on the particular nucleic acid molecule, the delivered agent, the particular genetic therapy, the subject to be administered the delivered agent, the target organ or portion thereof, the expected uptake, the needed therapeutic amount, and other factors.

Exemplary disease or disorder that can be treated by delivery of a nucleic acid molecule by the compartmentalized method herein include, but are not limited to, an inherited enzyme deficiency (e.g., mucopolysaccharidosis, glycogen storage disease, and lysosomal storage disease), cancer, hemophilia, diabetes, muscular dystrophy, cardiovascular disorder, cystic fibrosis, cancer, neurodegenerative disorder, trauma, pain, sickle cell anemia, autoimmune disease, inflammatory disease, inherited immune deficiency, hypertension and Parkinson's Disease. For example, the disease or condition is selected from among hemophilia A and B, type I diabetes mellitus, alpha-1-antitrypsin (AAT) deficiency, hemochromatosis, Wilson's disease, Crigler-Najjar syndrome type I, ornithine transcarbamylase deficiency, type II, familial hypercholesterolemia, afibrinogenemia, glycogen storage disease (GSD) type Ia, GSD type Ib, GSD type II (Pompe), mucopolysaccharidosis (MPS1), MPS IIIA, MPS IIIB, MPS VII, Fabry disease, Gaucher's disease, Niemann-Pick syndrome, ornithine transcarbamylase deficiency (OTC) deficiency, phenylketonuria, liver fibrosis, liver ischemia reperfusion injury, Alzheimer's disease, Amyotrophic Lateral Sclerosis (ALS), galactosemia, phenylketonuria, maple syrup urine disease, tyrosinemia type 1, methylmalonic acidemia, citrullinemia, Gout and Lesch Nyan syndrome, Sly syndrome, Zellweger syndrome, severe combined immunodeficiency disease (SCID), cystic fibrosis, acute intermittent *porphyria*, lipoprotein lipase deficiency (LPLD), or multiple sclerosis.

With exemplification to the liver, the methods herein can be used in the delivery of a delivered agent containing any nucleic acid, such as any described in Section D.1, to a compartmentalized liver or portion of the liver to treat any disease in which gene therapy has been used in the art. For example, the liver (or other tissue or organ) can be compartmentalized in the method herein for delivery of and treatment of diseases and conditions including, but not limited to: delivery of Factor VIII for treatment of hemophilia A; delivery of Factor IX for treatment of hemophilia B; delivery of α(alpha)1-antitrypsin for treatment of α(alpha)1-antitrypsin deficiency; delivery of glucose-6-phosphate-α for the treatment of glycogen storage disease (GSD) type Ia; delivery of G6PT for treatment of GSD type Ib; delivery of acid-α-glucosidase for treatment of GSD type II (Pompe); delivery of α-L-iduronidase for treatment of mucopolysaccharidosis (MPS1); delivery of sulphamidase for treatment of MPS IIIA; delivery of α-N-acetylglucosaminidase (NaGlu) for treatment of MPS IIIB; delivery of 3-glucuronidase for treatment of MPS VII; delivery of α-galactosidase A for treatment of Fabry disease; delivery of glucocerebrosidase for treatment of Gaucher's disease; delivery of acid sphingomyelinase for treatment of Niemann-Pick syndrome; delivery of ornithine transcarbamylase deficiency (OTC) for treatment of OTC deficiency; UDP glucuronosyltransferase 1A1 (UGT1A1) for treatment of Crigler-Najjar syndrome; LDL receptor for treatment of familial hypercholesterolemia; phenylalanine hydroxylase for treatment of phenylketonuria; metalloprotease (MMP1 or MMP8); u-PA, TIMP antagonist or anti-HSC molecules for treatment of liver fibrosis; anti-ROS molecules for treatment of liver ischemia reperfusion injury; proinsulin precursor or transcription factors for β cell trans-differentiation for treatment of diabetes mellitus; RNAi against viral RNA for treatment of Hepatitis B; RNAi against viral RNA for treatment of hepatitis C; p53 for treatment of liver cancers; IFN-β or other anti-inflammatory cytokine for the treatment of multiple sclerosis; interferon-α for the treatment of induced hepatitis; or lipoprotein lipase for the treatment of lipoprotein lipase deficiency (LPLD).

This list is not intended to be limiting, as any disease or condition that can be addressed with a therapeutic nucleic acid or a therapeutic polypeptide encoded by the nucleic acid could be addressed. Exemplary diseases and conditions are described below.

a. Hemophilia A and B

An example of a condition that can be treated by the compartmentalized method and materials herein is hemophilia. There are two types of hemophilia, A and B. Patients with hemophilia A lack a protein known as factor VIII while those with hemophilia B lack factor IX. Either low levels or complete absence of these blood clotting factors causes a severe impediment in the patient's ability to stop bleeding when suffering from a wound or when a blood vessels structure is compromised. This results in prolonged bleeding with potential fatal consequences. Current treatments for hemophilia include periodic transfusion with blood products or recombinant versions of the required blood factor. However, despite improved screening of donor blood the risk of viral infection through blood or blood product transfusion remains a problem. Furthermore, with both blood product-derived and recombinant-derived factor VIII or 1× therapy, the development of antibodies that block the activity of the clotting factors has complicated treatment for some patients. Hemophilia has been considered an ideal candidate for gene therapy since a modest rise in Factor VIII or Factor IX levels has been shown to be sufficient to ameliorate many of the clinical consequences of hemophilia A or B, respectively.

Using the method herein, a delivered agent containing a gene for Factor VIII can be used to treat hemophilia A. In another example, using the methods herein, a delivered agent containing a gene for Factor IX can be used to treat hemophilia B. In The present method permits the liver, for example a small portion of the liver, to become a de novo endocrine gland that can permanently secrete the required blood clotting factor into the circulation, thus, potentially ameliorating the consequences of the disease. This can be achieved using the methods herein by directly delivering to the parenchyma of a compartmentalized tissue or organ, for example a compartmentalized liver, such a small portion of the liver, a recombinant virus (e.g. adenovirus) or some other type of vector of delivered agent encoding the clotting factor. For example, the particular clotting factor can be either Factor VIII or IX depending on the underlying deficiency. The genetic information is be transcribed and transduced and thus the clotting factor is synthesized and secreted into the circulation correcting the blood clotting impairment/deficiency.

b. Familial Hypercholesterolemia

An example of a condition that can be treated by the compartmentalized method and materials herein is familial hypercholesterolemia. Familial hypercholesterolemia is an autosomal dominant disorder due to a mutation in the low-density lipoprotein receptor (LDLR) gene. Although lowering plasma cholesterol decreases the risk of coronary artery disease, patients with familial hypercholesterolemia generally respond poorly to pharmacologic treatment. Subjects that have familial hypercholesterolemia have been treated by administering nucleic acid encoding a low density lipoprotein receptor (see e.g. Grossman et al. (1995) *Nat. Med.*, 1:1148-1154; Shichiri et al. (2003) *Gene Ther.*, 10:827-31; Yang et al. (1994) *Immunity*, 1:433-442; Yang et al. (1995) *J. Virol.*, 69:2004-2015; Yang et al. (2004) *Biochem. J.*, 379:89-97). Similarly, using the compartmentalized method herein, a delivered agent containing a gene for LDLR can be used to treat familial hypercholesterolemia. This can be achieved using the methods herein by directly delivering to the parenchyma of a compartmentalized tissue or organ, for example a compartmentalized liver, such a small portion of the liver, a recombinant virus (e.g. adenovirus) or some other type of vector of delivered agent encoding LDLR.

c. Type I Diabetes Mellitus

A further example of a condition that can be treated by the compartmentalized method and materials herein is Type I Diabetes. Type I diabetes results from a failure to produce insulin, this in turn leads to a marked increase in blood glucose levels. Furthermore, sustained high glucose blood levels leads to several consequences that severely diminish patient's quality of life and life expectancy. Diabetes is a chronic disease that presently has no cure.

Alleviation of some of the pathological effects of diabetes can be achieved by partially restoring insulin levels using the present method. Using the compartmentalized method herein, a delivered agent containing a gene for insulin can be used to treat diabetes. This can be achieved using the methods herein by directly delivering to the parenchyma of a compartmentalized tissue or organ, for example a compartmentalized liver, such as to a small portion of the patients liver, a delivered agent (e.g. viral vector or other vector) encoding the insulin gene. This can result in the stable, long-term, synthesis and secretion of insulin by the transduced liver cells.

d. Alpha-1-Antitrypsin (AAT) Deficiency

A further example of a condition that can be treated by the compartmentalized method and materials herein is the common monogenic lung disease Alpha-1-antitrypsin (AAT) deficiency. AAT is produced by the liver and secreted to the circulation where it finds its way to the lungs where it protects elastin fibers and other connective tissue components of the alveolar wall from degradation by neutrophil elastase. AAT deficiency can lead to the patient's death due to emphysema. The gene encoding AAT has been isolated and exogenous administration with recombinant human AAT protein represents one form of current therapy.

A number of studies have also shown promise toward the development of a therapeutic approach based on gene therapy. Gene therapy methods include, for example, transduction of skeletal muscle cells or liver cells to express AAT (Song et al. (1998) *Proc. Natl. Acad. Sci.*, 95:14384-14388; Song et al. (2001) *Proc. Natl. Acad. Sci.*, 98:4084-8; Song et al. (2001) *Gene Ther.*, 8:1299-1306; Song et al. (2004) *Hepatology*, 40:918-24; Zhang et al. (2003) *Gene Therapy*, 10:2148-52; Ferkol et al. (1998) *Am. J. Respir. Cell Mol. Biol.*, 18:591-601).

Using the method herein, a delivered agent containing a gene for AAT can be used to treat AAT deficiency. This can be achieved using the methods herein by directly delivering to the parenchyma of a compartmentalized tissue or organ (e.g. such as the muscle or liver, e.g. a small portion of the liver) a delivered agent (e.g. a non-viral or viral vector such as adenovirus) encoding AAT. By incorporation of a nucleic acid sequence encoding AAT into a vector and transducing a portion of a tissue organ using the present method, stable long term expression of AAT can be achieved and could potentially resolve the emphysema.

e. Angiogenesis and Cancer

An example of a disease or condition that can be treated by the compartmentalized method herein is angiogenesis. Angiogenesis is the process by which new capillaries are formed from pre-existing vasculature. It is a complex process that involves proliferation and migration of endothelial cells. Angiogenesis plays a fundamental role in reproduction, embryonic development and wound repair. Unregulated angiogenesis, however, plays a central role in the progression of many diseases, such as solid tumor growth and metastasis, arthritis, diabetes, and some forms of blindness. For example, angiogenesis play a role in the growth and spread of cancer due to the formation of blood supply to tumors that can feed growing tumors and promote metastasis. Hence, anti-angiogenic agents can be used to treat cancer and other diseases in which angiogenesis plays a role.

Angiogenesis is controlled by complex interactions between pro-angiogenic growth factors such as VEGF, FGF and PDGF and anti-angiogenic factors such as endostatin and angiostatin. An imbalance between these two groups of factors generates pathologic angiogenesis. Several lines of research have proposed that the infusion of anti-angiogenesis factors into patients with cancer, such as endostatin or angiostatin, would reestablish the balance between these two forces, arrest abnormal angiogenesis and thus arrest tumor growth and metastasis.

Using the method herein, a delivered agent containing a nucleic acid encoding an anti-angiogenesis factor can be used to treat angiogenic diseases and conditions, such as cancer, arthritis, diabetes and blindness. This can be achieved using the methods herein by directly delivering to the parenchyma of a compartmentalized tissue or organ (e.g. such as the liver, e.g. a small portion of the liver) a delivered agent (e.g. a non-viral or viral vector such as adenovirus) encoding an anti-angiogenic factor, such as endostatin or angiostatin. By incorporation of a nucleic acid sequence encoding the anti-angiogenic factor into a vector and transducing a portion of a tissue organ using the present method, stable long term expression of the anti-angiogenic agent can be achieved.

f. Autoimmune and Inflammatory Disorders (e.g. Multiple Sclerosis)

An example of a disease or condition that can be treated by the compartmentalized method herein are autoimmune and inflammatory disorders, such as multiple sclerosis (MS), rheumatoid arthritis, osteoarthritis, diabetes, Crohn's disease, Sjogrens syndrome, cystic fibrosis, myositis and lupus. For example, MS is an autoimmune inflammatory disease of the central nervous system (CNS) in which fatty myelin sheaths around the axons of the brain and spinal cord are damaged. The result is that the axons can no longer conduct signals.

Treatment of autoimmune inflammatory disorders, such as MS and other conditions, by gene therapy targets immune activation using cytokines, cytokine antagonists, anti-T cell monoclonal antibodies, inhibitors of signal transduction. For example, anti-inflammatory genes can be introduced to down-modulate the immune response (Neumann et al. (2005) *Gene Therapy and Molecular Biology*, 9:61-76). Exemplary anti-inflammatory genes include cytokines or other immunomodulatory agents such as, but not limited to, by interleukin-4, interleukin-10, transforming growth factor b, interferon-beta (IFNβ), interleukin-1 receptor alpha (IL-1Rα), soluble TNF receptor (sTNF-R), soluble interleukin-1 receptor (sIL-1R) or soluble interferon-gamma receptor (sIFNγR). For example, treatment with interferon beta has been approved for MS (Kieseier et al. (2007) *Exp. Neurol.*, 203:1-4). In addition to viral and non-viral gene therapy approaches, treatments of MS include the use of cells harvested from the target subject to be treated (e.g. dendritic cells or T cells) that are engineered to express an anti-inflammatory cytokine (e.g. IFN-β, IL-10 or IL-4), which are then reintroduced to the host subject for delivery of the gene products.

Using the method herein, a delivered agent containing a nucleic acid encoding an anti-inflammatory gene or cytokine can be used to treat an autoimmune and inflammatory disorder, such as multiple sclerosis (MS), rheumatoid arthritis, osteoarthritis, diabetes, Crohn's disease, Sjogrens syndrome, cystic fibrosis, myositis and lupus. In particular examples, a delivered agent encoding a nucleic acid encoding an anti-inflammatory gene or cytokine (e.g. IFN-β, IL-10 or IL-4) is used to treat MS. This can be achieved using the methods herein by directly delivering to the parenchyma of a compartmentalized tissue or organ (e.g. such as the liver, e.g. a small portion of the liver) a delivered agent (e.g. a non-viral, viral vector such as adenovirus, or whole cells) encoding an anti-inflammatory gene or cytokine (e.g. IFN-β, IL-10 or IL-4). By incorporation of a nucleic acid sequence encoding the anti-inflammatory gene or cytokine into a vector and transducing a portion of a tissue organ using the present method, stable long term expression of the anti-inflammatory agent can be achieved.

g. Acute Intermittent Porphyria (AIP)

An example of a disease or condition that can be treated by the compartmentalized method herein is Acute Intermittent Porphyria (AIP). AIP is an inherited metabolic disease characterized by a deficiency of porphobilinogen deaminase (PBGD), the third enzyme of the heme synthesis pathway. The enzyme activity is ~50% of normal in those who inherit the genetic trait. The disease is inherited in an autosomal dominant manner and is the most common of acute porphyrias. Although it occurs in all races it is most prevalent in North Europe, mainly in Sweden, Britain and Ireland. In USA and other countries the estimated prevalence is 5/100, 000 and in Northern Sweden it is as high as 60-100/100,000. More than 225 mutations in the PBGD gene have been described to date. The dominant clinical feature is an acute intermittent attack due to dysfunction of the nervous system, including abdominal pain and neurovisceral and circulatory disturbances. Abdominal pain has been reported in 85-95% of cases and is the most common feature, followed by or associated with the neurological changes. Progression to respiratory and bulbar paralysis and death can occur if AIP is not recognized and harmful drugs are not withdrawn, such as drugs metabolized by the hepatic cytochrome P450 enzymes which may precipitate an attack. Sudden death can also occur as result of cardiac arrhythmia. Primary liver cancer and impaired renal function sometimes occur as well.

A high proportion of subjects that inherit PBGD mutation never develop porphyric symptoms, i.e. there is very low clinical penetrance. Clinical symptoms in AIP carriers are associated with increased production and excretion of the porphyrin precursors delta-aminolevulinic acid (ALA) and porphobilinogen (PBG) as result of increased demand of heme synthesis due to a drug or other precipitating factors that provoke the acute attack. In these conditions PBDG deficiency limits heme synthesis and as a result heme-mediated repression of ALA synthetase (ALAS1) is impaired. There is evidence indicating that the liver is the main source of the excess of porphyrin precursors. These compounds remain elevated between attacks in those subjects prone to repeated porphyric crises and increase further during the crisis. They may decrease to normal if the disease remains inactive for a long period of time.

Acute attacks usually occur after puberty and can be induced in latent individuals by endocrine factors and steroid hormones and a variety of environmental factors including drug, nutritional factors, restricted carbohydrate and caloric intake, smoking, steroid hormones and oral contraceptives, lead poisoning, intercurrent infections, surgery and psychological stress. Drugs are among the most important factors that precipitate acute attacks and a list of safe drugs is available in drugs-porphyria.com. Smoking, ethanol and drugs metabolized by CYP450, greatly increase hepatic heme demand and result in the induction of ALAS1, which increases the production of porphyrin precursors and precipitates an acute attack. Also, ALAS1 is positively regulated by the peroxisome proliferator-activated receptor γ coactivator 1α (PGC1α), which is induced in the liver during fasting. Among the precipitating factors steroid hormones seem to play an important role. This concept is supported by the fact that the disease rarely manifests before puberty and that oral contraceptives can exacerbate attacks in some females with PBGD deficiency. Also women (80%) are affected more often than men (20%).

Acute attacks are treated with infusions of glucose and hemin (Normosang, Orphan Europe). Glucose appears to antagonize the ALAS1 induction mediated by PGC-1α. Hemin restores the regulatory heme pool and suppresses hepatic ALAS1 induction. Some women develop premenstrual attacks which can be prevented by gonadotropin-releasing hormone (GnRH) analogs. Some patients exhibit recurrent acute attacks and significant, disabling neurological dysfunction. Advanced neurologic damage and subacute and chronic symptoms are generally unresponsive to heme therapy. This is a life-threatening condition that can be cured only by allogeneic liver transplantation that, in three patients to date, prevents the accumulation of neurotoxic ALA and PBG. Nevertheless liver transplantation has limited availability of compatible donors, and a significant morbidity and mortality.

Gene-replacement therapy is an alternative to liver transplantation, in particular in patients where the liver function is entirely normal except for the PBGD deficiency. Adenoviral vector-mediated gene transfer of PBGD to porphyric mice revealed short-term therapeutically efficacy as a result of the transient hepatic expression of PBGD (Johansson, 2004, *Mol. Ther.* 10(2):337-43). Adenovirus and adeno-associated virus-mediated gene therapy of a gene encoding gene therapy are also under development by Amsterdam Molecular Therapeutics and other companies (see e.g. U.S. Published Application No. US2011/0262399 and EP Patent No. EP1049487).

Using the method herein, a delivered agent containing a nucleic acid encoding PBDG can be used to treat Acute Intermittent Porphyria (AIP). This can be achieved using the methods herein by directly delivering to the parenchyma of a compartmentalized tissue or organ (e.g. such as the liver, e.g. a small portion of the liver) a delivered agent (e.g. a non-viral, viral vector such as adenovirus, or whole cells) encoding PBDG. By incorporation of a nucleic acid sequence encoding PBDG into a vector and transducing a portion of a tissue organ using the present method, stable long term expression of PBDG can be achieved for the treatment of AIP.

h. Sanfilippo Syndrome

An example of a condition that can be treated by the compartmentalized method and materials herein is Sanfilippo syndrome. Sanfilippo Syndrome or Mucopolysaccharidosis type III (MPSIII) is a lysosomal storage disease in which an autosomal recessive defect results in the accumulation of partially degraded oligosaccharides of heparan sulfate. It occurs in about 1 in 70,000 births. Sanfilippo syndrome is associated with a decline in learning ability in early childhood, delayed or stunted growth, delayed development and deteriorating mental status. There are four subtypes of Sanfilippo syndrome: Sanfilippo type A (MPSIIIA) occurs when the enzyme heparan N-sulfatase is missing or is altered; Sanfilippo type B (MPSIIIB) occurs when the enzyme alpha-N-acetylglucosaminidase (NaGlu) is missing, altered or is not produced enough; Sanfilippo C (MPSIIIC) occurs when the enzyme acetyl-CoAlpha-glucosaminide acetyltransferase is missing, altered or is not produced enough; and Sanfilippo type D (MPSIIID) occurs when the enzyme N-acetylglucosamine 6-sulfatase is missing, altered or is not produced enough. For example, Sanfilippo type B is caused by mutations in the NaGlu gene, which causes deficiency of the enzyme alpha-N-acetylglusosaminidase.

Treatment of Sanfilippo Syndrome, such as MPS IIIA, IIIB, IIIC or IIID, can be achieved by delivery of the missing or defective gene. Delivery can be directly to the central nervous system (CNS). Delivery also can be achieved by delivery methods that achieve efficient CNS delivery across the blood brain barrier, such as by using an adeno-associated virus serotype that is able to cross the blood brain barrier from the vasculature. Exemplary of such a serotype is AAV9 (see e.g., Fu et al. (2011) *Mol. Ther.*, 19:1025-33).

Using the method herein, a delivered agent containing a nucleic acid encoding heparan N-sulfatase can be used to treat MPSIIIA, a delivered agent containing a nucleic acid encoding alpha-N-acetylglusaminidase (NaGlu) can be used to treat MPSIIIB, a delivered agent containing nucleic acid encoding acetyl-CoAlpha-glucosaminide acetyltransferase can be use to treat MPSIIIC or a delivered agent containing nucleic acid encoding N-acetylglusocsamine 6-sulfatase can be used to treat MPSIIID. This can be achieved using the methods herein by directly delivering to the parenchyma of a compartmentalized tissue or organ (e.g. such as the liver, e.g. a small portion of the liver; or directly to the brain) a delivered agent (e.g. a non-viral, viral vector such as adenovirus, or whole cells) encoding the missing or defective enzyme for the particular MPSIII disorder. In particular examples, the delivered agent is a recombinant adenovirus-associated 9 containing nucleic acid encoding the missing or defective enzyme (e.g. rAAV9-hNAGLU) so as to achieve delivery across the blood brain barrier. By incorporation of a nucleic acid sequence encoding the missing or defective enzyme into a vector and transducing a portion of a tissue organ (e.g. liver) using the present method, stable long term expression of the missing or defective enzyme can be achieved in the CNS for the treatment of MPSIII (Sanfillipo Syndrome).

i. Lipoprotein Lipase Deficiency (LPLD)

An example of a condition that can be treated by the compartmentalized method and materials herein is lipoprotein lipase deficiency (LPLD; also known as type 1 hyperlipidemia, primary hyperlipoproteinemia or familial hyper chylomicronemia). LPLD is caused by alterations in the gene that encodes lipoprotein lipase (LPL). In the absence of LPL or a defective LPL, fat levels in the blood increase due to defects in metabolism of long-chain fatty acids. The symptoms associated with LPLD include, for example, abdominal pain and pancreatitis. LPLD also is associated with high blood triglyceride levels, which can predispose subjects to early-onset diabetes and atherosclerosis.

Gene therapy can be used to treat LPLD. For example, an adeno-associated virus (AAV) containing nucleic acid encoding the LPL gene has been approved in Europe for delivery to the skeletal muscle for treatment of LPLD (marketed as Glybera®).

Using the method herein, a delivered agent containing a nucleic acid encoding LPL can be used to treat lipoprotein lipase deficiency (LPLD). This can be achieved using the methods herein by directly delivering to the parenchyma of a compartmentalized tissue or organ (e.g. such as the liver, e.g. a small portion of the liver; or skeletal muscle) a delivered agent (e.g. a non-viral, viral vector such as adenovirus, or whole cells) encoding LPL. By incorporation of a nucleic acid sequence encoding LPL into a vector and transducing a portion of a tissue organ using the present method, stable long term expression of LPL can be achieved for the treatment of LPLD.

2. Protein Expression and Production

Provided herein is a method of making a polypeptide in an animal. Therapeutic production of proteins in animals, including therapeutic proteins or nutritional supplements, are well known to one of skill in the art. For example, products such as tissue plasminogen activator, (t-PA), insulin, growth hormone and coagulation factors have been produced in animals, such as cows, sheep or goats (see e.g. Mercier J. C. (1987) *Exploiting New Technologies in Animal Breeding*, p. 122-131, Oxford University Press; Lillico et al. (2005) *Drug Discovery Today*, 10:191-196; Echelard et al. (2006) *Biopharm International*, 19:36; Prather et al. (2003) *Theriogenology*, 59:115-123). Production of gene products in insect cells using viral vectors expressing a product of interest also has been described (see e.g. U.S. Published Application No. US2011/0119777)

The method of producing a protein, such as any described herein or known in the art, in an animal includes the steps of administering a delivered agent containing a nucleic acid molecule encoding the polypeptide to a compartmentalized organ or portion thereof of a production animal, maintaining the production animal under conditions that allow expression of the polypeptide, and isolating the expressed polypeptide from the production animal (e.g., from the blood or other biological fluid of the production animal). The encoded polypeptide can be any protein that is desired to be produced, in particular any therapeutic protein or protein that can be used as a nutritional supplement. Exemplary of such proteins include, but are not limited to, coagulation factors (e.g. Factor VIII, Factor IX, fibrinogen blood clotting factor), lactoferrin, haemoglobin, human protein C, alpha-1-antitrypsin, tissue plasminogen activator (t-PA), cystic fibrosis transmembrane conductance regulator (CFTR), insulin, growth hormones, cytokines, monoclonal antibodies, vaccines (e.g. antigens), cholesterol oxidase and others.

The polypeptide can be isolated from a biological sample from the production animal. The biological sample can be blood, urine, milk, plasma, saliva, or other similar sample. In particular examples, the protein products appears in the milk and can be used or isolated therefrom. The production animal can be a rabbit, rat, mouse, goat, horse, sheep, chicken, hen, porcine, or bovine animal. The method provides advantages over current production methods because the delivered agent can be scaled to produce high quantities of the polypeptide, particularly in large animals such as pigs and cows. Furthermore, as described above, the polypeptides can be posttranslationally modified (e.g., glycosylated) by the cells of the production animal.

3. Agricultural and Veterinary Applications

The method provided herein can be used in gene therapy applications in animals, and in particular for veterinary, agricultural or industrial applications. In such examples, a delivered agent for delivery in the methods herein contains a nucleic acid molecule that effects an increase in productivity and/or controls disease in an animal. Application in animals include, but are not limited to, applications that alter or produce animals having a desired trait, increase the quality of animals (e.g. muscle, milk, wool), increase resistance to disease, or produce products for industrial applications (e.g. silk). For example, gene therapy applications include those that increase hair production in an animal, increases wool production in an animal, increases growth of an animal, or regulate nutrient synthesis or utilization. In such examples, the nucleic acid molecule encodes a protein that increases muscle production in an animal, increases hair production in an animal, increases wool production in an animal, increases growth of an animal, or is involved in nutrient synthesis or utilization.

Such applications are well known to one of skill in the art. For example, a delivered agent containing a nucleic acid can be administered to an animal to increases muscle production in an animal, for example, by administering a nucleic acid encoding a growth hormone (e.g. somatotropin) or agents that mediate growth hormone (e.g. IGF-1, growth hormone releasing factor or chicken Ski (cSki) (see e.g., Lee (1997) *Theriogenology*, 47:225; Palmiter et al. (1982) *Nature*, 300: 611-615). In another example, a nucleic acid molecule can be or encode a myostatin inhibitor, which can be useful in meat production. For example, the nucleic acid molecule can encode follistatin that blocks the binding of myostatin to its receptor, thereby resulting in the development of larger muscles.

In another example, the quality of an animal, and products therefrom, can be improved. In such examples, the improvement of the overall quality of an animal can aid agricultural applications (e.g. for utilization of milk, eggs or meat). In one example, a delivered agent containing a nucleic acid can be administered to an animal to increase milk production or to increase the quality of milk (see e.g., Mercier J. C. (1987) Exploiting New Technologies in Animal Breeding, p. 122-131, Oxford University Press). In addition, the milk of animals also have been modified by gene therapy methods to increase or improve the quality of the milk, for example, for human consumption. For example, lactoferrin has been engineered to be expressed in the milk of cows to provide for a more nutritionally balanced product to be given to babies or the elderly (see e.g. van Berkel et al. (2002) *Nat. Biotech.*, 20:484-487). Also, milk in an animal can be improved by inhibiting the growth of bacteria that cause mastitis (e.g. Maga et al. (2006) *Foodborne Pathog. Dis.*, 3:384-392). In other examples, animals can be engineered to express a fatty acid desaturase gene (see e.g. Saeki et al. (2004) *Proc. Natl. Acad. Sci.*, 101:6361-6366), to be rich in omega-3 fatty acids (see e.g. Lai et al. (2006) *Nature Biotechnology*, 24:435-436); to produce milk with higher levels of beta-casein and kappa-casein (see e.g. Brophy et al. (2003) *Nature Biotechnology*, 21:157-162), or to express salivary phytase to produce low-phosphorous manure (see e.g. Golovan et al. (2001) *Nature Biotechnology*, 19:741-745). In a further example, nucleic acid molecules include those involved in amino acid biosynthesis or glyoxylate cycle genes, which can be use to improve nutrient utilization. For examples, a delivered agent can be administered that contains a nucleic acid molecule such as cysE and cssK genes that encode serine transacetylase and o-acetylserine sulphydrylase.

In additional examples, a delivered agent containing a nucleic acid molecule can be administered to an animal to increase the resistance of animals to disease. For example, an animal can be produced to lack prion protein (Richt et al. (2007) *Nature Biotechnology,* 25:132-138). In other examples, and animal can be engineered to be resistant to bacterial infection such as infection by *Staphylococcus aureus* (Wall et al. (2005) *Nature Biotechnology,* 23:445-451).

In addition examples, nucleic acid molecules can encode polypeptides that increase hair growth or increase wool production in an animal. For example, wool production can be increased by administering a delivered agent that contains a nucleic acid molecule encoding cysteine, which is a limiting amino acid in wool synthesis; a nucleic acid molecule encoding keratin, or nucleic acid molecules encoding growth factors (e.g. EGF or IGF-1) in wool follicles or the skin. Animals also can be engineered for industrial application, for example, to produce silk by engineering the spider gene that produce silk into animals, such as goats (see e.g. Lazaris et al. (2002) *Science,* 295:472-476).

H. Examples

The following examples are included for illustrative purposes only and are not intended to limit the scope of the invention.

Example 1

Compartmentalization of Adenovirus Transduction to the Caudate Lobe

Adenovirus was injected to the caudate lobe that was compartmentalized by isolation from the vasculature using a parenchymal clamp. The adenovirus, designated Ad-CMV-Luc, was provided from David T. Curiel (University of Alabama, see e.g. Bass et al. (1995) *Cancer Gene Ther.,* 2:97-104; published International PCT Application No. WO 1995/026411). Ad-CMV-Luc was derived from human adenovirus type 5 and encodes the luciferase gene driven by the cytomegalovirus (CMV) promoter. Specifically, for adenoviral transduction analysis, the adenovirus was made replication deficient by deleting the E1 region. Into this deleted E1 region, the reporter gene luciferase (Adluc) was cloned and constructed to be driven by the human cytomegalovirus promoter (designated rAd-CMV-Luciferase or Ad.CMV.Luc).

Specifically, to determine the extent of adenovirus transduction that could be compartmentalized to the caudate lobe of the liver, ten (10) rats were anesthetized with an intraperitoneal (i.p.) injection of sodium pentobarbital (50 mg/kg) (Abbott Laboratories, Chicago, Ill.). Each rat was then placed in a supine position, the abdominal region was shaved, and the abdominal cavity was exposed following a 3 cm ventral midline incision from the xiphoid process to the umbilical region. The upper portion of the caudate lobe was located and dissected, severing the interlobular and hepatogastric ligaments. The pedicle of the caudate lobe was identified and clamped using a 10 mm micro-serrefine (Fine Science Tools-USA Inc., Foster City, Calif.).

Once the caudate lobe was clamped, $1\times10^9$ pfu recombinant Ad.CMV.Luc, in 50 µl phosphate-buffered saline (PBS) in a 1 ml syringe (Becton & Dickinson Corp., Franklin, N.J.), were injected into the parenchyma of the caudate lobes of five (5) rats. Another five (5) rats were injected with $1\times10^9$ pfu Ad.CMV.Luc in a total volume of 100 µl PBS into the vena cava as a control. The clamp was held for 30 minutes. The rats were then sutured in two planes (muscle and skin) with 5-0 Vicryl (Ethicon Inc., Somerville, N.J.) and allowed to recover.

Seventy two (72) hours post-surgery, the rats were euthanized with an i.p. overdose of sodium pentobarbital. The livers were harvested and the caudate, right lateral, left lateral, and median lobes of the liver were separated and processed for histopathological evaluation, luciferase activity assay, and for nucleotide (DNA and RNA) extraction.

For DNA extraction: Ten mg tissue was placed in 400 µL of solution of 100 mM NaCl, 10 mM Tris×Cl, pH 8, 0.5% SDS, 0.1 mg/ml proteinase K and incubated until most of the cellular protein was degraded. The digest was deproteinized by successive phenol/chloroform/isoamyl alcohol extractions, the DNA was recovered by ethanol precipitation, and dried and resuspended in TE pH 8 buffer.

Formalin-fixed tissue was paraffin-embedded and used for routine histopathology. For histopathology, formalin-fixed, paraffin-embedded tissue blocks were sectioned at 5 µm, stained with hematoxylin and eosin and examined microscopically by a certified pathologist.

For the Luciferase activity assay, the dissected lobes were homogenized using Fast Prep 24, Sample Preparation System, (MP Biomedicals) by using the Lysing Matrix D (MP Biomedicals) in 500 µL Lysis buffer (Luciferase assay system, Promega, Madison, Wis.). Twenty microliters of supernatant were added to 100 ul of luciferase assay reagent and then used for measurement of luciferase activity using a luminometer (Biotek, USA) to measure photons for 10 s. Protein concentrations of the liver extract were determined by Bradford's method using a protein assay kit (Bio-Rad, Hercules, Calif., USA). Luciferase activities were normalized to the total protein in the homogenates (relative light units per gram (rlu/g) of total protein) for comparison and statistical analysis among the different lobes of the liver.

Results

Histological analysis for liver inflammation was performed. To compare the effects of compartmentalization and i.v transfusion on hepatic inflammation, liver sections obtained at 72 hrs were analyzed for signs of neutrophil infiltration. Liver histology performed on samples from I.V controls showed intense focal hepatocellular necrosis particularly in periportal regions. These focal necrotic areas were infiltrated with neutrophils. Hepatocellular necrosis, nonparenchymal cells or infiltrated inflammatory cells were completely absent in tissues obtained from compartmentalized animals.

For luciferase activity, the results show that similar levels of luciferase activity were measured in all lobes recovered from control animals, which received intravenous (IV) infusion of the adenovirus. In contrast, animals having received adenovirus injection into the caudate lobe, following clamping, exhibited greater than 3 orders of magnitude greater Luciferase activity than any of the other lobes of the liver, indicating that adenoviral transduction was restricted to the injected tissue and the surrounding tissues were spared from exposure to the vector. The results are set forth in FIG. 2.

Example 2

Determination of Clamp Duration to Minimize Systemic Release

A. Systemic Viral Expression Following Clamp Release

To determine the optimal length of clamping time to effect compartmentalization of the adenovirus to the injected tissue, the surgical procedure was performed as described in Example 1, followed by injection of $1\times10^{10}$ pfu Ad.CMV-.Luc suspended in a total volume of 50 µl into the parenchyma of the caudate lobe using a 1 mL insulin syringe. The micro-serrefine clamp was released from the pedicle at 7, 15, 30, and 60 min post adenoviral injection (n=6 per time point). One minute post clamp release, 200 µl of peripheral blood were collected from the vena cava and processed for PCR. The Luciferase gene was amplified using the following primers: sense 5'-ATGGAAGACGCCAAAAACATAAAG-3' (SEQ ID NO:1 and antisense 5'-AAAACCGGGAGGTA-GATGAGATGT-3' (SEQ ID NO:2) in a total reaction volume of 20l. PCR conditions were: 94° C. for 5 min, followed by cycles at 94° C. for 30 s, 55° C. for 30 s, and 72° C. for 30 s and 7 min at 72° C. extension.

The results are set forth in FIG. 3, panel A. The adenovirus DNA (Luciferase) was detectable in the peripheral blood after 7 min of clamp time. Increasing the clamp time to 15 min reduced the adenovirus DNA detected in the blood to about half that observed following 7 min of clamp time. Adenovirus DNA was undetectable in the peripheral blood following 30 and 60 min of clamp time, indicating a clamp duration of at least 30 min promotes restriction of the adenovirus to the injected tissue.

B. Systemic Presence of Adenoviral DNA During and Following Clamp Release

To confirm the results above assessing presence of adenoviral DNA in the peripheral blood after 30 minutes of clamp time, a time course study was conducted to measure adenovirus presence in the peripheral blood during and following a clamp time of 30 min (n=3). Specifically, once the caudate lobe was clamped, the surgical procedure described in Example 1 was performed, followed by injection of $1\times10^{10}$ pfu Ad.CMV.Luc suspended in a total volume of 50 µl into the parenchyma of the caudate lobe using a 1 mL insulin syringe. Then, 100 µl of blood were drawn from the vena cava at 1, 3, and 5 min post adenoviral injection (during clamping) and at 1, 3, and 5 min after release of the clamp (post clamp release). The clamp was held in place for 30 minutes. The blood samples were analyzed for the presence of adenoviral DNA by amplifying the Luciferase gene by PCR as described above. Ten microliters of Ad.CMV.Luc adenovirus was used as a positive control (C+).

The results are set forth in FIG. 3, panel B. Adenoviral DNA was not detectable in the blood at any of the time points tested, but was detected in the positive control sample. These results indicate the clamp procedure prevents the injected adenovirus from entering the blood stream while the clamp is in place. The results also confirm that a clamp time of 30 minutes is sufficient for transduction of the virus into the injected tissue cells as evidenced by an undetectable amount of virus in the blood up to 5 min after clamp removal.

Example 3

Dose-Response Kinetics of Transgene Expression

To determine the relationship between protein expression and adenoviral administration, a dose response curve was generated. Following the surgical and clamping procedures described in Example 1 (n=6/dose group). Each group received an injection of $1\times10^3$, $1\times10^6$, $1\times10^9$, or $1\times10^{12}$ pfu Ad.CMV.Luc in 50 µL PBS as described previously. Control groups of rats that were submitted to the surgical procedure and injected with the corresponding adenoviral doses in a total volume of 100 µL PBS directly into the vena cava (n=6/dose group). After injection, the rats were sutured as described in Example 1 and allowed to recover. Seventy two (72) hours post surgery, the rats were euthanized as described in Example 1, and the caudate lobes of the livers were harvested and processed for Luciferase activity assay, as described in Example 1. Because Luciferase activity is proportional to the amount of synthesized Luciferase protein present in the sample, this metric was used as a measure of synthesized transgenic protein.

The results are set forth in FIG. 4. Luciferase activity/expression increased linearly with increased vector dose, ranging from about $2.5\times10^2$ rlu/g of protein from tissues receiving injections of $10^3$ pfu adenovirus to greater than $5\times10^9$ rlu/g of protein for tissues receiving injections of $10^{12}$ pfu. These results show that there is a correlation between vector dose and protein output.

Example 4

Duration of Transgene Expression

The sustainability of transgene expression was determined by measuring transgene expression (Luciferase activity) at progressive time points following adenovirus administration. To this end, rats (n=6/time point) were subjected to the surgical procedure as described in Example 1, and after the caudate lobe was clamped, $1\times10^9$ pfu of Ad.CMV.Luc, in 50 µl PBS were injected into the caudate lobe, of each animal, following the protocol set forth in Example 1. A control group of rats (n=5) were submitted to the same surgical procedure as the experimental group, but received an intravenous (IV) injection of $1\times10^9$ pfu of Ad.CMV.Luc, in 100 µl PBS, into the vena cava. Following adenovirus administration, the rats were sutured as described in Example 1 and allowed to recover. Five (5) rats per time point were euthanized at 30, 60, 90, 120, 150, 180, and 365 days post adenovirus injection as described in Example 1 above. The caudate lobes of the livers were then harvested and processed to assay Luciferase activity, as described in Example 1.

The results are set forth in FIG. 5. At day 30, approximately $10^3$ rlu/g of protein, on average, were detected in caudate lobe extracts. The Luciferase activity increased over 100-fold between 30 and 90 days post adenovirus administration (~$10^3$ rlu/g of protein to ~$10^5$ rlu/g of protein). At 120 days post adenoviral transduction, the protein expression dropped to about half that observed at 30 days post transduction (~500 rlu/g of protein). Expression then rebounded up to over $10^4$ rlu/g of protein by 150 days post transduction. This level of protein expression was maintained at 180 days post injection and dropped only slightly at 1 year (365 days) post adenoviral transduction. These results demonstrate sustained transgene expression for at least 1 year post transduction.

Example 5

Cytokine mRNA Expression

Cytokine expression levels induced in the liver upon delivery of Adenovirus to the compartmentalized caudate lobe and cytokine expression levels induced in the peripheral blood upon delivery of Adenovirus to the vena cava were determined. Briefly, once the caudate lobe was clamped, the surgical procedure described in Example 1 was performed followed by injection of $1 \times 10^9$ pfu recombinant Ad.CMV.Luc, in 50 µl phosphate-buffered saline (PBS) into the parenchyma of the caudate lobes as described in Example 1. As a control group, animals were injected with $1 \times 10^9$ pfu Ad.CMV.Luc in a total volume of 50 µl PBS into the vena cava as described in Example 1.

Seventy Two (72) hours post procedure the rats were euthanized with an i.p. dose of sodium pentobarbital. The livers were harvested and the caudate lobe, right lateral, left lateral and median lobes of the liver were separated. Total RNA was extracted using the Trizol kit (Gibco/Life Technologies) according to the manufacturer's protocol. One µg of total RNA was used for reverse transcription, which was performed with a RNA PCR Kit (Applied Biosystems, Branchburg N.J.) following the manufacturer instructions. For tumor necrosis factor alpha (TNFα) mRNA detection, the following primers were used: sense 5'-ACTCCCA-GAAAAGCAAGCAA-3' (SEQ ID NO:3) and antisense 5'-CGAGCAGGAATGAGAAGAGG-3' (SEQ ID NO:4) in a total reaction volume of 1 µl. PCR conditions were: 94° C. for 5 min, followed by 25 cycles at 94° C. for 30 s, 58° C. for 30 s, and 72° C. for 30 s and 7 min at 72° C. extension. For transforming growth factor beta (TGFβ), the following primers were used: sense 5'-ATACGCCTGAGTGGCT-GTCT-3' (SEQ ID NO:5) and antisense 5'-TGGGACT-GATCCCATTGATT-3' (SEQ ID NO:6) in a total reaction volume of 20 µl. PCR conditions were: 94° C. for 5 min, followed by 25 cycles at 94° C. for 30 s, 58° C. for 30 s, and 72° C. for 30 s and 7 min at 72° C. extension, For interferon gamma (IFNγ), the following primers were used: sense 5'-GCCCTCTCTGGCTGTTACTTG-3' (SEQ ID NO:7) and antisense 5'-CTGATGGCCTGGTTGTCTTT-3' (SEQ ID NO:8) in a total reaction volume of 20 µl. PCR conditions were: 94° C. for 5 min, followed by 25 cycles at 94° C. for 30 s, 60° C. for 30 s, and 72° C. for 30 s and 7 min at 72° C. extension. For interleukin 6 (IL-6), the following primers were used: sense 5'-CCGGAGAGGAGACTTCACAG-3' (SEQ ID NO:9) and antisense 5'-ACAGTGCATCATCGCT-GTTC-3' (SEQ ID NO:10) in a total reaction volume of 20 µl. PCR conditions were: 94° C. for 5 min, followed by 25 cycles at 94° C. for 30 s, 55° C. for 30 s, and 72° C. for 30 s and 7 min at 72° C. extension. PCR primers for beta-actin was used as a internal control, and were as follows: sense 5'TGAAGATCAAGATCATTGCTCCTCC-3' (SEQ ID NO:11) and antisense 5'-CTAGAAGCATTTGCGGTG-GACGATG-3'(SEQ ID NO:12) in a total reaction volume of 20 µl. PCR conditions were: 94° C. for 5 min, followed by 25 cycles at 94° C. for 30 s, 55° C. for 30 s, and 72° C. for 30 s and 7 min at 72° C. extension.

The results are depicted in FIG. 6. The results show that delivery of adenovirus to the vena cava resulted in detection of TNFα and IFNγ in all liver lobes, while TGFβ and IL-6 were detected in all lobes, except the right lateral lobe. In contrast, delivery of the adenovirus to the compartmentalized caudate lobe resulted in detection of TGFβ and IFNγ in the caudate lobe and low level expression of TNFα in the caudate lobe. Expression of these cytokines in the other lobes was not detected. IL-6 was not detected in any lobe. Thus, the results show low hepatic cytokine expression.

Example 6

Ex-Vivo Clamping Studies on Cadaver Pig Liver

Preliminary ex vivo studies were performed on pig livers. The pig was chosen as an animal model given that the size, weight and gross anatomy closely resemble that of a human. Fresh whole/complete livers were obtained from a local butchery. Using a laparoscopic device, the left median lobe was clamped and 5 ml bromophenol blue were injected into the parenchyma. After 30 minutes, the clamp was removed and the tissue on both sides of where the clamp had been placed were dissected and analyzed for the presence of blue dye. While blue dye was observed at the clamping boundary on the side of the tissue proximal to the injection, the blue dye did not penetrate the tissue at the edge of the clamping boundary that was distal to the site of injection. Thus, the clamping device was capable of compartmentalizing the dye by preventing transfer of the solution to the distal side of the device.

Example 7

Compartmentalization of Adenovirus Transduction in Pigs

The procedure described in Example 1 was next tested in pigs using the clamping device described in Example 6. The pigs were housed under standard conditions with 12 hr day/night cycles and were provided with water and food ad libitum. The pigs were placed under general anesthesia, and following aseptic cleaning of the abdominal area, a 5 cm infra-xyphoid medial incision was made. The left median lobe of the liver was then located and exposed, and the surgical clamp described in Example 5 was placed on the distal portion of the left median lobe. 500 µL of phosphate buffered solution (PBS) containing $1 \times 10^9$ infective viral particles of rAd-CMV-Luciferase were then injected into the isolated parenchyma of the left median lobe using an insulin syringe.

After an elapsed time of 30 minutes, the clamp was removed, the abdominal cavity was sutured in two planes, and the animals were allowed to recover. Seventy two (72) hours after the surgery, the animals were euthanized and the livers were harvested. Tissue samples were taken from the site of injection, the left lateral lobe, right lateral lobe, and right median lobe at sites proximal, medial, and distal to the site of injection. The tissue samples were frozen for use in luciferase activity and viral DNA nested polymerase chain reaction (PCR) analysis.

Compartmentalization of the adenoviral transduction was assessed in the tissue samples. Briefly, tissue samples were homogenized and Luciferase activity assays were performed as described in Example 1. The results are set forth in FIG. 7. Background luciferase activity was observed on lobes from all samples from the right lateral, right median and left lateral lobes. In contrast, luciferase activity measured from the site of injection was approximately 20-fold higher than any of the other samples. These results demonstrate that Luciferase activity was limited to the injected, clamped tissue and support the conclusion that the adenoviral transduction was compartmentalized in pigs.

To confirm the compartmentalized transduction of the adenovirus, the tissue samples were further analyzed by nested-PCR. The initial run of PCR was conducted by amplifying the Luciferase gene for 50 cycles using specific primers. Ten microliters of Ad.CMV.Luc adenovirus was used as a positive control and the plasmid pcDNA3 (Invitrogen, Life Technologies, Carlsbad, Calif.) was used as a negative control. The initial product was analyzed by agarose gel electrophoresis. The results showed a band similar in size to that observed for the positive control amplified from the adenovirus-injected tissue, but not in any of the other tissue samples or in the negative control sample. The second PCR run, using the initial PCR product and nested primers was carried out with sense 5'-CAACTGCATAAGGCTATGAAGAGA-3' (SEQ ID NO:13) and antisense 5'-ATTTGTATTCAGCCCATATCGTTT-3' (SEQ ID NO: 14) primers in a total reaction volume of 20 µL. PCR conditions were: 94° C. for 5 min, followed by 25 cycles at 94° C. for 30 s, 53° C. for 30 s, and 72° C. for 30 s and 7 min at 72° C. extension. Upon analysis by agarose gel electrophoresis, a clear band corresponding to the Luciferase gene was present in the injected tissue and positive control samples and was completely absent in the other tissue and negative control samples. The presence of viral DNA sequence in the injected, clamped tissue and not in any of the adjacent tissue indicate successful compartmentalization of viral transduction.

Example 8

Soluble Reporter Protein Expression in Blood Following Delivery to Compartmentalized Liver Lobe To determine if a soluble protein can be expressed and detected in the blood, adenovirus expressing a soluble protein was injected into the caudate lobe of rats that was compartmentalized using a parenchymal clamp. The adenovirus designated Ad-ALB-AFP was derived from human adenovirus type 5 and encodes the rat alpha fetoprotein (AFP) gene driven by a rat albumin promoter sequence (Herbomel et al. (1989) *Molecular and Cellular Biology*, 9:4750-4758; Tronche et al. (1989) *Molecular and Cellular Biology*, 9:4759-4766). The adenovirus was made replication deficient by deleting the E1 region. Into this deleted E1 region, the reporter gene alpha fetoprotein (AFP) was cloned and constructed to be driven by the rat albumin (ALB) promoter for specificity to the liver. pUC57 plasmid encoding rat AFP under control of the ALB promoter was synthesized by Genscript (Piscataway, N.J.). The AFP expression cassette from the pUC57 plasmid was subcloned into the Dual-Basic adenoviral shuttle vector and recombined with Ad5 (DE1/DE3) vector (Vector Biolabs, Philadelphia, Pa.). The adenovirus was packaged in HEK293 cells and purified with cesium chloride ultracentrifugation. The ALB-AFP virus was administered at $3.25 \times 10^9$ in a total volume of 50 µL. On day 5 after injection, animals were sacrificed and livers were harvested.

Compartmentalization was performed similar to the procedures described in Example 1. Briefly, eight (8) rats were anesthetized with an intraperitoneal (i.p.) injection of 60 mg/kg ketamine-HCl and 10 mg/kg Xylazine-HCl (Baxter Healthcare Corporation, Deerfield, Ill.). Each rat was then placed in a supine position, the abdominal region was shaved, and the abdominal cavity was exposed following a 3 cm ventral midline incision from the xiphoid process to the umbilical region. The upper portion of the caudate lobe was located and dissected, severing the interlobular and hepatogastric ligaments. The pedicle of the caudate lobe was identified and clamped using a 10 mm micro-serrefine (Fine Science Tools-USA Inc., Foster City, Calif.).

Once the caudate lobe was clamped, $3.75 \times 10^9$ pfu recombinant Ad.ALB-AFP, in 50 µL phosphate-buffered saline (PBS) in a 1 mL syringe (Becton Dickinson Corp., Franklin, N.J.), were injected into the parenchyma of the caudate lobe of six (6) rats. Another 2 rats were used as non-injected controls. The clamp was held for 30 minutes. The rats were then sutured in two planes (muscle and skin) with 5-0 Vicryl (Ethicon, Inc., Somerville, N.J.) and allowed to recover.

Seven (7) days post-surgery, 1 mL of peripheral blood was collected from the vena cava. The blood was collected using a serum separator tube (Becton Dickinson Corp., Franklin, N.J.) and samples were allowed to clot for 30 minutes before centrifugation at 1000 g fro 15 minutes. Serum was removed, aliquoted and samples stored at −20° C. AFP was detected in the serum using the Rat Alpha-fetoprotein, AFP ELISA Kit (Cusabio Biotech Co., Ltd., Wuhan China) according to the manufacturer's protocol.

The results are depicted in FIG. 8. The results show detection of AFP in the blood of control rats that were not injected with virus. The results show that rats injected with Ad.ALB-AFP had higher AFP in the serum than the control animals. Thus, the results show that injection of adenovirus expressing a soluble protein into a compartmentalized lobe of the liver results in expression of the soluble protein that is detectable in the blood.

Since modifications will be apparent to those of skill in this art, it is intended that this invention be limited only by the scope of the appended claims.

What is claimed:

1. A method of delivering a nucleic acid molecule to a subject, comprising:
   a) compartmentalizing a tissue or organ or portion of the tissue or organ from systemic circulation of the subject, wherein:
   the tissue or organ is the liver of the subject or a portion of the liver of a subject;
   the portion has a volume of at least 5 mm³; and
   compartmentalization includes clamping the tissue, organ or portion thereof, and effects isolation of the tissue, organ or portion from systemic circulation;
   b) administering a delivered agent directly to the parenchyma of the compartmentalized tissue or organ or portion of the tissue or organ, wherein:
   the delivered agent comprises the nucleic acid molecule, wherein, upon administration directly into the parenchyma, the delivered agent enters parenchymal cells of the compartmentalized tissue or organ or portion of the tissue or organ, and is not delivered into systemic circulation; and administration is effected by injection directly into the parenchyma in the compartmentalized tissue or organ or portion thereof, and does not include administration to connective tissue, blood vessels, nerves or ducts;

c) maintaining the compartmentalization after administering the delivered agent for a predetermined time to effect cellular uptake of the delivered agent into cells of the parenchyma, wherein the predetermined time is at least 20 minutes up to 60 minutes; and d) after the predetermined time to effect cellular uptake of the delivered agent, restoring communication between the tissue, organ or portion of the tissue or organ and the systemic circulation.

2. The method of claim 1, wherein compartmentalizing the tissue or organ or portion of the tissue or organ is effected prior to or when administering the delivered agent.

3. The method of claim 1, wherein compartmentalizing the tissue or organ or portion of the tissue or organ is effected prior to administering the delivered agent, whereby the delivered agent is administered after compartmentalizing the tissue or organ or portion of the tissue or organ.

4. The method of claim 3, wherein administering the delivered agent is effected no more than 5 minutes after compartmentalizing the tissue or organ or portion of the tissue or organ.

5. The method of claim 1, wherein compartmentalization is achieved by applying pressure to the organ, tissue or portion thereof with a clamp, thereby compressing any arteries, veins, ducts and/or vessels and blocking the blood supply and flow to the arteries, veins, ducts and/or vessels in the tissue or organ or portion of the tissue or organ that is clamped, thereby eliminating the blood supply and flow to the tissue or organ or portion thereof that is clamped.

6. The method of claim 5, wherein all arteries, veins, ducts and/or vessels servicing or traversing the tissue or organ or portion of the tissue or organ are blocked from communication with the compartmentalized organ, tissue or portion thereof.

7. The method of claim 6, wherein the blocking of the arteries, veins, ducts and/or vessels is effected with a device or technique selected from among manual compression, an arterial or venous clamp, an occlusion catheter, a stapling device, a band, a tourniquet and a cable.

8. The method of claim 5, wherein a tissue or organ or portion of a tissue or organ is compartmentalized by clamping the tissue, organ or portion thereof with a parenchymal clamp.

9. The method of claim 8, wherein the clamp is a laparoscopic clamp.

10. The method of claim 1, wherein after compartmentalizing the tissue or organ or portion thereof, further comprising applying suction to reduce or eliminate blood in the tissue or organ or portion thereof.

11. The method of claim 1, wherein the predetermined time to effect cellular uptake is at least 30 minutes.

12. The method of claim 11, wherein restoring communication with the systemic circulation comprises removing the device or technique used to compartmentalize the tissue, organ or portion of the tissue or organ.

13. The method of claim 11, the method steps (a)-(d) are repeated a plurality of times.

14. The method of claim 13, wherein in a subsequent iteration of the method, the delivered agent is administered to the same compartmentalized locus or a different compartmentalized locus.

15. The method of claim 11, wherein the predetermined time is up to 45 minutes after administering the delivered agent.

16. The method of claim 11, wherein the predetermined time is less than 60 minutes.

17. The method of claim 11, wherein the predetermined time is 25 minutes to 60 minutes.

18. The method of claim 1, wherein the predetermined time is sufficient for the administered delivered agent to enter the parenchymal cells, whereby no more than 5% of the delivered agent is exposed to the systemic circulation.

19. The method of claim 18, wherein the predetermined time is up to 50 minutes after administering the delivered agent.

20. The method of claim 19, wherein the predetermined time is at least 30 minutes after administering the delivered agent.

21. The method of claim 1, wherein the tissue or organ or portion of the tissue or organ is a lobe of the liver or portion thereof.

22. The method of claim 1, wherein the portion of the liver is an area of that has a length ranging from about 0.5 cm to 25 cm, a height of 0.5 cm to 20 cm and a depth from 0.5 cm to 15 cm.

23. The method of claim 1, wherein:
the predetermined time before restoring communication with the systemic circulation is between about 20 minutes and 50 minutes.

24. The method of claim 1, wherein a portion of the tissue or organ is compartmentalized.

25. The method of claim 1, wherein a portion of the liver is compartmentalized and the portion is a lobe, segment or a portion of a lobe or segment of the liver.

26. The method of claim 25, wherein the lobe or portion of a lobe is selected from among the right lobe, the left lobe, the quadrate lobe and the caudate lobe or is a portion thereof.

27. The method of claim 1, wherein the delivered agent is selected from among a non-viral vector, a virus, a virus-like particle, a minicircle, a nanoparticle and a whole cell that comprise the nucleic acid molecule.

28. The method of claim 27, wherein the delivered agent is a nanoparticle and the nanoparticle is targeted or radiolabeled.

29. The method of claim 27, wherein the delivered agent is a virus and the virus is selected from among an adenovirus, an adeno-associated virus (AAV), a retrovirus, vaccinia virus and herpes simplex virus.

30. The method of claim 29, wherein the retrovirus is a lentivirus.

31. The method of claim 29, wherein the virus is an adenovirus.

32. The method of claim 31, wherein the adenovirus comprises a deletion in an E1, E2a, E2b, E3, or E4 coding region.

33. The method of claim 31, wherein the adenovirus is adenovirus type 2 or adenovirus type 5.

34. The method of claim 33, wherein the adenovirus comprises a deletion in an E1, E2a, E2b, E3, or E4 coding region.

35. The method of claim 29, wherein the virus comprises the nucleic acid molecule and the nucleic acid molecule is heterologous to the virus genome.

36. The method of claim 1, wherein the nucleic acid molecule encodes a polypeptide, whereby the polypeptide is expressed.

37. The method of claim 36, wherein the encoded polypeptide is selected from the among an enzyme, a hormone, a coagulation or clotting factor, a cytokine, a growth factor or active portion thereof, an antibody or antigen binding portions of antibodies, an angiogenesis modulator, an immunomodulator, a pain modulator, a receptor or active portion thereof, a transport protein, a regulatory protein, an antigen and an allergen.

38. The method of claim 36, wherein the encoded polypeptide is selected from among adenosine deaminase, cystic fibrosis transmembrane conductance regulator (CTFR), galsulfase, laronidase, N-acetylgalactosamine 6-sulfatase, phenylalanine ammonia lyase, acid alpha glucosidase, imiglucerase, alglucosidase alpha, thyrotropin, growth hormone, insulin, thyroid hormone, erythropoietin (EPO), interleukin-1 (IL-1), IL-2, IL-3, IL-4, IL-5, IL-7, interferon-α (IFN-α), IFN-β, IFN-γ, tumor necrosis factor (TNF), IL-12, IL-18, fms-related tyrosine kinase 3 (flt3), neuropilin-2 (NP2), bone morphogenic protein (BMPs), epidermal growth factor (EGF), erythropoietin (EPO), fibroblast growth factor (FGF), granulocyte colony stimulating factor (G-CSF), granulocyte macrophage colony stimulating factor (GM-CSF), hepatocyte growth factor (HGF), insulin-like growth factor (IGF), platelet derived growth factor (PDGF), transforming growth factor α or β, vascular endothelial growth factor (VEGF), epidermal growth factor receptor (EGFR), fibroblast growth factor receptor (FGFR), FGFR antagonist (sFGFR) transforming growth factor receptor (TGFR), vascular endothelial growth factor receptor (VEGFR), plasminogen activator, urokinase, Factor VIII, Factor IX, von Willebrand factor, growth hormone, metalloproteinase thrombospondin motifs 1 (METH-1), METH-2, tryptophanyl-tRNA synthetase (TrpRS) fragments, proliferin-related protein, prolactin fragment, pigment epithelium-derived factor (PEDF), vasostatin, angiostatin, endostatin, kininostatin, fibrinogen-E fragment, thrombospondin, tumstatin, canstatin, restin, soluble fms-like tyrosine kinase-1 (sFlt-1), soluble vascular endothelial growth factor receptors (sFlk), soluble Neuropilin 1 (sNRP1), Interferon gamma-induced protein 10 (IP-10), Platelet factor 4 (PF-4), Gro-beta, soluble Ephrin type-B receptor 4 (sEphB4), sephrinB2, IGF-1, herpes simplex virus thymidine kinase (HSV-TK), carboxypeptidase G2 (CPG2), carboxylesterase (CA), cytosine deaminase (CD), cytochrome P450 (cyt-450), deoxycytidine kinase (dCK), nitroreductase (NR), purine nucleoside phosphorylase (PNP), thymidine phosphorylase (TP), varicella zoster virus thymidine kinase (VZV-TK), xanthine-guanine phosphoribosyl transferase (XGPRT), Aspartylglucosaminidase, α-Galactosidase A, Palmitoyl Protein Thioesterase, Tripeptidyl Peptidase, Lysosomal transmembrane protein, cysteine transporter, Acid ceramidase, acid α-L-fucosidase, protective protein/cathepsin A, acid β-glucosidase or glucocerebrosidase, acid β-galactosidase, iduronate-2-sulfatase, α-L-Iduronidase, galactocerebrosidase, acid α-mannosidase, acid β-mannosidase, arylsulfatase B, arylsulfatase A, N-Acetylgalactosamine-6-sulfate sulfatase, N-Acetylglucosamine-1-phosphotransferase, Acid sphingomyelinase, NPC-1, β-Hexosaminidase B, Heparan N-sulfatase, α-N-Acetylglucosaminidase (NaGlu), Acetyl-CoA: αglucosamininde N-acetyltransferase, N-Acetylglucosamine-6-sulfate sulfatase, β-Glucuronidase, acid lipase, neprilysin, the insulin-degrading enzyme insulysin, thimet oligopeptidase, calbindin D28, parvalbumin, HIF1-alpha, SIRT-2, SMN-1, SMN-2, GDNF, ciliary neurotrophic factor (CNF), low density lipoprotein receptor (LDLR), lipoprotein lipase (LPL), Alpha-1-Antitrypsin (AAT), UDP-glucuronyl-transferase (UGT), UGT1A1, glucose-6 phosphatase, phosphoenolpyruvate-carboxykinase, galactose-1 phosphate uridyl transferase, phenylalanine hydroxylase, branched chain alpha-ketoacid dehydrogenase, fumarylacetoacetate hydrolase, methylmalonyl-CoA mutase, ornithine transcarbamylase, argininosuccinic acid synthetase, adenosine deaminase, hyposanthine guanine phosphoribosyl transferase, biotinidase, beta-glucocerebrosidase, beta-gluronidase, porphobilinogen deaminase (PBDG) and p53.

39. The method of claim 36, wherein the nucleic acid molecule is a therapeutic nucleic acid molecule that encodes a therapeutic product.

40. The method of claim 39, wherein the disease or condition is selected from among an arthritis, chronic pain, HIV-related AIDS, atherosclerosis, restenosis, inherited enzyme deficiency, inherited immune deficiency, cancer, a retrovirus infection, hemophilia, diabetes, a muscular dystrophy, a cardiovascular disorder, cystic fibrosis, a neurodegenerative disorder, trauma, pain, sickle cell anemia, autoimmune disease, inflammatory disease, and hypertension.

41. The method of claim 39, wherein the nucleic acid molecule encode a protein selected from among a Factor VIII for the treatment of hemophilia A; a Factor IX for the treatment of hemophilia B; an insulin gene for treatment of type I diabetes mellitus; an alpha-1-antitrypsin (AAT) for the treatment of alpha-1-antitrypsin (AAT) deficiency; a hemochromatosis protein (HFE) for treatment of hemochromatosis; a copper-transporting ATPase 2 for treatment of Wilson's disease; UDP glucuronosyltransferase 1A1 (UGT1A1) for the treatment of Crigler-Najjar syndrome type I; ornithine transcarbamylase (OTC) for the treatment of ornithine transcarbamylase deficiency, type II; low density lipoprotein receptor (LDLR) for the treatment of familial hypercholesterolemia; fibrinogen alpha (FGA), beta (FGB) or gamma (FGB) for the treatment of afibrinogenemia; glucose-6-phosphate-α for the treatment of glycogen storage disease (GSD) type Ia; G6PT for the treatment of GSD type Ib; acid-α-glucosidase for the treatment of GSD type II (Pompe); α-L-iduronidase for the treatment of mucopolysaccharidosis (MPSI); sulfamidase for the treatment of MPS IIIA; α-N-acetylglucosaminidase (NaGlu) for the treatment of MPS IIIB; β-glucuronidase for the treatment of MPS VII; α-galactosidase A for the treatment of Fabry disease; glucocerebrosidase for the treatment of Gaucher's disease; acid sphingomyelinase for the treatment of Niemann-Pick syndrome; phenylalanine hydroxylase for the treatment of phenylketonuria; TIMP antagonist or anti-HSC molecules for the treatment of liver fibrosis; anti-ROS molecules for the treatment of liver ischemia reperfusion injury; amyloid-beta degrading enzyme neprilysin, the insulin-degrading enzyme insulysin, or thimet oligopeptidase for the treatment of Alzheimer's disease; insulin growth factor-1 (IGF-1), calbindin D28, parvalbumin, HIF1-alpha, SIRT-2, VEGF, SMN-1, SMN-2, GDNF or ciliary neurotrophic factor (CNF) for the treatment of Amyotrophic Lateral Sclerosis (ALS); galactose-1 phosphate uridyl transferase for the treatment of galactosemia; branched chain alpha-ketoacid dehydrogenase for the treatment of maple syrup urine disease; fumarylacetoacetate hydrolase for the treatment of tyrosinemia type 1; methylmalonyl-CoA mutase for the treatment of methylmalonic acidemia; argininosuccinic acid synthetase for the treatment of citrullinemia; hyposanthine guanine phosphoribosyl transferase for the treatment of Gout and Lesch Nyan syndrome; beta-gluronidase for the treatment of Sly syndrome; peroxisome membrane protein 70 kDa for the treatment of Zellweger syndrome, enfuvirtide for the treatment of Human immunodeficiency virus (HIV) infection; adenosine deaminase (ADA) for the treatment of combined immunodeficiency disease (SCID); CFTR for the treatment of cystic fibrosis; porphobilinogen deaminase (PBDG) for the treatment of acute intermittent *porphyria*; interferon-beta for the treatment of multiple sclerosis; lipoprotein lipase for the treatment of lipoprotein lipase deficiency (LPLD), p53 for the treatment of cancer; and glutamic acid decarboxylase (GAD) for the treatment of Parkinson's Disease.

42. The method of claim 36, wherein the nucleic acid molecule encodes a polypeptide that increases muscle production in an animal, increases hair production in an animal, increases wool production in an animal, increases growth of an animal, or is involved in nutrient synthesis or utilization.

43. The method of claim 42, wherein the encoded polypeptide is selected from among:
a polypeptide that increases muscle production in an animal that is a myostatin inhibitor;
a polypeptide that increases growth in an animal that is a growth hormone, IGF-1, a growth hormone releasing factor or chicken Ski; and
a polypeptide that is involved in nutrient synthesis or utilization that is a serine transacetylase and o-acetylserine sulphydrylase.

44. The method of claim 43, wherein the myostatin inhibitor is follistatin.

45. The method of claim 1, wherein the nucleic acid molecule is selected from among a DNA molecule, a RNA molecule, and an aptamer.

46. The method of claim 45, wherein the nucleic acid molecule is selected from among a microRNA, a small interfering RNA, a ribozyme and an antisense nucleic acid.

47. The method of claim 1, comprising imaging the tissue or organ to identify the parenchymal tissue prior to administration of the delivered agent.

48. The method of claim 47, wherein the imaging is magnetic resonance imaging (MRI), sonography (ultrasound), or computed tomography (ct).

49. The method of claim 1, wherein the delivered agent is formulated with lipids, polymer reagents or other agents to facilitate entry into the parenchymal cells.

50. The method of claim 1, wherein the delivered agent is delivered in the presence of a physical method to facilitate entry into parenchymal cells.

51. The method of claim 50, wherein the physical method is selected from among electroporation, sonoporation, hydrodynamic pressure, ultrasound and a gene gun.

52. The method of claim 1, further comprising administering an agent that promotes cellular uptake of the delivered agent, wherein the agent is administered prior to, simultaneously or subsequent to administration of the delivered agent.

53. The method of claim 52, wherein the agent is a transcriptional enhancer of a virus-specific cell surface receptor or of the therapeutic transgene.

54. The method of claim 53, wherein the agent is a histone deacetylase (HDAC) inhibitor.

55. The method of claim 1, wherein the amount of delivered agent that is administered is 100-fold or less than the amount of the same delivered agent administered intravenously for the same purpose.

56. The method of claim 1, wherein:
the delivered agent is an adenovirus or adeno-associated virus comprising a heterologous nucleic acid molecule in its genome; and
the amount of delivered agent administered is between about 10 to $1 \times 10^{12}$ viral particles.

57. The method of claim 56, wherein:
the amount of delivered agent administered is up to about $1 \times 10^{10}$ to about $1 \times 10^{11}$ viral particles.

58. The method of claim 56, wherein:
the amount of delivered agent administered is up to about $1 \times 10^{7}$ viral particles.

59. The method of claim 1, wherein the delivered agent is administered to more than one locus in the compartmentalized tissue, organ or portion of the tissue or organ.

60. The method of claim 1, wherein prior to restoring communication to the tissue, organ or portion of the tissue or organ with the systemic circulation, further comprising removing from the parenchyma of the tissue or organ or portion of the tissue or organ any delivered agent that is extracellular.

61. The method of claim 1, wherein the subject is selected from among a mouse, rat, cow, pig, sheep, goat, horse and human.

62. The method of claim 1, wherein the subject is a human child under the age of 18 or is a human fetus.

63. The method of claim 1, wherein the subject has been diagnosed with a genetic deficiency.

64. The method of claim 1 the method steps (a)-(d) are performed via laparoscopy.

65. The method of claim 1, wherein the predetermined time is no more than 30 minutes after administering the delivered agent.

66. The method of claim 1, wherein the portion has a volume of at least 10 $mm^3$.

67. The method of claim 1, wherein the predetermined time is 20 minutes to 30 minutes.

68. The method of claim 1, wherein the nucleic acid encodes insulin.

69. The method of claim 1, wherein the nucleic acid encodes a coagulation or clotting factor.

70. The method of claim 1, wherein the nucleic acid encodes factor VIII.

71. The method of claim 1, wherein the predetermined time is 30 to 60 minutes after compartmentalization.

72. The method of claim 1, wherein the predetermined time is at least 25 minutes after compartmentalization.

73. A method of delivering a nucleic acid molecule to a subject, comprising:
a) compartmentalizing a tissue or organ or portion of the tissue or organ to isolate it from systemic circulation of the subject, wherein:
the portion has a volume of at least 5 $mm^3$; and
compartmentalization is effected by clamping the tissue or organ or portion of the tissue or organ to effect isolation of the tissue, organ or portion from systemic circulation;
b) administering a delivered agent directly by injection into the parenchyma of the compartmentalized tissue or organ or portion of the tissue or organ, wherein:
the delivered agent comprises the nucleic acid molecule, whereby the delivered agent directly enters parenchymal cells of the compartmentalized tissue or organ or portion of the tissue or organ; and the parenchyma in the compartmentalized tissue or organ or portion of the tissue or organ does not include connective tissue, blood vessels, nerves or ducts; and c) maintaining the compartmentalization for a predetermined time to effect cellular uptake of the delivered agent in to the cells of the parenchyma, wherein the predetermined time is more than 15 minutes up to about 1 hour; and d) after the predetermined time to effect cellular uptake of the delivered agent, restoring communication between the tissue, organ or portion of the tissue or organ and the systemic circulation.

74. The method of claim 73, wherein the predetermined time is at least 30 minutes.

75. The method of claim 73, wherein the predetermined time is at least 25 minutes after compartmentalization.

\* \* \* \* \*

SEQUENCE LISTING

<160> NUMBER OF SEQ ID NOS: 14

<210> SEQ ID NO 1
<211> LENGTH: 24
<212> TYPE: DNA
<213> ORGANISM: Artificial Sequence
<220> FEATURE:
<223> OTHER INFORMATION: Luciferase primer - sense

<400> SEQUENCE: 1
atggaagacg ccaaaaacat aaag            24

<210> SEQ ID NO 2
<211> LENGTH: 24
<212> TYPE: DNA
<213> ORGANISM: Artificial Sequence
<220> FEATURE:
<223> OTHER INFORMATION: Luciferase primer - antisense

<400> SEQUENCE: 2

```
aaaaccggga ggtagatgag atgt                                              24

<210> SEQ ID NO 3
<211> LENGTH: 20
<212> TYPE: DNA
<213> ORGANISM: Artificial Sequence
<220> FEATURE:
<223> OTHER INFORMATION: TNF alpha primer - sense

<400> SEQUENCE: 3
actcccagaa aagcaagcaa                                                   20

<210> SEQ ID NO 4
<211> LENGTH: 20
<212> TYPE: DNA
<213> ORGANISM: Artificial Sequence
<220> FEATURE:
<223> OTHER INFORMATION: TNF alpha primer - antisense

<400> SEQUENCE: 4
cgagcaggaa tgagaagagg                                                   20

<210> SEQ ID NO 5
<211> LENGTH: 20
<212> TYPE: DNA
<213> ORGANISM: Artificial Sequence
<220> FEATURE:
<223> OTHER INFORMATION: TGF beta primer - sense

<400> SEQUENCE: 5
atacgcctga gtggctgtct                                                   20

<210> SEQ ID NO 6
<211> LENGTH: 20
<212> TYPE: DNA
<213> ORGANISM: Artificial Sequence
<220> FEATURE:
<223> OTHER INFORMATION: TGF beta primer - antisense

<400> SEQUENCE: 6
tgggactgat cccattgatt                                                   20

<210> SEQ ID NO 7
<211> LENGTH: 21
<212> TYPE: DNA
<213> ORGANISM: Artificial Sequence
<220> FEATURE:
<223> OTHER INFORMATION: IFN gamma primer - sense

<400> SEQUENCE: 7
gccctctctg gctgttactt g                                                 21

<210> SEQ ID NO 8
<211> LENGTH: 20
<212> TYPE: DNA
<213> ORGANISM: Artificial Sequence
<220> FEATURE:
<223> OTHER INFORMATION: IFN gamma primer - antisense

<400> SEQUENCE: 8
ctgatggcct ggttgtcttt                                                   20

<210> SEQ ID NO 9
<211> LENGTH: 20
<212> TYPE: DNA
```

```
<213> ORGANISM: Artificial Sequence
<220> FEATURE:
<223> OTHER INFORMATION: IL-6 primer - sense

<400> SEQUENCE: 9
ccggagagga gacttcacag                                          20

<210> SEQ ID NO 10
<211> LENGTH: 20
<212> TYPE: DNA
<213> ORGANISM: Artificial Sequence
<220> FEATURE:
<223> OTHER INFORMATION: IL-6 primer - antisense

<400> SEQUENCE: 10
acagtgcatc atcgctgttc                                          20

<210> SEQ ID NO 11
<211> LENGTH: 25
<212> TYPE: DNA
<213> ORGANISM: Artificial Sequence
<220> FEATURE:
<223> OTHER INFORMATION: beta-actin primer - sense

<400> SEQUENCE: 11
tgaagatcaa gatcattgct cctcc                                    25

<210> SEQ ID NO 12
<211> LENGTH: 25
<212> TYPE: DNA
<213> ORGANISM: Artificial Sequence
<220> FEATURE:
<223> OTHER INFORMATION: beta-actin primer - antisense

<400> SEQUENCE: 12
ctagaagcat ttgcggtgga cgatg                                    25

<210> SEQ ID NO 13
<211> LENGTH: 24
<212> TYPE: DNA
<213> ORGANISM: Artificial Sequence
<220> FEATURE:
<223> OTHER INFORMATION: Second (nested) Luciferase primer - sense

<400> SEQUENCE: 13
caactgcata aggctatgaa gaga                                     24

<210> SEQ ID NO 14
<211> LENGTH: 24
<212> TYPE: DNA
<213> ORGANISM: Artificial Sequence
<220> FEATURE:
<223> OTHER INFORMATION: Second (nested) Luciferase primer - antisense

<400> SEQUENCE: 14
atttgtattc agcccatatc gttt                                     24
```

UNITED STATES PATENT AND TRADEMARK OFFICE
CERTIFICATE OF CORRECTION

Page 1 of 1

PATENT NO. : 9,821,114 B2
APPLICATION NO. : 13/815206
DATED : November 21, 2017
INVENTOR(S) : Jose Gustavo Cabrera Aquino It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 32 days.

Signed and Sealed this
Twenty-seventh Day of March, 2018

Andrei Iancu
*Director of the United States Patent and Trademark Office*